US008394379B2

(12) United States Patent
Imboden et al.

(10) Patent No.: US 8,394,379 B2
(45) Date of Patent: Mar. 12, 2013

(54) TARGETED CRYPTOSPORIDIUM BIOCIDES

(75) Inventors: Michael Imboden, Madison, WI (US); Michael Warren Riggs, Tucson, AZ (US); Deborah A. Schaefer, Tucson, AZ (US); Jane Homan, Hillpoint, WI (US)

(73) Assignee: ioGenetics, LLC, Madison, WI (US)

( * ) Notice: Subject to any disclaimer, the term of this patent is extended or adjusted under 35 U.S.C. 154(b) by 284 days.

(21) Appl. No.: 12/686,879

(22) Filed: Jan. 13, 2010

(65) Prior Publication Data

US 2010/0183611 A1 Jul. 22, 2010

Related U.S. Application Data

(60) Continuation-in-part of application No. 12/536,291, filed on Aug. 5, 2009, now abandoned, which is a division of application No. 11/545,601, filed on Oct. 10, 2006, now abandoned, which is a continuation-in-part of application No. 11/254,500, filed on Oct. 20, 2005, now Pat. No. 7,566,447, which is a continuation-in-part of application No. 10/844,837, filed on May 13, 2004, now abandoned.

(60) Provisional application No. 61/144,299, filed on Jan. 13, 2009, provisional application No. 60/470,841, filed on May 15, 2003.

(51) Int. Cl.
*A61K 39/00* (2006.01)
*A61K 39/395* (2006.01)

(52) U.S. Cl. ............... 424/134.1; 424/133.1; 424/141.1; 424/151.1

(58) Field of Classification Search ........................ None
See application file for complete search history.

(56) References Cited

U.S. PATENT DOCUMENTS 4,816,567 A 3/1989 Cabilly et al.
5,019,411 A 5/1991 Johnson et al.
5,433,955 A 7/1995 Bredehorst et al.
5,550,145 A 8/1996 Olund
5,601,825 A 2/1997 Hansen
5,618,840 A 4/1997 Wright
5,750,496 A 5/1998 Forney
5,871,714 A 2/1999 Budny et al.
5,874,079 A 2/1999 Weinrauch
5,891,490 A 4/1999 Merabet
6,013,918 A 1/2000 Bushnell et al.
6,015,882 A 1/2000 Petersen et al.
6,063,905 A 5/2000 Capra
6,086,936 A 7/2000 Wilson et al.
6,093,573 A 7/2000 Beamer et al.
6,103,505 A 8/2000 Clausen
6,110,463 A 8/2000 Riggs et al.
6,159,447 A 12/2000 Budny et al.
6,162,788 A 12/2000 Lambert, Jr.
6,165,526 A 12/2000 Newman
6,172,040 B1 1/2001 Naidu
6,265,187 B1 7/2001 Scott et al.
6,323,020 B1 11/2001 Perryman et al.
6,376,450 B1 4/2002 Ghosh
6,475,484 B1 11/2002 Weiss
6,562,617 B1 5/2003 Anderson et al.
6,682,737 B1 1/2004 Riggs et al.
6,830,745 B1 12/2004 Budny et al.
6,984,503 B1 1/2006 Wang et al.
7,063,837 B2 6/2006 Fischetti et al.
7,566,447 B2 7/2009 Homan et al.
2002/0015697 A1 2/2002 Beckman et al.
2002/0048576 A1 4/2002 Anderson
2003/0056244 A1 3/2003 Huang et al.
2003/0114377 A1 6/2003 Kirkland et al.
2004/0009167 A1 1/2004 Rider
2004/0052814 A1 3/2004 Shi et al.
2004/0115207 A1 6/2004 Irwin et al.
2005/0014932 A1 1/2005 Imboden
2005/0170334 A1 8/2005 Mikayama et al.

FOREIGN PATENT DOCUMENTS

WO 94/25476 3/1996
WO 96/09398 3/1996
WO 97/03693 6/1997
WO 98/06430 2/1998
WO 98/07320 2/1998
WO 00/23593 4/2000
WO 00/61190 10/2000
WO 02/13857 2/2002
WO 03/007989 1/2003
WO 2004/050846 A2 6/2004
WO 2004/110143 12/2004
WO 2005/040201 A1 5/2005
WO 2006/132665 12/2006
WO 2007/047189 4/2007

OTHER PUBLICATIONS

Brown et al. J. immunol. 1996 156(9):3285-3291.*
Vadjos et al. J. Mol. Biol. 2002. 320:415-428.*
Paul, William E. Ed. Fundamental Immunology, 3rd Edition, 1993, p. 292-295.*
Abbas et al. Cellular and Molecular Immunology 4th edition, 2000 Chapter 48, p. 42-43 and p. 48.*
Forney J.R. et al., "Antagonistic Effect of Human Alpha 1 Antitrypsin on Excystation of Cryptosporidium parvum Oocysts", J Parasitol., 83:771-774 (1997).
US Dept. Ag.: Animal and Plant Health Inspection Service, Veterinary Services, National Daily Heifer Evaluation Project, "Dairy Heifer Morbidity, Mortality, and Health Management Focusing on Preweaned Heifers", pp. 1-22 (1994).
Novello, A., "Public Health Dispatch: Outbreak of *Escherichia coli* O157:H7 and Campylobacter Among Attendees of the Washington County Fair" MMWR Morb. Mortal. Wkly. Rep., 48(36):803-805 (1999).
Grau F., "Prevention of Microbial contamination in the export of beef abattoir", In: Smulders FJM ed. Amsterdam: Elsevier, 221-234 (1987).
Perryman, L.E., "Protection of claves against cyrptosporidiosis with immune bovine colostrums induced by a *Cryptosporidium parvum* recombinant protein", Vaccine, 17:2142-2149 (1999).

(Continued)

*Primary Examiner* — Oluwatosin Ogunbiyi
(74) *Attorney, Agent, or Firm* — Casimir Jones, S.C.

(57) ABSTRACT

The present invention relates to fusion proteins comprising a microorganism targeting molecule (e.g., immunoglobulin) and a biocide. The present invention also relates to therapeutic and prophylactic methods of using a fusion protein comprising a microorganism targeting molecule and a biocide in diverse fields.

4 Claims, 71 Drawing Sheets

OTHER PUBLICATIONS

Pritchard, G.C. et al, "Verocytotoxin-producing *Escheria coli* 0157 on a farm open to the public: outbreak investigation and longitudinal bacteriological study,"Vet. Rec., 147:259-264 (2000).
Characklis, W.G. "Biofilm processes", In: Characklis WG and Marshall KC eds. New York: John Wiley & Sons, pp. 195-231 (1990).
Kim, C.W., "Cryptosporidiosis in Pigs and Horses", In: J.P. Dubey, C.A. Speer, and R. Faye reds. Boca Raton, FL: CRC Press, pp. 105-111 (1990).
Chappell, C. et al., "Infectivity of *Cyrptosporidium parvum* in Healthy Adults with Preexisting Anti-C. Parvum Serum Immunoglobulin G", Am J. Trop Med Hyg., 60 (1) pp. 157-164 (1999).
Eisenhauer, P., "Purification and Antimicrobial Properties of three Defensins from Rat Neutorphils", Infect and Immun., 57(7) pp. 2021-2027 (1989).
Fore, J., "The effects of business practices, licensing, and intellectual property on development and dissemination of the polymerase chain reaction: case study", J. Biomed. Disc. & Callabo., 1(7) (2006).
Ganz, T., et al. "Defensins, Natural Peptide Antibiotics of Human Neutrophils", J. Clin. Invest. 76 pp. 1427-1435 Oct. 1985.
Langer, R. & Riggs, M., "Cryptosporidium parvum Apical Complex Glycoprotein CSL Contains a Sporozoite Ligand for Intestinal Epithelial Cells", Infect. & Immun. 67(10) pp. 5282-5291 (1999).
Langer, R. et al., "Characterization of an intestinal Epithelial Cell Receptor Recognized by the *Cryptosporidium parvum* Sporozoite Ligand CLS", Infect Y Immun. 69(3) pp. 1661-1670 (2001).
Moreira, L., et al., "Bee Venom Phospholipase Inhibits Malaria Parasite Development in Transgenic Mosquitoes", J. Biol.Chem. 277(43) pp. 40839-40843 (2002).
Selsted, M. and Harwig, S. "Purification, Primary Structure, and Antimicrobial Activities of a Guinea Pig Neutrophil Defensin", Infect. & Immun. 55(9) pp. 2281-2286 (1987).
Wilde, C., et al., "Purification and Characterization of Human Neutrophil Peptide 4, a Novel Member of the Defensin Family", Jul. 5, 1989;264(19):11200-3.
Wong, A. "Biofilms in Food Processing Environments", J. Dairy Sci. 81 pp. 2765-2770 (1998).
McGwire, B. "Killing of African Trypanosomes by Antimicrobial Peptides", J. Infect. Disease; 188 pp. 146-152 (2003).
Flint, S.H., et al., "Biofilms in Dairy Manufacturing Plant-Description, Current Concerns and Methods of Control", Biofouling, vol. 11(1) pp. 81-97 (1997).
Riggs, M.W., et al., "Protective Monoclonal Antibody Defines a Circumsporozite-Like Glycoprotein Exoantigen of *Cryptosaporidium parvum* Sporozoites and Merozoites", J. of Immunology, 158 pp. 1787-1795 (1997).
Ibrahim, H.R., et al., "Genetic evidence that antibacterial activity off lysozyme is independent of its catlaytic function", FEBS Letters, 506 pp. 27-32 (2001).
Tzipori, S., and Ward, H., "Cryptosporidiosus: biology, pathogenesis and disease", Microbes and Infection, 4 pp. 1047-1058 (2002).
Zeya et al., "Antimicrobial Specificity of Leukocyte Lysosomal Cationic Proteins," Science, 154:1049-1051 (1966).
Hancock, D.D., et al., "The prevalence of *Escheria coli* 0157.H7 in dairy and beef cattle in Washington State", Epidemiol. Infect., 113(2):199-207 (1994).
Riggs, M. , Microbes Infect., Recent advances in cryptosporidiosis: the immune response. Microbes. Infect 4:1067-1080, 2002 4:1067 (2002).
Robinson, C. and Sauer, R. "Optimizing the stability of single-chain proteins by linker length and composition mutagenesis", Poc.Natl. Acad. Sci. 95 pp. 5929-5934 (1998).
Schaefer, D.A., et al., "Characterization and Formulation of Multiple Epitope-Specific Neutralizing Monoclonal Antibodies for Passive Immunization against Cryptosporidiosus", Infection and Immunity 68(5):2608-2616 (May 2000).
Pellegrini, A., et al., Biochem. Biophys. Res. Commun., Identification and Isolation of the Bactericidal Domains in the Proteinase Inhibitor Aprotinin, 222(2):559-565 (1996).
Gerhard, et al., "Prospects for Universal Influenza Virus Vaccine", Emerging Infectious Diseases, vol. 12, pp. 569-574 (2006).
Zebedee, et al., "Influenza A Virus M2 Protein: Monoclonal Antibody Restriction of Virus Growth and Detection of M2 in Virions", Journal of Virology, vol. 62, pp. 2762-2772 (1988).
Riggs, et al., "Efficacy of Monoclonal Antibodies against Defined Antigens for Passive Immunotherapy of Chronic Gastrointestinal Cryptosporidiosis", Antimicrobial Agents and Chemotherapy, vol. 46, pp. 275-282 (2002).
Rehg, et al., "Effect on Interferon-γ in Experimental *Cryptosporidium parvum* Infection", J. of Infectious Diseases, vol. 174, pp. 229-232 (1996).
Hunt, et al., "Oral Bovine Serum Concentrate Improves Cryptosporidial Enteritis in Calves", Pediatric Research, vol. 51, pp. 370-376 (2002).
Carey, et al., "Biology, persistence and detection of *Cryptosporidium parvum* and *Cryptosporidium hominis* oocyst", Water Research, vol. 38, pp. 818-862 (2004).
Howe, et al. "Cryptosporidium Oocysts in a Water Supply Associated with a Cryptosporidosis Outbreak", Emerging Infectious Diseases, vol. 8, pp. 619-624 (2002).
Searcy, et al. "Capture and Retention of *Cryptosporidium parvum* Oocysts by *Pseudomonas aeruginosa* Biofilms", Applied Environmental Microbiology, vol. 72, pp. 6242-6247 (2006).
Kato, et al. "Effects of Freeze-Thaw Events on the Viability of *Cryptosporidium parvum* Oocysts in Soil", J. Parasitol., vol. 88, pp. 718-722 (2002).
Sitaram, et al. "The Therapeutic Potential of Host-Defense Antimicrobial Peptides", Current Drug Targets, vol. 3, pp. 259-267 (2002).
Saito, et al. "Potent Bactericidal Activity of Bovine Lactoferrin Hydrolysate Produced by Heat Treament at Acidic pH", J. Dairy Science, vol. 74, pp. 3724-3730 (1991).
Yoshida, et al. "Separation of Lactoferrin-a and -b from Bovine Colostrum", J. Dairy Science, vol. 83, pp. 2211-2215 (2000).
Barker, et al. "Survival of *Salmonella* in bathrooms and toilets in domestic homes following salmonellosis", Journal of Applied Microbiology, vol. 89, pp. 137-144 (2000).
Tzipori, "Cryptosporidosus: Laboratory Investigations and Chemotherapy" Advances in Parasitology, vol. 40, pp. 187-221(1998).
Abbas et al. Cellular and Molecular Immunology 4th ed. 2000 p. 50-51.
Okuda et al. "New Type of Antibody-Enzyme Conjugate Which Specifically Kills Candida albicans." Infection and Immunity Feb. 1980, p. 690-692.
Cortruvo et al. Waterborne Zoonoses: Identfication, Causes and Control. Emerging Issues in Water and Infectious Diseases series, World Health Organizatiion, Section V Pl. 209-212, 2004.
Merriam Webster Dictionary definition of foodstuff, retrieved Feb. 24, 2007, http://www.m-w.com/cgi-bin/dictionary?book+dictionary &va=foodstuff.
Merriam Webster Dictionary definition of microorganism, http://www.m-w.com/cgi-bin/dictionary?book-Dictionary &va=microorganism, retrieved Feb. 24, 2007.
Randall et al., "J Chain Synthesis and secretion of hesameric IgM is differentially regulated by lipopolysaccharide and interleukin 5."PNAS V. 89 P. 962-966 1992.
Lis et al.,"Galactose Oxidase-Glucan Binding Domain Fusiion Proteins as Targeting Inhibitors of Dental Plaque Bacteria." Antimicrobial Agents and Chemotherapy, May 1997, p. 999-1003.
Triiantafilou et al., "Lipopolysaccharide recognition: CD14, TLRs and the LPS-activation cluster." Trends in Immunology vol. 23 Jun. 2002 p. 301-304.
Kim et al., "Cyrstal Structure of CD14 and its Implications for Lipopolysaccharide Signaling." The Journal of Biological Chemistry V. 280 p. 11347-11351, 2005.
Pietrella et al., "Mannoproteins from Cyrptococcus neoformans Promote Dentritic Cell Maturation and Activation." Infection and Immunity, Feb. 2005 p. 820-827.
Kitchens et al. "Plasma CD14 decreases monocyte responses to LPS by transferring cell-bound LPS to plasma lipoproteins." The Journal of Investigation, 2001 108:485-493.
Palmer et al. "Functional Glycosylphosphatidylinositol Anchor signal sequences in the *Pneumocystis carinii* PRT1 Family." Am J. Respir. Cell Mol. Biol. 25:466-473 2001.

Kitchens et al. "Bacterial lipopolysaccharide Can Enter Monocytes via Two CD14-Dependent Pathways." The Journal of Immunology, 1998 161:5534-5545.
Pugin et al., "CD14 Is a Pattern Recognition Receptor." Immunity Sep. 1994; 1(6):509-516.
Jack et al., "Both Membrane-bound and soluble forms of CD14 bind to Gram-negative bacteria." Eur. J. Immunol. 1995 25:1436-1441.
Definition of Kitchenware—Merriam-Webster Online Dictionary, retrieved Oct. 3, 2006, http://www.m-w.com/cgi-bin/dictionary?book=Dictionary&va=kitchenware.
Definition of Treatment—American Heritage Dictionary of the English Language: 4th edition. 2000—Online Copy.
Labeta et al., "Innate Recognition of Bacteria in Human Milk Is Mediated by a Milk-derived Highly Expressed Pattern Recognition Receptor, Soluable CD14." J. Exp. Med. May 15, 2000 191(10):1807-1812.
Thomas et al., "Prevention of Microbial Contamination in the poultry processing plant", Smulders FJM ed. Amsterdam: Elsevier, 1987:163-180.
Jenkins. "Advances and protocols for subunit vaccines against protozoa of vetinary importance." Vetrinary Parasitology 101(2001) p. 291-310.
Garcia et al., "Intestinal Protozoa: Coccidia and Microsporidia." Diagnostic Medical Parasitology 2nd Edition 1993 p. 49-51.
Carryn et al., "Phospholipases and cationic peptides neutralize *Cyrptosporidium parvum* sporozolite Infectivity by either parasiticidal or non-parasiticidal Mechanisms." International Journal of Antimicrobial Agents vol. 24S p. S117 (2004).
Freshney. "Culture of Animal Cells, A manual of Basic Technique." Alan R. Liss, Inc., 1983, New York, p. 4).
Cayman Chemical CPLA2 Assay Kit Technical Bulletin pp. 1-8 Catalog No. 765021, Caymen chemical Company, Ann Arbor, MI. Feb. 17, 2003.
Calbiochem, Lactoferrin ELISA kit, Catalog No. 427275, Rev. Nov. 4, 2005 RFH 6 pages.
Graczyk et al., *Giardia* sp. Cysts and Infectiouis *Cyrptosporidium parvum* Oocysts in the Feces of Migratory Canada Gees (*Branta canadensis*)Applied and Environmental Microbiology Jul. 1998 p. 2736-2738.
Prins Etfoye's Principles of Medical Chemistry, Fifth Edition, D.A. 2002, Ch. 6, p. 119, Left Column Under Alternative Drug Delievery Methods for Peptides and Proteins AL., Antonie van Leeuwehoek 1983 49:585-595.
Hammerling et al., "Monoclonal Antibodies and T Cell Hybridomas Perspectives and technical advances" Elsevier/North Holland Biomedical Press 1981.
Oi et al., "Chimeric Antibodies." Biotechniques 1986 4:214-221.
Presta et al., "Antibody Engineering." Current Opinion in Structural Biology 1992 2:593-596.
Reichmann et al., Reshaping human antibodies for therapyNature 1998 332(6162): 323-7.
Jones et al., "Replacing the complementarity-determining regions in a human antibody with those from a mouse." Nature 1986 321(6069):522-5.
Orlandi et al. "Cloning immunoglbulin variable domains for expression by the polymerase chain reaction." PNAS May 1989 86:3833-3837.
Coloma et al. "Primer Design for the Cloning of Immuno-globulin Heavy-Chain Leader-Variable Regions from Mouse Hybridoma Cells Using the PCR." Biotechniques 1991 11:152-156.
Sastry et al. "Cloning of the immunological repertoire in *Escherichia coli* for generation of monoclonal catalytic antibodies: Construction of a heavy chain variable region-specific cDNA library." PNAS 1989 86:5728-5732.
Bendig et al., "Humanization of Rodent Monoclonals Antibodies by CDR Grafting." Methods: A Companion to Methods in Enzymology 1995 8:83-93.
Falla et al, "Mode of Action of the Antimicrobial Peptide Inolicidin." The Journal of Biological Chemistry, vol. 271, No. 32, pp. 19298-19303, 1996.
Florack et al, "Thionins: Properties, possible biological roles and mechanisms of action." Plant Molecular Biology 26: 25-37, 1994.
Huettinger et al, "Lactoferrin Specifically Inhibits Endocytosis of Chylomicron Remnants but Not α-Macroglobulin." The Journal of Biological Chemistry 267 (26) 18551-18557, 1992.
Weiner et al., "The Antimicrobial Activity of the Cathelicidin LL37 Is Inhibited by F-actin Bundles and Restored by Gelsolin." American Journal of Respiratory Cell and Molecular Biology 2003 28:738-745.
Gomi et al., "Immunological Detection of Lipopolysaccharide Antigens of Thermophilic Campylobacters Capurted on Polymyxin-Coated Polyester Cloth." Immunological Investigations 25(3):177-183 (1996).
Cohen et al., "Serum Antibodies to Lipopolysaccharide and Natural Immunity to Shigellosis in an Israeli Military Population." The Journal of Infectious Diseases 157(5): 1068-1071 (May 1988).
Priya et al., "Identification and evaluation of LPS antigen for serodiagnosis of uveitis associated with leptospirosis." J Med Microbiol 52:667-673 (2003).
Petrov et al., "Toxicity and Immunogenicity of Neisseria Meningitidis Lipopolysaccharide Incorporated into Liposomes." Infection and Immunity 60(9):3897-3903 (Sep. 1992).
Takkinen et al., "An Active single-chain antibody containing a cellulase linker domain is secreted by *Escherichia coli*." Protein Engineering Design and Selection 4:837-841 (1991).
Greenspan et al., "Defining epitopes: It's not as easy as it seems." Nature Biotechnology 7:936-937 (1999).
Baral, T.N. et al., "Experimental therapy of African trypanosomasis with a nanobody-conjugated human trypanolytic factor" Nat. Med., 12(5):580-584 (May 2006).
Bowdish D.M. et al., "Impact of LL-37 on antim-infective Immunity" J. Leukoc. Biol., 77(4):451-459 (Apr. 2005).
Giocometti, A. et al., "In vitro effect on *Cyrptosporidium parvum* of short-term exposure to cathelicidin peptides" J. Antimicrob. Chemoth. 51(4):843-847, 2003.
Arrowood et al, "Effects of Immune Colostrum and Orally Administered Atisporozoite Monoclonal Antibodies on the Outcome of *Cryptosporidium parvum* Infections in Neonatal Micel." Infection and Immunity 57(8):2283-2288 (1989).
Colman et al., "Effects of amino acid sequence changes on antibody-antigen interactions." Research in Immunology 145:33-36 (1994).
Khan et al., "Biological and Chemical Terrorism: Strategic Plan for Preparedness and Response Recommendations of the CDC Strategic Planning Workgroup." MMWR Report Apr. 21, 2009 (RR04); 1-14.
Millar et al., "*Cryptosporidium* in foodstuffs-an emerging aetiological route of human foodborne illness." Trends in Food Science and Technology 13(5):168-187 (2002).
Fletcher et al., "A Novel Peptide-IgG Conjugate, CAP18106-138-IgG, that binds and neutralizes Endotoxin and Kills Gram-Negative Bacteria." J. Infectious Diseases 1997, 175(3):621-632.
Shaw et al., "Protection Efficacy of CAP18 106-138-Immunoglobulin G in Sepsis." J. Infectious Diseases 2003, 188 (9): 1382-1393.
Imboden et al., "Antibodies Fused to Innate Immune Molecules Reduce Initiation of *Cryptosporidium parvum* Infection in Mice." Antimicrobial Agent and Chemotherapy 2010, 54(4): 1385-1392.
Schultz et al., "BPI ANCA is found in reactive arthritis caused by *Yersinia* and *Salmonell* infection and recognize exclusively the C-terminal part of the BPI molecule" Scand. J Rheumaltol. 2000 v.29 pp. 226-231.
Randall et al., "J Chain Synthesis and secretion of hesameric IgM is differentially regulated by lipopolysaccharide and interleukin 5." PNAS V. 89 p. 962-966 1992.
Yoshida, Shigeto, "Bacteria expressing single-chain immunotoxin inhibit malaria parasite development in mosquitos", Molecular and Biochemical Parasitology 113(1):89-96 Mar. 2001 XP002429871, ISSN: 0166-6851.
Oren et al., "Structure and organization of the human antimicrobial peptide LL-37 in phospholipid membranes: relevance to the molecular basis for its non-cell-selective activity" Biochem J. Aug. 1, 1999. vol. 341 Pt.3, pp. 501-513 abstract p. 502 para. 1.
Perryman, et al., "Kinetics of *Cryptosporidium parvum* Sporozoite Neutralization by Monoclonal Antibodies". Immune Bovine Serum, and immune Bovine Colostrum Infect. Immun. Jan. 1990 58(1):257-259.

Cohen, S., "Colorado Firm Recalls Beef Trim and Ground Beef Products for Possible *E. coli* O157:H7" Recall Release, FSIS-RC-055-2002.
Buzby et al., "Bacterial Foodborne Disease: Medical Costs and Producliviry Losses", Food and Consumer Economics Division, Economic Research Service U.S. Department of Agriculture, Economic Report No. 741 (1996).
During, K., et al., "The non-enzymatic microbicidal activity of lysozymes", FEBS Lett., 449(2-3):93-100 (1999).
Reusens-Billen, at al., "Prevention of the cytotoxic effect of IL-1 by human lysozyme on isolated rat islets", Diabetes Res. Clin. Pract. vol. 23(2), pp. 85-94 (1994).
Takada, K., et al.,"Binding of Lysozyme to Lipopolysaccharide Supresses Tumor Necrosis Factor Production In Vivo", Infect. Immun., vol. 62(4), pp. 1171-1175 (1994).
Takada,K., et al., "Lysozyme RegUlates LPS-Induced Interleuken-6 Release in Mice", Circ. Shock, 44(4):169-174 (1994).
Qu, X.D. and Lehrer,R.I. "Secretory Phospholipase A2. is the Principal Bactericide for *Staphylococci* and other Gram-Positive Bacteria in Human Tears", Infect. Immun., 66:2791-2797 (1998).
Qu, X.D., et al., "Secretion of Type II Phospholipase A2 and Cryptdin by Rat Small Intestinal Paneth Cells", Infect. Immun., 64:5161-5165 (1996).
Buckland, A.G. and Wilton, D.C.,"The antibacterial properties of secreted phospholipases A2", Biochim. Biophys. Acta, 1488(1-2):71-82 (2000).
Gronroos, J.O., et al., "Bactericidal Group IIA Phospholipase A2 in Serum of Patients with Bacterial Infections", J. Infect. Dis., 185:1767-1772 (2002).
Laine,V.J., at al., "Resistance of Transgenic Mica Expressing Human Group II Phospholipase A2 to *Escheria coli* Infection", Infect. Immun., 68(1):87-92 (2000).
Koduri, R.S., et al., "Action of Huma Group LLa Secreted Phospholipase A2 on Cell Membranes." J. Biol. Chem., 273:32142-32153 (1998).
Laine V.J. et al, "Protection Group II Phospholipase A2 Against *Staphyloccus aureus*" J Immunol 162: 7402-7408 (1999).
Okhuysen, P.C., et al., "*Cryptosporidium parvum* Metalloaminopeptidase Inhibitors Prevent In Vitro Excystation", Antimicrob. Agents Chemother. 40: 2781-2784 (1996).
Forney, J.R. et al., "Efficacy of Serine Protease Inhibitors Against *Cryptosporidium parvum* Infection in a Bovine Fallopian Tube Epithelial Cell Culture", J. Parasitol., 82(4) 638-640 (1996).
Forney, J.R. et al., "A Role for Host Phosphoinositide 3-Kinase and Cytoskeletal Remodeling during *Cryptosporidium parvum* Infection", Infect. Immun., 67 (2) 844-852 (1999).
Nesterenko, M.V., et al., "A metallo-dependent cysteine proteinase of *Cryptosporidium parvum* associated with the surface of sporozites", Microbios., 83:77-88 (1995).
Mannion, B.A., et al., "Separation of Sublethal and Lethal Effects of the Bactericidal/Permeability Increasing Protein on *Escheria coli*", J. Clin. Invest., 85(3):853-860 (1990).
Prohinar, P. et al., "OmpR-dependent and OmpR-independent responses of *Escheria coli* to sublethal attack by the neutrophil bactericidal/permeability increasing protein", Mol. Microbiol., 43(6):1493-1504 (2002).
Selstad et al., "Purification and Antibacterial Activity of Antimicrobial Peptides if Rabbit Granulocytes", Infect. Immuno., 45:150-154 (1984).
Zeya et al., "Arginne-Rich Proteins of Polmorphonuclear Leukocyte Lysosomes", J. Exp. Med., 127:927-941 (1968).
Zeya et al., "Characterization of Cationic Protein-Bearing Granules of Polymorphonuclear Leukocytes", Lab. Invest., 24:229-236 (1971).
Lehrer et al., "Direct Inactivation of Viruses by MCP-1 and MCP-2, Natural Peptide Antibiotics from Rabbit Leukocytes", J. Virol. 54(2) pp. 467-472 (1985).
Selstad et al., "Activity of Rabbit Leukocyte Peptides Against Candida albicans", Infect. Immun., 49:202-206 (1985).
Segal et al., "In Vitro Effect of Phagocyte Cationic Peptides on *Coccidioides immitis*", J. Infect. Disease 151:890-894 (1985).
Costerton et al., "Microbial Biolfilms", Annu Rev Microbiol.; 49:711-45 (1995).
Lehrer et al., "Nonoxidative fungicidal mechanisms of mammalian granulocytes: demonstration of Components with Candidacidal Activity in Human, Rabbit . . . " Infect. & Immun. Infect Immuno. Jun. 1975; 11(6): 1226-1234.
Tomkin et al., "Guidelines to Prevent Post-Processing Contamination from Listeria Monocytogenes", Dairy, Food Environ Sanit; 19-551-62 (1999).
Welbourn and Williams "New Listeria Control Measures Under Considerations", Dairy, Food Environ Sanit 19:399-401 (1999).
Tuttle, J. et al., "Lessons from a large outbreak of *Escheria coli* 0157:H7 infections: insights into the infectious dose and method of widespread contamination of hamburger patties" Epidemiol. Infect., 122:185-192 (1999).
Beumer et al., "Listeria species in domestic environments" Epidemiol Infect. 117(3):437-42 Dec. 1996.
Zichichi et al., "*Psuedomonas aeurginosa* folliculitis after shower/bath exposure" Int J Dermatol 39(4):270-3 Apr. 2000.
Kumar, C.G. & Anand, S.K., "Significance of microbial biofilms in food industry: a review", Int J food Microbiol; 42:9-27 (1998).
Zottola and Sasahara, "Mircobial biofilms in the fodd processing industry-Should they be a concern?", Int J Food Microbiol; 23:125-48 (1994).
Mattick et al., "The survival of foodborne pathogens during domestic washing-up and subsequent transfer onto washing-up sponges, kitchen surfaces and food", Int J Food Microbiol. 25:85(3):213-26(2003).
Kusumaningrum et al., "Survival of foodborne pathogens on stainless steel surfaces and cross-contamination to foods", Int J Food Microbiol. 85(3)227-36(2003).
Silverman and Nieland, "Hot tub Dermatitis: A familial outbreak of *Pseudomonas folliculitis*", J Am Acad Dermatol.; 8(2) pp. 153-156 Feb. 1983.
Murphy et al., "Defensins Are Mitogenic for Epithelial Cells and Fibroblasts", J. Cell. Physiol., 155:408-13(1993).
Blackman and Frank, "Growth of Listeria monocytogenes as a Biofilm on Various Food-Processing Surfaces", J Food Prot; 59:827-31 (1996).
Frank and Coffi, "Surface-adherant Growth of Listeria Monocytogenes is Associated with Increased Resistance to Surfactant Sanitizers and Heat", J Food Prot; 53:550-4 (1990).
Krysinski, "Effect of Cleaners and Sanitizers on Listeria monocytogenes Attached to Product Contact Surfaces" J Food Prot 55:246-51 (1992).
Ronner and Wong "Biofilm Development and Santizer Inactivation of *Listeria monocytogenes* and *Salmonella typhimurium* on stainless steel and . . . " J Food Prot; 56:750-8 (1993).
Dunsmore et al., "Design and Performance of Systems for Cleaning Product-Contact Surfaces of Food Equipment: A review", J Food Prot; 44:220-40 (1981).
Helke and Wong, "Survival and Growth Characteristics of *Listeria monocytogenes* and *Salmonella typhimurium* on stainless steel and Buna-N Rubber", J Food Prot; 57:963-8 (1994).
Lehrer and Ladra "Fungicidal Components of Mammalian Granulocytes Active against *Cryptococcus neoformans*", J Infect. Dis 136(1) pp. 96-99 (1977).

* cited by examiner

Figure 2

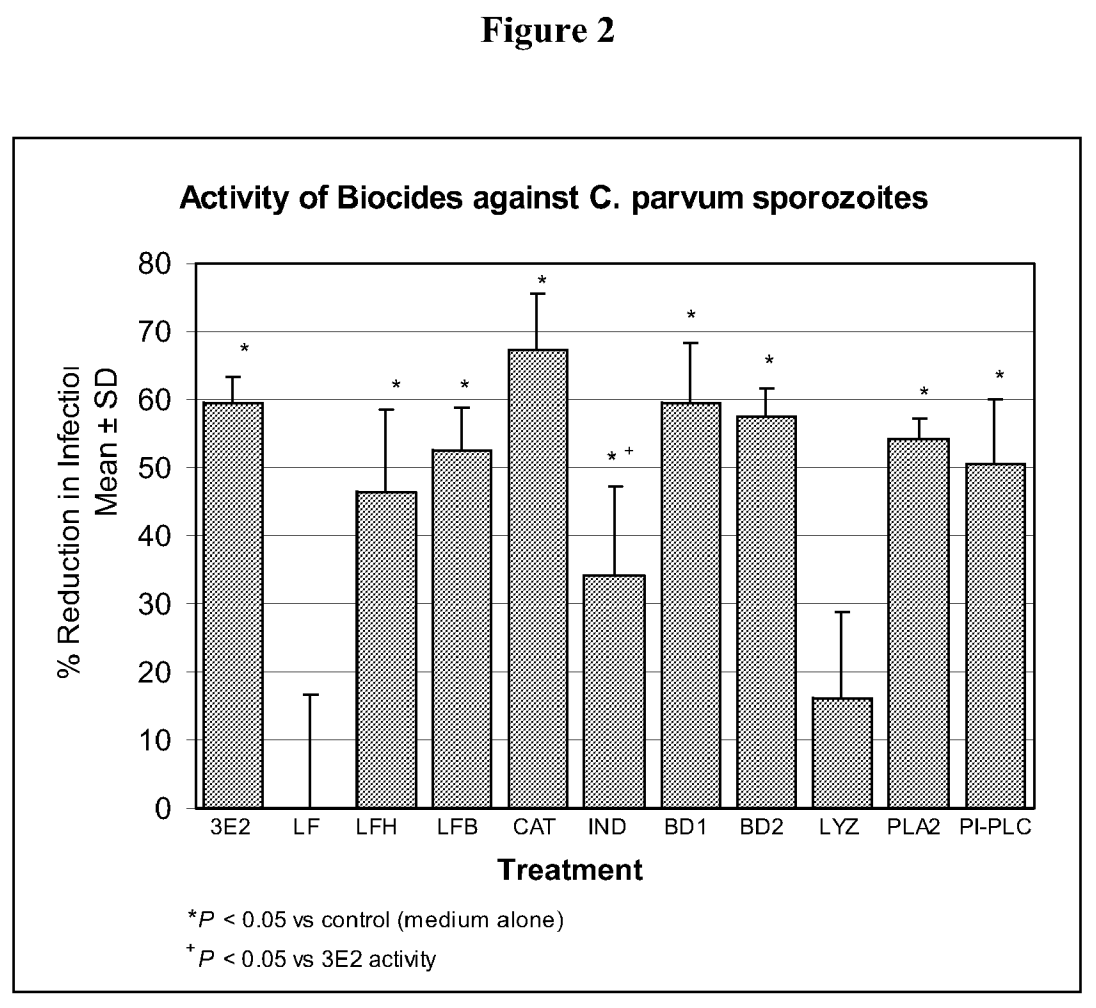

Activity of Biocides against C. parvum sporozoites

% Reduction in Infection
Mean ± SD 80
70
60
50
40
30
20
10
0

3E2
LF
LFH
LFB
CAT
IND
BD1
BD2
LYZ
PLA2
PI-PLC

Treatment

*$P < 0.05$ vs control (medium alone)

+$P < 0.05$ vs 3E2 activity

Figure 9

4H9-G1 Heavy Chain, 1395 bp including signal peptide (1-60) (SEQ ID NO:1)

ATGGAGACAGACACACTCCTGCTATGGGTACTGCTGCTCTGGGTTCCAGGTTCCACTGGTGACCAGGTCCAGCTTCAGCAGTCTGGGGC
TGAACTGGCAAAACCTGGGGCCTCAGTGAAGATGTCCTGCAAGGCTTCTGGCTACACCTTTACTAGCTACTGGATGCACTGGGTGAAAC
AGAGGCCTGGACAGGGTCTGGAATGGATTGGATACATTAATCCTAGCACTGGTTATCCTGAGTACAATCAGAAATTCAAGGACAAGGCC
ACATTGACTGCAGACAAATCCTCCAACACAGCCTACATGCAACTGAGCAGCCTGACATCTGAGGACTCTGCAGTCTATTACTGTGTAAG
AAGGAATTACTACGAGGACTTCTTTGACTACTGGGGCCAAGGCACCACTCTCACAGTCTCCTCAGCCAAAACGACACCCCCATCTGTCT
ATCCACTGGCCCCTGGATCTGCTGCCCAAACTAACTCCATGGTGACCCTGGGATGCCTGGTCAAGGGCTATTTCCCTGAGCCAGTGACA
GTGACCTGGAACTCTGGATCCCTGTCCAGCGGTGTGCACACCTTCCCAGCTGTCCTGCAGTCTGACCTCTACACTCTGAGCAGCTCAGT
GACTGTCCCCTCCAGCACCTGGCCCAGCGAGACCGTCACCTGCAACGTTGCCCACCCGGCCAGCAGCACCAAGGTGGACAAGAAAATTG
TGCCCAGGGATTGTGGTTGTAAGCCTTGCATATGTACAGTCCCAGAAGTATCATCTGTCTTCATCTTCCCCCCAAAGCCCAAGGATGTG
CTCACCATTACTCTGACTCCTAAGGTCACGTGTGTTGTGGTAGACATCAGCAAGGATGATCCCGAGGTCCAGTTCAGCTGGTTTGTAGA
TGATGTGGAGGTGCACACAGCTCAGACGCAACCCCGGGAGGAGCAGTTCAACAGCACTTTCCGCTCAGTCAGTGAACTTCCCATCATGC
ACCAGGACTGGCTCAATGGCAAGGAGTTCAAATGCAGGGTCAACAGTGCAGCTTTCCCTGCCCCCATCGAGAAAACCATCTCCAAAACC
AAAGGCAGACCGAAGGCTCCACAGGTGTACACCATTCCACCTCCCAAGGAGCAGATGGCCAAGGATAAAGTCAGTCTGACCTGCATGAT
AACAGACTTCTTCCCTGAAGACATTACTGTGGAGTGGCAGTGGAATGGGCAGCCAGCGGAGAACTACAAGAACACTCAGCCCATCATGG
ACACAGATGGCTCTTACTTCGTCTACAGCAAGCTCAATGTGCAGAAGAGCAACTGGGAGGCAGGAAATACTTTCACCTGCTCTGTGTTA
CATGAGGGCCTGCACAACCACCATACTGAGAAGAGCCTCTCCCACTCTCCTGGTAAATGA

Figure 9 Continued

Translation 4H9-G1, 464 residues including SP (1-20) (SEQ ID NO:2)

METDTLLLWVLLLWVPGSTGDQVQLQQSGAELAKPGASVKMSCKASGYTFTSYWMHWVKQRPGQGLEWIGYINPSTGYPEYNQKFKDKA

TLTADKSSNTAYMQLSSLTSEDSAVYYCVRRNYYEDFFDYWGQGTTLTVSSAKTTPPSVYPLAPGSAAQTNSMVTLGCLVKGYFPEPVT

VTWNSGSLSSGVHTFPAVLQSDLYTLSSSVTVPSSTWPSETVTCNVAHPASSTKVDKKIVPRDCGCKPCICTVPEVSSVFIFPPKPKDV

LTITLTPKVTCVVVDISKDDPEVQFSWFVDDVEVHTAQTQPREEQFNSTFRSVSELPIMHQDWLNGKEFKCRVNSAAFPAPIEKTISKT

KGRPKAPQVYTIPPPKEQMAKDKVSLTCMITDFFPEDITVEWQWNGQPAENYKNTQPIMDTDGSYFVYSKLNVQKSNWEAGNTFTCSVL

HEGLHNHHTEKSLSHSPGK

Figure 9 Continued

4H9-G1-LL37, 1554 bp, including signal peptide (1-60) (SEQ ID NO:3)

ATGGAGACAGACACACTCCTGCTATGGGTACTGCTGCTCTGGGTTCCAGGTTCCACTGGTGACCAGGTCCAGCTTCAGCAGTCTGGGGC
TGAACTGGCAAAACCTGGGGCCTCAGTGAAGATGTCCTGCAAGGCTTCTGGCTACACCTTTACTAGCTACTGGATGCACTGGGTGAAAC
AGAGGCCTGGACAGGGTCTGGAATGGATTGGATACATTAATCCTAGCACTGGTTATCCTGAGTACAATCAGAAATTCAAGGACAAGGCC
ACATTGACTGCAGACAAATCCTCCAACACAGCCTACATGCAACTGAGCAGCCTGACATCTGAGGACTCTGCAGTCTATTACTGTGTAAG
AAGGAATTACTACGAGGACTTCTTTGACTACTGGGGCCAAGGCACCACTCTCACAGTCTCCTCAGCCAAAACGACACCCCCATCTGTCT
ATCCACTGGCCCCTGGATCTGCTGCCCAAACTAACTCCATGGTGACCCTGGGATGCCTGGTCAAGGGCTATTTCCCTGAGCCAGTGACA
GTGACCTGGAACTCTGGATCCCTGTCCAGCGGTGTGCACACCTTCCCAGCTGTCCTGCAGTCTGACCTCTACACTCTGAGCAGCTCAGT
GACTGTCCCCTCCAGCACCTGGCCCAGCGAGACCGTCACCTGCAACGTTGCCCACCCGGCCAGCAGCACCAAGGTGGACAAGAAAATTG
TGCCCAGGGATTGTGGTTGTAAGCCTTGCATATGTACAGTCCCAGAAGTATCATCTGTCTTCATCTTCCCCCCAAAGCCCAAGGATGTG
CTCACCATTACTCTGACTCCTAAGGTCACGTGTGTTGTGGTAGACATCAGCAAGGATGATCCCGAGGTCCAGTTCAGCTGGTTTGTAGA
TGATGTGGAGGTGCACACAGCTCAGACGCAACCCCGGGAGGAGCAGTTCAACAGCACTTTCCGCTCAGTCAGTGAACTTCCCATCATGC
ACCAGGACTGGCTCAATGGCAAGGAGTTCAAATGCAGGGTCAACAGTGCAGCTTTCCCTGCCCCCATCGAGAAAACCATCTCCAAAACC
AAAGGCAGACCGAAGGCTCCACAGGTGTACACCATTCCACCTCCCAAGGAGCAGATGGCCAAGGATAAAGTCAGTCTGACCTGCATGAT
AACAGACTTCTTCCCTGAAGACATTACTGTGGAGTGGCAGTGGAATGGGCAGCCAGCGGAGAACTACAAGAACACTCAGCCcATCATGG
ACACAGATGGCTCTTACTTCGTCTACAGCAAGCTCAATGTGCAGAAGAGCAACTGGGAGGCAGGAAATACTTTCACCTGCTCTGTGTTA
CATGAGGGCCTGCACAACCACCATACTGAGAAGAGCCTCTCCCACTCTCCTGGTAAATCAGGTGGTGGCGGTTCAGGCGGAGGTGGCTC
TGGCGGTGGCGGATCGCTGCTGGGGGATTTCTTCCGGAAGTCTAAAGAGAAGATTGGGAAAGAGTTTAAAAGAATTGTCCAGAGAATCA
AGGATTTTTTGCGGAATCTTGTGCCCAGGACAGAATCCTAG

Figure 9 Continued

Translation 4H9-G1-LL37, 517 residues including SP (1-20) (SEQ ID NO:4)

METDTLLLWVLLLWVPGSTGDQVQLQQSGAELAKPGASVKMSCKASGYTFTSYWMHWVKQRPGQGLEWIGYINPSTGYPEYNQKFKDKA
TLTADKSSNTAYMQLSSLTSEDSAVYYCVRRNYYEDFFDYWGQGTTLTVSSAKTTPPSVYPLAPGSAAQTNSMVTLGCLVKGYFPEPVT
VTWNSGSLSSGVHTFPAVLQSDLYTLSSSVTVPSSTWPSETVTCNVAHPASSTKVDKKIVPRDCGCKPCICTVPEVSSVFIFPPKPKDV
LTITLTPKVTCVVVDISKDDPEVQFSWFVDDVEVHTAQTQPREEQFNSTFRSVSELPIMHQDWLNGKEFKCRVNSAAFPAPIEKTISKT
KGRPKAPQVYTIPPPKEQMAKDKVSLTCMITDFFPEDITVEWQWNGQPAENYKNTQPIMDTDGSYFVYSKLNVQKSNWEAGNTFTCSVL
HEGLHNHHTEKSLSHSPGKSGGGGSGGGGSGGGGSLLGDFFRKSKEKIGKEFKRIVQRIKDFLRNLVPRTES

Figure 9 Continued

4H9-G2b-LL37, 1590 bp, including signal peptide (1-60) (SEQ ID NO:5)

ATGGAGACAGACACACTCCTGCTATGGGTACTGCTGCTCTGGGTTCCAGGTTCCACTGGTGACCAGGTCCAGCTTCAGCAGTCTGGGGC
TGAACTGGCAAAACCTGGGGCCTCAGTGAAGATGTCCTGCAAGGCTTCTGGCTACACCTTTACTAGCTACTGGATGCACTGGGTGAAAC
AGAGGCCTGGACAGGGTCTGGAATGGATTGGATACATTAATCCTAGCACTGGTTATCCTGAGTACAATCAGAAATTCAAGGACAAGGCC
ACATTGACTGCAGACAAATCCTCCAACACAGCCTACATGCAACTGAGCAGCCTGACATCTGAGGACTCTGCAGTCTATTACTGTGTAAG
AAGGAATTACTACGAGGACTTCTTTGACTACTGGGGCCAAGGCACCACTCTCACAGTCTCCTCAGCCAAAACGACACCCCCATCTGTCT
ATCCAcTGGcCCCTGGGTGTGGAGATACAACTGGTTCCTCcGTGACTCTGGGATGCCTGGTCAAGGGCTACTTCCCTGAGTCAGTGACT
GTGACTTGGAACTCTGGATCCCTGTCCAGCAGTGTGCACACCTTCCCAGCTCTCCTGCAGTCTGGACTCTACACTATGAGCAGCTCAGT
GACTGTCCCCTCCAGCACCTGGCCAAGTCAGACCGTCACCTGCAGCGTTGCTCACCCAGCCAGCAGCACCACGGTGGACAAAAAACTTG
AGCCCAGCGGGCCCATTTCAACAATCAACCCCTGTCCTCCATGCAAGGAGTGTCACAAATGCCCAGCTCCTAACCTCGAGGGTGGACCA
TCCGTCTTCATCTTCCCTCCAAATATCAAGGATGTACTCATGATCTCCCTGACACCCAAGGTCACGTGTGTGGTGGTGGATGTGAGCGA
GGATGACCCAGACGTCCAGATCAGCTGGTTTGTGAACAACGTGGAAGTACACACAGCTCAGACACAAACCCATAGAGAGGATTACAACA
GTACTATCCGGGTGGTCAGCACCCTCCCCATCCAGCACCAGGACTGGATGAGTGGCAAGGAGTTCAAATGCAAGGTCAACAACAAAGAC
CTCCCATCACCCATCGAGAGAACCATCTCAAAAATTAAAGGGCTAGTCAGAGCTCCACAAGTATACATCTTGCCGCCACCAGCAGAGCA
GTTGTCCAGGAAAGATGTCAGTCTCACTTGCCTGGTCGTGGGCTTCAACCCTGGAGACATCAGTGTGGAGTGGACCAGCAATGGGCATA
CAGAGGAGAACTACAAGGACACCGCACCAGTCCTGGACTCTGACGGTTCTTACTTCATATATAGCAAGCTCAATATGAAAACAAGCAAG
TGGGAGAAAACAGATTCCTTCTCATGCAACGTGAGACACGAGGGTCTGAAAAATTACTACCTGAAGAAGACCATCTCCCGGTCTCCGGG
TAAATCAGGTGGTGGCGGTTCAGGCGGAGGTGGCTCTGGCGGTGGCGGATCGCTGCTGGGGGATTTCTTCCGGAAGTCTAAAGAGAAGA
TTGGGAAAGAGTTTAAAAGAATTGTCCAGAGAATCAAGGATTTTTTGCGGAATCTTGTGCCCAGGACAGAATCCTAG

Figure 9 Continued

Translation 4H9-G2b-LL37, 529 residues including SP (1-20) (SEQ ID NO:6)

METDTLLLWVLLLWVPGSTGDQVQLQQSGAELAKPGASVKMSCKASGYTFTSYWMHWVKQRPGQGLEWIGYINPSTGYPEYNQKFKDKA
TLTADKSSNTAYMQLSSLTSEDSAVYYCVRRNYYEDFFDYWGQGTTLTVSSAKTTPPSVYPLAPGCGDTTGSSVTLGCLVKGYFPESVT
VTWNSGSLSSSVHTFPALLQSGLYTMSSSVTVPSSTWPSQTVTCSVAHPASSTTVDKKLEPSGPISTINPCPPCKECHKCPAPNLEGGP
SVFIFPPNIKDVLMISLTPKVTCVVVDVSEDDPDVQISWFVNNVEVHTAQTQTHREDYNSTIRVVSTLPIQHQDWMSGKEFKCKVNNKD
LPSPIERTISKIKGLVRAPQVYILPPPAEQLSRKDVSLTCLVVGFNPGDISVEWTSNGHTEENYKDTAPVLDSDGSYFIYSKLNMKTSK
WEKTDSFSCNVRHEGLKNYYLKKTISRSPGKSGGGGSGGGGSGGGGSLLGDFFRKSKEKIGKEFKRIVQRIKDFLRNLVPRTES

Figure 9 Continued

4H9-G1-PLA2, 1815 bp, including signal peptide (1-60) (SEQ ID NO:7)

ATGGAGACAGACACACTCCTGCTATGGGTACTGCTGCTCTGGGTTCCAGGTTCCACTGGTGACCAGGTCCAGCTTCAGCAGTCTGGGGC
TGAACTGGCAAAACCTGGGGCCTCAGTGAAGATGTCCTGCAAGGCTTCTGGCTACACCTTTACTAGCTACTGGATGCACTGGGTGAAAC
AGAGGCCTGGACAGGGTCTGGAATGGATTGGATACATTAATCCTAGCACTGGTTATCCTGAGTACAATCAGAAATTCAAGGACAAGGCC
ACATTGACTGCAGACAAATCCTCCAACACAGCCTACATGCAACTGAGCAGCCTGACATCTGAGGACTCTGCAGTCTATTACTGTGTAAG
AAGGAATTACTACGAGGACTTCTTTGACTACTGGGGCCAAGGCACCACTCTCACAGTCTCCTCAGCCAAAACGACACCCCCATCTGTCT
ATCCACTGGCCCCTGGATCTGCTGCCCAAACTAACTCCATGGTGACCCTGGGATGCCTGGTCAAGGGCTATTTCCCTGAGCCAGTGACA
GTGACCTGGAACTCTGGATCCCTGTCCAGCGGTGTGCACACCTTCCCAGCTGTCCTGCAGTCTGACCTCTACACTCTGAGCAGCTCAGT
GACTGTCCCCTCCAGCACCTGGCCCAGCGAGACCGTCACCTGCAACGTTGCCCACCCGGCCAGCAGCACCAAGGTGGACAAGAAAATTG
TGCCCAGGGATTGTGGTTGTAAGCCTTGCATATGTACAGTCCCAGAAGTATCATCTGTCTTCATCTTCCCCCCAAAGCCCAAGGATGTG
CTCACCATTACTCTGACTCCTAAGGTCACGTGTGTTGTGGTAGACATCAGCAAGGATGATCCCGAGGTCCAGTTCAGCTGGTTTGTAGA
TGATGTGGAGGTGCACACAGCTCAGACGCAACCCCGGGAGGAGCAGTTCAACAGCACTTTCCGCTCAGTCAGTGAACTTCCCATCATGC
ACCAGGACTGGCTCAATGGCAAGGAGTTCAAATGCAGGGTCAACAGTGCAGCTTTCCCTGCCCCCATCGAGAAAACCATCTCCAAAACC
AAAGGCAGACCGAAGGCTCCACAGGTGTACACCATTCCACCTCCCAAGGAGCAGATGGCCAAGGATAAAGTCAGTCTGACCTGCATGAT
AACAGACTTCTTCCCTGAAGACATTACTGTGGAGTGGCAGTGGAATGGGCAGCCAGCGGAGAACTACAAGAACACTCAGCCcATCATGG
ACACAGATGGCTCTTACTTCGTCTACAGCAAGCTCAATGTGCAGAAGAGCAACTGGGAGGCAGGAAATACTTTCACCTGCTCTGTGTTA
CATGAGGGCCTGCACAACCACCATACTGAGAAGAGCCTCTCCCACTCTCCTGGTAAATCAGGTGGTGGCGGTTCAGGCGGAGGTGGCTC
TGGCGGTGGCGGATCGAATTTGGTGAATTTCCACAGAATGATCAAGTTGACGACAGGAAAGGAAGCCGCACTCAGTTATGGCTTCTACG
GCTGCCACTGTGGCGTGGGTGGCAGAGGATCCCCCAAGGATGCAACGGATCGCTGCTGTGTCACTCATGACTGTTGCTACAAACGTCTG
GAGAAACGTGGATGTGGCACCAAATTTCTGAGCTACAAGTTTAGCAACTCGGGGAGCAGAATCACCTGTGCAAAACAGGACTCCTGCAG

Figure 9 Continued

AAGTCAACTGTGTGAGTGTGATAAGGCTGCTGCCACCTGTTTTGCTAGAAACAAGACGACCTACAATAAAAAGTACCAGTACTATTCCA
ATAAACACTGCAGAGGGAGCACCCCTCGTTGCTGA

Translation 4H9-G1-PLA2, 604 residues including SP (1-20) (SEQ ID NO:8)

METDTLLLWVLLLWVPGSTGDQVQLQQSGAELAKPGASVKMSCKASGYTFTSYWMHWVKQRPGQGLEWIGYINPSTGYPEYNQKFKDKA
TLTADKSSNTAYMQLSSLTSEDSAVYYCVRRNYYEDFFDYWGQGTTLTVSSAKTTPPSVYPLAPGSAAQTNSMVTLGCLVKGYFPEPVT
VTWNSGSLSSGVHTFPAVLQSDLYTLSSSVTVPSSTWPSETVTCNVAHPASSTKVDKKIVPRDCGCKPCICTVPEVSSVFIFPPKPKDV
LTITLTPKVTCVVVDISKDDPEVQFSWFVDDVEVHTAQTQPREEQFNSTFRSVSELPIMHQDWLNGKEFKCRVNSAAFPAPIEKTISKT
KGRPKAPQVYTIPPPKEQMAKDKVSLTCMITDFFPEDITVEWQWNGQPAENYKNTQPIMDTDGSYFVYSKLNVQKSNWEAGNTFTCSVL
HEGLHNHHTEKSLSHSPGKSGGGGSGGGGSGGGGSNLVNFHRMIKLTTGKEAALSYGFYGCHCGVGGRGSPKDATDRCCVTHDCCYKRL
EKRGCGTKFLSYKFSNSGSRITCAKQDSCRSQLCECDKAAATCFARNKTTYNKKYQYYSNKHCRGSTPRC

Figure 9 Continued

4H9-LC, 720 bp, including signal peptide (1-60) (SEQ ID NO:9)

ATGGAGACAGACACACTCCTGCTATGGGTACTGCTGCTCTGGGTTCCAGGTTCCACTGGTGACGTTGTGATGACCCAAATTCCACTCTC
CCTGCCTGTCAGTCTTGGAGATCAAGCCTCCATCTCTTGCAGATCTAGTCAGAGCCTTGTACACAGTAATGGAAACACCTATTTACATT
GGTACCTGCAGAAGCCAGGCCAGTCTCCAAAGGTCCTGATCTACAAAGTTTCCAACCGATTTTCTGGGGTCCCAGACAGGTTCAGTGGC
AGTGGATCAGGGACAGATTTCACACTCAAGATCAGCAGAGTGGAGGCTGAGGATCTGGGAGTTTATTTCTGCTCTCAAAGTACACATGT
TCCGCTCACGTTCGGTGCTGGGACCAAGCTGGAGCTGAAACGGGCTGATGCTGCACCAACTGTATCCATCTTCCCACCATCCAGTGAGC
AGTTAACATCTGGAGGTGCCTCAGTCGTGTGCTTCTTGAACAACTTCTACCCCAAAGACATCAATGTCAAGTGGAAGATTGATGGCAGT
GAACGACAAAATGGCGTCCTGAACAGTTGGACTGATCAGGACAGCAAAGACAGCACCTACAGCATGAGCAGCACCCTCACGTTGACCAA
GGACGAGTATGAACGACATAACAGCTATACCTGTGAGGCCACTCACAAGACATCAACTTCACCCATTGTCAAGAGCTTCAACAGGAATG
AGTGTTAG

Translation 4H9-LC, 239 residues including SP (1-20) (SEQ ID NO:10)

METDTLLLWVLLLWVPGSTGDVVMTQIPLSLPVSLGDQASISCRSSQSLVHSNGNTYLHWYLQKPGQSPKVLIYKVSNRFSGVPDRFSG
SGSGTDFTLKISRVEAEDLGVYFCSQSTHVPLTFGAGTKLELKRADAAPTVSIFPPSSEQLTSGGASVVCFLNNFYPKDINVKWKIDGS
ERQNGVLNSWTDQDSKDSTYSMSSTLTLTKDEYERHNSYTCEATHKTSTSPIVKSFNRNEC

Figure 9 Continued

3E2-M-HC, 1791 bp including SP (1-60) (SEQ ID NO:11)

ATGGAGACAGACACACTCCTGCTATGGGTACTGCTGCTCTGGGTTCCAGGTTCCACTGGTGACCAGGTGCAGCTGAAGGAGTCAGGACC
TGGCCTGGTGGCGCCCTCACAGAGCCTGTCCATCACTTGCACTGTCTCTGGGTTTTCATTAACCAACTATGGTGTACATTGGGTTCGCC
AGCCTCCAGGAAAGGGTCTGGAGTGGCTGGGAGTAATATGGGCTGGTGGAAACACAAATTATAATTCGGCTTTTATGTCCAGACTGAGC
ATCACCAAAGACAACTCCAAGAGCCAAGTTTTCATAAAAATGAACAGTCTGCAAACTGATGACACAGCCATGTACTACTGTGCCAGAGA
ATATAGGCACGGGGCTTACTATGCTATGGACTACTGGGGTCAAGGAACCTCAGTCACCGTCTCCTCAGAGAGTCAGTCCTTCCCAAATG
TCTTCCCCCTCGTCTCCTGCGAGAGCCCCCTGTCTGATAAGAATCTGGTGGCCATGGGCTGCCTGGCCCGGGACTTCCTGCCCAGCACC
ATTTCCTTCACCTGGAACTACCAGAACAACACTGAAGTCATCCAGGGTATCAGAACCTTCCCAACACTGAGGACAGGGGGCAAGTACCT
AGCCACCTCGCAGGTGTTGCTGTCTCCCAAGAGCATCCTTGAAGGTTCAGATGAATACCTGGTATGCAAAATCCACTACGGAGGCAAAA
ACAGAGATCTGCATGTGCCCATTCCAGCTGTCGCAGAGATGAACCCCAATGTAAATGTGTTCGTCCCACCACGGGATGGCTTCTCTGGC
CCTGCACCACGCAAGTCTAAACTCATCTGCGAGGCCACGAACTTCACTCCAAAACCGATCACAGTATCCTGGCTAAAGGATGGGAAGCT
CGTGGAATCTGGCTTCACCACAGatccggtgaccatcgagaacaaaggatccacaccccaaaCCTACAAGGTCATAAGCACACTTACCA
TCTCTGAAATCGACTGGCTGAACCTGAATGTGTACACCTGCCGTGTGGATCACAGGGGTCTCACCTTCTTGAAGAACGTGTCCTCCACA
TGTGCTGCCAGTCCCTCCACAGACATCCTGACCTTCACCATCCCCCCCTCCTTTGCCGACATCTTCCTCAGCAAGTCCGCTAACCTGAC
CTGTCTGGTCTCAAACCTGGCAACCTATGAAACCCTGAATATCTCCTGGGCTTCTCAAAGTGGTGAACCACTGGAAACCAAAATTAAAA
TCATGGAAAGCCATCCCAATGGCACCTTCAGTGCTAAGGGTGTGGCTAGTGTTTGTGTGGAAGACTGGAATAACAGGAAGGAATTTGTG
TGTACTGTGACTCACAGGGATCTGCCTTCACCACAGAAGAAATTCATCTCAAAACCCAATGAGGTGCACAAACATCCACCTGCTGTGTA
CCTGCTGCCACCAGCTCGTGAGCAACTGAACCTGAGGGAGTCAGCCACAGTCACCTGCCTGGTGAAGGGCTTCTCTCCTGCAGACATCA
GTGTGCAGTGGCTTCAGAGAGGGCAACTCTTGCCCCAAGAGAAGTATGTGACCAGTGCCCCGATGCCAGAGCCTGGGGCCCCAGGCTTC
TACTTTACCCACAGCATCCTGACTGTGACAGAGGAGGAATGGAACTCCGGAGAGACCTATACCTGTGTTGTAGGCCACGAGGCCCTGCC
ACACCTGGTGACCGAGAGGACCGTGGACAAGTCCACTGGTAAACCCACACTGTACAATGTCTCCCTGATCATGTCTGACACAGGCGGCA
CCTGCTATTGA

Figure 9 Continued

Translation 3E2-M-HC, 596 residues including SP (1-20) (SEQ ID NO:12)

METDTLLLWVLLLWVPGSTGDQVQLKESGPGLVAPSQSLSITCTVSGFSLTNYGVHWVRQPPGKGLEWLGVIWAGGNTNYNSAFMSRLS
ITKDNSKSQVFIKMNSLQTDDTAMYYCAREYRHGAYYAMDYWGQGTSVTVSSESQSFPNVFPLVSCESPLSDKNLVAMGCLARDFLPST
ISFTWNYQNNTEVIQGIRTFPTLRTGGKYLATSQVLLSPKSILEGSDEYLVCKIHYGGKNRDLHVPIPAVAEMNPNVNVFVPPRDGFSG
PAPRKSKLICEATNFTPKPITVSWLKDGKLVESGFTTDPVTIENKGSTPQTYKVISTLTISEIDWLNLNVYTCRVDHRGLTFLKNVSST
CAASPSTDILTFTIPPSFADIFLSKSANLTCLVSNLATYETLNISWASQSGEPLETKIKIMESHPNGTFSAKGVASVCVEDWNNRKEFV
CTVTHRDLPSPQKKFISKPNEVHKHPPAVYLLPPAREQLNLRESATVTCLVKGFSPADISVQWLQRGQLLPQEKYVTSAPMPEPGAPGF
YFTHSILTVTEEEWNSGETYTCVVGHEALPHLVTERTVDKSTGKPTLYNVSLIMSDTGGTCY

Figure 9 Continued

3E2-M-LL37, 2013 bp including SP (1-60) (SEQ ID NO:13)

ATGGAGACAGACACACTCCTGCTATGGGTACTGCTGCTCTGGGTTCCAGGTTCCACTGGTGACCATCACCATCACCATCACGGATCTGG
CTCTGGATCTGGTATCGAGGGAAGGacgcgtCAGGTGCAGCTGAAGGAGTCAGGACCTGGCCTGGTGGCGCCCTCACAGAGCCTGTCCA
TCACTTGCACTGTCTCTGGGTTTTCATTAACCAACTATGGTGTACATTGGGTTCGCCAGCCTCCAGGAAAGGGTCTGGAGTGGCTGGGA
GTAATATGGGCTGGTGGAAACACAAATTATAATTCGGCTTTTATGTCCAGACTGAGCATCACCAAAGACAACTCCAAGAGCCAAGTTTT
CATAAAAATGAACAGTCTGCAAACTGATGACACAGCCATGTACTACTGTGCCAGAGAATATAGGCACGGGGCTTACTATGCTATGGACT
ACTGGGGTCAAGGAACCTCAGTCACCGTCTCCTCAGAGAGTCAGTCCTTCCCAAATGTCTTCCCCCTCGTCTCCTGCGAGAGCCCCCTG
TCTGATAAGAATCTGGTGGCCATGGGCTGCCTGGCCCGGGACTTCCTGCCCAGCACCATTTCCTTCACCTGGAACTACCAGAACAACAC
TGAAGTCATCCAGGGTATCAGAACCTTCCCAACACTGAGGACAGGGGGCAAGTACCTAGCCACCTCGCAGGTGTTGCTGTCTCCCAAaA
GCATCCTTGAAGGTTCAGATGAATACCTGGTATGCAAAATCCACTACGGAGGCAAAAACAGAGATCTGCATGTGCCCATTCCAGCTGTC
GCAGAGATGAACCCCAATGTAAATGTGTTCGTCCCACCACGGGATGGCTTCTCTGGCCCTGCACCACGCAAGTCTAAACTCATCTGCGA
GGCCACGAACTTCACTCCAAAACCGATCACAGTATCCTGGCTAAAGGATGGGAAGCTCGTGGAATCTGGCTTCACCACAGatccggtga
ccatcgagaacaaaggatccacaccccaaaCCTACAAGGTCATAAGCACACTTACCATCTCTGAAATCGACTGGCTGAACCTGAATGTG
TACACCTGCCGTGTGGATCACAGGGGTCTCACCTTCTTGAAGAACGTGTCCTCCACATGTGCTGCCAGTCCCTCCACAGACATCCTGAC
CTTCACCATCCCCCCCTCCTTTGCCGACATCTTCCTCAGCAAGTCCGCTAACCTGACCTGTCTGGTCTCAAACCTGGCAACCTATGAAA
CCCTGAATATCTCCTGGGCTTCTCAAAGTGGTGAACCACTGGAAACCAAAATTAAAATCATGGAAAGCCATCCCAATGGCACCTTCAGT
GCTAAGGGTGTGGCTAGTGTTTGTGTGGAAGACTGGAATAACAGGAAGGAATTTGTGTGTACTGTGACTCACAGGGATCTGCCTTCACC
ACAGAAGAAATTCATCTCAAAACCCAATGAGGTGCACAAACATCCACCTGCTGTGTACCTGCTGCCACCAGCTCGTGAGCAACTGAACC
TGAGGGAGTCAGCCACAGTCACCTGCCTGGTGAAGGGCTTCTCTCCTGCAGACATCAGTGTGCAGTGGCTTCAGAGAGGGCAACTCTTG
CCCCAAGAGAAGTATGTGACCAGTGCCCCGATGCCAGAGCCTGGGGCCCCAGGCTTCTACTTTACCCACAGCATCCTGACTGTGACAGA
GGAGGAATGGAACTCCGGAGAGACCTATACCTGTGTTGTAGGCCACGAGGCCCTGCCACACCTGGTGACCGAGAGGACCGTGGACAAGT
CCACTGGTAAACCCACACTGTACAATGTCTCCCTGATCATGTCTGACACAGGCGGCACCTGCTATgcggccgcaGGTGGTGGCGGTTCA

Figure 9 Continued

GGCGGAGGTGGCTCTGGCGGTGGCGGATCcCTGCTGGGGGATTTCTTCCGGAAGTCTAAAGAGAAGATTGGGAAAGAGTTTAAAAGAAT
TGTCCAGAGAATCAAGGATTTTTTGCGGAATCTTGTGCCCAGGACAGAATCCTAG

Translation 3E2-M-LL37, 670 residues including SP (1-20) (SEQ ID NO:14)

METDTLLLWVLLLWVPGSTGDHHHHHHGSGSGSGIEGRTRQVQLKESGPGLVAPSQSLSITCTVSGFSLTNYGVHWVRQPPGKGLEWLG
VIWAGGNTNYNSAFMSRLSITKDNSKSQVFIKMNSLQTDDTAMYYCAREYRHGAYYAMDYWGQGTSVTVSSESQSFPNVFPLVSCESPL
SDKNLVAMGCLARDFLPSTISFTWNYQNNTEVIQGIRTFPTLRTGGKYLATSQVLLSPKSILEGSDEYLVCKIHYGGKNRDLHVPIPAV
AEMNPNVNVFVPPRDGFSGPAPRKSKLICEATNFTPKPITVSWLKDGKLVESGFTTDPVTIENKGSTPQTYKVISTLTISEIDWLNLNV
YTCRVDHRGLTFLKNVSSTCAASPSTDILTFTIPPSFADIFLSKSANLTCLVSNLATYETLNISWASQSGEPLETKIKIMESHPNGTFS
AKGVASVCVEDWNNRKEFVCTVTHRDLPSPQKKFISKPNEVHKHPPAVYLLPPAREQLNLRESATVTCLVKGFSPADISVQWLQRGQLL
PQEKYVTSAPMPEPGAPGFYFTHSILTVTEEEWNSGETYTCVVGHEALPHLVTERTVDKSTGKPTLYNVSLIMSDTGGTCYAAAGGGGS
GGGGSGGGGSLLGDFFRKSKEKIGKEFKRIVQRIKDFLRNLVPRTES

Figure 9 Continued

3E2-Mmono-LL37, 2013 bp including SP (1-60) (SEQ ID NO:15)

ATGGAGACAGACACACTCCTGCTATGGGTACTGCTGCTCTGGGTTCCAGGTTCCACTGGTGACCATCACCATCACCATCACGGATCTGGCTCTGGATC
TGGTATCGAGGGAAGGacgcgtCAGGTGCAGCTGAAGGAGTCAGGACCTGGCCTGGTGGCGCCCTCACAGAGCCTGTCCATCACTTGCACTGTCTCTG
GGTTTTCATTAACCAACTATGGTGTACATTGGGTTCGCCAGCCTCCAGGAAAGGGTCTGGAGTGGCTGGGAGTAATATGGGCTGGTGGAAACACAAAT
TATAATTCGGCTTTTATGTCCAGACTGAGCATCACCAAAGACAACTCCAAGAGCCAAGTTTTCATAAAAATGAACAGTCTGCAAACTGATGACACAGC
CATGTACTACTGTGCCAGAGAATATAGGCACGGGGCTTACTATGCTATGGACTACTGGGGTCAAGGAACCTCAGTCACCGTCTCCTCAGAGAGTCAGT
CCTTCCCAAATGTCTTCCCCCTCGTCTCCTGCGAGAGCCCCCTGTCTGATAAGAATCTGGTGGCCATGGGCTGCCTGGCCCGGGACTTCCTGCCCAGC
ACCATTTCCTTCACCTGGAACTACCAGAACAACACTGAAGTCATCCAGGGTATCAGAACCTTCCCAACACTGAGGACAGGGGGCAAGTACCTAGCCAC
CTCGCAGGTGTTGCTGTCTCCCAAGAGCATCCTTGAAGGTTCAGATGAATACCTGGTATGCAAAATCCACTACGGAGGCAAAAACAGAGATCTGCATG
TGCCCATTCCAGCTGTCGCAGAGATGAACCCCAATGTAAATGTGTTCGTCCCACCACGGGATGGCTTCTCTGGCCCTGCACCACGCAAGTCTAAACTC
ATCTGCGAGGCCACGAACTTCACTCCAAAACCGATCACAGTATCCTGGCTAAAGGATGGGAAGCTCGTGGAATCTGGCTTCACCACAGatccggtgac
catcgagaacaaaggatccacaccccaaaCCTACAAGGTCATAAGCACACTTACCATCTCTGAAATCGACTGGCTGAACCTGAATGTGTACACCTGCC
GTGTGGATCACAGGGGTCTCACCTTCTTGAAGAACGTGTCCTCCACATGTGCTGCCAGTCCCTCCACAGACATCCTaACCTTCACCATCCCCCCCTCC
TTTGCCGACATCTTCCTCAGCAAGTCCGCTAACCTGACCTGTCTGGTCTCAAACCTGGCAACCTATGAAACCCTGAATATCTCCTGGGCTTCTCAAAG
TGGTGAACCACTGGAAACCAAAATTAAAATCATGGAAAGCCATCCCAATGGCACCTTCAGTGCTAAGGGTGTGGCTAGTGTTTCTGTGGAAGACTGGA
ATAACAGGAAGGAATTTGTGTGTACTGTGACTCACAGGGATCTGCCTTCACCACAGAAGAAATTCATCTCAAAACCCAATGAGGTGCACAAACATCCA
CCTGCTGTGTACCTGCTGCCACCAGCTCGTGAGCAACTGAACCTGAGGGAGTCAGCCACAGTCACCTGCCTGGTGAAGGGCTTCTCTCCTGCAGACAT
CAGTGTGCAGTGGCTTCAGAGAGGGCAACTCTTGCCCCAAGAGAAGTATGTGACCAGTGCCCCGATGCCAGAGCCTGGGGCCCCAGGCTTCTACTTTA
CCCACAGCATCCTGACTGTGACAGAGGAGGAATGGAACTCCGGAGAGACCTATACCTGTGTTGTAGGCCACGAGGCCCTGCCACACCTGGTGACCGAG
AGGACCGTGGACAAGTCCACTGGTAAACCCACACTGTACAATGTCTCCCTGATCATGTCTGACACAGGCGGCACCTGCTATgcggccgcaGGTGGTGG
CGGTTCAGGCGGAGGTGGCTCTGGCGGTGGCGGATCcCTGCTGGGGGATTTCTTCCGGAAGTCTAAAGAGAAGATTGGGAAAGAGTTTAAAAGAATTG
TCCAGAGAATCAAGGATTTTTTGCGGAATCTTGTGCCCAGGACAGAATCCTAG

Figure 9 Continued

Highlighted: Two Mutations to induce Cys to Ser change, results in 60% Monomers and 40% Halfmers

- position 1358, from G to C resulting in amino acid residue change from Cys to Ser
- position 1841, from G to C resulting in amino acid residue change from Cys to Ser

Translation 3E2-Mmono-LL37, 670 residues including SP (1-20) (SEQ ID NO:16)

METDTLLLWVLLLWVPGSTGDHHHHHHGSGSGSGIEGRTRQVQLKESGPGLVAPSQSLSITCTVSGFSLTNYGVHWVRQPPGKGLEWLGVIWAGGNTN
YNSAFMSRLSITKDNSKSQVFIKMNSLQTDDTAMYYCAREYRHGAYYAMDYWGQGTSVTVSSESQSFPNVFPLVSCESPLSDKNLVAMGCLARDFLPS
TISFTWNYQNNTEVIQGIRTFPTLRTGGKYLATSQVLLSPKSILEGSDEYLVCKIHYGGKNRDLHVPIPAVAEMNPNVNVFVPPRDGFSGPAPRKSKL
ICEATNFTPKPITVSWLKDGKLVESGFTTDPVTIENKGSTPQTYKVISTLTISEIDWLNLNVYTCRVDHRGLTFLKNVSSTCAASPSTDILTFTIPPS
FADIFLSKSANLTCLVSNLATYETLNISWASQSGEPLETKIKIMESHPNGTFSAKGVASVSVEDWNNRKEFVCTVTHRDLPSPQKKFISKPNEVHKHP
PAVYLLPPAREQLNLRESATVTCLVKGFSPADISVQWLQRGQLLPQEKYVTSAPMPEPGAPGFYFTHSILTVTEEEWNSGETYTCVVGHEALPHLVTE
RTVDKSTGKPTLYNVSLIMSDTGGTSYAAAGGGGSGGGGSGGGGSLLGDFFRKSKEKIGKEFKRIVQRIKDFLRNLVPRTES

Highlighted amino acids indicate changes from cysteine to serine to disable disulfide bond formation:

$C_{453} \rightarrow S_{453}$ $C_{614} \rightarrow S_{614}$

Figure 9 Continued

3E2-Mhalf-LL37, 2013 bp including SP (1-60) (SEQ ID NO:17)

ATGGAGACAGACACACTCCTGCTATGGGTACTGCTGCTCTGGGTTCCAGGTTCCACTGGTGACCATCACCATCACCATCACGGATCTGGCTCTGGATC
TGGTATCGAGGGAAGGacgcgtCAGGTGCAGCTGAAGGAGTCAGGACCTGGCCTGGTGGCGCCCTCACAGAGCCTGTCCATCACTTGCACTGTCTCTG
GGTTTTCATTAACCAACTATGGTGTACATTGGGTTCGCCAGCCTCCAGGAAAGGGTCTGGAGTGGCTGGGAGTAATATGGGCTGGTGGAAACACAAAT
TATAATTCGGCTTTTATGTCCAGACTGAGCATCACCAAAGACAACTCCAAGAGCCAAGTTTTCATAAAAATGAACAGTCTGCAAACTGATGACACAGC
CATGTACTACTGTGCCAGAGAATATAGGCACGGGGCTTACTATGCTATGGACTACTGGGGTCAAGGAACCTCAGTCACCGTCTCCTCAGAGAGTCAGT
CCTTCCCAAATGTCTTCCCCCTCGTCTCCTGCGAGAGCCCCCTGTCTGATAAGAATCTGGTGGCCATGGGCTGCCTGGCCCGGGACTTCCTGCCCAGC
ACCATTTCCTTCACCTGGAACTACCAGAACAACACTGAAGTCATCCAGGGTATCAGAACCTTCCCAACACTGAGGACAGGGGGCAAGTACCTAGCCAC
CTCGCAGGTGTTGCTGTCTCCCAAGAGCATCCTTGAAGGTTCAGATGAATACCTGGTATGCAAAATCCACTACGGAGGCAAAAACAGAGATCTGCATG
TGCCCATTCCAGCTGTCGCAGAGATGAACCCCAATGTAAATGTGTTCGTCCCACCACGGGATGGCTTCTCTGGCCCTGCACCACGCAAGTCTAAACTC
ATCTGCGAGGCCACGAACTTCACTCCAAAACCGATCACAGTATCCTGGCTAAAGGATGGGAAGCTCGTGGAATCTGGCTTCACCACAGatccggtgac
catcgagaacaaaggatccacaccccaaaCCTACAAGGTCATAAGCACACTTACCATCTCTGAAATCGACTGGCTGAACCTGAATGTGTACACCTGCC
GTGTGGATCACAGGGGTCTCACCTTCTTGAAGAACGTGTCCTCCACATCTGCTGCCAGTCCCTCCACAGACATCCTaACCTTCACCATCCCCCCCTCC
TTTGCCGACATCTTCCTCAGCAAGTCCGCTAACCTGACCTGTCTGGTCTCAAACCTGGCAACCTATGAAACCCTGAATATCTCCTGGGCTTCTCAAAG
TGGTGAACCACTGGAAACCAAAATTAAAATCATGGAAAGCCATCCCAATGGCACCTTCAGTGCTAAGGGTGTGGCTAGTGTTTCTGTGGAAGACTGGA
ATAACAGGAAGGAATTTGTGTGTACTGTGACTCACAGGGATCTGCCTTCACCACAGAAGAAATTCATCTCAAAACCCAATGAGGTGCACAAACATCCA
CCTGCTGTGTACCTGCTGCCACCAGCTCGTGAGCAACTGAACCTGAGGGAGTCAGCCACAGTCACCTGCCTGGTGAAGGGCTTCTCTCCTGCAGACAT
CAGTGTGCAGTGGCTTCAGAGAGGGCAACTCTTGCCCCAAGAGAAGTATGTGACCAGTGCCCCGATGCCAGAGCCTGGGGCCCCAGGCTTCTACTTTA
CCCACAGCATCCTGACTGTGACAGAGGAGGAATGGAACTCCGGAGAGACCTATACCTGTGTTGTAGGCCACGAGGCCCTGCCACACCTGGTGACCGAG
AGGACCGTGGACAAGTCCACTGGTAAACCCACACTGTACAATGTCTCCCTGATCATGTCTGACACAGGCGGCACCTCCTATgcggccgcaGGTGGTGG
CGGTTCAGGCGGAGGTGGCTCTGGCGGTGGCGGATCcCTGCTGGGGGATTTCTTCCGGAAGTCTAAAGAGAAGATTGGGAAAGAGTTTAAAAGAATTG
TCCAGAGAATCAAGGATTTTTTGCGGAATCTTGTGCCCAGGACAGAATCCTAG

Figure 9 Continued

Highlighted: Three Mutations that induce Cys to Ser change, results in 60% Monomers and 40% Halfmers

- position 1127, from G to C resulting in amino acid residue change from Cys to Ser
- position 1358, from G to C resulting in amino acid residue change from Cys to Ser
- position 1841, from G to C resulting in amino acid residue change from Cys to Ser

Translation 3E2-Mhalf-LL37, 670 residues including SP (1-20) (SEQ ID NO:18)

METDTLLLWVLLLWVPGSTGDHHHHHHGSGSGSGIEGRTRQVQLKESGPGLVAPSQSLSITCTVSGFSLTNYGVHWVRQPPGKGLEWLGVIWAGGNTN
YNSAFMSRLSITKDNSKSQVFIKMNSLQTDDTAMYYCAREYRHGAYYAMDYWGQGTSVTVSSESQSFPNVFPLVSCESPLSDKNLVAMGCLARDFLPS
TISFTWNYQNNTEVIQGIRTFPTLRTGGKYLATSQVLLSPKSILEGSDEYLVCKIHYGGKNRDLHVPIPAVAEMNPNVNVFVPPRDGFSGPAPRKSKL
ICEATNFTPKPITVSWLKDGKLVESGFTTDPVTIENKGSTPQTYKVISTLTISEIDWLNLNVYTCRVDHRGLTFLKNVSSTSAASPSTDILTFTIPPS
FADIFLSKSANLTCLVSNLATYETLNISWASQSGEPLETKIKIMESHPNGTFSAKGVASVSVEDWNNRKEFVCTVTHRDLPSPQKKFISKPNEVHKHP
PAVYLLPPAREQLNLRESATVTCLVKGFSPADISVQWLQRGQLLPQEKYVTSAPMPEPGAPGFYFTHSILTVTEEEWNSGETYTCVVGHEALPHLVTE
RTVDKSTGKPTLYNVSLIMSDTGGTSYAAAGGGGSGGGGSGGGGSLLGDFFRKSKEKIGKEFKRIVQRIKDFLRNLVPRTES

Highlighted amino acids indicate changes from cysteine to serire to disable disulfide bond formation:

$C_{376} \rightarrow S_{376}$ $C_{453} \rightarrow S_{453}$ $C_{614} \rightarrow S_{614}$

Figure 9 Continued

3E2-G1, 1461 bp including SP (1-60) (SEQ ID NO:19)

ATGGAGACAGACACACTCCTGCTATGGGTACTGCTGCTCTGGGTTCCAGGTTCCACTGGTGACCATCACCATCACCATCACGGATCTGG
CTCTGGATCTGGTATCGAGGGAAGGacgcgtCAGGTGCAGCTGAAGGAGTCAGGACCTGGCCTGGTGGCGCCCTCACAGAGCCTGTCCA
TCACTTGCACTGTCTCTGGGTTTTCATTAACCAACTATGGTGTACATTGGGTTCGCCAGCCTCCAGGAAAGGGTCTGGAGTGGCTGGGA
GTAATATGGGCTGGTGGAAACACAAATTATAATTCGGCTTTTATGTCCAGACTGAGCATCACCAAAGACAACTCCAAGAGCCAAGTTTT
CATAAAAATGAACAGTCTGCAAACTGATGACACAGCCATGTACTACTGTGCCAGAGAATATAGGCACGGGGCTTACTATGCTATGGACT
ACTGGGGTCAAGGAACCTCAGTCACCGTCTCCTCAGAGAGTCAGTCCTTCTCTGTCTATCCACTGGCCCCTGGATCTGCTGCCCAAACT
AACTCCATGGTGACCCTGGGATGCCTGGTCAAGGGCTATTTCCCTGAGCCAGTGACAGTGACCTGGAACTCTGGATCCCTGTCCAGCGG
TGTGCACACCTTCCCAGCTGTCCTGCAGTCTGACCTCTACACTCTGAGCAGCTCAGTGACTGTCCCCTCCAGCACCTGGCCCAGCGAGA
CCGTCACCTGCAACGTTGCCCACCCGGCCAGCAGCACCAAGGTGGACAAGAAAATTGTGCCCAGGGATTGTGGTTGTAAGCCTTGCATA
TGTACAGTCCCAGAAGTATCATCTGTCTTCATCTTCCCCCCAAAGCCCAAGGATGTGCTCACCATTACTCTGACTCCTAAGGTCACGTG
TGTTGTGGTAGACATCAGCAAGGATGATCCCGAGGTCCAGTTCAGCTGGTTTGTAGATGATGTGGAGGTGCACACAGCTCAGACGCAAC
CCCGGGAGGAGCAGTTCAACAGCACTTTCCGCTCAGTCAGTGAACTTCCCATCATGCACCAGGACTGGCTCAATGGCAAGGAGTTCAAA
TGCAGGGTCAACAGTGCAGCTTTCCCTGCCCCCATCGAGAAAACCATCTCCAAAACCAAAGGCAGACCGAAGGCTCCACAGGTGTACAC
CATTCCACCTCCCAAGGAGCAGATGGCCAAGGATAAAGTCAGTCTGACCTGCATGATAACAGACTTCTTCCCTGAAGACATTACTGTGG
AGTGGCAGTGGAATGGGCAGCCAGCGGAGAACTACAAGAACACTCAGCCCATCATGGACACAGATGGCTCTTACTTCGTCTACAGCAAG
CTCAATGTGCAGAAGAGCAACTGGGAGGCAGGAAATACTTTCACCTGCTCTGTGTTACATGAGGGCCTGCACAACCACCATACTGAGAA
GAGCCTCTCCCACTCTCCTGGTAAAgcGGCCGCATGA

Figure 9 Continued

Translation 3E2-G1, 486 residues including SP (1-20) (SEQ ID NO:20)

```
METDTLLLWVLLLWVPGSTGDHHHHHHGSGSGSGIEGRTRQVQLKESGPGLVAPSQSLSITCTVSGFSLTNYGVHWVRQPPGKGLEWLG
VIWAGGNTNYNSAFMSRLSITKDNSKSQVFIKMNSLQTDDTAMYYCAREYRHGAYYAMDYWGQGTSVTVSSESQSFSVYPLAPGSAAQT
NSMVTLGCLVKGYFPEPVTVTWNSGSLSSGVHTFPAVLQSDLYTLSSSVTVPSSTWPSETVTCNVAHPASSTKVDKKIVPRDCGCKPCI
CTVPEVSSVFIFPPKPKDVLTITLTPKVTCVVVDISKDDPEVQFSWFVDDVEVHTAQTQPREEQFNSTFRSVSELPIMHQDWLNGKEFK
CRVNSAAFPAPIEKTISKTKGRPKAPQVYTIPPPKEQMAKDKVSLTCMITDFFPEDITVEWQWNGQPAENYKNTQPIMDTDGSYFVYSK
LNVQKSNWEAGNTFTCSVLHEGLHNHHTEKSLSHSPGKAAA
```

Figure 9 Continued

3E2-G1-LL37, 1617 bp including SP (1-60) (SEQ ID NO:21)

ATGGAGACAGACACACTCCTGCTATGGGTACTGCTGCTCTGGGTTCCAGGTTCCACTGGTGACCATCACCATCACCATCACGGATCTGG
CTCTGGATCTGGTATCGAGGGAAGGacgcgtCAGGTGCAGCTGAAGGAGTCAGGACCTGGCCTGGTGGCGCCCTCACAGAGCCTGTCCA
TCACTTGCACTGTCTCTGGGTTTTCATTAACCAACTATGGTGTACATTGGGTTCGCCAGCCTCCAGGAAAGGGTCTGGAGTGGCTGGGA
GTAATATGGGCTGGTGGAAACACAAATTATAATTCGGCTTTTATGTCCAGACTGAGCATCACCAAAGACAACTCCAAGAGCCAAGTTTT
CATAAAAATGAACAGTCTGCAAACTGATGACACAGCCATGTACTACTGTGCCAGAGAATATAGGCACGGGGCTTACTATGCTATGGACT
ACTGGGGTCAAGGAACCTCAGTCACCGTCTCCTCAGAGAGTCAGTCCTTCTCTGTCTATCCACTGGCCCCTGGATCTGCTGCCCAAACT
AACTCCATGGTGACCCTGGGATGCCTGGTCAAGGGCTATTTCCCTGAGCCAGTGACAGTGACCTGGAACTCTGGATCCCTGTCCAGCGG
TGTGCACACCTTCCCAGCTGTCCTGCAGTCTGACCTCTACACTCTGAGCAGCTCAGTGACTGTCCCCTCCAGCACCTGGCCCAGCGAGA
CCGTCACCTGCAACGTTGCCCACCCGGCCAGCAGCACCAAGGTGGACAAGAAAATTGTGCCCAGGGATTGTGGTTGTAAGCCTTGCATA
TGTACAGTCCCAGAAGTATCATCTGTCTTCATCTTCCCCCCAAAGCCCAAGGATGTGCTCACCATTACTCTGACTCCTAAGGTCACGTG
TGTTGTGGTAGACATCAGCAAGGATGATCCCGAGGTCCAGTTCAGCTGGTTTGTAGATGATGTGGAGGTGCACACAGCTCAGACGCAAC
CCCGGGAGGAGCAGTTCAACAGCACTTTCCGCTCAGTCAGTGAACTTCCCATCATGCACCAGGACTGGCTCAATGGCAAGGAGTTCAAA
TGCAGGGTCAACAGTGCAGCTTTCCCTGCCCCCATCGAGAAAACCATCTCCAAAACCAAAGGCAGACCGAAGGCTCCACAGGTGTACAC
CATTCCACCTCCCAAGGAGCAGATGGCCAAGGATAAAGTCAGTCTGACCTGCATGATAACAGACTTCTTCCCTGAAGACATTACTGTGG
AGTGGCAGTGGAATGGGCAGCCAGCGGAGAACTACAAGAACACTCAGCCCATCATGGACACAGATGGCTCTTACTTCGTCTACAGCAAG
CTCAATGTGCAGAAGAGCAACTGGGAGGCAGGAAATACTTTCACCTGCTCTGTGTTACATGAGGGCCTGCACAACCACCATACTGAGAA
GAGCCTCTCCCACTCTCCTGGTAAAgcggccgcaGGTGGTGGCGGTTCAGGCGGAGGTGGCTCTGGCGGTGGCGGATCcCTGCTGGGGG
ATTTCTTCCGGAAGTCTAAAGAGAAGATTGGGAAAGAGTTTAAAAGAATTGTCCAGAGAATCAAGGATTTTTTGCGGAATCTTGTGCCC
AGGACAGAATCCTAG

Figure 9 Continued

Translation 3E2-G1-LL37, 538 residues including SP (1-20) (SEQ ID NO:22)

METDTLLLWVLLLWVPGSTGDHHHHHHGSGSGSGIEGRTRQVQLKESGPGLVAPSQSLSITCTVSGFSLTNYGVHWVRQPPGKGLEWLG
VIWAGGNTNYNSAFMSRLSITKDNSKSQVFIKMNSLQTDDTAMYYCAREYRHGAYYAMDYWGQGTSVTVSSESQSFSVYPLAPGSAAQT
NSMVTLGCLVKGYFPEPVTVTWNSGSLSSGVHTFPAVLQSDLYTLSSSVTVPSSTWPSETVTCNVAHPASSTKVDKKIVPRDCGCKPCI
CTVPEVSSVFIFPPKPKDVLTITLTPKVTCVVVDISKDDPEVQFSWFVDDVEVHTAQTQPREEQFNSTFRSVSELPIMHQDWLNGKEFK
CRVNSAAFPAPIEKTISKTKGRPKAPQVYTIPPPKEQMAKDKVSLTCMITDFFPEDITVEWQWNGQPAENYKNTQPIMDTDGSYFVYSK
LNVQKSNWEAGNTFTCSVLHEGLHNHHTEKSLSHSPGKAAAGGGGSGGGGSGGGGSLLGDFFRKSKEKIGKEFKRIVQRIKDFLRNLVP
RTES

Figure 9 Continued

3E2-LC, 708 bp including SP (1-60) (SEQ ID NO:23)

ATGGAGACAGACACACTCCTGCTATGGGTACTGCTGCTCTGGGTTCCAGGTTCCACTGGTGACGACATCCAGATGACTCAGTCTCCAGC
CTCCCTATCTGCATCTGTGGGAGAAACTGTCACCATCACATGTCGAGCAAGTGAGAACATTTACAGTTATTTAGCATGGTATCAGCAGA
AACAGGGAAAATCTCCTCAGTTCCTGGTCTATAATGCAGAAACCTTAGCAGAAGGTGTGCCATCAAGGTTCAGTGGCAGTGGATCAGGC
AAACAGTTTTCTCTGAAGATCAACAGCCTGCAGCCTGAAGATTTTGGGAGTTATTACTGTCAACATCATTATGGTACTCATCCGACGTT
CGGTGGAGGCACCAAGCTGGAAATCAAACGGGCTGATGCTGCACCAACTGTATCCATCTTCCCACCATCCAGTGAGCAGTTAACATCTG
GAGGTGCCTCAGTCGTGTGCTTCTTGAACAACTTCTACCCCAAAGACATCAATGTCAAGTGGAAGATTGATGGCAGTGAACGACAAAAT
GGCGTCCTGAACAGTTGGACTGATCAGGACAGCAAAGACAGCACCTACAGCATGAGCAGCACCCTCACGTTGACCAAGGACGAGTATGA
ACGACATAACAGCTATACCTGTGAGGCCACTCACAAGACATCAACTTCACCCATTGTCAAGAGCTTCAACAGGAATGAGTGTTAG

Translation 3E2-LC, 235 residues including SP (1-20) (SEQ ID NO:24)

METDTLLLWVLLLWVPGSTGDDIQMTQSPASLSASVGETVTITCRASENIYSYLAWYQQKQGKSPQFLVYNAETLAEGVPSRFSGSGSG
KQFSLKINSLQPEDFGSYYCQHHYGTHPTFGGGTKLEIKRADAAPTVSIFPPSSEQLTSGGASVVCFLNNFYPKDINVKWKIDGSERQN
GVLNSWTDQDSKDSTYSMSSTLTLTKDEYERHNSYTCEATHKTSTSPIVKSFNRNEC

Figure 9 Continued

18.44-G1, 1401 bp including SP (1-60)(SEQ ID NO:25)

ATGGAGACAGACACACTCCTGCTATGGGTACTGCTGCTCTGGGTTCCAGGTTCCACTGGTGACGAGGTGAAGCTGGTGGAGTCTGGAGG

AGGCTTGGTACAGTCTGGGGGTTCTCTGAGACTCTCCTGTGCAACTTCTGGGTTCACCTTCACTGATTATTACATGAGTTGGGTCCGCC

AGCCTCCAGGAAAGGCACTTGAGTGGTTGGGCTTTATTAGAGACAGAGATAATGGTTACACAACAGAATACAGTGCTTCTGTGAAGGGT

CGGTTCACCATCTCCAGAGATAATTCCCAAAGCATCCTCTATCTTCAAATGAACTCCCTGCGAGCTGAGGACAGTGCCACTTATTACTG

TGCAAGAGATATAAGGACTAACGAAGCTTTTGCTTACTGGGGCCAAGGGACTCTGGTCACTGTCTCTGCAGCtAcAACaACAgCCCCAT

CTGTCTATCCACTGGCCCCTGGATCTGCTGCCCAAACTAACTCCATGGTGACCCTGGGATGCCTGGTCAAGGGCTATTTCCCTGAGCCA

GTGACAGTGACCTGGAACTCTGGATCCCTGTCCAGCGGTGTGCACACCTTCCCAGCTGTCCTGCAGTCTGACCTCTACACTCTGAGCAG

CTCAGTGACTGTCCCCTCCAGCACCTGGCCCAGCGAGACCGTCACCTGCAACGTTGCCCACCCGGCCAGCAGCACCAAGGTGGACAAGA

AAATTGTGCCCAGGGATTGTGGTTGTAAGCCTTGCATATGTACAGTCCCAGAAGTATCATCTGTCTTCATCTTCCCCCCAAAGCCCAAG

GATGTGCTCACCATTACTCTGACTCCTAAGGTCACGTGTGTTGTGGTAGACATCAGCAAGGATGATCCCGAGGTCCAGTTCAGCTGGTT

TGTAGATGATGTGGAGGTGCACACAGCTCAGACGCAACCCCGGGAGGAGCAGTTCAACAGCACTTTCCGCTCAGTCAGTGAACTTCCCA

TCATGCACCAGGACTGGCTCAATGGCAAGGAGTTCAAATGCAGGGTCAACAGTGCAGCTTTCCCTGCCCCCATCGAGAAAACCATCTCC

AAAACCAAAGGCAGACCGAAGGCTCCACAGGTGTACACCATTCCACCTCCCAAGGAGCAGATGGCCAAGGATAAAGTCAGTCTGACCTG

CATGATAACAGACTTCTTCCCTGAAGACATTACTGTGGAGTGGCAGTGGAATGGGCAGCCAGCGGAGAACTACAAGAACACTCAGCCCA

TCATGGACACAGATGGCTCTTACTTCGTCTACAGCAAGCTCAATGTGCAGAAGAGCAACTGGGAGGCAGGAAATACTTTCACCTGCTCT

GTGTTACATGAGGGCCTGCACAACCACCATACTGAGAAGAGCCTCTCCCACTCTCCTGGTAAATGA

Figure 9 Continued

Translation 18.44-G1, 466 residues including SP (1-20) (SEQ ID NO:26)

METDTLLLWVLLLWVPGSTGDEVKLVESGGGLVQSGGSLRLSCATSGFTFTDYYMSWVRQPPGKALEWLGFIRDRDNGYTTEYSASVKG
RFTISRDNSQSILYLQMNSLRAEDSATYYCARDIRTNEAFAYWGQGTLVTVSAATTTAPSVYPLAPGSAAQTNSMVTLGCLVKGYFPEP
VTVTWNSGSLSSGVHTFPAVLQSDLYTLSSSVTVPSSTWPSETVTCNVAHPASSTKVDKKIVPRDCGCKPCICTVPEVSSVFIFPPKPK
DVLTITLTPKVTCVVVDISKDDPEVQFSWFVDDVEVHTAQTQPREEQFNSTFRSVSELPIMHQDWLNGKEFKCRVNSAAFPAPIEKTIS
KTKGRPKAPQVYTIPPPKEQMAKDKVSLTCMITDFFPEDITVEWQWNGQPAENYKNTQPIMDTDGSYFVYSKLNVQKSNWEAGNTFTCS
VLHEGLHNHHTEKSLSHSPGK

Figure 9 Continued

18.44-G1-LL37, 1560 bp including SP (1-60) (SEQ ID NO:27)

ATGGAGACAGACACACTCCTGCTATGGGTACTGCTGCTCTGGGTTCCAGGTTCCACTGGTGACGAGGTGAAGCTGGTGGAGTCTGGAGG
AGGCTTGGTACAGTCTGGGGGTTCTCTGAGACTCTCCTGTGCAACTTCTGGGTTCACCTTCACTGATTATTACATGAGTTGGGTCCGCC
AGCCTCCAGGAAAGGCACTTGAGTGGTTGGGCTTTATTAGAGACAGAGATAATGGTTACACAACAGAATACAGTGCTTCTGTGAAGGGT
CGGTTCACCATCTCCAGAGATAATTCCCAAAGCATCCTCTATCTTCAAATGAACTCCCTGCGAGCTGAGGACAGTGCCACTTATTACTG
TGCAAGAGATATAAGGACTAACGAAGCTTTTGCTTACTGGGGCCAAGGGACTCTGGTCACTGTCTCTGCAGCtAcAACaACAgCCCCAT
CTGTCTATCCACTGGCCCCTGGATCTGCTGCCCAAACTAACTCCATGGTGACCCTGGGATGCCTGGTCAAGGGCTATTTCCCTGAGCCA
GTGACAGTGACCTGGAACTCTGGATCCCTGTCCAGCGGTGTGCACACCTTCCCAGCTGTCCTGCAGTCTGACCTCTACACTCTGAGCAG
CTCAGTGACTGTCCCCTCCAGCACCTGGCCCAGCGAGACCGTCACCTGCAACGTTGCCCACCCGGCCAGCAGCACCAAGGTGGACAAGA
AAATTGTGCCCAGGGATTGTGGTTGTAAGCCTTGCATATGTACAGTCCCAGAAGTATCATCTGTCTTCATCTTCCCCCCAAAGCCCAAG
GATGTGCTCACCATTACTCTGACTCCTAAGGTCACGTGTGTTGTGGTAGACATCAGCAAGGATGATCCCGAGGTCCAGTTCAGCTGGTT
TGTAGATGATGTGGAGGTGCACACAGCTCAGACGCAACCCCGGGAGGAGCAGTTCAACAGCACTTTCCGCTCAGTCAGTGAACTTCCCA
TCATGCACCAGGACTGGCTCAATGGCAAGGAGTTCAAATGCAGGGTCAACAGTGCAGCTTTCCCTGCCCCCATCGAGAAAACCATCTCC
AAAACCAAAGGCAGACCGAAGGCTCCACAGGTGTACACCATTCCACCTCCCAAGGAGCAGATGGCCAAGGATAAAGTCAGTCTGACCTG
CATGATAACAGACTTCTTCCCTGAAGACATTACTGTGGAGTGGCAGTGGAATGGGCAGCCAGCGGAGAACTACAAGAACACTCAGCCcA
TCATGGACACAGATGGCTCTTACTTCGTCTACAGCAAGCTCAATGTGCAGAAGAGCAACTGGGAGGCAGGAAATACTTTCACCTGCTCT
GTGTTACATGAGGGCCTGCACAACCACCATACTGAGAAGAGCCTCTCCCACTCTCCTGGTAAATCAGGTGGTGGCGGTTCAGGCGGAGG
TGGCTCTGGCGGTGGCGGATCGCTGCTGGGGGATTTCTTCCGGAAGTCTAAAGAGAAGATTGGGAAAGAGTTTAAAAGAATTGTCCAGA
GAATCAAGGATTTTTTGCGGAATCTTGTGCCCAGGACAGAATCCTAG

Figure 9 Continued

Translation 18.44-G1-LL37, 519 residues including SP (1-20) (SEQ ID NO:28)

METDTLLLWVLLLWVPGSTGDEVKLVESGGGLVQSGGSLRLSCATSGFTFTDYYMSWVRQPPGKALEWLGFIRDRDNGYTTEYSASVKG
RFTISRDNSQSILYLQMNSLRAEDSATYYCARDIRTNEAFAYWGQGTLVTVSAATTTAPSVYPLAPGSAAQTNSMVTLGCLVKGYFPEP
VTVTWNSGSLSSGVHTFPAVLQSDLYTLSSSVTVPSSTWPSETVTCNVAHPASSTKVDKKIVPRDCGCKPCICTVPEVSSVFIFPPKPK
DVLTITLTPKVTCVVVDISKDDPEVQFSWFVDDVEVHTAQTQPREEQFNSTFRSVSELPIMHQDWLNGKEFKCRVNSAAFPAPIEKTIS
KTKGRPKAPQVYTIPPPKEQMAKDKVSLTCMITDFFPEDITVEWQWNGQPAENYKNTQPIMDTDGSYFVYSKLNVQKSNWEAGNTFTCS
VLHEGLHNHHTEKSLSHSPGKSGGGGSGGGGSGGGGSLLGDFFRKSKEKIGKEFKRIVQRIKDFLRNLVPRTES

Figure 9 Continued

18.44-G1-PLA2, 1821 bp including SP (1-60) (SEQ ID NO:29)

ATGGAGACAGACACACTCCTGCTATGGGTACTGCTGCTCTGGGTTCCAGGTTCCACTGGTGACGAGGTGAAGCTGGTGGAGTCTGGAGG
AGGCTTGGTACAGTCTGGGGGTTCTCTGAGACTCTCCTGTGCAACTTCTGGGTTCACCTTCACTGATTATTACATGAGTTGGGTCCGCC
AGCCTCCAGGAAAGGCACTTGAGTGGTTGGGCTTTATTAGAGACAGAGATAATGGTTACACAACAGAATACAGTGCTTCTGTGAAGGGT
CGGTTCACCATCTCCAGAGATAATTCCCAAAGCATCCTCTATCTTCAAATGAACTCCCTGCGAGCTGAGGACAGTGCCACTTATTACTG
TGCAAGAGATATAAGGACTAACGAAGCTTTTGCTTACTGGGGCCAAGGGACTCTGGTCACTGTCTCTGCAGCtAcAACaACAgCCCCAT
CTGTCTATCCACTGGCCCCTGGATCTGCTGCCCAAACTAACTCCATGGTGACCCTGGGATGCCTGGTCAAGGGCTATTTCCCTGAGCCA
GTGACAGTGACCTGGAACTCTGGATCCCTGTCCAGCGGTGTGCACACCTTCCCAGCTGTCCTGCAGTCTGACCTCTACACTCTGAGCAG
CTCAGTGACTGTCCCCTCCAGCACCTGGCCCAGCGAGACCGTCACCTGCAACGTTGCCCACCCGGCCAGCAGCACCAAGGTGGACAAGA
AAATTGTGCCCAGGGATTGTGGTTGTAAGCCTTGCATATGTACAGTCCCAGAAGTATCATCTGTCTTCATCTTCCCCCCAAAGCCCAAG
GATGTGCTCACCATTACTCTGACTCCTAAGGTCACGTGTGTTGTGGTAGACATCAGCAAGGATGATCCCGAGGTCCAGTTCAGCTGGTT
TGTAGATGATGTGGAGGTGCACACAGCTCAGACGCAACCCCGGGAGGAGCAGTTCAACAGCACTTTCCGCTCAGTCAGTGAACTTCCCA
TCATGCACCAGGACTGGCTCAATGGCAAGGAGTTCAAATGCAGGGTCAACAGTGCAGCTTTCCCTGCCCCCATCGAGAAAACCATCTCC
AAAACCAAAGGCAGACCGAAGGCTCCACAGGTGTACACCATTCCACCTCCCAAGGAGCAGATGGCCAAGGATAAAGTCAGTCTGACCTG
CATGATAACAGACTTCTTCCCTGAAGACATTACTGTGGAGTGGCAGTGGAATGGGCAGCCAGCGGAGAACTACAAGAACACTCAGCCCA
TCATGGACACAGgTGGCTCTTACTTCGTCTACAGCAAGCTCAATGTGCAGAAGAGCAACTGGGAGGCAGGAAATACTTTCACCTGCTCT
GTGTTACATGAGGGCCTGCACAACCACCATACTGAGAAGAGCCTCTCCCACTCTCCTGGTAAATCAGGTGGTGGCGGTTCAGGCGGAGG
TGGCTCTGGCGGTGGCGGATCGAATTTGGTGAATTTCCACAGAATGATCAAGTTGACGACAGGAAAGGAAGCCGCACTCAGTTATGGCT
TCTACGGCTGCCACTGTGGCGTGGGTGGCAGAGGATCCCCCAAGGATGCAACGGATCGCTGCTGTGTCACTCATGACTGTTGCTACAAA
CGTCTGGAGAAACGTGGATGTGGCACCAAATTTCTGAGCTACAAGTTTAGCAACTCGGGGAGCAGAATCACCTGTGCAAAACAGGACTC

Figure 9 Continued

CTGCAGAAGTCAACTGTGTGAGTGTGATAAGGCTGCTGCCACCTGTTTTGCTAGAAACAAGACGACCTACAATAAAAAGTACCAGTACT
ATTCCAATAAACACTGCAGAGGGAGCACCCCTCGTTGCTGA

Translation 18.44-G1-PLA2, 606 residues including SP (1-20) (SEQ ID NO:30)

METDTLLLWVLLLWVPGSTGDEVKLVESGGGLVQSGGSLRLSCATSGFTFTDYYMSWVRQPPGKALEWLGFIRDRDNGYTTEYSASVKG
RFTISRDNSQSILYLQMNSLRAEDSATYYCARDIRTNEAFAYWGQGTLVTVSAATTTAPSVYPLAPGSAAQTNSMVTLGCLVKGYFPEP
VTVTWNSGSLSSGVHTFPAVLQSDLYTLSSSVTVPSSTWPSETVTCNVAHPASSTKVDKKIVPRDCGCKPCICTVPEVSSVFIFPPKPK
DVLTITLTPKVTCVVVDISKDDPEVQFSWFVDDVEVHTAQTQPREEQFNSTFRSVSELPIMHQDWLNGKEFKCRVNSAAFPAPIEKTIS
KTKGRPKAPQVYTIPPPKEQMAKDKVSLTCMITDFFPEDITVEWQWNGQPAENYKNTQPIMDTGGSYFVYSKLNVQKSNWEAGNTFTCS
VLHEGLHNHHTEKSLSHSPGKSGGGGSGGGGSGGGGSNLVNFHRMIKLTTGKEAALSYGFYGCHCGVGGRGSPKDATDRCCVTHDCCYK
RLEKRGCGTKFLSYKFSNSGSRITCAKQDSCRSQLCECDKAAATCFARNKTTYNKKYQYYSNKHCRGSTPRC

Figure 9 Continued

18.44-LC, 723 bp including SP (1-60) (SEQ ID NO:31)

ATGGAGACAGACACACTCCTGCTATGGGTACTGCTGCTCTGGGTTCCAGGTTCCACTGGTGACGATGTTTTGATGACCCAAACTCCACT
CTCCCTGCCTGTCAGTCTTGGAGATCAAGCCTCCATCTCTTGCAGATCTAGTCAGAGCACTGTACATAGGAATGGAAACACCTATTTAG
AATGGTACCTGCAGAAACCAGGCCAGTCTCCAAAGCTCCTGATCTACAGAGTTTCCAACCGATTTTCTGGGGTCCCAGACAGGTTCAGT
GGCAGTGGATCAGGGACAGATTTCACACTCAAGATCAGCAGAGTGGAGGCTGAGGATCTGGGAGTTTATTACTGCTTTCAAGGTTCACA
TGTTCCGTGGACGTTCGGTGGAGGCACCAAGCTGGAAATCAAACGGGCTGATGCTGCACCAACTGTATCCATCTTCCCACCATCCAGTG
AGCAGTTAACATCTGGAGGTGCCTCAGTCGTGTGCTTCTTGAACAACTTCTACCCCAAAGACATCAATGTCAAGTGGAAGATTGATGGC
AGTGAACGACAAAATGGCGTCCTGAACAGTTGGACTGATCAGGACAGCAAAGACAGCACCTACAGCATGAGCAGCACCCTCACGTTGAC
CAAGGACGAGTATGAACGACATAACAGCTATACCTGTGAGGCCACTCACAAGACATCAACTTCACCCATTGTCAAGAGCTTCAACAGGA
ATGAGTGTTAG

Translation 18.44-LC, 240 residues including SP (1-20) (SEQ ID NO:32)

METDTLLLWVLLLWVPGSTGDDVLMTQTPLSLPVSLGDQASISCRSSQSTVHRNGNTYLEWYLQKPGQSPKLLIYRVSNRFSGVPDRFS
GSGSGTDFTLKISRVEAEDLGVYYCFQGSHVPWTFGGGTKLEIKRADAAPTVSIFPPSSEQLTSGGASVVCFLNNFYPKDINVKWKIDG
SERQNGVLNSWTDQDSKDSTYSMSSTLTLTKDEYERHNSYTCEATHKTSTSPIVKSFNRNEC

Figure 9 Continued

Variable Regions Only

---

4H9 heavy chain variable region nucleotide sequence, 423 bp, including signal peptide (1-60) (SEQ ID NO:33)

ATGGAGACAGACACACTCCTGCTATGGGTACTGCTGCTCTGGGTTCCAGGTTCCACTGGTGACCAGGTCCAGCTTCAGCAGTCTGGGGC
TGAACTGGCAAAACCTGGGGCCTCAGTGAAGATGTCCTGCAAGGCTTCTGGCTACACCTTTACTAGCTACTGGATGCACTGGGTGAAAC
AGAGGCCTGGACAGGGTCTGGAATGGATTGGATACATTAATCCTAGCACTGGTTATCCTGAGTACAATCAGAAATTCAAGGACAAGGCC
ACATTGACTGCAGACAAATCCTCCAACACAGCCTACATGCAACTGAGCAGCCTGACATCTGAGGACTCTGCAGTCTATTACTGTGTAAG
AAGGAATTACTACGAGGACTTCTTTGACTACTGGGGCCAAGGCACCACTCTCACAGTCTCCTCAGCC

4H9 heavy chain variable region amino acid sequence, 141 residues, including SP (1-20)(SEQ ID NO:34)

METDTLLLWVLLLWVPGSTGDQVQLQQSGAELAKPGASVKMSCKASGYTFTSYWMHWVKQRPGQGLEWIGYINPSTGYPEYNQKFKDKA
TLTADKSSNTAYMQLSSLTSEDSAVYYCVRRNYYEDFFDYWGQGTTLTVSSA

4H9 light chain variable region nucleotide sequence, 402 bp including signal peptide (1-60) (SEQ ID NO:35)

ATGGAGACAGACACACTCCTGCTATGGGTACTGCTGCTCTGGGTTCCAGGTTCCACTGGTGACGTTGTGATGACCCAAATTCCACTCTC
CCTGCCTGTCAGTCTTGGAGATCAAGCCTCCATCTCTTGCAGATCTAGTCAGAGCCTTGTACACAGTAATGGAAACACCTATTTACATT
GGTACCTGCAGAAGCCAGGCCAGTCTCCAAAGGTCCTGATCTACAAAGTTTCCAACCGATTTTCTGGGGTCCCAGACAGGTTCAGTGGC
AGTGGATCAGGGACAGATTTCACACTCAAGATCAGCAGAGTGGAGGCTGAGGATCTGGGAGTTTATTTCTGCTCTCAAAGTACACATGT
TCCGCTCACGTTCGGTGCTGGGACCAAGCTGGAGCTGAAACGGGCT

Figure 9 Continued

4H9 light chain variable region amino acid sequence, 134 residues, including SP (1-20) (SEQ ID NO:36)

METDTLLLWVLLLWVPGSTGDVVMTQIPLSLPVSLGDQASISCRSSQSLVHSNGNTYLHWYLQKPGQSPKVLIYKVSNRFSGVPDRFSG
SGSGTDFTLKISRVEAEDLGVYFCSQSTHVPLTFGAGTKLELKRA

Figure 9 Continued

3E2 heavy chain variable region nucleotide sequence, 426 bp, including SP (1-60) (SEQ ID NO:37)

ATGGAGACAGACACACTCCTGCTATGGGTACTGCTGCTCTGGGTTCCAGGTTCCACTGGTGACCAGGTGCAGCTGAAGGAGTCAGGACC

TGGCCTGGTGGCGCCCTCACAGAGCCTGTCCATCACTTGCACTGTCTCTGGGTTTTCATTAACCAACTATGGTGTACATTGGGTTCGCC

AGCCTCCAGGAAAGGGTCTGGAGTGGCTGGGAGTAATATGGGCTGGTGGAAACACAAATTATAATTCGGCTTTTATGTCCAGACTGAGC

ATCACCAAAGACAACTCCAAGAGCCAAGTTTTCATAAAAATGAACAGTCTGCAAACTGATGACACAGCCATGTACTACTGTGCCAGAGA

ATATAGGCACGGGGCTTACTATGCTATGGACTACTGGGGTCAAGGAACCTCAGTCACCGTCTCCTCAGAG

3E2 heavy chain variable region amino acid sequence, 142 residues, including SP (1-20) (SEQ ID NO:38)

METDTLLLWVLLLWVPGSTGDQVQLKESGPGLVAPSQSLSITCTVSGFSLTNYGVHWVRQPPGKGLEWLGVIWAGGNTNYNSAFMSRLS

ITKDNSKSQVFIKMNSLQTDDTAMYYCAREYRHGAYYAMDYWGQGTSVTVSSE

3E2 light chain variable region nucleotide sequence, 390 bp, including SP (1-60) (SEQ ID NO:39)

ATGGAGACAGACACACTCCTGCTATGGGTACTGCTGCTCTGGGTTCCAGGTTCCACTGGTGACGACATCCAGATGACTCAGTCTCCAGC

CTCCCTATCTGCATCTGTGGGAGAAACTGTCACCATCACATGTCGAGCAAGTGAGAACATTTACAGTTATTTAGCATGGTATCAGCAGA

AACAGGGAAAATCTCCTCAGTTCCTGGTCTATAATGCAGAAACCTTAGCAGAAGGTGTGCCATCAAGGTTCAGTGGCAGTGGATCAGGC

AAACAGTTTTCTCTGAAGATCAACAGCCTGCAGCCTGAAGATTTTGGGAGTTATTACTGTCAACATCATTATGGTACTCATCCGACGTT

CGGTGGAGGCACCAAGCTGGAAATCAAACGGGCT

3E2 light chain variable region – amino acid sequence, including SP (1-20) (SEQ ID NO:40)

Figure 9 Continued

METDTLLLWVLLLWVPGSTGDDIQMTQSPASLSASVGETVTITCRASENIYSYLAWYQQKQGKSPQFLVYNAETLAEGVPSRFSGSGSG

KQFSLKINSLQPEDFGSYYCQHHYGTHPTFGGGTKLEIKRA

Figure 9 Continued

18.44 Light chain variable region, 405 bp, including SP (1-60) (SEQ ID NO:41)

ATGGAGACAGACACACTCCTGCTATGGGTACTGCTGCTCTGGGTTCCAGGTTCCACTGGTGACGATGTTTTGATGACCCAAACTCCACT
CTCCCTGCCTGTCAGTCTTGGAGATCAAGCCTCCATCTCTTGCAGATCTAGTCAGAGCACTGTACATAGGAATGGAAACACCTATTTAG
AATGGTACCTGCAGAAACCAGGCCAGTCTCCAAAGCTCCTGATCTACAGAGTTTCCAACCGATTTTCTGGGGTCCCAGACAGGTTCAGT
GGCAGTGGATCAGGGACAGATTTCACACTCAAGATCAGCAGAGTGGAGGCTGAGGATCTGGGAGTTTATTACTGCTTTCAAGGTTCACA
TGTTCCGTGGACGTTCGGTGGAGGCACCAAGCTGGAAATCAAACGGGCT

18.44 light chain variable region amino acid sequence, 135 residues, including SP (1-20) (SEQ ID NO:42)

METDTLLLWVLLLWVPGSTGDDVLMTQTPLSLPVSLGDQASISCRSSQSTVHRNGNTYLEWYLQKPGQSPKLLIYRVSNRFSGVPDRFS
GSGSGTDFTLKISRVEAEDLGVYYCFQGSHVPWTFGGGTKLEIKRA

18.44 heavy chain variable region, 429 bp including SP (1-60) (SEQ ID NO:43)

ATGGAGACAGACACACTCCTGCTATGGGTACTGCTGCTCTGGGTTCCAGGTTCCACTGGTGACGAGGTGAAGCTGGTGGAGTCTGGAGG
AGGCTTGGTACAGTCTGGGGGTTCTCTGAGACTCTCCTGTGCAACTTCTGGGTTCACCTTCACTGATTATTACATGAGTTGGGTCCGCC
AGCCTCCAGGAAAGGCACTTGAGTGGTTGGCTTTATTAGAGACAGAGATAATGGTTACACAACAGAATACAGTGCTTCTGTGAAGGGT
CGGTTCACCATCTCCAGAGATAATTCCCAAAGCATCCTCTATCTTCAAATGAACTCCCTGCGAGCTGAGGACAGTGCCACTTATTACTG
TGCAAGAGATATAAGGACTAACGAAGCTTTTGCTTACTGGGGCCAAGGGACTCTGGTCACTGTCTCTGCAGCt

18.44 heavy chain variable region, 143 residues, including SP (1-20) (SEQ ID NO:44)

Figure 9 Continued

METDTLLLWVLLLWVPGSTGDEVKLVESGGGLVQSGGSLRLSCATSGFTFTDYYMSWVRQPPGKALEWLGFIRDRDNGYTTEYSASVKG
RFTISRDNSQSILYLQMNSLRAEDSATYYCARDIRTNEAFAYWGQGTLVTVSAA

4H9-LC nucleotide sequence coding region (1-714 bp)as in transgenics bicistronic construct (SEQ ID NO:157)

ATGGCCTCCTTTGTCTCTCTGCTCCTGGTTGGCATCCTATTCCATGCCACCCAGGCCGTTGTGATGACCCAAATTCCACTCTCCCTGCCTGTCAGTCT
TGGAGATCAAGCCTCCATCTCTTGCAGATCTAGTCAGAGCCTTGTACACAGTAATGGAAACACCTATTTACATTGGTACCTGCAGAAGCCAGGCCAGT
CTCCAAAGGTCCTGATCTACAAAGTTTCCAACCGATTTTCTGGGGTCCCAGACAGGTTCAGTGGCAGTGGATCAGGGACAGATTTCACACTCAAGATC
AGCAGAGTGGAGGCTGAGGATCTGGGAGTTTATTTCTGCTCTCAAAGTACACATGTTCCGCTCACGTTCGGTGCTGGGACCAAGCTGGAGCTGAAACG
GGCTGATGCTGCACCAACTGTATCCATCTTCCCACCATCCAGTGAGCAGTTAACATCTGGAGGTGCCTCAGTCGTGTGCTTCTTGAACAACTTCTACC
CCAAAGACATCAATGTCAAGTGGAAGATTGATGGCAGTGAACGACAAAATGGCGTCCTGAACAGTTGGACTGATCAGGACAGCAAAGACAGCACCTAC
AGCATGAGCAGCACCCTCACGTTGACCAAGGACGAGTATGAACGACATAACAGCTATACCTGTGAGGCCACTCACAAGACATCAACTTCACCCATTGT
CAAGAGCTTCAACAGGAATGAGTGTTAG

4H9-LC amino acid sequence, 238 residues, including alphalactalbumin signal peptide (residue 1-19) as in transgenic bicistronic construct (SEQ ID NO:158)

MASFVSLLLVGILFHATQAVVMTQIPLSLPVSLGDQASISCRSSQSLVHSNGNTYLHWYLQKPGQSPKVLIYKVSNRFSGVPDRFSGSGSGTDFTLKI
SRVEAEDLGVYFCSQSTHVPLTFGAGTKLELKRADAAPTVSIFPPSSEQLTSGGASVVCFLNNFYPKDINVKWKIDGSERQNGVLNSWTDQDSKDSTY
SMSSTLTLTKDEYERHNSYTCEATHKTSTSPIVKSFNRNEC

Figure 9 Continued

Mouse-human Chimeric Variable Regions

1A9 light chain variable region nucleotide sequence, 411 bp, including signal peptide (1-60) (SEQ ID NO:159)

ATGGAGACAGACACACTCCTGCTATGGGTACTGCTGCTCTGGGTTCCAGGTTCCACTGGTGACaCGCGTGATGTTGTGATGACCCAAATTCCACTCTC
CCTGCCTGTCAGTCTTGGAGATCAAGCCTCCATCTCTTGCAGATCTAGTCAGAGCCTTGTACACAGTAATGGAAACACCTATTTACATTGGTACCTGC
AGAAGCCAGGCCAGTCTCCAAAGCTCCTGATCTACAAAGTTTCCAACCGATTTTCTGGGGTCCCAGACAGGTTCAGTGGCAGTGGATCAGGGACAGAT
TTCACACTCAAGATCAGCAGAGTGGAGGCTGAGGATCTGGGAGTTTATTTCTGCTCTCAAAGTACACATGTTCCTCCGTGGACGTTTGGTGGAGGCAC
CAAGCTGGAAATCAAACGG

1A9 light chain variable region amino acid sequence, 137 residues, including SP (1-20) (SEQ ID NO:160)

METDTLLLWVLLLWVPGSTGDTRDVVMTQIPLSLPVSLGDQASISCRSSQSLVHSNGNTYLHWYLQKPGQSPKLLIYKVSNRFSGVPDRFSGSGSGTD
FTLKISRVEAEDLGVYFCSQSTHVPPWTFGGGTKLEIKR

1A9 heavy chain variable region nucleotide sequence, 429 bp, including signal peptide (1-60) (SEQ ID NO:161)

ATGGAGACAGACACACTCCTGCTATGGGTACTGCTGCTCTGGGTTCCAGGTTCCACTGGTGACaCGCGTCAGATCCAGTTGGTGCAGTCTGGACCTGA
GCTGAAGAAGCCTGGAGAGACAGTCAAGATCTCCTGCAAGGCTTCTGGGTATACCTTCACAAACTATGGAATGAACTGGGTGAAGCAGGCTCCAGGAA
AGGGTTTAAAGTGGATGGGCTGGATAAACACCAACACTGGAGAGCCAACATATGCTGAAGAGTTCAAGGGGCGGTTTGCCTTCTCTTTGGAAACCTCT
GCCAGCACTGCCTATTTGCAGATCAACAACCTCAAAAATGAGGACACGGCTACATATTTCTGTGCAAGACACGGTGGTAGGAGCTGGTACTTCGATGT
CTGGGGCGCAGGGACCACGGTCACCGTCTCCTCAGCG

Figure 9 Continued

1A9 heavy chain variable region amino acid sequence, 143 residues, including SP (1-20) (SEQ ID NO:162)

METDTLLLWVLLLWVPGSTGDTRQIQLVQSGPELKKPGETVKISCKASGYTFTNYGMNWVKQAPGKGLKWMGWINTNTGEPTYAEEFKGRFAFSLETS
ASTAYLQINNLKNEDTATYFCARHGGRSWYFDVWGAGTTVTVSSA

2C6 light chain variable region nucleotide sequence, 393 bp, including signal peptide (1-60) (SEQ ID NO:163)

ATGGAGACAGACACACTCCTGCTATGGGTACTGCTGCTCTGGGTTCCAGGTTCCACTGGTGACacgcgtGACATTGTGATGACCCAGTCTCAAAAATT
CATGTCCACATCAGTAGGAGACAGGGTCAGCGTCACCTGCAAGGCCAGTCAGAATGTGGGTACTAATGTAGCCTGGTTTCAACAGAAACTAGGGCAAT
CTCCTAAAGCACTGATTTACTCGGCATCCTACCGGTTCAGTGGAGTCCCTGATCGCTTCACAGGCAGTGGATCTGGGACAGATTTCACTCTCACCATC
AGCAATGTGCAGTCTGAAGACTTGGCAGAGTATTTCTGTCAGCAATATAACAGCTTTCCATTCACGTTCGGCTCGGGGACAAAGTTGGAAATAAAACG
G

2C6 light chain variable region amino acid sequence, 131 residues, including SP (1-20) (SEQ ID NO:164)

METDTLLLWVLLLWVPGSTGDTRDIVMTQSQKFMSTSVGDRVSVTCKASQNVGTNVAWFQQKLGQSPKALIYSASYRFSGVPDRFTGSGSGTDFTLTI
SNVQSEDLAEYFCQQYNSFPFTFGSGTKLEIKR

2C6 heavy chain variable region nucleotide sequence, 417 bp, including signal peptide (1-60) (SEQ ID NO:165)

Figure 9 Continued

ATGGAGACAGACACACTCCTGCTATGGGTACTGCTGCTCTGGGTTCCAGGTTCCACTGGTGACaCGCGTCAGGTTCAGCTGCAGCAGTCTGACGCTGA
GTTGGTGAGACCTGGGGCTTCAGTGAAGATATCCTGCAAACCTTCTGGCTACACCTTCACTGACCATGCTATTCACTGGGTGAAGCAGAAGCCTGAAC
AGGGCCTGGAATGGATTGGATATATTTCTCCCGGAAATGGTGATATTAAGTACAATGAGAAGTTCAAGGGCAAGGCCACACTGACTGCAGACAAATCC
TCCAGCACTGCCTACATGCAGCTCAACAGCCTGACATCTGAGGATTCTGCAGTGTATTTCTGTAAAAGATCCTACGCCCAGTTTGCTTACTGGGGCCA
AGGGACTCTGGTCACTGTCTCTGCG

__2C6 heavy chain variable region amino acid sequence, 139 residues, including SP (1-20) (SEQ ID NO:166)__

METDTLLLWVLLLWVPGSTGDTRQVQLQQSDAELVRPGASVKISCKPSGYTFTDHAIHWVKQKPEQGLEWIGYISPGNGDIKYNEKFKGKATLTADKS
SSTAYMQLNSLTSEDSAVYFCKRSYAQFAYWGQGTLVTVSA

__3D1 light chain variable region nucleotide sequence, 408 bp, including signal peptide (1-60) (SEQ ID NO:167)__

ATGGAGACAGACACACTCCTGCTATGGGTACTGCTGCTCTGGGTTCCAGGTTCCACTGGTGACaCGCGTAACATTATGATGACACAGTCGCCATCATC
TCTGGCTGTGTCTGCAGGAGAAAAGGTCACTATGAGCTGTAAGTCCAGTCAAAGTGTTTTATACAGTTCAGATCAGAAGAACTACTTGGCCTGGTACC
AGCAGAAACCAGGGCAGTCTCCTAAACTGCTGATCTACTGGGCATCCACTAGGGAATCTGGTGTCCCTGATCGCTTCACAGGCAGTGGATCTGGGACA
GATTTTACTCTTACCATCAGCAGTGTACAATCTGAAGACCTGGCAGTTTATTACTGTCATCAATACCTCTCCTCATTCACGTTCGGCTCGGGGACAAA
GTTGGAAATAGAACGG

__3D1 light chain variable region amino acid sequence, 136 residues, including SP (1-20) (SEQ ID NO:168)__

Figure 9 Continued

METDTLLLWVLLLWVPGSTGDTRNIMMTQSPSSLAVSAGEKVTMSCKSSQSVLYSSDQKNYLAWYQQKPGQSPKLLIYWASTRESGVPDRFTGSGSGT
DFTLTISSVQSEDLAVYYCHQYLSSFTFGSGTKLEIER

3D1 heavy chain variable region nucleotide sequence, 420 bp, including signal peptide (1-60) (SEQ ID NO:169)

ATGGAGACAGACACACTCCTGCTATGGGTACTGCTGCTCTGGGTTCCAGGTTCCACTGGTGACaCGCGTGAGGTTCAGCTGCAGCAGTCTGGGGCAGA
GCTTGTGAAGCCAGGGGCCTCAGTCAAGTTGTCCTGCACAGCTTCTGGCTTCAACATTATAGACACCTATATGCACTGGGTGAAACAGAGGCCTGAAC
AGGGCCTGGAGTGGATTGGAAGGATTGATCCTGCGAATGATAATACTAAATATGACCCGAAATTCCAGGGCAAGGCCACTATAACAGCTGACACATCC
TCCAACACAGCCTACCTGCAGCTCAGCAGCCTGACATCTGAGGACACTGCCGTCTATTACTGTGCCCTCTTTATTACGAGGGCTATGGACTACTGGGG
TCAAGGAACCTCAGTCACCGTCTCCTCA

3D1 heavy chain variable region amino acid sequence, 140 residues, including SP (1-20) (SEQ ID NO:170)

METDTLLLWVLLLWVPGSTGDTREVQLQQSGAELVKPGASVKLSCTASGFNIIDTYMHWVKQRPEQGLEWIGRIDPANDNTKYDPKFQGKATITADTS
SNTAYLQLSSLTSEDTAVYYCALFITRAMDYWGQGTSVTVSS

4E4 light chain variable region nucleotide sequence, 411 bp, including signal peptide (1-60) (SEQ ID NO:171)

ATGGAGACAGACACACTCCTGCTATGGGTACTGCTGCTCTGGGTTCCAGGTTCCACTGGTGACaCGCGTGATGTTGTGATGACCCAAATTCCACTCTC
CCTGCCTGTCAGTCTTGGAGATCAAGCCTCCATCTCTTGCAGATCTAGTCAGAGCCTTGTACACAGTAATGGAAACACCTATTTACATTGGTACCTGC
AGAAGCCAGGCCAGTCTCCAAAGCTCCTGATCTACAAAGTTTCCAACCGATTTTCTGGGGTCCCAGACAGGTTCAGTGGCAGTGGATCAGGGACAGAT

Figure 9 Continued

TTCACACTCAAGATCAGCAGAGTGGAGGCTGAGGATCTGGGAGTTTATTTCTGCTCTCAAAGTACACATGTTCCTCCGTGGACGTTCGGTGGAGGCAC
CAAGCTGGAAATCAAACGG

4E4 light chain variable region amino acid sequence, 137 residues, including SP (1-20) (SEQ ID NO:172)

METDTLLLWVLLLWVPGSTGDTRDVVMTQIPLSLPVSLGDQASISCRSSQSLVHSNGNTYLHWYLQKPGQSPKLLIYKVSNRFSGVPDRFSGSGSGTD
FTLKISRVEAEDLGVYFCSQSTHVPPWTFGGGTKLEIKR

4E4 heavy chain variable region nucleotide sequence, 429 bp, including signal peptide (1-60) (SEQ ID NO:173)

ATGGAGACAGACACACTCCTGCTATGGGTACTGCTGCTCTGGGTTCCAGGTTCCACTGGTGACaCGCGTCAGATCCAGTTGGTGCAGTCTGGACCTGA
GCTGAAGAAGCCTGGAGAGACAGTCAAGATCTCCTGCAAGGCTTCTGGGTATACCTTCACAAACTATGGAATGAACTGGGTGAAGCAGGCTCCAGGAA
AGGGTTTAAAGTGGATGGGCTGGATAAACACCAACACTGGAGAGCCAACATATGCTGAAGAGTTCAAGGGGCGGTTTGCCTTCTCTTTGGAAACCTCT
GCCAGCACTGCCTATTTGCAGATCAACAACCTCAAAAATGAGGACACGGCTACATATTTCTGTGCAAGACACGGTGGTAGGAGCTGGTACTTCGATGT
CTGGGGCGCAGGGACCACGGTCACCGTCTCCTCAGCT

4E4 heavy chain variable region amino acid sequence, 142 residues, including SP (1-20) (SEQ ID NO:174)

METDTLLLWVLLLWVPGSTGDTRQIQLVQSGPELKKPGETVKISCKASGYTFTNYGMNWVKQAPGKGLKWMGWINTNTGEPTYAEEFKGRFAFSLETS
ASTAYLQINNLKNEDTATYFCARHGGRSWYFDVWGAGTTVTVSSA

Figure 9 Continued 8.2C6 light chain variable region nucleotide sequence, 390 bp, including signal peptide (1-60) (SEQ ID NO:175)

ATGGAGACAGACACACTCCTGCTATGGGTACTGCTGCTCTGGGTTCCAGGTTCCACTGGTGACaCGCGTCAAATTGTTCTCACCCAGTCTCCAGCAAT
CATGTCTGCATCTCCAGGGGAGAAGGTCACCATAACCTGCAGTGCCAGCTCAAGTGTAAGTTACATGCACTGGTTCCAGCAGAAGCCAGGCACTTCTC
CCAAACTCTGGATTTATAGCACATCCAACCTGGCTTCTGGAGTCCCTGCTCGCTTCAGTGGCAGTGGATCTGGGACCTCTTACTCTCTCACAATCAGC
CGAATGGAGGCTGAAGATGCTGCCACTTATTACTGCCAGCAAAGGAGTAGTTACCCACCTACGTTCGGTGCTGGGACCAAGCTGGAGCTGAAACGG 8.2C6 light chain variable region amino acid sequence, 130 residues, including SP (1-20) (SEQ ID NO:176)

METDTLLLWVLLLWVPGSTGDTRQIVLTQSPAIMSASPGEKVTITCSASSSVSYMHWFQQKPGTSPKLWIYSTSNLASGVPARFSGSGSGTSYSLTIS
RMEAEDAATYYCQQRSSYPPTFGAGTKLELKR 8.2C6 heavy chain variable region nucleotide sequence, 423 bp, including signal peptide (1-60) (SEQ ID NO:177)

ATGGAGACAGACACACTCCTGCTATGGGTACTGCTGCTCTGGGTTCCAGGTTCCACTGGTGACaCGCGTGAGGTCCAGCTGCAGCAGTCTGGACCTGA
GCTAGTGAAGACTGGGGCTTCAGTGAAGATATCCTGCAAGGCTTCTGGTTACTCATTCACTGGTTACTACATGCACTGGGTCAAGCAGAGCCATGGAA
AGAGCCTTGAGTGGATTGGATATATTAGTTGTTACAATGGTGCTACTAGCTACAACCAGAAGTTCAAGGGCAAGGCCACATTTACTGTAGACACATCC
TCCAGCACAGCCTACATGCAGTTCAACAGCCTGACATCTGAAGACTCTGCGGTCTATTACTGTGCAAGATCGACTATGAGGGGGGTTATGGACTACTG
GGGTCAAGGAACCTCAGTCACCGTCTCCTCA 8.2C6 heavy chain variable region amino acid sequence, 130 residues, including SP (1-20) (SEQ ID NO:178)

Figure 9 Continued

METDTLLLWVLLLWVPGSTGDTREVQLQQSGPELVKTGASVKISCKASGYSFTGYYMHWVKQSHGKSLEWIGYISCYNGATSYNQKFKGKATFTVDTS
SSTAYMQFNSLTSEDSAVYYCARSTMRGVMDYWGQGTSVTVSS

Figure 12

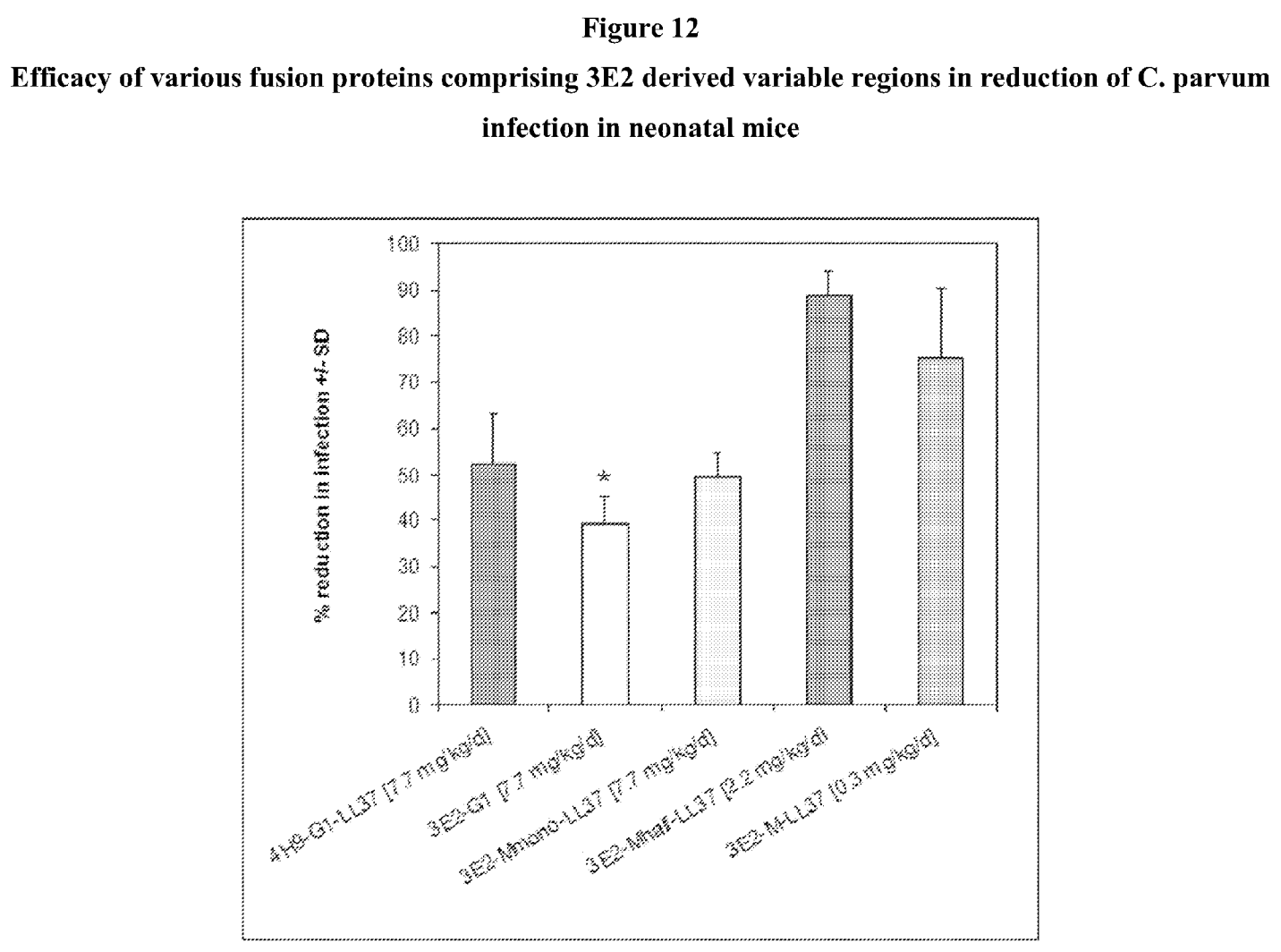

Efficacy of various fusion proteins comprising 3E2 derived variable regions in reduction of C. parvum infection in neonatal mice

Combinatorial Treatment of *C. parvum* in Neonatal Mouse Model
DBs binding different epitopes

Figure 14

| Parent Antibody | | Variable region | Recombinant Product Structure | Brief Structural Description | Nucleic acid sequences | Amino Acid sequences |
|---|---|---|---|---|---|---|
| 4H9 (native isotype G1) | | Recombinant variable region sequences<br><br>Nucleic Acid<br>Light Chain SEQ 35<br>Heavy Chain SEQ 33<br><br>Amino Acid<br>Light Chain SEQ 36<br>Heavy Chain SEQ 34 | 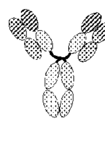 4H9-G1 | Recombinant IgG1 consisting of 2 full heavy chains and two full light chains assembled into one full size IgG1 antibody, no biocide | Light Chain SEQ 9<br>Heavy Chain SEQ 1 | Light Chain SEQ 10<br>Heavy Chain SEQ 2 |
| | | | 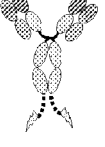 4H9-G1-LL37 | Recombinant IgG1 with LL37 biocide attached to each constant heavy chain c-terminus, 2 full size light chains | Light Chain SEQ 9<br>Heavy Chain SEQ 3<br>*For transgenic production*<br>Light Chain SEQ 157<br>Heavy Chain SEQ 3 | Light Chain SEQ 10<br>Heavy Chain SEQ 4<br>*For transgenic production*<br>Light Chain SEQ 158<br>Heavy Chain SEQ: 4 |
| | | | 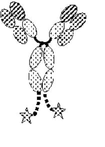 4H9-G1-PLA2 | Recombinant IgG1 with PLA2 biocide attached to each constant heavy chain C-terminus, 2 full size light chains | Light Chain SEQ 9<br>Heavy Chain SEQ 7 | Light Chain SEQ 10<br>Heavy Chain SEQ 8 |

Figure 14 Continued

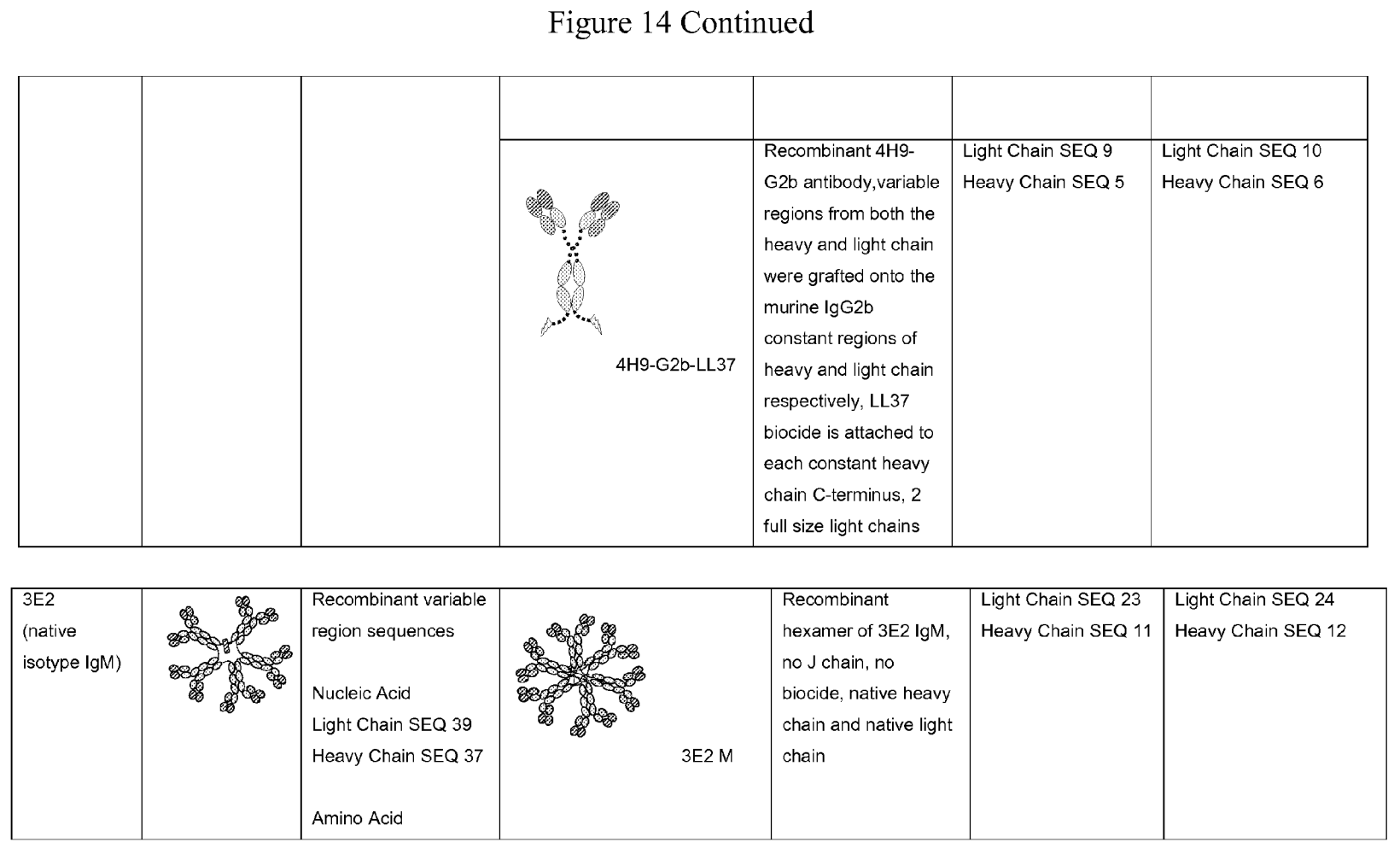

| | | | | | | |
|---|---|---|---|---|---|---|
| | | | 4H9-G2b-LL37 | Recombinant 4H9-G2b antibody,variable regions from both the heavy and light chain were grafted onto the murine IgG2b constant regions of heavy and light chain respectively, LL37 biocide is attached to each constant heavy chain C-terminus, 2 full size light chains | Light Chain SEQ 9<br>Heavy Chain SEQ 5 | Light Chain SEQ 10<br>Heavy Chain SEQ 6 |

| | | | | | | |
|---|---|---|---|---|---|---|
| 3E2 (native isotype IgM) | | Recombinant variable region sequences<br><br>Nucleic Acid<br>Light Chain SEQ 39<br>Heavy Chain SEQ 37<br><br>Amino Acid | 3E2 M | Recombinant hexamer of 3E2 IgM, no J chain, no biocide, native heavy chain and native light chain | Light Chain SEQ 23<br>Heavy Chain SEQ 11 | Light Chain SEQ 24<br>Heavy Chain SEQ 12 |

Figure 14 Continued

| | | | | | | |
|---|---|---|---|---|---|---|
| | | Light Chain SEQ 40<br>Heavy Chain SEQ 38 | 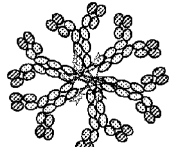 3E2-M-LL37 | Recombinant 3E2 hexamer, with one LL37 attached to c-terminus of each of 12 heavy chains. 12 biocides total | Light Chain SEQ 23<br>Heavy Chain SEQ 13 | Light Chain SEQ 24<br>Heavy Chain SEQ 14 |
| | | | 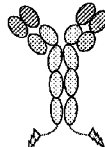 3E2-Mmono-LL37 | Single subunit of IgM pentamer, called IgM monomer, consists of two full size native light chains and two full size modified heavy chains which are linked to one biocide each, 2 biocides total | Light Chain SEQ 23<br>Heavy Chain SEQ 15 | Light Chain SEQ 24<br>Heavy Chain SEQ 16 |
| | | | 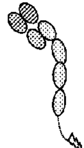 3E2-Mhalf-LL37 | Half of an IgM monomer, called IgM halfmer, consists of one full size native light chain and one fullsize modified heavy chain with one biocide attached to the heavy chain C- | Light Chain SEQ 23<br>Heavy Chain SEQ 17 | Light Chain SEQ 24<br>Heavy Chain SEQ 18 |

Figure 14 Continued

| | | | | | | |
|---|---|---|---|---|---|---|
| | | | | terminus | | |
| | | | 3E2 G1 | 3E2 heavy chain variable regions are grafted onto murine IgG1 heavy chain constant reagion, the 3E2 kappa LC is in its native form | Light Chain SEQ 23<br>Heavy Chain SEQ 19 | Light Chain SEQ 24<br>Heavy Chain SEQ 20 |
| | | | 3E2-G1-LL37 | 3E2 kappa LC is in its native form, 3E2-G1 heavy chains are linked to one biocide each (total of 2 biocides) | Light Chain SEQ 23<br>Heavy Chain SEQ 21 | Light Chain SEQ 24<br>Heavy Chain SEQ 22 |

| | | | | | | |
|---|---|---|---|---|---|---|
| 18.44 Native isotype IgG3 | | Recombinant variable region sequences<br><br>Nucleic Acid<br>Light Chain SEQ 41<br>Heavy Chain SEQ 43<br><br>Amino Acid<br>Light Chain SEQ 42 | 18.44 G1 | 18.44 light chain is in its native form, 18.44 heavy chain variable regions are grafted onto murine IgG1 heavy chain constant region | Light Chain SEQ 31<br>Heavy Chain SEQ 25 | Light Chain SEQ 32<br>Heavy Chain SEQ 26 |
| | | | | 18.44 light chain is in | Light Chain SEQ 31 | Light Chain SEQ 32 |

Figure 14 Continued

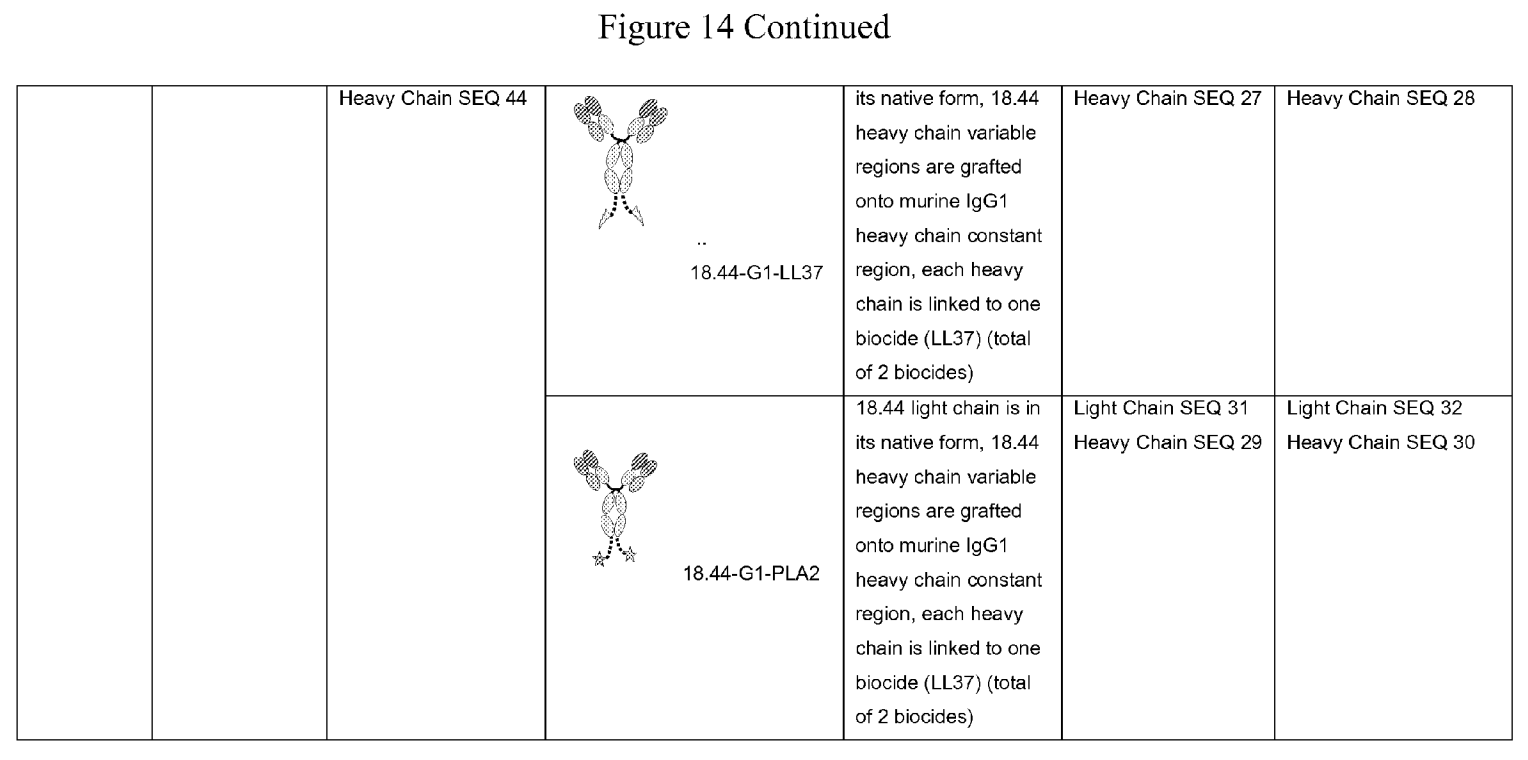

| | | | | | | |
|---|---|---|---|---|---|---|
| | | Heavy Chain SEQ 44 | .. 18.44-G1-LL37 | its native form, 18.44 heavy chain variable regions are grafted onto murine IgG1 heavy chain constant region, each heavy chain is linked to one biocide (LL37) (total of 2 biocides) | Heavy Chain SEQ 27 | Heavy Chain SEQ 28 |
| | | | 18.44-G1-PLA2 | 18.44 light chain is in its native form, 18.44 heavy chain variable regions are grafted onto murine IgG1 heavy chain constant region, each heavy chain is linked to one biocide (LL37) (total of 2 biocides) | Light Chain SEQ 31<br>Heavy Chain SEQ 29 | Light Chain SEQ 32<br>Heavy Chain SEQ 30 |

Figure 14 Continued

Mouse-human chimeric antibody constructs

| Parent Antibody | | Variable region | Chimeric Mouse-Human Product Structure | Brief Structural Description |
|---|---|---|---|---|
| 1A9 Native isotype IgG3 | | Recombinant variable region sequences<br><br>Nucleic Acid<br>Light Chain SEQ 159<br>Heavy Chain SEQ 161<br><br>Amino Acid<br>Light Chain SEQ 160<br>Heavy Chain SEQ 162 | 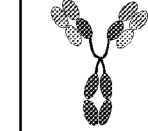 ch1A9-G1 | 1A9 light chain variable region is grafted onto human IgG1 light chain constant region, 1A9 heavy chain variable region is grafted onto human IgG1 heavy chain constant region |
| | | | ch1A9-G1-LL37 | 1A9 light chain variable region is grafted onto human IgG1 light chain constant region, 1A9 heavy chain variable region is grafted onto human IgG1 heavy chain constant region, each heavy chain is linked to one biocide (LL37) for a total of 2 biocides. |
| | | | ch1A9-G1-PLA2 | 1A9 light chain variable region is grafted onto human IgG1 light chain constant region, 1A9 heavy chain variable region is grafted onto human IgG1 heavy chain constant region, each heavy chain is linked to one biocide (PLA2) for a total of 2 biocides. |
| | | | ch1A9-G1-HBD2 | 1A9 light chain variable region is grafted onto human IgG1 light chain constant region, 1A9 heavy chain variable region is grafted onto human IgG1 heavy chain constant region, each heavy chain is linked to one biocide (HBD2) for a total of 2 biocides. |

Figure 14 Continued

| Parent Antibody | | Variable region | Chimeric Mouse-Human Product Structure | Brief Structural Description |
| --- | --- | --- | --- | --- |
| 2C6<br>Native<br>isotype IgM | | Recombinant variable region sequences<br><br>Nucleic Acid<br>Light Chain SEQ163<br>Heavy Chain SEQ165<br><br>Amino Acid<br>Light Chain SEQ164<br>Heavy Chain SEQ 166 | 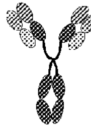 ch2C6-G1 | 2C6 light chain variable region is grafted onto human IgG1 light chain constant region, 1A9 heavy chain variable region is grafted onto human IgG1 heavy chain constant region |
| | | | 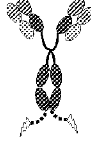 ch2C6-G1-LL37 | 2C6 light chain variable region is grafted onto human IgG1 light chain constant region, 1A9 heavy chain variable region is grafted onto human IgG1 heavy chain constant region, each heavy chain is linked to one biocide (LL37) for a total of 2 biocides. |
| | | | 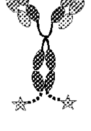 ch2C6-G1-PLA2 | 2C6 light chain variable region is grafted onto human IgG1 light chain constant region, 1A9 heavy chain variable region is grafted onto human IgG1 heavy chain constant region, each heavy chain is linked to one biocide (PLA2) for a total of 2 biocides. |
| | | | 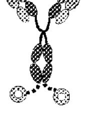 ch2C6-G1-HBD2 | 2C6 light chain variable region is grafted onto human IgG1 light chain constant region, 1A9 heavy chain variable region is grafted onto human IgG1 heavy chain constant region, each heavy chain is linked to one biocide (HBD2) for a total of 2 biocides. |

Figure 14 Continued

| Parent Antibody | | Variable region | Chimeric Mouse-Human Product Structure | Brief Structural Description |
|---|---|---|---|---|
| 3D1<br>Native<br>isotype IgM | | Recombinant variable region sequences<br><br>Nucleic Acid<br>Light Chain SEQ 167<br>Heavy Chain SEQ 169<br><br>Amino Acid<br>Light Chain SEQ 168<br>Heavy Chain SEQ 170 | ch3D1-G1 | 3D1 light chain variable region is grafted onto human IgG1 light chain constant region, 1A9 heavy chain variable region is grafted onto human IgG1 heavy chain constant region |
| | | | ..<br>ch3D1-G1-LL37 | 3D1 light chain variable region is grafted onto human IgG1 light chain constant region, 1A9 heavy chain variable region is grafted onto human IgG1 heavy chain constant region, each heavy chain is linked to one biocide (LL37) for a total of 2 biocides. |
| | | | ch3D1-G1-PLA2 | 3D1 light chain variable region is grafted onto human IgG1 light chain constant region, 1A9 heavy chain variable region is grafted onto human IgG1 heavy chain constant region, each heavy chain is linked to one biocide (PLA2) for a total of 2 biocides. |
| | | | ch3D1-G1-HBD2 | 3D1 light chain variable region is grafted onto human IgG1 light chain constant region, 1A9 heavy chain variable region is grafted onto human IgG1 heavy chain constant region, each heavy chain is linked to one biocide (HBD2) for a total of 2 biocides. |

Figure 14 Continued

| Parent Antibody | | Variable region | Chimeric Mouse-Human Product Structure | Brief Structural Description |
|---|---|---|---|---|
| 4E4<br>Native<br>isotype<br>IgG3 | | Recombinant variable region sequences<br><br>Nucleic Acid<br>Light Chain SEQ171<br>Heavy Chain SEQ 173<br><br>Amino Acid<br>Light Chain SEQ172<br>Heavy Chain SEQ174 | ch4E4-G1 | 4E4 light chain variable region is grafted onto human IgG1 light chain constant region, 1A9 heavy chain variable region is grafted onto human IgG1 heavy chain constant region |
| | | | ch4E4-G1-LL37 | 4E4 light chain variable region is grafted onto human IgG1 light chain constant region, 1A9 heavy chain variable region is grafted onto human IgG1 heavy chain constant region, each heavy chain is linked to one biocide (LL37) for a total of 2 biocides. |
| | | | ch4E4-G1-PLA2 | 4E4 light chain variable region is grafted onto human IgG1 light chain constant region, 1A9 heavy chain variable region is grafted onto human IgG1 heavy chain constant region, each heavy chain is linked to one biocide (PLA2) for a total of 2 biocides. |
| | | | ch4E4-G1-HBD2 | 4E4 light chain variable region is grafted onto human IgG1 light chain constant region, 1A9 heavy chain variable region is grafted onto human IgG1 heavy chain constant region, each heavy chain is linked to one biocide (HBD2) for a total of 2 biocides. |

Figure 14 Continued

| Parent Antibody | | Variable region | Chimeric Mouse-Human Product Structure | Brief Structural Description |
|---|---|---|---|---|
| 8.2C6<br>Native<br>isotype IgM | | Recombinant variable region sequences<br><br>Nucleic Acid<br>Light Chain SEQ 175<br>Heavy Chain SEQ 177<br><br>Amino Acid<br>Light Chain SEQ 176<br>Heavy Chain SEQ 178 | 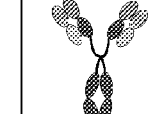 ch8.2C6-G1 | 8.2C6 light chain variable region is grafted onto human IgG1 light chain constant region, 1A9 heavy chain variable region is grafted onto human IgG1 heavy chain constant region |
| | | | ch8.2C6-G1-LL37 | 8.2C6 light chain variable region is grafted onto human IgG1 light chain constant region, 1A9 heavy chain variable region is grafted onto human IgG1 heavy chain constant region, each heavy chain is linked to one biocide (LL37) for a total of 2 biocides. |
| | | | ch8.2C6-G1-PLA2 | 8.2C6 light chain variable region is grafted onto human IgG1 light chain constant region, 1A9 heavy chain variable region is grafted onto human IgG1 heavy chain constant region, each heavy chain is linked to one biocide (PLA2) for a total of 2 biocides. |
| | | | ch8.2C6-G1-HBD2 | 8.2C6 light chain variable region is grafted onto human IgG1 light chain constant region, 1A9 heavy chain variable region is grafted onto human IgG1 heavy chain constant region, each heavy chain is linked to one biocide (HBD2) for a total of 2 biocides. |

SEQUENCE LISTING

```
<160> NUMBER OF SEQ ID NOS: 188

<210> SEQ ID NO 1
<211> LENGTH: 1395
<212> TYPE: DNA
<213> ORGANISM: Artificial Sequence
<220> FEATURE:
<223> OTHER INFORMATION: Synthetic

<400> SEQUENCE: 1

atggagacag acacactcct gctatgggta ctgctgctct gggttccagg ttccactggt      60

gaccaggtcc agcttcagca gtctggggct gaactggcaa aacctggggc ctcagtgaag     120

atgtcctgca aggcttctgg ctacaccttt actagctact ggatgcactg ggtgaaacag     180

aggcctggac agggtctgga atggattgga tacattaatc ctagcactgg ttatcctgag     240

tacaatcaga aattcaagga caaggccaca ttgactgcag acaaatcctc caacacagcc     300
```

```
tacatgcaac tgagcagcct gacatctgag gactctgcag tctattactg tgtaagaagg    360

aattactacg aggacttctt tgactactgg ggccaaggca ccactctcac agtctcctca    420

gccaaaacga cacccccatc tgtctatcca ctggcccctg gatctgctgc ccaaactaac    480

tccatggtga ccctgggatg cctggtcaag ggctatttcc ctgagccagt gacagtgacc    540

tggaactctg gatccctgtc cagcggtgtg cacaccttcc cagctgtcct gcagtctgac    600

ctctacactc tgagcagctc agtgactgtc ccctccagca cctggcccag cgagaccgtc    660

acctgcaacg ttgcccaccc ggccagcagc accaaggtgg acaagaaaat tgtgcccagg    720

gattgtggtt gtaagccttg catatgtaca gtcccagaag tatcatctgt cttcatcttc    780

cccccaaagc ccaaggatgt gctcaccatt actctgactc ctaaggtcac gtgtgttgtg    840

gtagacatca gcaaggatga tcccgaggtc cagttcagct ggtttgtaga tgatgtggag    900

gtgcacacag ctcagacgca accccgggag gagcagttca acagcacttt ccgctcagtc    960

agtgaacttc ccatcatgca ccaggactgg ctcaatggca aggagttcaa atgcagggtc   1020

aacagtgcag ctttccctgc ccccatcgag aaaaccatct ccaaaaccaa aggcagaccg   1080

aaggctccac aggtgtacac cattccacct cccaaggagc agatggccaa ggataaagtc   1140

agtctgacct gcatgataac agacttcttc cctgaagaca ttactgtgga gtggcagtgg   1200

aatgggcagc cagcggagaa ctacaagaac actcagccca tcatggacac agatggctct   1260

tacttcgtct acagcaagct caatgtgcag aagagcaact gggaggcagg aaatactttc   1320

acctgctctg tgttacatga gggcctgcac aaccaccata ctgagaagag cctctcccac   1380

tctcctggta aatga                                                    1395
```

```
<210> SEQ ID NO 2
<211> LENGTH: 464
<212> TYPE: PRT
<213> ORGANISM: Artificial Sequence
<220> FEATURE:
<223> OTHER INFORMATION: Synthetic

<400> SEQUENCE: 2

Met Glu Thr Asp Thr Leu Leu Leu Trp Val Leu Leu Leu Trp Val Pro
1               5                   10                  15

Gly Ser Thr Gly Asp Gln Val Gln Leu Gln Gln Ser Gly Ala Glu Leu
            20                  25                  30

Ala Lys Pro Gly Ala Ser Val Lys Met Ser Cys Lys Ala Ser Gly Tyr
        35                  40                  45

Thr Phe Thr Ser Tyr Trp Met His Trp Val Lys Gln Arg Pro Gly Gln
    50                  55                  60

Gly Leu Glu Trp Ile Gly Tyr Ile Asn Pro Ser Thr Gly Tyr Pro Glu
65                  70                  75                  80

Tyr Asn Gln Lys Phe Lys Asp Lys Ala Thr Leu Thr Ala Asp Lys Ser
                85                  90                  95

Ser Asn Thr Ala Tyr Met Gln Leu Ser Ser Leu Thr Ser Glu Asp Ser
            100                 105                 110

Ala Val Tyr Tyr Cys Val Arg Arg Asn Tyr Tyr Glu Asp Phe Phe Asp
        115                 120                 125

Tyr Trp Gly Gln Gly Thr Thr Leu Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
```

```
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460


<210> SEQ ID NO 3
<211> LENGTH: 1554
<212> TYPE: DNA
<213> ORGANISM: Artificial Sequence
<220> FEATURE:
<223> OTHER INFORMATION: Synthetic

<400> SEQUENCE: 3

atggagacag acacactcct gctatgggta ctgctgctct gggttccagg ttccactggt      60

gaccaggtcc agcttcagca gtctggggct gaactggcaa aacctggggc ctcagtgaag     120

atgtcctgca aggcttctgg ctacaccttt actagctact ggatgcactg ggtgaaacag     180

aggcctggac agggtctgga atggattgga tacattaatc ctagcactgg ttatcctgag     240

tacaatcaga aattcaagga caaggccaca ttgactgcag acaaatcctc caacacagcc     300

tacatgcaac tgagcagcct gacatctgag gactctgcag tctattactg tgtaagaagg     360

aattactacg aggacttctt tgactactgg ggccaaggca ccactctcac agtctcctca     420
```

```
gccaaaacga cacccccatc tgtctatcca ctggcccctg gatctgctgc ccaaactaac    480

tccatggtga ccctgggatg cctggtcaag ggctatttcc ctgagccagt gacagtgacc    540

tggaactctg gatccctgtc cagcggtgtg cacaccttcc cagctgtcct gcagtctgac    600

ctctacactc tgagcagctc agtgactgtc ccctccagca cctggcccag cgagaccgtc    660

acctgcaacg ttgcccaccc ggccagcagc accaaggtgg acaagaaaat tgtgcccagg    720

gattgtggtt gtaagccttg catatgtaca gtcccagaag tatcatctgt cttcatcttc    780

cccccaaagc ccaaggatgt gctcaccatt actctgactc ctaaggtcac gtgtgttgtg    840

gtagacatca gcaaggatga tcccgaggtc cagttcagct ggtttgtaga tgatgtggag    900

gtgcacacag ctcagacgca accccgggag gagcagttca acagcacttt ccgctcagtc    960

agtgaacttc ccatcatgca ccaggactgg ctcaatggca aggagttcaa atgcagggtc   1020

aacagtgcag ctttccctgc ccccatcgag aaaaccatct ccaaaaccaa aggcagaccg   1080

aaggctccac aggtgtacac cattccacct cccaaggagc agatggccaa ggataaagtc   1140

agtctgacct gcatgataac agacttcttc cctgaagaca ttactgtgga gtggcagtgg   1200

aatgggcagc cagcggagaa ctacaagaac actcagccca tcatggacac agatggctct   1260

tacttcgtct acagcaagct caatgtgcag aagagcaact gggaggcagg aaatactttc   1320

acctgctctg tgttacatga gggcctgcac aaccaccata ctgagaagag cctctcccac   1380

tctcctggta aatcaggtgg tggcggttca ggcggaggtg gctctggcgg tggcggatcg   1440

ctgctggggg atttcttccg gaagtctaaa gagaagattg ggaaagagtt taaaagaatt   1500

gtccagagaa tcaaggattt tttgcggaat cttgtgccca ggacagaatc ctag         1554
```

```
<210> SEQ ID NO 4
<211> LENGTH: 517
<212> TYPE: PRT
<213> ORGANISM: Artificial Sequence
<220> FEATURE:
<223> OTHER INFORMATION: Synthetic

<400> SEQUENCE: 4

Met Glu Thr Asp Thr Leu Leu Leu Trp Val Leu Leu Leu Trp Val Pro
1               5                   10                  15

Gly Ser Thr Gly Asp Gln Val Gln Leu Gln Gln Ser Gly Ala Glu Leu
            20                  25                  30

Ala Lys Pro Gly Ala Ser Val Lys Met Ser Cys Lys Ala Ser Gly Tyr
        35                  40                  45

Thr Phe Thr Ser Tyr Trp Met His Trp Val Lys Gln Arg Pro Gly Gln
    50                  55                  60

Gly Leu Glu Trp Ile Gly Tyr Ile Asn Pro Ser Thr Gly Tyr Pro Glu
65                  70                  75                  80

Tyr Asn Gln Lys Phe Lys Asp Lys Ala Thr Leu Thr Ala Asp Lys Ser
                85                  90                  95

Ser Asn Thr Ala Tyr Met Gln Leu Ser Ser Leu Thr Ser Glu Asp Ser
            100                 105                 110

Ala Val Tyr Tyr Cys Val Arg Arg Asn Tyr Tyr Glu Asp Phe Phe Asp
        115                 120                 125

Tyr Trp Gly Gln Gly Thr Thr Leu Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175
```

```
Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

Ser Gly Gly Gly Gly Ser Gly Gly Gly Gly Ser Gly Gly Gly Gly Ser
465                 470                 475                 480

Leu Leu Gly Asp Phe Phe Arg Lys Ser Lys Glu Lys Ile Gly Lys Glu
                485                 490                 495

Phe Lys Arg Ile Val Gln Arg Ile Lys Asp Phe Leu Arg Asn Leu Val
            500                 505                 510

Pro Arg Thr Glu Ser
        515
```

<210> SEQ ID NO 5
<211> LENGTH: 1590
<212> TYPE: DNA
<213> ORGANISM: Artificial Sequence
<220> FEATURE:
<223> OTHER INFORMATION: Synthetic

<400> SEQUENCE: 5

```
atggagacag acacactcct gctatgggta ctgctgctct gggttccagg ttccactggt      60

gaccaggtcc agcttcagca gtctggggct gaactggcaa aacctggggc ctcagtgaag     120
```

```
atgtcctgca aggcttctgg ctacaccttt actagctact ggatgcactg ggtgaaacag    180

aggcctggac agggtctgga atggattgga tacattaatc ctagcactgg ttatcctgag    240

tacaatcaga aattcaagga caaggccaca ttgactgcag acaaatcctc caacacagcc    300

tacatgcaac tgagcagcct gacatctgag gactctgcag tctattactg tgtaagaagg    360

aattactacg aggacttctt tgactactgg ggccaaggca ccactctcac agtctcctca    420

gccaaaacga cacccccatc tgtctatcca ctggcccctg ggtgtggaga tacaactggt    480

tcctccgtga ctctgggatg cctggtcaag ggctacttcc ctgagtcagt gactgtgact    540

tggaactctg gatccctgtc cagcagtgtg cacaccttcc cagctctcct gcagtctgga    600

ctctacacta tgagcagctc agtgactgtc ccctccagca cctggccaag tcagaccgtc    660

acctgcagcg ttgctcaccc agccagcagc accacggtgg acaaaaaact tgagcccagc    720

gggcccattt caacaatcaa cccctgtcct ccatgcaagg agtgtcacaa atgcccagct    780

cctaacctcg agggtggacc atccgtcttc atcttccctc caaatatcaa ggatgtactc    840

atgatctccc tgacacccaa ggtcacgtgt gtggtggtgg atgtgagcga ggatgaccca    900

gacgtccaga tcagctggtt tgtgaacaac gtggaagtac acacagctca gacacaaacc    960

catagagagg attacaacag tactatccgg gtggtcagca ccctccccat ccagcaccag   1020

gactggatga gtggcaagga gttcaaatgc aaggtcaaca acaaagacct cccatcaccc   1080

atcgagagaa ccatctcaaa aattaaaggg ctagtcagag ctccacaagt atacatcttg   1140

ccgccaccag cagagcagtt gtccaggaaa gatgtcagtc tcacttgcct ggtcgtgggc   1200

ttcaaccctg gagacatcag tgtggagtgg accagcaatg ggcatacaga ggagaactac   1260

aaggacaccg caccagtcct ggactctgac ggttcttact tcatatatag caagctcaat   1320

atgaaaacaa gcaagtggga gaaaacagat tccttctcat gcaacgtgag acacgagggt   1380

ctgaaaaatt actacctgaa gaagaccatc tcccggtctc cgggtaaatc aggtggtggc   1440

ggttcaggcg gaggtggctc tggcggtggc ggatcgctgc tgggggattt cttccggaag   1500

tctaaagaga agattgggaa agagtttaaa agaattgtcc agagaatcaa ggatttttg    1560

cggaatcttg tgcccaggac agaatcctag                                    1590
```

<210> SEQ ID NO 6
<211> LENGTH: 529
<212> TYPE: PRT
<213> ORGANISM: Artificial Sequence
<220> FEATURE:
<223> OTHER INFORMATION: Synthetic

<400> SEQUENCE: 6

```
Met Glu Thr Asp Thr Leu Leu Leu Trp Val Leu Leu Leu Trp Val Pro
1               5                   10                  15

Gly Ser Thr Gly Asp Gln Val Gln Leu Gln Gln Ser Gly Ala Glu Leu
            20                  25                  30

Ala Lys Pro Gly Ala Ser Val Lys Met Ser Cys Lys Ala Ser Gly Tyr
        35                  40                  45

Thr Phe Thr Ser Tyr Trp Met His Trp Val Lys Gln Arg Pro Gly Gln
    50                  55                  60

Gly Leu Glu Trp Ile Gly Tyr Ile Asn Pro Ser Thr Gly Tyr Pro Glu
65                  70                  75                  80

Tyr Asn Gln Lys Phe Lys Asp Lys Ala Thr Leu Thr Ala Asp Lys Ser
                85                  90                  95

Ser Asn Thr Ala Tyr Met Gln Leu Ser Ser Leu Thr Ser Glu Asp Ser
```

```
            100                 105                 110

Ala Val Tyr Tyr Cys Val Arg Arg Asn Tyr Tyr Glu Asp Phe Phe Asp
        115                 120                 125

Tyr Trp Gly Gln Gly Thr Thr Leu Thr Val Ser Ser Ala Lys Thr Thr
    130                 135                 140

Pro Pro Ser Val Tyr Pro Leu Ala Pro Gly Cys Gly Asp Thr Thr Gly
145                 150                 155                 160

Ser Ser Val Thr Leu Gly Cys Leu Val Lys Gly Tyr Phe Pro Glu Ser
                165                 170                 175

Val Thr Val Thr Trp Asn Ser Gly Ser Leu Ser Ser Ser Val His Thr
            180                 185                 190

Phe Pro Ala Leu Leu Gln Ser Gly Leu Tyr Thr Met Ser Ser Ser Val
        195                 200                 205

Thr Val Pro Ser Ser Thr Trp Pro Ser Gln Thr Val Thr Cys Ser Val
    210                 215                 220

Ala His Pro Ala Ser Ser Thr Thr Val Asp Lys Lys Leu Glu Pro Ser
225                 230                 235                 240

Gly Pro Ile Ser Thr Ile Asn Pro Cys Pro Pro Cys Lys Glu Cys His
                245                 250                 255

Lys Cys Pro Ala Pro Asn Leu Glu Gly Gly Pro Ser Val Phe Ile Phe
            260                 265                 270

Pro Pro Asn Ile Lys Asp Val Leu Met Ile Ser Leu Thr Pro Lys Val
        275                 280                 285

Thr Cys Val Val Val Asp Val Ser Glu Asp Asp Pro Asp Val Gln Ile
    290                 295                 300

Ser Trp Phe Val Asn Asn Val Glu Val His Thr Ala Gln Thr Gln Thr
305                 310                 315                 320

His Arg Glu Asp Tyr Asn Ser Thr Ile Arg Val Val Ser Thr Leu Pro
                325                 330                 335

Ile Gln His Gln Asp Trp Met Ser Gly Lys Glu Phe Lys Cys Lys Val
            340                 345                 350

Asn Asn Lys Asp Leu Pro Ser Pro Ile Glu Arg Thr Ile Ser Lys Ile
        355                 360                 365

Lys Gly Leu Val Arg Ala Pro Gln Val Tyr Ile Leu Pro Pro Pro Ala
    370                 375                 380

Glu Gln Leu Ser Arg Lys Asp Val Ser Leu Thr Cys Leu Val Val Gly
385                 390                 395                 400

Phe Asn Pro Gly Asp Ile Ser Val Glu Trp Thr Ser Asn Gly His Thr
                405                 410                 415

Glu Glu Asn Tyr Lys Asp Thr Ala Pro Val Leu Asp Ser Asp Gly Ser
            420                 425                 430

Tyr Phe Ile Tyr Ser Lys Leu Asn Met Lys Thr Ser Lys Trp Glu Lys
        435                 440                 445

Thr Asp Ser Phe Ser Cys Asn Val Arg His Glu Gly Leu Lys Asn Tyr
    450                 455                 460

Tyr Leu Lys Lys Thr Ile Ser Arg Ser Pro Gly Lys Ser Gly Gly Gly
465                 470                 475                 480

Gly Ser Gly Gly Gly Gly Ser Gly Gly Gly Gly Ser Leu Leu Gly Asp
                485                 490                 495

Phe Phe Arg Lys Ser Lys Glu Lys Ile Gly Lys Glu Phe Lys Arg Ile
            500                 505                 510

Val Gln Arg Ile Lys Asp Phe Leu Arg Asn Leu Val Pro Arg Thr Glu
        515                 520                 525
```

Ser

<210> SEQ ID NO 7
<211> LENGTH: 1815
<212> TYPE: DNA
<213> ORGANISM: Artificial Sequence
<220> FEATURE:
<223> OTHER INFORMATION: Synthetic

<400> SEQUENCE: 7

```
atggagacag acacactcct gctatgggta ctgctgctct gggttccagg ttccactggt     60

gaccaggtcc agcttcagca gtctggggct gaactggcaa aacctggggc ctcagtgaag    120

atgtcctgca aggcttctgg ctacaccttt actagctact ggatgcactg ggtgaaacag    180

aggcctggac agggtctgga atggattgga tacattaatc ctagcactgg ttatcctgag    240

tacaatcaga aattcaagga caaggccaca ttgactgcag acaaatcctc caacacagcc    300

tacatgcaac tgagcagcct gacatctgag gactctgcag tctattactg tgtaagaagg    360

aattactacg aggacttctt tgactactgg ggccaaggca ccactctcac agtctcctca    420

gccaaaacga cacccccatc tgtctatcca ctggcccctg gatctgctgc ccaaactaac    480

tccatggtga ccctgggatg cctggtcaag ggctatttcc ctgagccagt gacagtgacc    540

tggaactctg gatccctgtc cagcggtgtg cacaccttcc cagctgtcct gcagtctgac    600

ctctacactc tgagcagctc agtgactgtc ccctccagca cctggcccag cgagaccgtc    660

acctgcaacg ttgcccaccc ggccagcagc accaaggtgg acaagaaaat tgtgcccagg    720

gattgtggtt gtaagccttg catatgtaca gtcccagaag tatcatctgt cttcatcttc    780

cccccaaagc ccaaggatgt gctcaccatt actctgactc ctaaggtcac gtgtgttgtg    840

gtagacatca gcaaggatga tcccgaggtc cagttcagct ggtttgtaga tgatgtggag    900

gtgcacacag ctcagacgca accccgggag gagcagttca acagcacttt ccgctcagtc    960

agtgaacttc ccatcatgca ccaggactgg ctcaatggca aggagttcaa atgcagggtc   1020

aacagtgcag ctttccctgc ccccatcgag aaaaccatct ccaaaaccaa aggcagaccg   1080

aaggctccac aggtgtacac cattccacct cccaaggagc agatggccaa ggataaagtc   1140

agtctgacct gcatgataac agacttcttc cctgaagaca ttactgtgga gtggcagtgg   1200

aatgggcagc cagcggagaa ctacaagaac actcagccca tcatggacac agatggctct   1260

tacttcgtct acagcaagct caatgtgcag aagagcaact gggaggcagg aaatactttc   1320

acctgctctg tgttacatga gggcctgcac aaccaccata ctgagaagag cctctcccac   1380

tctcctggta aatcaggtgg tggcggttca ggcggaggtg gctctggcgg tggcggatcg   1440

aatttggtga atttccacag aatgatcaag ttgacgacag gaaaggaagc cgcactcagt   1500

tatggcttct acggctgcca ctgtggcgtg ggtggcagag gatcccccaa ggatgcaacg   1560

gatcgctgct gtgtcactca tgactgttgc tacaaacgtc tggagaaacg tggatgtggc   1620

accaaatttc tgagctacaa gtttagcaac tcggggagca gaatcacctg tgcaaaacag   1680

gactcctgca gaagtcaact gtgtgagtgt gataaggctg ctgccacctg ttttgctaga   1740

aacaagacga cctacaataa aaagtaccag tactattcca ataaacactg cagagggagc   1800

acccctcgtt gctga                                                    1815
```

<210> SEQ ID NO 8
<211> LENGTH: 604
<212> TYPE: PRT
<213> ORGANISM: Artificial Sequence
<220> FEATURE:

<223> OTHER INFORMATION: Synthetic

<400> SEQUENCE: 8

```
Met Glu Thr Asp Thr Leu Leu Leu Trp Val Leu Leu Leu Trp Val Pro
1               5                   10                  15

Gly Ser Thr Gly Asp Gln Val Gln Leu Gln Gln Ser Gly Ala Glu Leu
            20                  25                  30

Ala Lys Pro Gly Ala Ser Val Lys Met Ser Cys Lys Ala Ser Gly Tyr
        35                  40                  45

Thr Phe Thr Ser Tyr Trp Met His Trp Val Lys Gln Arg Pro Gly Gln
    50                  55                  60

Gly Leu Glu Trp Ile Gly Tyr Ile Asn Pro Ser Thr Gly Tyr Pro Glu
65                  70                  75                  80

Tyr Asn Gln Lys Phe Lys Asp Lys Ala Thr Leu Thr Ala Asp Lys Ser
                85                  90                  95

Ser Asn Thr Ala Tyr Met Gln Leu Ser Ser Leu Thr Ser Glu Asp Ser
            100                 105                 110

Ala Val Tyr Tyr Cys Val Arg Arg Asn Tyr Tyr Glu Asp Phe Phe Asp
        115                 120                 125

Tyr Trp Gly Gln Gly Thr Thr Leu Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
```

```
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

Ser Gly Gly Gly Gly Ser Gly Gly Gly Gly Ser Gly Gly Gly Gly Ser
465                 470                 475                 480

Asn Leu Val Asn Phe His Arg Met Ile Lys Leu Thr Thr Gly Lys Glu
                485                 490                 495

Ala Ala Leu Ser Tyr Gly Phe Tyr Gly Cys His Cys Gly Val Gly Gly
            500                 505                 510

Arg Gly Ser Pro Lys Asp Ala Thr Asp Arg Cys Cys Val Thr His Asp
        515                 520                 525

Cys Cys Tyr Lys Arg Leu Glu Lys Arg Gly Cys Gly Thr Lys Phe Leu
    530                 535                 540

Ser Tyr Lys Phe Ser Asn Ser Gly Ser Arg Ile Thr Cys Ala Lys Gln
545                 550                 555                 560

Asp Ser Cys Arg Ser Gln Leu Cys Glu Cys Asp Lys Ala Ala Ala Thr
                565                 570                 575

Cys Phe Ala Arg Asn Lys Thr Thr Tyr Asn Lys Lys Tyr Gln Tyr Tyr
            580                 585                 590

Ser Asn Lys His Cys Arg Gly Ser Thr Pro Arg Cys
        595                 600
```

<210> SEQ ID NO 9
<211> LENGTH: 720
<212> TYPE: DNA
<213> ORGANISM: Artificial Sequence
<220> FEATURE:
<223> OTHER INFORMATION: Synthetic

<400> SEQUENCE: 9

```
atggagacag acacactcct gctatgggta ctgctgctct gggttccagg ttccactggt     60

gacgttgtga tgacccaaat tccactctcc ctgcctgtca gtcttggaga tcaagcctcc    120

atctcttgca gatctagtca gagccttgta cacagtaatg gaaacaccta tttacattgg    180

tacctgcaga agccaggcca gtctccaaag gtcctgatct acaaagtttc caaccgattt    240

tctggggtcc cagacaggtt cagtggcagt ggatcaggga cagatttcac actcaagatc    300

agcagagtgg aggctgagga tctgggagtt tatttctgct ctcaaagtac acatgttccg    360

ctcacgttcg gtgctgggac caagctggag ctgaaacggg ctgatgctgc accaactgta    420

tccatcttcc caccatccag tgagcagtta acatctggag gtgcctcagt cgtgtgcttc    480

ttgaacaact tctaccccaa agacatcaat gtcaagtgga agattgatgg cagtgaacga    540

caaaatggcg tcctgaacag ttggactgat caggacagca aagacagcac ctacagcatg    600

agcagcaccc tcacgttgac caaggacgag tatgaacgac ataacagcta tacctgtgag    660

gccactcaca agacatcaac ttcacccatt gtcaagagct tcaacaggaa tgagtgttag    720
```

<210> SEQ ID NO 10
<211> LENGTH: 239
<212> TYPE: PRT
<213> ORGANISM: Artificial Sequence
<220> FEATURE:
<223> OTHER INFORMATION: Synthetic

<400> SEQUENCE: 10

```
Met Glu Thr Asp Thr Leu Leu Leu Trp Val Leu Leu Leu Trp Val Pro
1               5                   10                  15

Gly Ser Thr Gly Asp Val Val Met Thr Gln Ile Pro Leu Ser Leu Pro
            20                  25                  30

Val Ser Leu Gly Asp Gln Ala Ser Ile Ser Cys Arg Ser Ser Gln Ser
        35                  40                  45

Leu Val His Ser Asn Gly Asn Thr Tyr Leu His Trp Tyr Leu Gln Lys
    50                  55                  60

Pro Gly Gln Ser Pro Lys Val Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Phe
            100                 105                 110

Cys Ser Gln Ser Thr His Val Pro Leu Thr Phe Gly Ala Gly Thr Lys
        115                 120                 125

Leu Glu Leu Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235
```

<210> SEQ ID NO 11
<211> LENGTH: 1791
<212> TYPE: DNA
<213> ORGANISM: Artificial Sequence
<220> FEATURE:
<223> OTHER INFORMATION: Synthetic

<400> SEQUENCE: 11

```
atggagacag acacactcct gctatgggta ctgctgctct gggttccagg ttccactggt     60

gaccaggtgc agctgaagga gtcaggacct ggcctggtgg cgccctcaca gagcctgtcc    120

atcacttgca ctgtctctgg gttttcatta accaactatg gtgtacattg ggttcgccag    180

cctccaggaa agggtctgga gtggctggga gtaatatggg ctggtggaaa cacaaattat    240

aattcggctt ttatgtccag actgagcatc accaaagaca actccaagag ccaagttttc    300

ataaaaatga acagtctgca aactgatgac acagccatgt actactgtgc cagagaatat    360

aggcacgggg cttactatgc tatggactac tggggtcaag gaacctcagt caccgtctcc    420

tcagagagtc agtccttccc aaatgtcttc cccctcgtct cctgcgagag ccccctgtct    480

gataagaatc tggtggccat gggctgcctg gcccgggact tcctgcccag caccatttcc    540

ttcacctgga actaccagaa caacactgaa gtcatccagg gtatcagaac cttcccaaca    600

ctgaggacag gggcaagta cctagccacc tcgcaggtgt tgctgtctcc caagagcatc    660

cttgaaggtt cagatgaata cctggtatgc aaaatccact acggaggcaa aaacagagat    720
```

```
ctgcatgtgc ccattccagc tgtcgcagag atgaacccca atgtaaatgt gttcgtccca    780

ccacgggatg gcttctctgg ccctgcacca cgcaagtcta aactcatctg cgaggccacg    840

aacttcactc caaaaccgat cacagtatcc tggctaaagg atgggaagct cgtggaatct    900

ggcttcacca cagatccggt gaccatcgag aacaaaggat ccacacccca aacctacaag    960

gtcataagca cacttaccat ctctgaaatc gactggctga acctgaatgt gtacacctgc   1020

cgtgtggatc acaggggtct caccttcttg aagaacgtgt cctccacatg tgctgccagt   1080

ccctccacag acatcctgac cttcaccatc ccccctcct ttgccgacat cttcctcagc    1140

aagtccgcta acctgacctg tctggtctca aacctggcaa cctatgaaac cctgaatatc   1200

tcctgggctt ctcaaagtgg tgaaccactg gaaaccaaaa ttaaaatcat ggaaagccat   1260

cccaatggca ccttcagtgc taagggtgtg gctagtgttt gtgtggaaga ctggaataac   1320

aggaaggaat ttgtgtgtac tgtgactcac agggatctgc cttcaccaca gaagaaattc   1380

atctcaaaac ccaatgaggt gcacaaacat ccacctgctg tgtacctgct gccaccagct   1440

cgtgagcaac tgaacctgag ggagtcagcc acagtcacct gcctggtgaa gggcttctct   1500

cctgcagaca tcagtgtgca gtggcttcag agagggcaac tcttgcccca agagaagtat   1560

gtgaccagtg ccccgatgcc agagcctggg gccccaggct tctactttac ccacagcatc   1620

ctgactgtga cagaggagga atggaactcc ggagagacct atacctgtgt tgtaggccac   1680

gaggccctgc cacacctggt gaccgagagg accgtggaca agtccactgg taaacccaca   1740

ctgtacaatg tctccctgat catgtctgac acaggcggca cctgctattg a            1791
```

```
<210> SEQ ID NO 12
<211> LENGTH: 596
<212> TYPE: PRT
<213> ORGANISM: Artificial Sequence
<220> FEATURE:
<223> OTHER INFORMATION: Synthetic

<400> SEQUENCE: 12

Met Glu Thr Asp Thr Leu Leu Leu Trp Val Leu Leu Leu Trp Val Pro
1               5                   10                  15

Gly Ser Thr Gly Asp Gln Val Gln Leu Lys Glu Ser Gly Pro Gly Leu
            20                  25                  30

Val Ala Pro Ser Gln Ser Leu Ser Ile Thr Cys Thr Val Ser Gly Phe
        35                  40                  45

Ser Leu Thr Asn Tyr Gly Val His Trp Val Arg Gln Pro Pro Gly Lys
    50                  55                  60

Gly Leu Glu Trp Leu Gly Val Ile Trp Ala Gly Gly Asn Thr Asn Tyr
65                  70                  75                  80

Asn Ser Ala Phe Met Ser Arg Leu Ser Ile Thr Lys Asp Asn Ser Lys
                85                  90                  95

Ser Gln Val Phe Ile Lys Met Asn Ser Leu Gln Thr Asp Asp Thr Ala
            100                 105                 110

Met Tyr Tyr Cys Ala Arg Glu Tyr Arg His Gly Ala Tyr Tyr Ala Met
        115                 120                 125

Asp Tyr Trp Gly Gln Gly Thr Ser Val Thr Val Ser Ser Glu Ser Gln
    130                 135                 140

Ser Phe Pro Asn Val Phe Pro Leu Val Ser Cys Glu Ser Pro Leu Ser
145                 150                 155                 160

Asp Lys Asn Leu Val Ala Met Gly Cys Leu Ala Arg Asp Phe Leu Pro
                165                 170                 175
```

```
Ser Thr Ile Ser Phe Thr Trp Asn Tyr Gln Asn Asn Thr Glu Val Ile
            180                 185                 190

Gln Gly Ile Arg Thr Phe Pro Thr Leu Arg Thr Gly Gly Lys Tyr Leu
        195                 200                 205

Ala Thr Ser Gln Val Leu Leu Ser Pro Lys Ser Ile Leu Glu Gly Ser
    210                 215                 220

Asp Glu Tyr Leu Val Cys Lys Ile His Tyr Gly Gly Lys Asn Arg Asp
225                 230                 235                 240

Leu His Val Pro Ile Pro Ala Val Ala Glu Met Asn Pro Asn Val Asn
                245                 250                 255

Val Phe Val Pro Pro Arg Asp Gly Phe Ser Gly Pro Ala Pro Arg Lys
            260                 265                 270

Ser Lys Leu Ile Cys Glu Ala Thr Asn Phe Thr Pro Lys Pro Ile Thr
        275                 280                 285

Val Ser Trp Leu Lys Asp Gly Lys Leu Val Glu Ser Gly Phe Thr Thr
    290                 295                 300

Asp Pro Val Thr Ile Glu Asn Lys Gly Ser Thr Pro Gln Thr Tyr Lys
305                 310                 315                 320

Val Ile Ser Thr Leu Thr Ile Ser Glu Ile Asp Trp Leu Asn Leu Asn
                325                 330                 335

Val Tyr Thr Cys Arg Val Asp His Arg Gly Leu Thr Phe Leu Lys Asn
            340                 345                 350

Val Ser Ser Thr Cys Ala Ala Ser Pro Ser Thr Asp Ile Leu Thr Phe
        355                 360                 365

Thr Ile Pro Pro Ser Phe Ala Asp Ile Phe Leu Ser Lys Ser Ala Asn
    370                 375                 380

Leu Thr Cys Leu Val Ser Asn Leu Ala Thr Tyr Glu Thr Leu Asn Ile
385                 390                 395                 400

Ser Trp Ala Ser Gln Ser Gly Glu Pro Leu Glu Thr Lys Ile Lys Ile
                405                 410                 415

Met Glu Ser His Pro Asn Gly Thr Phe Ser Ala Lys Gly Val Ala Ser
            420                 425                 430

Val Cys Val Glu Asp Trp Asn Asn Arg Lys Glu Phe Val Cys Thr Val
        435                 440                 445

Thr His Arg Asp Leu Pro Ser Pro Gln Lys Lys Phe Ile Ser Lys Pro
    450                 455                 460

Asn Glu Val His Lys His Pro Pro Ala Val Tyr Leu Leu Pro Pro Ala
465                 470                 475                 480

Arg Glu Gln Leu Asn Leu Arg Glu Ser Ala Thr Val Thr Cys Leu Val
                485                 490                 495

Lys Gly Phe Ser Pro Ala Asp Ile Ser Val Gln Trp Leu Gln Arg Gly
            500                 505                 510

Gln Leu Leu Pro Gln Glu Lys Tyr Val Thr Ser Ala Pro Met Pro Glu
        515                 520                 525

Pro Gly Ala Pro Gly Phe Tyr Phe Thr His Ser Ile Leu Thr Val Thr
    530                 535                 540

Glu Glu Glu Trp Asn Ser Gly Glu Thr Tyr Thr Cys Val Val Gly His
545                 550                 555                 560

Glu Ala Leu Pro His Leu Val Thr Glu Arg Thr Val Asp Lys Ser Thr
                565                 570                 575

Gly Lys Pro Thr Leu Tyr Asn Val Ser Leu Ile Met Ser Asp Thr Gly
            580                 585                 590

Gly Thr Cys Tyr
        595
```

<210> SEQ ID NO 13
<211> LENGTH: 2013
<212> TYPE: DNA
<213> ORGANISM: Artificial Sequence
<220> FEATURE:
<223> OTHER INFORMATION: Synthetic

<400> SEQUENCE: 13
atggagacag acacactcct gctatgggta ctgctgctct gggttccagg ttccactggt 60
gaccatcacc atcaccatca cggatctggc tctggatctg gtatcgaggg aaggacgcgt 120
caggtgcagc tgaaggagtc aggacctggc ctggtggcgc cctcacagag cctgtccatc 180
acttgcactg tctctgggtt ttcattaacc aactatggtg tacattgggt tcgccagcct 240
ccaggaaagg gtctggagtg gctgggagta atatgggctg gtggaaacac aaattataat 300
tcggctttta tgtccagact gagcatcacc aaagacaact ccaagagcca agttttcata 360
aaaatgaaca gtctgcaaac tgatgacaca gccatgtact actgtgccag agaatatagg 420
cacggggctt actatgctat ggactactgg ggtcaaggaa cctcagtcac cgtctcctca 480
gagagtcagt ccttcccaaa tgtcttcccc ctcgtctcct gcgagagccc cctgtctgat 540
aagaatctgg tggccatggg ctgcctggcc cgggacttcc tgcccagcac catttccttc 600
acctggaact accagaacaa cactgaagtc atccagggta tcagaacctt cccaacactg 660
aggacagggg gcaagtacct agccacctcg caggtgttgc tgtctcccaa aagcatcctt 720
gaaggttcag atgaatacct ggtatgcaaa atccactacg gaggcaaaaa cagagatctg 780
catgtgccca ttccagctgt cgcagagatg aaccccaatg taaatgtgtt cgtcccacca 840
cgggatggct tctctggccc tgcaccacgc aagtctaaac tcatctgcga ggccacgaac 900
ttcactccaa aaccgatcac agtatcctgg ctaaaggatg ggaagctcgt ggaatctggc 960
ttcaccacag atccggtgac catcgagaac aaaggatcca caccccaaac ctacaaggtc 1020
ataagcacac ttaccatctc tgaaatcgac tggctgaacc tgaatgtgta cacctgccgt 1080
gtggatcaca ggggtctcac cttcttgaag aacgtgtcct ccacatgtgc tgccagtccc 1140
tccacagaca tcctgacctt caccatcccc ccctcctttg ccgacatctt cctcagcaag 1200
tccgctaacc tgacctgtct ggtctcaaac ctggcaacct atgaaaccct gaatatctcc 1260
tgggcttctc aaagtggtga accactggaa accaaaatta aaatcatgga aagccatccc 1320
aatggcacct tcagtgctaa gggtgtggct agtgtttgtg tggaagactg gaataacagg 1380
aaggaatttg tgtgtactgt gactcacagg gatctgcctt caccacagaa gaaattcatc 1440
tcaaaaccca atgaggtgca caaacatcca cctgctgtgt acctgctgcc accagctcgt 1500
gagcaactga acctgaggga gtcagccaca gtcacctgcc tggtgaaggg cttctctcct 1560
gcagacatca gtgtgcagtg gcttcagaga gggcaactct tgccccaaga gaagtatgtg 1620
accagtgccc cgatgccaga gcctggggcc ccaggcttct actttaccca cagcatcctg 1680
actgtgacag aggaggaatg gaactccgga gagacctata cctgtgttgt aggccacgag 1740
gccctgccac acctggtgac cgagaggacc gtggacaagt ccactggtaa acccacactg 1800
tacaatgtct ccctgatcat gtctgacaca ggcggcacct gctatgcggc cgcaggtggt 1860
ggcggttcag gcggaggtgg ctctggcggt ggcggatccc tgctggggga tttcttccgg 1920
aagtctaaag agaagattgg gaaagagttt aaaagaattg tccagagaat caaggatttt 1980
ttgcggaatc ttgtgcccag gacagaatcc tag 2013

```
<210> SEQ ID NO 14
<211> LENGTH: 670
<212> TYPE: PRT
<213> ORGANISM: Artificial Sequence
<220> FEATURE:
<223> OTHER INFORMATION: Synthetic

<400> SEQUENCE: 14

Met Glu Thr Asp Thr Leu Leu Leu Trp Val Leu Leu Leu Trp Val Pro
1               5                   10                  15

Gly Ser Thr Gly Asp His His His His His His Gly Ser Gly Ser Gly
            20                  25                  30

Ser Gly Ile Glu Gly Arg Thr Arg Gln Val Gln Leu Lys Glu Ser Gly
        35                  40                  45

Pro Gly Leu Val Ala Pro Ser Gln Ser Leu Ser Ile Thr Cys Thr Val
    50                  55                  60

Ser Gly Phe Ser Leu Thr Asn Tyr Gly Val His Trp Val Arg Gln Pro
65                  70                  75                  80

Pro Gly Lys Gly Leu Glu Trp Leu Gly Val Ile Trp Ala Gly Gly Asn
                85                  90                  95

Thr Asn Tyr Asn Ser Ala Phe Met Ser Arg Leu Ser Ile Thr Lys Asp
            100                 105                 110

Asn Ser Lys Ser Gln Val Phe Ile Lys Met Asn Ser Leu Gln Thr Asp
        115                 120                 125

Asp Thr Ala Met Tyr Tyr Cys Ala Arg Glu Tyr Arg His Gly Ala Tyr
    130                 135                 140

Tyr Ala Met Asp Tyr Trp Gly Gln Gly Thr Ser Val Thr Val Ser Ser
145                 150                 155                 160

Glu Ser Gln Ser Phe Pro Asn Val Phe Pro Leu Val Ser Cys Glu Ser
                165                 170                 175

Pro Leu Ser Asp Lys Asn Leu Val Ala Met Gly Cys Leu Ala Arg Asp
            180                 185                 190

Phe Leu Pro Ser Thr Ile Ser Phe Thr Trp Asn Tyr Gln Asn Asn Thr
        195                 200                 205

Glu Val Ile Gln Gly Ile Arg Thr Phe Pro Thr Leu Arg Thr Gly Gly
    210                 215                 220

Lys Tyr Leu Ala Thr Ser Gln Val Leu Leu Ser Pro Lys Ser Ile Leu
225                 230                 235                 240

Glu Gly Ser Asp Glu Tyr Leu Val Cys Lys Ile His Tyr Gly Gly Lys
                245                 250                 255

Asn Arg Asp Leu His Val Pro Ile Pro Ala Val Ala Glu Met Asn Pro
            260                 265                 270

Asn Val Asn Val Phe Val Pro Pro Arg Asp Gly Phe Ser Gly Pro Ala
        275                 280                 285

Pro Arg Lys Ser Lys Leu Ile Cys Glu Ala Thr Asn Phe Thr Pro Lys
    290                 295                 300

Pro Ile Thr Val Ser Trp Leu Lys Asp Gly Lys Leu Val Glu Ser Gly
305                 310                 315                 320

Phe Thr Thr Asp Pro Val Thr Ile Glu Asn Lys Gly Ser Thr Pro Gln
                325                 330                 335

Thr Tyr Lys Val Ile Ser Thr Leu Thr Ile Ser Glu Ile Asp Trp Leu
            340                 345                 350

Asn Leu Asn Val Tyr Thr Cys Arg Val Asp His Arg Gly Leu Thr Phe
        355                 360                 365

Leu Lys Asn Val Ser Ser Thr Cys Ala Ala Ser Pro Ser Thr Asp Ile
    370                 375                 380
```

```
Leu Thr Phe Thr Ile Pro Pro Ser Phe Ala Asp Ile Phe Leu Ser Lys
385                 390                 395                 400

Ser Ala Asn Leu Thr Cys Leu Val Ser Asn Leu Ala Thr Tyr Glu Thr
                405                 410                 415

Leu Asn Ile Ser Trp Ala Ser Gln Ser Gly Glu Pro Leu Glu Thr Lys
            420                 425                 430

Ile Lys Ile Met Glu Ser His Pro Asn Gly Thr Phe Ser Ala Lys Gly
        435                 440                 445

Val Ala Ser Val Cys Val Glu Asp Trp Asn Asn Arg Lys Glu Phe Val
    450                 455                 460

Cys Thr Val Thr His Arg Asp Leu Pro Ser Pro Gln Lys Lys Phe Ile
465                 470                 475                 480

Ser Lys Pro Asn Glu Val His Lys His Pro Pro Ala Val Tyr Leu Leu
                485                 490                 495

Pro Pro Ala Arg Glu Gln Leu Asn Leu Arg Glu Ser Ala Thr Val Thr
            500                 505                 510

Cys Leu Val Lys Gly Phe Ser Pro Ala Asp Ile Ser Val Gln Trp Leu
        515                 520                 525

Gln Arg Gly Gln Leu Leu Pro Gln Glu Lys Tyr Val Thr Ser Ala Pro
    530                 535                 540

Met Pro Glu Pro Gly Ala Pro Gly Phe Tyr Phe Thr His Ser Ile Leu
545                 550                 555                 560

Thr Val Thr Glu Glu Glu Trp Asn Ser Gly Glu Thr Tyr Thr Cys Val
                565                 570                 575

Val Gly His Glu Ala Leu Pro His Leu Val Thr Glu Arg Thr Val Asp
            580                 585                 590

Lys Ser Thr Gly Lys Pro Thr Leu Tyr Asn Val Ser Leu Ile Met Ser
        595                 600                 605

Asp Thr Gly Gly Thr Cys Tyr Ala Ala Ala Gly Gly Gly Gly Ser Gly
    610                 615                 620

Gly Gly Gly Ser Gly Gly Gly Gly Ser Leu Leu Gly Asp Phe Phe Arg
625                 630                 635                 640

Lys Ser Lys Glu Lys Ile Gly Lys Glu Phe Lys Arg Ile Val Gln Arg
                645                 650                 655

Ile Lys Asp Phe Leu Arg Asn Leu Val Pro Arg Thr Glu Ser
            660                 665                 670


<210> SEQ ID NO 15
<211> LENGTH: 2013
<212> TYPE: DNA
<213> ORGANISM: Artificial Sequence
<220> FEATURE:
<223> OTHER INFORMATION: Synthetic

<400> SEQUENCE: 15

atggagacag acacactcct gctatgggta ctgctgctct gggttccagg ttccactggt      60

gaccatcacc atcaccatca cggatctggc tctggatctg gtatcgaggg aaggacgcgt     120

caggtgcagc tgaaggagtc aggacctggc ctggtggcgc cctcacagag cctgtccatc     180

acttgcactg tctctgggtt ttcattaacc aactatggtg tacattgggt tcgccagcct     240

ccaggaaagg gtctggagtg gctgggagta atatgggctg gtggaaacac aaattataat     300

tcggctttta tgtccagact gagcatcacc aaagacaact ccaagagcca agttttcata     360

aaaatgaaca gtctgcaaac tgatgacaca gccatgtact actgtgccag agaatatagg     420

cacggggctt actatgctat ggactactgg ggtcaaggaa cctcagtcac cgtctcctca     480
```

```
gagagtcagt ccttcccaaa tgtcttcccc ctcgtctcct gcgagagccc cctgtctgat    540

aagaatctgg tggccatggg ctgcctggcc cgggacttcc tgcccagcac catttccttc    600

acctggaact accagaacaa cactgaagtc atccagggta tcagaacctt cccaacactg    660

aggacagggg gcaagtacct agccacctcg caggtgttgc tgtctcccaa gagcatcctt    720

gaaggttcag atgaatacct ggtatgcaaa atccactacg gaggcaaaaa cagagatctg    780

catgtgccca ttccagctgt cgcagagatg aaccccaatg taaatgtgtt cgtcccacca    840

cgggatggct tctctggccc tgcaccacgc aagtctaaac tcatctgcga ggccacgaac    900

ttcactccaa aaccgatcac agtatcctgg ctaaaggatg ggaagctcgt ggaatctggc    960

ttcaccacag atccggtgac catcgagaac aaaggatcca caccccaaac ctacaaggtc   1020

ataagcacac ttaccatctc tgaaatcgac tggctgaacc tgaatgtgta cacctgccgt   1080

gtggatcaca ggggtctcac cttcttgaag aacgtgtcct ccacatgtgc tgccagtccc   1140

tccacagaca tcctaacctt caccatcccc ccctcctttg ccgacatctt cctcagcaag   1200

tccgctaacc tgacctgtct ggtctcaaac ctggcaacct atgaaaccct gaatatctcc   1260

tgggcttctc aaagtggtga accactggaa accaaaatta aaatcatgga aagccatccc   1320

aatggcacct tcagtgctaa gggtgtggct agtgtttctg tggaagactg gaataacagg   1380

aaggaatttg tgtgtactgt gactcacagg gatctgcctt caccacagaa gaaattcatc   1440

tcaaaaccca atgaggtgca caaacatcca cctgctgtgt acctgctgcc accagctcgt   1500

gagcaactga acctgaggga gtcagccaca gtcacctgcc tggtgaaggg cttctctcct   1560

gcagacatca gtgtgcagtg gcttcagaga gggcaactct tgccccaaga gaagtatgtg   1620

accagtgccc cgatgccaga gcctggggcc ccaggcttct actttaccca cagcatcctg   1680

actgtgacag aggaggaatg gaactccgga gagacctata cctgtgttgt aggccacgag   1740

gccctgccac acctggtgac cgagaggacc gtggacaagt ccactggtaa acccacactg   1800

tacaatgtct ccctgatcat gtctgacaca ggcggcacct cctatgcggc cgcaggtggt   1860

ggcggttcag gcggaggtgg ctctggcggt ggcggatccc tgctggggga tttcttccgg   1920

aagtctaaag agaagattgg gaaagagttt aaaagaattg tccagagaat caaggatttt   1980

ttgcggaatc ttgtgcccag gacagaatcc tag                                2013
```

```
<210> SEQ ID NO 16
<211> LENGTH: 670
<212> TYPE: PRT
<213> ORGANISM: Artificial Sequence
<220> FEATURE:
<223> OTHER INFORMATION: Synthetic

<400> SEQUENCE: 16

Met Glu Thr Asp Thr Leu Leu Leu Trp Val Leu Leu Leu Trp Val Pro
1               5                   10                  15

Gly Ser Thr Gly Asp His His His His His His Gly Ser Gly Ser Gly
            20                  25                  30

Ser Gly Ile Glu Gly Arg Thr Arg Gln Val Gln Leu Lys Glu Ser Gly
        35                  40                  45

Pro Gly Leu Val Ala Pro Ser Gln Ser Leu Ser Ile Thr Cys Thr Val
    50                  55                  60

Ser Gly Phe Ser Leu Thr Asn Tyr Gly Val His Trp Val Arg Gln Pro
65                  70                  75                  80

Pro Gly Lys Gly Leu Glu Trp Leu Gly Val Ile Trp Ala Gly Gly Asn
                85                  90                  95
```

```
Thr Asn Tyr Asn Ser Ala Phe Met Ser Arg Leu Ser Ile Thr Lys Asp
            100                 105                 110

Asn Ser Lys Ser Gln Val Phe Ile Lys Met Asn Ser Leu Gln Thr Asp
        115                 120                 125

Asp Thr Ala Met Tyr Tyr Cys Ala Arg Glu Tyr Arg His Gly Ala Tyr
    130                 135                 140

Tyr Ala Met Asp Tyr Trp Gly Gln Gly Thr Ser Val Thr Val Ser Ser
145                 150                 155                 160

Glu Ser Gln Ser Phe Pro Asn Val Phe Pro Leu Val Ser Cys Glu Ser
                165                 170                 175

Pro Leu Ser Asp Lys Asn Leu Val Ala Met Gly Cys Leu Ala Arg Asp
            180                 185                 190

Phe Leu Pro Ser Thr Ile Ser Phe Thr Trp Asn Tyr Gln Asn Asn Thr
        195                 200                 205

Glu Val Ile Gln Gly Ile Arg Thr Phe Pro Thr Leu Arg Thr Gly Gly
    210                 215                 220

Lys Tyr Leu Ala Thr Ser Gln Val Leu Leu Ser Pro Lys Ser Ile Leu
225                 230                 235                 240

Glu Gly Ser Asp Glu Tyr Leu Val Cys Lys Ile His Tyr Gly Gly Lys
                245                 250                 255

Asn Arg Asp Leu His Val Pro Ile Pro Ala Val Ala Glu Met Asn Pro
            260                 265                 270

Asn Val Asn Val Phe Val Pro Pro Arg Asp Gly Phe Ser Gly Pro Ala
        275                 280                 285

Pro Arg Lys Ser Lys Leu Ile Cys Glu Ala Thr Asn Phe Thr Pro Lys
    290                 295                 300

Pro Ile Thr Val Ser Trp Leu Lys Asp Gly Lys Leu Val Glu Ser Gly
305                 310                 315                 320

Phe Thr Thr Asp Pro Val Thr Ile Glu Asn Lys Gly Ser Thr Pro Gln
                325                 330                 335

Thr Tyr Lys Val Ile Ser Thr Leu Thr Ile Ser Glu Ile Asp Trp Leu
            340                 345                 350

Asn Leu Asn Val Tyr Thr Cys Arg Val Asp His Arg Gly Leu Thr Phe
        355                 360                 365

Leu Lys Asn Val Ser Ser Thr Cys Ala Ala Ser Pro Ser Thr Asp Ile
    370                 375                 380

Leu Thr Phe Thr Ile Pro Pro Ser Phe Ala Asp Ile Phe Leu Ser Lys
385                 390                 395                 400

Ser Ala Asn Leu Thr Cys Leu Val Ser Asn Leu Ala Thr Tyr Glu Thr
                405                 410                 415

Leu Asn Ile Ser Trp Ala Ser Gln Ser Gly Glu Pro Leu Glu Thr Lys
            420                 425                 430

Ile Lys Ile Met Glu Ser His Pro Asn Gly Thr Phe Ser Ala Lys Gly
        435                 440                 445

Val Ala Ser Val Ser Val Glu Asp Trp Asn Asn Arg Lys Glu Phe Val
    450                 455                 460

Cys Thr Val Thr His Arg Asp Leu Pro Ser Pro Gln Lys Lys Phe Ile
465                 470                 475                 480

Ser Lys Pro Asn Glu Val His Lys His Pro Pro Ala Val Tyr Leu Leu
                485                 490                 495

Pro Pro Ala Arg Glu Gln Leu Asn Leu Arg Glu Ser Ala Thr Val Thr
            500                 505                 510

Cys Leu Val Lys Gly Phe Ser Pro Ala Asp Ile Ser Val Gln Trp Leu
```

```
        515                 520                 525

Gln Arg Gly Gln Leu Leu Pro Gln Glu Lys Tyr Val Thr Ser Ala Pro
    530                 535                 540

Met Pro Glu Pro Gly Ala Pro Gly Phe Tyr Phe Thr His Ser Ile Leu
545                 550                 555                 560

Thr Val Thr Glu Glu Glu Trp Asn Ser Gly Glu Thr Tyr Thr Cys Val
                565                 570                 575

Val Gly His Glu Ala Leu Pro His Leu Val Thr Glu Arg Thr Val Asp
            580                 585                 590

Lys Ser Thr Gly Lys Pro Thr Leu Tyr Asn Val Ser Leu Ile Met Ser
        595                 600                 605

Asp Thr Gly Gly Thr Ser Tyr Ala Ala Ala Gly Gly Gly Gly Ser Gly
    610                 615                 620

Gly Gly Gly Ser Gly Gly Gly Gly Ser Leu Leu Gly Asp Phe Phe Arg
625                 630                 635                 640

Lys Ser Lys Glu Lys Ile Gly Lys Glu Phe Lys Arg Ile Val Gln Arg
                645                 650                 655

Ile Lys Asp Phe Leu Arg Asn Leu Val Pro Arg Thr Glu Ser
            660                 665                 670


<210> SEQ ID NO 17
<211> LENGTH: 2013
<212> TYPE: DNA
<213> ORGANISM: Artificial Sequence
<220> FEATURE:
<223> OTHER INFORMATION: Synthetic

<400> SEQUENCE: 17

atggagacag acacactcct gctatgggta ctgctgctct gggttccagg ttccactggt     60

gaccatcacc atcaccatca cggatctggc tctggatctg gtatcgaggg aaggacgcgt    120

caggtgcagc tgaaggagtc aggacctggc ctggtggcgc cctcacagag cctgtccatc    180

acttgcactg tctctgggtt ttcattaacc aactatggtg tacattgggt tcgccagcct    240

ccaggaaagg gtctggagtg gctgggagta atatgggctg gtggaaacac aaattataat    300

tcggctttta tgtccagact gagcatcacc aaagacaact ccaagagcca agttttcata    360

aaaatgaaca gtctgcaaac tgatgacaca gccatgtact actgtgccag agaatatagg    420

cacggggctt actatgctat ggactactgg ggtcaaggaa cctcagtcac cgtctcctca    480

gagagtcagt ccttcccaaa tgtcttcccc ctcgtctcct gcgagagccc cctgtctgat    540

aagaatctgg tggccatggg ctgcctggcc cgggacttcc tgcccagcac catttccttc    600

acctggaact accagaacaa cactgaagtc atccagggta tcagaacctt cccaacactg    660

aggacagggg gcaagtacct agccacctcg caggtgttgc tgtctcccaa gagcatcctt    720

gaaggttcag atgaatacct ggtatgcaaa atccactacg gaggcaaaaa cagagatctg    780

catgtgccca ttccagctgt cgcagagatg aaccccaatg taaatgtgtt cgtcccacca    840

cgggatggct tctctggccc tgcaccacgc aagtctaaac tcatctgcga ggccacgaac    900

ttcactccaa aaccgatcac agtatcctgg ctaaaggatg ggaagctcgt ggaatctggc    960

ttcaccacag atccggtgac catcgagaac aaaggatcca caccccaaac ctacaaggtc   1020

ataagcacac ttaccatctc tgaaatcgac tggctgaacc tgaatgtgta cacctgccgt   1080

gtggatcaca ggggtctcac cttcttgaag aacgtgtcct ccacatctgc tgccagtccc   1140

tccacagaca tcctaacctt caccatcccc ccctcctttg ccgacatctt cctcagcaag   1200

tccgctaacc tgacctgtct ggtctcaaac ctggcaacct atgaaaccct gaatatctcc   1260
```

```
tgggcttctc aaagtggtga accactggaa accaaaatta aaatcatgga aagccatccc   1320

aatggcacct tcagtgctaa gggtgtggct agtgtttctg tggaagactg gaataacagg   1380

aaggaatttg tgtgtactgt gactcacagg gatctgcctt caccacagaa gaaattcatc   1440

tcaaaaccca atgaggtgca caaacatcca cctgctgtgt acctgctgcc accagctcgt   1500

gagcaactga acctgaggga gtcagccaca gtcacctgcc tggtgaaggg cttctctcct   1560

gcagacatca gtgtgcagtg gcttcagaga gggcaactct tgccccaaga gaagtatgtg   1620

accagtgccc cgatgccaga gcctggggcc ccaggcttct actttaccca cagcatcctg   1680

actgtgacag aggaggaatg gaactccgga gagacctata cctgtgttgt aggccacgag   1740

gccctgccac acctggtgac cgagaggacc gtggacaagt ccactggtaa acccacactg   1800

tacaatgtct ccctgatcat gtctgacaca ggcggcacct cctatgcggc cgcaggtggt   1860

ggcggttcag gcggaggtgg ctctggcggt ggcggatccc tgctggggga tttcttccgg   1920

aagtctaaag agaagattgg gaaagagttt aaaagaattg tccagagaat caaggatttt   1980

ttgcggaatc ttgtgcccag gacagaatcc tag                                 2013
```

<210> SEQ ID NO 18
<211> LENGTH: 670
<212> TYPE: PRT
<213> ORGANISM: Artificial Sequence
<220> FEATURE:
<223> OTHER INFORMATION: Synthetic

<400> SEQUENCE: 18

```
Met Glu Thr Asp Thr Leu Leu Leu Trp Val Leu Leu Leu Trp Val Pro
1               5                   10                  15

Gly Ser Thr Gly Asp His His His His His His Gly Ser Gly Ser Gly
            20                  25                  30

Ser Gly Ile Glu Gly Arg Thr Arg Gln Val Gln Leu Lys Glu Ser Gly
        35                  40                  45

Pro Gly Leu Val Ala Pro Ser Gln Ser Leu Ser Ile Thr Cys Thr Val
    50                  55                  60

Ser Gly Phe Ser Leu Thr Asn Tyr Gly Val His Trp Val Arg Gln Pro
65                  70                  75                  80

Pro Gly Lys Gly Leu Glu Trp Leu Gly Val Ile Trp Ala Gly Gly Asn
                85                  90                  95

Thr Asn Tyr Asn Ser Ala Phe Met Ser Arg Leu Ser Ile Thr Lys Asp
            100                 105                 110

Asn Ser Lys Ser Gln Val Phe Ile Lys Met Asn Ser Leu Gln Thr Asp
        115                 120                 125

Asp Thr Ala Met Tyr Tyr Cys Ala Arg Glu Tyr Arg His Gly Ala Tyr
    130                 135                 140

Tyr Ala Met Asp Tyr Trp Gly Gln Gly Thr Ser Val Thr Val Ser Ser
145                 150                 155                 160

Glu Ser Gln Ser Phe Pro Asn Val Phe Pro Leu Val Ser Cys Glu Ser
                165                 170                 175

Pro Leu Ser Asp Lys Asn Leu Val Ala Met Gly Cys Leu Ala Arg Asp
            180                 185                 190

Phe Leu Pro Ser Thr Ile Ser Phe Thr Trp Asn Tyr Gln Asn Asn Thr
        195                 200                 205

Glu Val Ile Gln Gly Ile Arg Thr Phe Pro Thr Leu Arg Thr Gly Gly
    210                 215                 220

Lys Tyr Leu Ala Thr Ser Gln Val Leu Leu Ser Pro Lys Ser Ile Leu
```

```
225                 230                 235                 240

Glu Gly Ser Asp Glu Tyr Leu Val Cys Lys Ile His Tyr Gly Gly Lys
                245                 250                 255

Asn Arg Asp Leu His Val Pro Ile Pro Ala Val Ala Glu Met Asn Pro
            260                 265                 270

Asn Val Asn Val Phe Val Pro Pro Arg Asp Gly Phe Ser Gly Pro Ala
        275                 280                 285

Pro Arg Lys Ser Lys Leu Ile Cys Glu Ala Thr Asn Phe Thr Pro Lys
    290                 295                 300

Pro Ile Thr Val Ser Trp Leu Lys Asp Gly Lys Leu Val Glu Ser Gly
305                 310                 315                 320

Phe Thr Thr Asp Pro Val Thr Ile Glu Asn Lys Gly Ser Thr Pro Gln
                325                 330                 335

Thr Tyr Lys Val Ile Ser Thr Leu Thr Ile Ser Glu Ile Asp Trp Leu
            340                 345                 350

Asn Leu Asn Val Tyr Thr Cys Arg Val Asp His Arg Gly Leu Thr Phe
        355                 360                 365

Leu Lys Asn Val Ser Ser Thr Ser Ala Ala Ser Pro Ser Thr Asp Ile
    370                 375                 380

Leu Thr Phe Thr Ile Pro Pro Ser Phe Ala Asp Ile Phe Leu Ser Lys
385                 390                 395                 400

Ser Ala Asn Leu Thr Cys Leu Val Ser Asn Leu Ala Thr Tyr Glu Thr
                405                 410                 415

Leu Asn Ile Ser Trp Ala Ser Gln Ser Gly Glu Pro Leu Glu Thr Lys
            420                 425                 430

Ile Lys Ile Met Glu Ser His Pro Asn Gly Thr Phe Ser Ala Lys Gly
        435                 440                 445

Val Ala Ser Val Ser Val Glu Asp Trp Asn Asn Arg Lys Glu Phe Val
    450                 455                 460

Cys Thr Val Thr His Arg Asp Leu Pro Ser Pro Gln Lys Lys Phe Ile
465                 470                 475                 480

Ser Lys Pro Asn Glu Val His Lys His Pro Pro Ala Val Tyr Leu Leu
                485                 490                 495

Pro Pro Ala Arg Glu Gln Leu Asn Leu Arg Glu Ser Ala Thr Val Thr
            500                 505                 510

Cys Leu Val Lys Gly Phe Ser Pro Ala Asp Ile Ser Val Gln Trp Leu
        515                 520                 525

Gln Arg Gly Gln Leu Leu Pro Gln Glu Lys Tyr Val Thr Ser Ala Pro
    530                 535                 540

Met Pro Glu Pro Gly Ala Pro Gly Phe Tyr Phe Thr His Ser Ile Leu
545                 550                 555                 560

Thr Val Thr Glu Glu Glu Trp Asn Ser Gly Glu Thr Tyr Thr Cys Val
                565                 570                 575

Val Gly His Glu Ala Leu Pro His Leu Val Thr Glu Arg Thr Val Asp
            580                 585                 590

Lys Ser Thr Gly Lys Pro Thr Leu Tyr Asn Val Ser Leu Ile Met Ser
        595                 600                 605

Asp Thr Gly Gly Thr Ser Tyr Ala Ala Ala Gly Gly Gly Gly Ser Gly
    610                 615                 620

Gly Gly Gly Ser Gly Gly Gly Gly Ser Leu Leu Gly Asp Phe Phe Arg
625                 630                 635                 640

Lys Ser Lys Glu Lys Ile Gly Lys Glu Phe Lys Arg Ile Val Gln Arg
                645                 650                 655
```

Ile Lys Asp Phe Leu Arg Asn Leu Val Pro Arg Thr Glu Ser
660 665 670

<210> SEQ ID NO 19
<211> LENGTH: 1461
<212> TYPE: DNA
<213> ORGANISM: Artificial Sequence
<220> FEATURE:
<223> OTHER INFORMATION: Synthetic

<400> SEQUENCE: 19
atggagacag acacactcct gctatgggta ctgctgctct gggttccagg ttccactggt 60
gaccatcacc atcaccatca cggatctggc tctggatctg gtatcgaggg aaggacgcgt 120
caggtgcagc tgaaggagtc aggacctggc ctggtggcgc cctcacagag cctgtccatc 180
acttgcactg tctctgggtt ttcattaacc aactatggtg tacattgggt tcgccagcct 240
ccaggaaagg gtctggagtg gctgggagta atatgggctg gtggaaacac aaattataat 300
tcggctttta tgtccagact gagcatcacc aaagacaact ccaagagcca agttttcata 360
aaaatgaaca gtctgcaaac tgatgacaca gccatgtact actgtgccag agaatatagg 420
cacggggctt actatgctat ggactactgg ggtcaaggaa cctcagtcac cgtctcctca 480
gagagtcagt ccttctctgt ctatccactg gcccctggat ctgctgccca aactaactcc 540
atggtgaccc tgggatgcct ggtcaagggc tatttccctg agccagtgac agtgacctgg 600
aactctggat ccctgtccag cggtgtgcac accttcccag ctgtcctgca gtctgacctc 660
tacactctga gcagctcagt gactgtcccc tccagcacct ggcccagcga gaccgtcacc 720
tgcaacgttg cccacccggc cagcagcacc aaggtggaca agaaaattgt gcccagggat 780
tgtggttgta agccttgcat atgtacagtc ccagaagtat catctgtctt catcttcccc 840
ccaaagccca aggatgtgct caccattact ctgactccta aggtcacgtg tgttgtggta 900
gacatcagca aggatgatcc cgaggtccag ttcagctggt ttgtagatga tgtggaggtg 960
cacacagctc agacgcaacc ccgggaggag cagttcaaca gcactttccg ctcagtcagt 1020
gaacttccca tcatgcacca ggactggctc aatggcaagg agttcaaatg cagggtcaac 1080
agtgcagctt tccctgcccc catcgagaaa accatctcca aaaccaaagg cagaccgaag 1140
gctccacagg tgtacaccat tccacctccc aaggagcaga tggccaagga taaagtcagt 1200
ctgacctgca tgataacaga cttcttccct gaagacatta ctgtggagtg gcagtggaat 1260
gggcagccag cggagaacta caagaacact cagcccatca tggacacaga tggctcttac 1320
ttcgtctaca gcaagctcaa tgtgcagaag agcaactggg aggcaggaaa tactttcacc 1380
tgctctgtgt tacatgaggg cctgcacaac caccatactg agaagagcct ctcccactct 1440
cctggtaaag cggccgcatg a 1461

<210> SEQ ID NO 20
<211> LENGTH: 486
<212> TYPE: PRT
<213> ORGANISM: Artificial Sequence
<220> FEATURE:
<223> OTHER INFORMATION: Synthetic

<400> SEQUENCE: 20

Met Glu Thr Asp Thr Leu Leu Leu Trp Val Leu Leu Leu Trp Val Pro
1 5 10 15

Gly Ser Thr Gly Asp His His His His His His Gly Ser Gly Ser Gly
20 25 30

Ser Gly Ile Glu Gly Arg Thr Arg Gln Val Gln Leu Lys Glu Ser Gly

```
        35                  40                  45

Pro Gly Leu Val Ala Pro Ser Gln Ser Leu Ser Ile Thr Cys Thr Val
    50                  55                  60

Ser Gly Phe Ser Leu Thr Asn Tyr Gly Val His Trp Val Arg Gln Pro
65                  70                  75                  80

Pro Gly Lys Gly Leu Glu Trp Leu Gly Val Ile Trp Ala Gly Gly Asn
                85                  90                  95

Thr Asn Tyr Asn Ser Ala Phe Met Ser Arg Leu Ser Ile Thr Lys Asp
            100                 105                 110

Asn Ser Lys Ser Gln Val Phe Ile Lys Met Asn Ser Leu Gln Thr Asp
        115                 120                 125

Asp Thr Ala Met Tyr Tyr Cys Ala Arg Glu Tyr Arg His Gly Ala Tyr
    130                 135                 140

Tyr Ala Met Asp Tyr Trp Gly Gln Gly Thr Ser Val Thr Val Ser Ser
145                 150                 155                 160

Glu Ser Gln Ser Phe Ser Val Tyr Pro Leu Ala Pro Gly Ser Ala Ala
                165                 170                 175

Gln Thr Asn Ser Met Val Thr Leu Gly Cys Leu Val Lys Gly Tyr Phe
            180                 185                 190

Pro Glu Pro Val Thr Val Thr Trp Asn Ser Gly Ser Leu Ser Ser Gly
        195                 200                 205

Val His Thr Phe Pro Ala Val Leu Gln Ser Asp Leu Tyr Thr Leu Ser
    210                 215                 220

Ser Ser Val Thr Val Pro Ser Ser Thr Trp Pro Ser Glu Thr Val Thr
225                 230                 235                 240

Cys Asn Val Ala His Pro Ala Ser Ser Thr Lys Val Asp Lys Lys Ile
                245                 250                 255

Val Pro Arg Asp Cys Gly Cys Lys Pro Cys Ile Cys Thr Val Pro Glu
            260                 265                 270

Val Ser Ser Val Phe Ile Phe Pro Pro Lys Pro Lys Asp Val Leu Thr
        275                 280                 285

Ile Thr Leu Thr Pro Lys Val Thr Cys Val Val Val Asp Ile Ser Lys
    290                 295                 300

Asp Asp Pro Glu Val Gln Phe Ser Trp Phe Val Asp Asp Val Glu Val
305                 310                 315                 320

His Thr Ala Gln Thr Gln Pro Arg Glu Glu Gln Phe Asn Ser Thr Phe
                325                 330                 335

Arg Ser Val Ser Glu Leu Pro Ile Met His Gln Asp Trp Leu Asn Gly
            340                 345                 350

Lys Glu Phe Lys Cys Arg Val Asn Ser Ala Ala Phe Pro Ala Pro Ile
        355                 360                 365

Glu Lys Thr Ile Ser Lys Thr Lys Gly Arg Pro Lys Ala Pro Gln Val
    370                 375                 380

Tyr Thr Ile Pro Pro Pro Lys Glu Gln Met Ala Lys Asp Lys Val Ser
385                 390                 395                 400

Leu Thr Cys Met Ile Thr Asp Phe Phe Pro Glu Asp Ile Thr Val Glu
                405                 410                 415

Trp Gln Trp Asn Gly Gln Pro Ala Glu Asn Tyr Lys Asn Thr Gln Pro
            420                 425                 430

Ile Met Asp Thr Asp Gly Ser Tyr Phe Val Tyr Ser Lys Leu Asn Val
        435                 440                 445

Gln Lys Ser Asn Trp Glu Ala Gly Asn Thr Phe Thr Cys Ser Val Leu
    450                 455                 460
```

```
His Glu Gly Leu His Asn His His Thr Glu Lys Ser Leu Ser His Ser
465                 470                 475                 480

Pro Gly Lys Ala Ala Ala
                485
```

<210> SEQ ID NO 21
<211> LENGTH: 1617
<212> TYPE: DNA
<213> ORGANISM: Artificial Sequence
<220> FEATURE:
<223> OTHER INFORMATION: Synthetic

<400> SEQUENCE: 21

```
atggagacag acacactcct gctatgggta ctgctgctct gggttccagg ttccactggt     60

gaccatcacc atcaccatca cggatctggc tctggatctg gtatcgaggg aaggacgcgt    120

caggtgcagc tgaaggagtc aggacctggc ctggtggcgc cctcacagag cctgtccatc    180

acttgcactg tctctgggtt ttcattaacc aactatggtg tacattgggt tcgccagcct    240

ccaggaaagg gtctggagtg gctgggagta atatgggctg gtggaaacac aaattataat    300

tcggctttta tgtccagact gagcatcacc aaagacaact ccaagagcca agttttcata    360

aaaatgaaca gtctgcaaac tgatgacaca gccatgtact actgtgccag agaatatagg    420

cacggggctt actatgctat ggactactgg ggtcaaggaa cctcagtcac cgtctcctca    480

gagagtcagt ccttctctgt ctatccactg gcccctggat ctgctgccca aactaactcc    540

atggtgaccc tgggatgcct ggtcaagggc tatttccctg agccagtgac agtgacctgg    600

aactctggat ccctgtccag cggtgtgcac accttcccag ctgtcctgca gtctgacctc    660

tacactctga gcagctcagt gactgtcccc tccagcacct ggcccagcga gaccgtcacc    720

tgcaacgttg cccacccggc cagcagcacc aaggtggaca agaaaattgt gcccagggat    780

tgtggttgta agccttgcat atgtacagtc ccagaagtat catctgtctt catcttcccc    840

ccaaagccca aggatgtgct caccattact ctgactccta aggtcacgtg tgttgtggta    900

gacatcagca aggatgatcc cgaggtccag ttcagctggt ttgtagatga tgtggaggtg    960

cacacagctc agacgcaacc ccgggaggag cagttcaaca gcactttccg ctcagtcagt   1020

gaacttccca tcatgcacca ggactggctc aatggcaagg agttcaaatg cagggtcaac   1080

agtgcagctt tccctgcccc catcgagaaa accatctcca aaaccaaagg cagaccgaag   1140

gctccacagg tgtacaccat tccacctccc aaggagcaga tggccaagga taaagtcagt   1200

ctgacctgca tgataacaga cttcttccct gaagacatta ctgtggagtg gcagtggaat   1260

gggcagccag cggagaacta caagaacact cagcccatca tggacacaga tggctcttac   1320

ttcgtctaca gcaagctcaa tgtgcagaag agcaactggg aggcaggaaa tactttcacc   1380

tgctctgtgt tacatgaggg cctgcacaac caccatactg agaagagcct ctcccactct   1440

cctggtaaag cggccgcagg tggtggcggt tcaggcggag gtggctctgg cggtggcgga   1500

tccctgctgg gggatttctt ccggaagtct aaagagaaga ttgggaaaga gtttaaaaga   1560

attgtccaga gaatcaagga tttttgcgg aatcttgtgc ccaggacaga atcctag      1617
```

<210> SEQ ID NO 22
<211> LENGTH: 538
<212> TYPE: PRT
<213> ORGANISM: Artificial Sequence
<220> FEATURE:
<223> OTHER INFORMATION: Synthetic

<400> SEQUENCE: 22

```
Met Glu Thr Asp Thr Leu Leu Leu Trp Val Leu Leu Leu Trp Val Pro
1               5                   10                  15

Gly Ser Thr Gly Asp His His His His His His Gly Ser Gly Ser Gly
            20                  25                  30

Ser Gly Ile Glu Gly Arg Thr Arg Gln Val Gln Leu Lys Glu Ser Gly
        35                  40                  45

Pro Gly Leu Val Ala Pro Ser Gln Ser Leu Ser Ile Thr Cys Thr Val
    50                  55                  60

Ser Gly Phe Ser Leu Thr Asn Tyr Gly Val His Trp Val Arg Gln Pro
65                  70                  75                  80

Pro Gly Lys Gly Leu Glu Trp Leu Gly Val Ile Trp Ala Gly Gly Asn
                85                  90                  95

Thr Asn Tyr Asn Ser Ala Phe Met Ser Arg Leu Ser Ile Thr Lys Asp
            100                 105                 110

Asn Ser Lys Ser Gln Val Phe Ile Lys Met Asn Ser Leu Gln Thr Asp
        115                 120                 125

Asp Thr Ala Met Tyr Tyr Cys Ala Arg Glu Tyr Arg His Gly Ala Tyr
    130                 135                 140

Tyr Ala Met Asp Tyr Trp Gly Gln Gly Thr Ser Val Thr Val Ser Ser
145                 150                 155                 160

Glu Ser Gln Ser Phe Ser Val Tyr Pro Leu Ala Pro Gly Ser Ala Ala
                165                 170                 175

Gln Thr Asn Ser Met Val Thr Leu Gly Cys Leu Val Lys Gly Tyr Phe
            180                 185                 190

Pro Glu Pro Val Thr Val Thr Trp Asn Ser Gly Ser Leu Ser Ser Gly
        195                 200                 205

Val His Thr Phe Pro Ala Val Leu Gln Ser Asp Leu Tyr Thr Leu Ser
    210                 215                 220

Ser Ser Val Thr Val Pro Ser Ser Thr Trp Pro Ser Glu Thr Val Thr
225                 230                 235                 240

Cys Asn Val Ala His Pro Ala Ser Ser Thr Lys Val Asp Lys Lys Ile
                245                 250                 255

Val Pro Arg Asp Cys Gly Cys Lys Pro Cys Ile Cys Thr Val Pro Glu
            260                 265                 270

Val Ser Ser Val Phe Ile Phe Pro Pro Lys Pro Lys Asp Val Leu Thr
        275                 280                 285

Ile Thr Leu Thr Pro Lys Val Thr Cys Val Val Val Asp Ile Ser Lys
    290                 295                 300

Asp Asp Pro Glu Val Gln Phe Ser Trp Phe Val Asp Asp Val Glu Val
305                 310                 315                 320

His Thr Ala Gln Thr Gln Pro Arg Glu Glu Gln Phe Asn Ser Thr Phe
                325                 330                 335

Arg Ser Val Ser Glu Leu Pro Ile Met His Gln Asp Trp Leu Asn Gly
            340                 345                 350

Lys Glu Phe Lys Cys Arg Val Asn Ser Ala Ala Phe Pro Ala Pro Ile
        355                 360                 365

Glu Lys Thr Ile Ser Lys Thr Lys Gly Arg Pro Lys Ala Pro Gln Val
    370                 375                 380

Tyr Thr Ile Pro Pro Pro Lys Glu Gln Met Ala Lys Asp Lys Val Ser
385                 390                 395                 400

Leu Thr Cys Met Ile Thr Asp Phe Phe Pro Glu Asp Ile Thr Val Glu
                405                 410                 415

Trp Gln Trp Asn Gly Gln Pro Ala Glu Asn Tyr Lys Asn Thr Gln Pro
            420                 425                 430
```

```
Ile Met Asp Thr Asp Gly Ser Tyr Phe Val Tyr Ser Lys Leu Asn Val
        435                 440                 445

Gln Lys Ser Asn Trp Glu Ala Gly Asn Thr Phe Thr Cys Ser Val Leu
    450                 455                 460

His Glu Gly Leu His Asn His His Thr Glu Lys Ser Leu Ser His Ser
465                 470                 475                 480

Pro Gly Lys Ala Ala Ala Gly Gly Gly Gly Ser Gly Gly Gly Gly Ser
                485                 490                 495

Gly Gly Gly Gly Ser Leu Leu Gly Asp Phe Phe Arg Lys Ser Lys Glu
            500                 505                 510

Lys Ile Gly Lys Glu Phe Lys Arg Ile Val Gln Arg Ile Lys Asp Phe
        515                 520                 525

Leu Arg Asn Leu Val Pro Arg Thr Glu Ser
    530                 535
```

<210> SEQ ID NO 23
<211> LENGTH: 708
<212> TYPE: DNA
<213> ORGANISM: Artificial Sequence
<220> FEATURE:
<223> OTHER INFORMATION: Synthetic

<400> SEQUENCE: 23

```
atggagacag acacactcct gctatgggta ctgctgctct gggttccagg ttccactggt     60

gacgacatcc agatgactca gtctccagcc tccctatctg catctgtggg agaaactgtc    120

accatcacat gtcgagcaag tgagaacatt tacagttatt tagcatggta tcagcagaaa    180

cagggaaaat ctcctcagtt cctggtctat aatgcagaaa ccttagcaga aggtgtgcca    240

tcaaggttca gtggcagtgg atcaggcaaa cagttttctc tgaagatcaa cagcctgcag    300

cctgaagatt ttgggagtta ttactgtcaa catcattatg gtactcatcc gacgttcggt    360

ggaggcacca agctggaaat caaacgggct gatgctgcac caactgtatc catcttccca    420

ccatccagtg agcagttaac atctggaggt gcctcagtcg tgtgcttctt gaacaacttc    480

taccccaaag acatcaatgt caagtggaag attgatggca gtgaacgaca aaatggcgtc    540

ctgaacagtt ggactgatca ggacagcaaa gacagcacct acagcatgag cagcaccctc    600

acgttgacca aggacgagta tgaacgacat aacagctata cctgtgaggc cactcacaag    660

acatcaactt cacccattgt caagagcttc aacaggaatg agtgttag                 708
```

<210> SEQ ID NO 24
<211> LENGTH: 235
<212> TYPE: PRT
<213> ORGANISM: Artificial Sequence
<220> FEATURE:
<223> OTHER INFORMATION: Synthetic

<400> SEQUENCE: 24

```
Met Glu Thr Asp Thr Leu Leu Leu Trp Val Leu Leu Leu Trp Val Pro
1               5                   10                  15

Gly Ser Thr Gly Asp Asp Ile Gln Met Thr Gln Ser Pro Ala Ser Leu
            20                  25                  30

Ser Ala Ser Val Gly Glu Thr Val Thr Ile Thr Cys Arg Ala Ser Glu
        35                  40                  45

Asn Ile Tyr Ser Tyr Leu Ala Trp Tyr Gln Gln Lys Gln Gly Lys Ser
    50                  55                  60

Pro Gln Phe Leu Val Tyr Asn Ala Glu Thr Leu Ala Glu Gly Val Pro
65                  70                  75                  80
```

```
Ser Arg Phe Ser Gly Ser Gly Ser Gly Lys Gln Phe Ser Leu Lys Ile
                85                  90                  95

Asn Ser Leu Gln Pro Glu Asp Phe Gly Ser Tyr Tyr Cys Gln His His
            100                 105                 110

Tyr Gly Thr His Pro Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 25
<211> LENGTH: 1401
<212> TYPE: DNA
<213> ORGANISM: Artificial Sequence
<220> FEATURE:
<223> OTHER INFORMATION: Synthetic

<400> SEQUENCE: 25

```
atggagacag acacactcct gctatgggta ctgctgctct gggttccagg ttccactggt      60

gacgaggtga agctggtgga gtctggagga ggcttggtac agtctggggg ttctctgaga     120

ctctcctgtg caacttctgg gttcaccttc actgattatt acatgagttg ggtccgccag     180

cctccaggaa aggcacttga gtggttgggc tttattagag acagagataa tggttacaca     240

acagaataca gtgcttctgt gaagggtcgg ttcaccatct ccagagataa ttcccaaagc     300

atcctctatc ttcaaatgaa ctccctgcga gctgaggaca gtgccactta ttactgtgca     360

agagatataa ggactaacga agcttttgct tactggggcc aagggactct ggtcactgtc     420

tctgcagcta caacaacagc cccatctgtc tatccactgg cccctggatc tgctgcccaa     480

actaactcca tggtgaccct gggatgcctg gtcaagggct atttccctga gccagtgaca     540

gtgacctgga actctggatc cctgtccagc ggtgtgcaca ccttcccagc tgtcctgcag     600

tctgacctct acactctgag cagctcagtg actgtcccct ccagcacctg gcccagcgag     660

accgtcacct gcaacgttgc ccacccggcc agcagcacca aggtggacaa gaaaattgtg     720

cccagggatt gtggttgtaa gccttgcata tgtacagtcc cagaagtatc atctgtcttc     780

atcttccccc caaagcccaa ggatgtgctc accattactc tgactcctaa ggtcacgtgt     840

gttgtggtag acatcagcaa ggatgatccc gaggtccagt tcagctggtt tgtagatgat     900

gtggaggtgc acacagctca gacgcaaccc cgggaggagc agttcaacag cactttccgc     960

tcagtcagtg aacttcccat catgcaccag gactggctca atggcaagga gttcaaatgc    1020

agggtcaaca gtgcagcttt ccctgccccc atcgagaaaa ccatctccaa aaccaaaggc    1080

agaccgaagg ctccacaggt gtacaccatt ccacctccca aggagcagat ggccaaggat    1140

aaagtcagtc tgacctgcat gataacagac ttcttccctg aagacattac tgtggagtgg    1200
```

```
cagtggaatg ggcagccagc ggagaactac aagaacactc agcccatcat ggacacagat   1260

ggctcttact tcgtctacag caagctcaat gtgcagaaga gcaactggga ggcaggaaat   1320

actttcacct gctctgtgtt acatgagggc ctgcacaacc accatactga gaagagcctc   1380

tcccactctc ctggtaaatg a                                              1401


<210> SEQ ID NO 26
<211> LENGTH: 466
<212> TYPE: PRT
<213> ORGANISM: Artificial Sequence
<220> FEATURE:
<223> OTHER INFORMATION: Synthetic

<400> SEQUENCE: 26

Met Glu Thr Asp Thr Leu Leu Leu Trp Val Leu Leu Leu Trp Val Pro
1               5                   10                  15

Gly Ser Thr Gly Asp Glu Val Lys Leu Val Glu Ser Gly Gly Gly Leu
            20                  25                  30

Val Gln Ser Gly Gly Ser Leu Arg Leu Ser Cys Ala Thr Ser Gly Phe
        35                  40                  45

Thr Phe Thr Asp Tyr Tyr Met Ser Trp Val Arg Gln Pro Pro Gly Lys
    50                  55                  60

Ala Leu Glu Trp Leu Gly Phe Ile Arg Asp Arg Asp Asn Gly Tyr Thr
65                  70                  75                  80

Thr Glu Tyr Ser Ala Ser Val Lys Gly Arg Phe Thr Ile Ser Arg Asp
                85                  90                  95

Asn Ser Gln Ser Ile Leu Tyr Leu Gln Met Asn Ser Leu Arg Ala Glu
            100                 105                 110

Asp Ser Ala Thr Tyr Tyr Cys Ala Arg Asp Ile Arg Thr Asn Glu Ala
        115                 120                 125

Phe Ala Tyr Trp Gly Gln Gly Thr Leu Val Thr Val Ser Ala Ala Thr
    130                 135                 140

Thr Thr Ala Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
```

```
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465


<210> SEQ ID NO 27
<211> LENGTH: 1560
<212> TYPE: DNA
<213> ORGANISM: Artificial Sequence
<220> FEATURE:
<223> OTHER INFORMATION: Synthetic

<400> SEQUENCE: 27

atggagacag acacactcct gctatgggta ctgctgctct gggttccagg ttccactggt     60

gacgaggtga agctggtgga gtctggagga ggcttggtac agtctggggg ttctctgaga    120

ctctcctgtg caacttctgg gttcaccttc actgattatt acatgagttg ggtccgccag    180

cctccaggaa aggcacttga gtggttgggc tttattagag acagagataa tggttacaca    240

acagaataca gtgcttctgt gaagggtcgg ttcaccatct ccagagataa ttcccaaagc    300

atcctctatc ttcaaatgaa ctccctgcga gctgaggaca gtgccactta ttactgtgca    360

agagatataa ggactaacga agcttttgct tactggggcc aagggactct ggtcactgtc    420

tctgcagcta caacaacagc cccatctgtc tatccactgg cccctggatc tgctgcccaa    480

actaactcca tggtgaccct gggatgcctg gtcaagggct atttccctga gccagtgaca    540

gtgacctgga actctggatc cctgtccagc ggtgtgcaca ccttcccagc tgtcctgcag    600

tctgacctct acactctgag cagctcagtg actgtcccct ccagcacctg gcccagcgag    660

accgtcacct gcaacgttgc ccacccggcc agcagcacca aggtggacaa gaaaattgtg    720

cccagggatt gtggttgtaa gccttgcata tgtacagtcc cagaagtatc atctgtcttc    780

atcttccccc caaagcccaa ggatgtgctc accattactc tgactcctaa ggtcacgtgt    840

gttgtggtag acatcagcaa ggatgatccc gaggtccagt tcagctggtt tgtagatgat    900

gtggaggtgc acacagctca gacgcaaccc cgggaggagc agttcaacag cactttccgc    960

tcagtcagtg aacttcccat catgcaccag gactggctca atggcaagga gttcaaatgc   1020

agggtcaaca gtgcagcttt ccctgccccc atcgagaaaa ccatctccaa aaccaaaggc   1080

agaccgaagg ctccacaggt gtacaccatt ccacctccca aggagcagat ggccaaggat   1140

aaagtcagtc tgacctgcat gataacagac ttcttccctg aagacattac tgtggagtgg   1200

cagtggaatg gcagccagc ggagaactac aagaacactc agcccatcat ggacacagat   1260
```

```
ggctcttact tcgtctacag caagctcaat gtgcagaaga gcaactggga ggcaggaaat   1320

actttcacct gctctgtgtt acatgagggc ctgcacaacc accatactga gaagagcctc   1380

tcccactctc ctggtaaatc aggtggtggc ggttcaggcg gaggtggctc tggcggtggc   1440

ggatcgctgc tgggggattt cttccggaag tctaaagaga agattgggaa agagtttaaa   1500

agaattgtcc agagaatcaa ggattttttg cggaatcttg tgcccaggac agaatcctag   1560
```

<210> SEQ ID NO 28
<211> LENGTH: 519
<212> TYPE: PRT
<213> ORGANISM: Artificial Sequence
<220> FEATURE:
<223> OTHER INFORMATION: Synthetic

<400> SEQUENCE: 28

```
Met Glu Thr Asp Thr Leu Leu Leu Trp Val Leu Leu Leu Trp Val Pro
1               5                   10                  15

Gly Ser Thr Gly Asp Glu Val Lys Leu Val Glu Ser Gly Gly Gly Leu
            20                  25                  30

Val Gln Ser Gly Gly Ser Leu Arg Leu Ser Cys Ala Thr Ser Gly Phe
        35                  40                  45

Thr Phe Thr Asp Tyr Tyr Met Ser Trp Val Arg Gln Pro Pro Gly Lys
    50                  55                  60

Ala Leu Glu Trp Leu Gly Phe Ile Arg Asp Arg Asp Asn Gly Tyr Thr
65                  70                  75                  80

Thr Glu Tyr Ser Ala Ser Val Lys Gly Arg Phe Thr Ile Ser Arg Asp
                85                  90                  95

Asn Ser Gln Ser Ile Leu Tyr Leu Gln Met Asn Ser Leu Arg Ala Glu
            100                 105                 110

Asp Ser Ala Thr Tyr Tyr Cys Ala Arg Asp Ile Arg Thr Asn Glu Ala
        115                 120                 125

Phe Ala Tyr Trp Gly Gln Gly Thr Leu Val Thr Val Ser Ala Ala Thr
    130                 135                 140

Thr Thr Ala Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320
```

```
Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys Ser Gly Gly Gly Gly Ser Gly Gly Gly Gly Ser Gly Gly Gly
465                 470                 475                 480

Gly Ser Leu Leu Gly Asp Phe Phe Arg Lys Ser Lys Glu Lys Ile Gly
                485                 490                 495

Lys Glu Phe Lys Arg Ile Val Gln Arg Ile Lys Asp Phe Leu Arg Asn
            500                 505                 510

Leu Val Pro Arg Thr Glu Ser
        515
```

<210> SEQ ID NO 29
<211> LENGTH: 1821
<212> TYPE: DNA
<213> ORGANISM: Artificial Sequence
<220> FEATURE:
<223> OTHER INFORMATION: Synthetic

<400> SEQUENCE: 29

```
atggagacag acacactcct gctatgggta ctgctgctct gggttccagg ttccactggt      60

gacgaggtga agctggtgga gtctggagga ggcttggtac agtctggggg ttctctgaga     120

ctctcctgtg caacttctgg gttcaccttc actgattatt acatgagttg ggtccgccag     180

cctccaggaa aggcacttga gtggttgggc tttattagag acagagataa tggttacaca     240

acagaataca gtgcttctgt gaagggtcgg ttcaccatct ccagagataa ttcccaaagc     300

atcctctatc ttcaaatgaa ctccctgcga gctgaggaca gtgccactta ttactgtgca     360

agagatataa ggactaacga agcttttgct tactggggcc aagggactct ggtcactgtc     420

tctgcagcta caacaacagc cccatctgtc tatccactgg cccctggatc tgctgcccaa     480

actaactcca tggtgaccct gggatgcctg gtcaagggct atttccctga gccagtgaca     540

gtgacctgga actctggatc cctgtccagc ggtgtgcaca ccttcccagc tgtcctgcag     600

tctgacctct acactctgag cagctcagtg actgtcccct ccagcacctg gcccagcgag     660

accgtcacct gcaacgttgc ccacccggcc agcagcacca aggtggacaa gaaaattgtg     720

cccagggatt gtggttgtaa gccttgcata tgtacagtcc cagaagtatc atctgtcttc     780

atcttccccc caaagcccaa ggatgtgctc accattactc tgactcctaa ggtcacgtgt     840

gttgtggtag acatcagcaa ggatgatccc gaggtccagt tcagctggtt tgtagatgat     900
```

```
gtggaggtgc acacagctca gacgcaaccc cgggaggagc agttcaacag cactttccgc    960

tcagtcagtg aacttcccat catgcaccag gactggctca atggcaagga gttcaaatgc   1020

agggtcaaca gtgcagcttt ccctgccccc atcgagaaaa ccatctccaa aaccaaaggc   1080

agaccgaagg ctccacaggt gtacaccatt ccacctccca aggagcagat ggccaaggat   1140

aaagtcagtc tgacctgcat gataacagac ttcttccctg aagacattac tgtggagtgg   1200

cagtggaatg ggcagccagc ggagaactac aagaacactc agcccatcat ggacacaggt   1260

ggctcttact tcgtctacag caagctcaat gtgcagaaga gcaactggga ggcaggaaat   1320

actttcacct gctctgtgtt acatgagggc ctgcacaacc accatactga gaagagcctc   1380

tcccactctc ctggtaaatc aggtggtggc ggttcaggcg gaggtggctc tggcggtggc   1440

ggatcgaatt tggtgaattt ccacagaatg atcaagttga cgacaggaaa ggaagccgca   1500

ctcagttatg gcttctacgg ctgccactgt ggcgtgggtg gcagaggatc ccccaaggat   1560

gcaacggatc gctgctgtgt cactcatgac tgttgctaca aacgtctgga gaaacgtgga   1620

tgtggcacca aatttctgag ctacaagttt agcaactcgg ggagcagaat cacctgtgca   1680

aaacaggact cctgcagaag tcaactgtgt gagtgtgata aggctgctgc cacctgtttt   1740

gctagaaaca agacgaccta caataaaaag taccagtact attccaataa acactgcaga   1800

gggagcaccc ctcgttgctg a                                              1821


<210> SEQ ID NO 30
<211> LENGTH: 606
<212> TYPE: PRT
<213> ORGANISM: Artificial Sequence
<220> FEATURE:
<223> OTHER INFORMATION: Synthetic

<400> SEQUENCE: 30

Met Glu Thr Asp Thr Leu Leu Leu Trp Val Leu Leu Leu Trp Val Pro
1               5                   10                  15

Gly Ser Thr Gly Asp Glu Val Lys Leu Val Glu Ser Gly Gly Gly Leu
            20                  25                  30

Val Gln Ser Gly Gly Ser Leu Arg Leu Ser Cys Ala Thr Ser Gly Phe
        35                  40                  45

Thr Phe Thr Asp Tyr Tyr Met Ser Trp Val Arg Gln Pro Pro Gly Lys
    50                  55                  60

Ala Leu Glu Trp Leu Gly Phe Ile Arg Asp Arg Asp Asn Gly Tyr Thr
65                  70                  75                  80

Thr Glu Tyr Ser Ala Ser Val Lys Gly Arg Phe Thr Ile Ser Arg Asp
                85                  90                  95

Asn Ser Gln Ser Ile Leu Tyr Leu Gln Met Asn Ser Leu Arg Ala Glu
            100                 105                 110

Asp Ser Ala Thr Tyr Tyr Cys Ala Arg Asp Ile Arg Thr Asn Glu Ala
        115                 120                 125

Phe Ala Tyr Trp Gly Gln Gly Thr Leu Val Thr Val Ser Ala Ala Thr
    130                 135                 140

Thr Thr Ala Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205
```

```
Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Gly Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys Ser Gly Gly Gly Gly Ser Gly Gly Gly Gly Ser Gly Gly Gly
465                 470                 475                 480

Gly Ser Asn Leu Val Asn Phe His Arg Met Ile Lys Leu Thr Thr Gly
                485                 490                 495

Lys Glu Ala Ala Leu Ser Tyr Gly Phe Tyr Gly Cys His Cys Gly Val
            500                 505                 510

Gly Gly Arg Gly Ser Pro Lys Asp Ala Thr Asp Arg Cys Cys Val Thr
        515                 520                 525

His Asp Cys Cys Tyr Lys Arg Leu Glu Lys Arg Gly Cys Gly Thr Lys
    530                 535                 540

Phe Leu Ser Tyr Lys Phe Ser Asn Ser Gly Ser Arg Ile Thr Cys Ala
545                 550                 555                 560

Lys Gln Asp Ser Cys Arg Ser Gln Leu Cys Glu Cys Asp Lys Ala Ala
                565                 570                 575

Ala Thr Cys Phe Ala Arg Asn Lys Thr Thr Tyr Asn Lys Lys Tyr Gln
            580                 585                 590

Tyr Tyr Ser Asn Lys His Cys Arg Gly Ser Thr Pro Arg Cys
        595                 600                 605
```

<210> SEQ ID NO 31
<211> LENGTH: 723
<212> TYPE: DNA

<213> ORGANISM: Artificial Sequence
<220> FEATURE:
<223> OTHER INFORMATION: Synthetic

<400> SEQUENCE: 31

```
atggagacag acacactcct gctatgggta ctgctgctct gggttccagg ttccactggt     60

gacgatgttt tgatgaccca aactccactc tccctgcctg tcagtcttgg agatcaagcc    120

tccatctctt gcagatctag tcagagcact gtacatagga atggaaacac ctatttagaa    180

tggtacctgc agaaaccagg ccagtctcca aagctcctga tctacagagt ttccaaccga    240

ttttctgggg tcccagacag gttcagtggc agtggatcag ggacagattt cacactcaag    300

atcagcagag tggaggctga ggatctggga gtttattact gctttcaagg ttcacatgtt    360

ccgtggacgt tcggtggagg caccaagctg gaaatcaaac gggctgatgc tgcaccaact    420

gtatccatct tcccaccatc cagtgagcag ttaacatctg gaggtgcctc agtcgtgtgc    480

ttcttgaaca acttctaccc caaagacatc aatgtcaagt ggaagattga tggcagtgaa    540

cgacaaaatg gcgtcctgaa cagttggact gatcaggaca gcaaagacag cacctacagc    600

atgagcagca ccctcacgtt gaccaaggac gagtatgaac gacataacag ctatacctgt    660

gaggccactc acaagacatc aacttcaccc attgtcaaga gcttcaacag gaatgagtgt    720

tag                                                                  723
```

<210> SEQ ID NO 32
<211> LENGTH: 240
<212> TYPE: PRT
<213> ORGANISM: Artificial Sequence
<220> FEATURE:
<223> OTHER INFORMATION: Synthetic

<400> SEQUENCE: 32

```
Met Glu Thr Asp Thr Leu Leu Leu Trp Val Leu Leu Leu Trp Val Pro
1               5                   10                  15

Gly Ser Thr Gly Asp Asp Val Leu Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Thr Val His Arg Asn Gly Asn Thr Tyr Leu Glu Trp Tyr Leu Gln
    50                  55                  60

Lys Pro Gly Gln Ser Pro Lys Leu Leu Ile Tyr Arg Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Tyr Cys Phe Gln Gly Ser His Val Pro Trp Thr Phe Gly Gly Gly Thr
        115                 120                 125

Lys Leu Glu Ile Lys Arg Ala Asp Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205
```

```
Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240
```

<210> SEQ ID NO 33
<211> LENGTH: 423
<212> TYPE: DNA
<213> ORGANISM: Artificial Sequence
<220> FEATURE:
<223> OTHER INFORMATION: Synthetic

<400> SEQUENCE: 33

```
atggagacag acacactcct gctatgggta ctgctgctct gggttccagg ttccactggt     60

gaccaggtcc agcttcagca gtctggggct gaactggcaa aacctggggc ctcagtgaag    120

atgtcctgca aggcttctgg ctacaccttt actagctact ggatgcactg ggtgaaacag    180

aggcctggac agggtctgga atggattgga tacattaatc ctagcactgg ttatcctgag    240

tacaatcaga aattcaagga caaggccaca ttgactgcag acaaatcctc caacacagcc    300

tacatgcaac tgagcagcct gacatctgag gactctgcag tctattactg tgtaagaagg    360

aattactacg aggacttctt tgactactgg ggccaaggca ccactctcac agtctcctca    420

gcc                                                                  423
```

<210> SEQ ID NO 34
<211> LENGTH: 141
<212> TYPE: PRT
<213> ORGANISM: Artificial Sequence
<220> FEATURE:
<223> OTHER INFORMATION: Synthetic

<400> SEQUENCE: 34

```
Met Glu Thr Asp Thr Leu Leu Leu Trp Val Leu Leu Leu Trp Val Pro
1               5                   10                  15

Gly Ser Thr Gly Asp Gln Val Gln Leu Gln Gln Ser Gly Ala Glu Leu
            20                  25                  30

Ala Lys Pro Gly Ala Ser Val Lys Met Ser Cys Lys Ala Ser Gly Tyr
        35                  40                  45

Thr Phe Thr Ser Tyr Trp Met His Trp Val Lys Gln Arg Pro Gly Gln
    50                  55                  60

Gly Leu Glu Trp Ile Gly Tyr Ile Asn Pro Ser Thr Gly Tyr Pro Glu
65                  70                  75                  80

Tyr Asn Gln Lys Phe Lys Asp Lys Ala Thr Leu Thr Ala Asp Lys Ser
                85                  90                  95

Ser Asn Thr Ala Tyr Met Gln Leu Ser Ser Leu Thr Ser Glu Asp Ser
            100                 105                 110

Ala Val Tyr Tyr Cys Val Arg Arg Asn Tyr Tyr Glu Asp Phe Phe Asp
        115                 120                 125

Tyr Trp Gly Gln Gly Thr Thr Leu Thr Val Ser Ser Ala
    130                 135                 140
```

<210> SEQ ID NO 35
<211> LENGTH: 402
<212> TYPE: DNA
<213> ORGANISM: Artificial Sequence
<220> FEATURE:
<223> OTHER INFORMATION: Synthetic

<400> SEQUENCE: 35

```
atggagacag acacactcct gctatgggta ctgctgctct gggttccagg ttccactggt      60

gacgttgtga tgacccaaat tccactctcc ctgcctgtca gtcttggaga tcaagcctcc     120

atctcttgca gatctagtca gagccttgta cacagtaatg gaaacaccta tttacattgg     180

tacctgcaga agccaggcca gtctccaaag gtcctgatct acaaagtttc caaccgattt     240

tctggggtcc cagacaggtt cagtggcagt ggatcaggga cagatttcac actcaagatc     300

agcagagtgg aggctgagga tctgggagtt tatttctgct ctcaaagtac acatgttccg     360

ctcacgttcg gtgctgggac caagctggag ctgaaacggg ct                        402
```

<210> SEQ ID NO 36
<211> LENGTH: 134
<212> TYPE: PRT
<213> ORGANISM: Artificial Sequence
<220> FEATURE:
<223> OTHER INFORMATION: Synthetic

<400> SEQUENCE: 36

```
Met Glu Thr Asp Thr Leu Leu Leu Trp Val Leu Leu Leu Trp Val Pro
1               5                   10                  15

Gly Ser Thr Gly Asp Val Val Met Thr Gln Ile Pro Leu Ser Leu Pro
            20                  25                  30

Val Ser Leu Gly Asp Gln Ala Ser Ile Ser Cys Arg Ser Ser Gln Ser
        35                  40                  45

Leu Val His Ser Asn Gly Asn Thr Tyr Leu His Trp Tyr Leu Gln Lys
    50                  55                  60

Pro Gly Gln Ser Pro Lys Val Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Phe
            100                 105                 110

Cys Ser Gln Ser Thr His Val Pro Leu Thr Phe Gly Ala Gly Thr Lys
        115                 120                 125

Leu Glu Leu Lys Arg Ala
    130
```

<210> SEQ ID NO 37
<211> LENGTH: 426
<212> TYPE: DNA
<213> ORGANISM: Artificial Sequence
<220> FEATURE:
<223> OTHER INFORMATION: Synthetic

<400> SEQUENCE: 37

```
atggagacag acacactcct gctatgggta ctgctgctct gggttccagg ttccactggt      60

gaccaggtgc agctgaagga gtcaggacct ggcctggtgg cgccctcaca gagcctgtcc     120

atcacttgca ctgtctctgg gttttcatta accaactatg gtgtacattg ggttcgccag     180

cctccaggaa agggtctgga gtggctggga gtaatatggg ctggtggaaa cacaaattat     240

aattcggctt ttatgtccag actgagcatc accaaagaca actccaagag ccaagttttc     300

ataaaaatga acagtctgca aactgatgac acagccatgt actactgtgc cagagaatat     360

aggcacgggg cttactatgc tatggactac tggggtcaag gaacctcagt caccgtctcc     420

tcagag                                                                426
```

<210> SEQ ID NO 38
<211> LENGTH: 142

<212> TYPE: PRT
<213> ORGANISM: Artificial Sequence
<220> FEATURE:
<223> OTHER INFORMATION: Synthetic

<400> SEQUENCE: 38

```
Met Glu Thr Asp Thr Leu Leu Leu Trp Val Leu Leu Leu Trp Val Pro
1               5                   10                  15

Gly Ser Thr Gly Asp Gln Val Gln Leu Lys Glu Ser Gly Pro Gly Leu
            20                  25                  30

Val Ala Pro Ser Gln Ser Leu Ser Ile Thr Cys Thr Val Ser Gly Phe
        35                  40                  45

Ser Leu Thr Asn Tyr Gly Val His Trp Val Arg Gln Pro Pro Gly Lys
    50                  55                  60

Gly Leu Glu Trp Leu Gly Val Ile Trp Ala Gly Gly Asn Thr Asn Tyr
65                  70                  75                  80

Asn Ser Ala Phe Met Ser Arg Leu Ser Ile Thr Lys Asp Asn Ser Lys
                85                  90                  95

Ser Gln Val Phe Ile Lys Met Asn Ser Leu Gln Thr Asp Asp Thr Ala
            100                 105                 110

Met Tyr Tyr Cys Ala Arg Glu Tyr Arg His Gly Ala Tyr Tyr Ala Met
        115                 120                 125

Asp Tyr Trp Gly Gln Gly Thr Ser Val Thr Val Ser Ser Glu
    130                 135                 140
```

<210> SEQ ID NO 39
<211> LENGTH: 390
<212> TYPE: DNA
<213> ORGANISM: Artificial Sequence
<220> FEATURE:
<223> OTHER INFORMATION: Synthetic

<400> SEQUENCE: 39

```
atggagacag acacactcct gctatgggta ctgctgctct gggttccagg ttccactggt     60

gacgacatcc agatgactca gtctccagcc tccctatctg catctgtggg agaaactgtc    120

accatcacat gtcgagcaag tgagaacatt tacagttatt tagcatggta tcagcagaaa    180

cagggaaaat ctcctcagtt cctggtctat aatgcagaaa ccttagcaga aggtgtgcca    240

tcaaggttca gtggcagtgg atcaggcaaa cagttttctc tgaagatcaa cagcctgcag    300

cctgaagatt ttgggagtta ttactgtcaa catcattatg gtactcatcc gacgttcggt    360

ggaggcacca agctggaaat caaacgggct                                      390
```

<210> SEQ ID NO 40
<211> LENGTH: 130
<212> TYPE: PRT
<213> ORGANISM: Artificial Sequence
<220> FEATURE:
<223> OTHER INFORMATION: Synthetic

<400> SEQUENCE: 40

```
Met Glu Thr Asp Thr Leu Leu Leu Trp Val Leu Leu Leu Trp Val Pro
1               5                   10                  15

Gly Ser Thr Gly Asp Asp Ile Gln Met Thr Gln Ser Pro Ala Ser Leu
            20                  25                  30

Ser Ala Ser Val Gly Glu Thr Val Thr Ile Thr Cys Arg Ala Ser Glu
        35                  40                  45

Asn Ile Tyr Ser Tyr Leu Ala Trp Tyr Gln Gln Lys Gln Gly Lys Ser
    50                  55                  60
```

```
Pro Gln Phe Leu Val Tyr Asn Ala Glu Thr Leu Ala Glu Gly Val Pro
65              70                  75                  80

Ser Arg Phe Ser Gly Ser Gly Ser Gly Lys Gln Phe Ser Leu Lys Ile
                85                  90                  95

Asn Ser Leu Gln Pro Glu Asp Phe Gly Ser Tyr Tyr Cys Gln His His
            100                 105                 110

Tyr Gly Thr His Pro Thr Phe Gly Gly Gly Thr Lys Leu Glu Ile Lys
        115                 120                 125

Arg Ala
    130


<210> SEQ ID NO 41
<211> LENGTH: 405
<212> TYPE: DNA
<213> ORGANISM: Artificial Sequence
<220> FEATURE:
<223> OTHER INFORMATION: Synthetic

<400> SEQUENCE: 41

atggagacag acacactcct gctatgggta ctgctgctct gggttccagg ttccactggt     60

gacgatgttt tgatgaccca aactccactc tccctgcctg tcagtcttgg agatcaagcc    120

tccatctctt gcagatctag tcagagcact gtacatagga atggaaacac ctatttagaa    180

tggtacctgc agaaaccagg ccagtctcca aagctcctga tctacagagt ttccaaccga    240

ttttctgggg tcccagacag gttcagtggc agtggatcag ggacagattt cacactcaag    300

atcagcagag tggaggctga ggatctggga gtttattact gctttcaagg ttcacatgtt    360

ccgtggacgt tcggtggagg caccaagctg gaaatcaaac gggct                    405


<210> SEQ ID NO 42
<211> LENGTH: 135
<212> TYPE: PRT
<213> ORGANISM: Artificial Sequence
<220> FEATURE:
<223> OTHER INFORMATION: Synthetic

<400> SEQUENCE: 42

Met Glu Thr Asp Thr Leu Leu Leu Trp Val Leu Leu Leu Trp Val Pro
1               5                   10                  15

Gly Ser Thr Gly Asp Asp Val Leu Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Thr Val His Arg Asn Gly Asn Thr Tyr Leu Glu Trp Tyr Leu Gln
    50                  55                  60

Lys Pro Gly Gln Ser Pro Lys Leu Leu Ile Tyr Arg Val Ser Asn Arg
65              70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Tyr Cys Phe Gln Gly Ser His Val Pro Trp Thr Phe Gly Gly Gly Thr
        115                 120                 125

Lys Leu Glu Ile Lys Arg Ala
    130                 135


<210> SEQ ID NO 43
<211> LENGTH: 429
<212> TYPE: DNA
```

<213> ORGANISM: Artificial Sequence
<220> FEATURE:
<223> OTHER INFORMATION: Synthetic

<400> SEQUENCE: 43

```
atggagacag acacactcct gctatgggta ctgctgctct gggttccagg ttccactggt     60

gacgaggtga agctggtgga gtctggagga ggcttggtac agtctggggg ttctctgaga    120

ctctcctgtg caacttctgg gttcaccttc actgattatt acatgagttg ggtccgccag    180

cctccaggaa aggcacttga gtggttgggc tttattagag acagagataa tggttacaca    240

acagaataca gtgcttctgt gaagggtcgg ttcaccatct ccagagataa ttcccaaagc    300

atcctctatc ttcaaatgaa ctccctgcga gctgaggaca gtgccactta ttactgtgca    360

agagatataa ggactaacga agcttttgct tactggggcc aagggactct ggtcactgtc    420

tctgcagct                                                            429
```

<210> SEQ ID NO 44
<211> LENGTH: 143
<212> TYPE: PRT
<213> ORGANISM: Artificial Sequence
<220> FEATURE:
<223> OTHER INFORMATION: Synthetic

<400> SEQUENCE: 44

```
Met Glu Thr Asp Thr Leu Leu Leu Trp Val Leu Leu Leu Trp Val Pro
1               5                   10                  15

Gly Ser Thr Gly Asp Glu Val Lys Leu Val Glu Ser Gly Gly Gly Leu
            20                  25                  30

Val Gln Ser Gly Gly Ser Leu Arg Leu Ser Cys Ala Thr Ser Gly Phe
        35                  40                  45

Thr Phe Thr Asp Tyr Tyr Met Ser Trp Val Arg Gln Pro Pro Gly Lys
    50                  55                  60

Ala Leu Glu Trp Leu Gly Phe Ile Arg Asp Arg Asp Asn Gly Tyr Thr
65                  70                  75                  80

Thr Glu Tyr Ser Ala Ser Val Lys Gly Arg Phe Thr Ile Ser Arg Asp
                85                  90                  95

Asn Ser Gln Ser Ile Leu Tyr Leu Gln Met Asn Ser Leu Arg Ala Glu
            100                 105                 110

Asp Ser Ala Thr Tyr Tyr Cys Ala Arg Asp Ile Arg Thr Asn Glu Ala
        115                 120                 125

Phe Ala Tyr Trp Gly Gln Gly Thr Leu Val Thr Val Ser Ala Ala
    130                 135                 140
```

<210> SEQ ID NO 45
<211> LENGTH: 64
<212> TYPE: PRT
<213> ORGANISM: Bos taurus

<400> SEQUENCE: 45

```
Met Arg Leu His His Leu Leu Leu Ala Leu Leu Phe Leu Val Leu Ser
1               5                   10                  15

Ala Gly Ser Gly Phe Thr Gln Gly Val Arg Asn Ser Gln Ser Cys Arg
            20                  25                  30

Arg Asn Lys Gly Ile Cys Val Pro Ile Arg Cys Pro Gly Ser Met Arg
        35                  40                  45

Gln Ile Gly Thr Cys Leu Gly Ala Gln Val Lys Cys Cys Arg Arg Lys
    50                  55                  60
```

```
<210> SEQ ID NO 46
<211> LENGTH: 24
<212> TYPE: PRT
<213> ORGANISM: Xenopus laevis

<400> SEQUENCE: 46

Gly Val Leu Ser Asn Val Ile Gly Tyr Leu Lys Lys Leu Gly Thr Gly
1               5                   10                  15

Ala Leu Asn Ala Val Leu Lys Gln
            20


<210> SEQ ID NO 47
<211> LENGTH: 81
<212> TYPE: PRT
<213> ORGANISM: Xenopus laevis

<400> SEQUENCE: 47

Met Tyr Lys Gly Ile Phe Leu Cys Val Leu Leu Ala Val Ile Cys Ala
1               5                   10                  15

Asn Ser Leu Ala Thr Pro Ser Ser Asp Ala Asp Glu Asp Asn Asp Glu
            20                  25                  30

Val Glu Arg Tyr Val Arg Gly Trp Ala Ser Lys Ile Gly Gln Thr Leu
        35                  40                  45

Gly Lys Ile Ala Lys Val Gly Leu Lys Glu Leu Ile Gln Pro Lys Arg
    50                  55                  60

Glu Ala Met Leu Arg Ser Ala Glu Ala Gln Gly Lys Arg Pro Trp Ile
65                  70                  75                  80

Leu


<210> SEQ ID NO 48
<211> LENGTH: 303
<212> TYPE: PRT
<213> ORGANISM: Xenopus laevis

<400> SEQUENCE: 48

Met Phe Lys Gly Leu Phe Ile Cys Ser Leu Ile Ala Val Ile Cys Ala
1               5                   10                  15

Asn Ala Leu Pro Gln Pro Glu Ala Ser Ala Asp Glu Asp Met Asp Glu
            20                  25                  30

Arg Glu Val Arg Gly Ile Gly Lys Phe Leu His Ser Ala Gly Lys Phe
        35                  40                  45

Gly Lys Ala Phe Val Gly Glu Ile Met Lys Ser Lys Arg Asp Ala Glu
    50                  55                  60

Ala Val Gly Pro Glu Ala Phe Ala Asp Glu Asp Leu Asp Glu Arg Glu
65                  70                  75                  80

Val Arg Gly Ile Gly Lys Phe Leu His Ser Ala Lys Lys Phe Gly Lys
                85                  90                  95

Ala Phe Val Gly Glu Ile Met Asn Ser Lys Arg Asp Ala Glu Ala Val
            100                 105                 110

Gly Pro Glu Ala Phe Ala Asp Glu Asp Leu Asp Glu Arg Glu Val Arg
        115                 120                 125

Gly Ile Gly Lys Phe Leu His Ser Ala Lys Lys Phe Gly Lys Ala Phe
    130                 135                 140

Val Gly Glu Ile Met Asn Ser Lys Arg Asp Ala Glu Ala Val Gly Pro
145                 150                 155                 160

Glu Ala Phe Ala Asp Glu Asp Leu Asp Glu Arg Glu Val Arg Gly Ile
                165                 170                 175

Gly Lys Phe Leu His Ser Ala Lys Lys Phe Gly Lys Ala Phe Val Gly
```

```
            180                 185                 190

Glu Ile Met Asn Ser Lys Arg Asp Ala Glu Ala Val Gly Pro Glu Ala
        195                 200                 205

Phe Ala Asp Glu Asp Phe Asp Glu Arg Glu Val Arg Gly Ile Gly Lys
    210                 215                 220

Phe Leu His Ser Ala Lys Lys Phe Gly Lys Ala Phe Val Gly Glu Ile
225                 230                 235                 240

Met Asn Ser Lys Arg Asp Ala Glu Ala Val Gly Pro Glu Ala Phe Ala
                245                 250                 255

Asp Glu Asp Leu Asp Glu Arg Glu Val Arg Gly Ile Gly Lys Phe Leu
            260                 265                 270

His Ser Ala Lys Lys Phe Gly Lys Ala Phe Val Gly Glu Ile Met Asn
        275                 280                 285

Ser Lys Arg Asp Ala Glu Ala Val Asp Asp Arg Arg Trp Val Glu
    290                 295                 300


<210> SEQ ID NO 49
<211> LENGTH: 17
<212> TYPE: PRT
<213> ORGANISM: Tachypleus gigas

<400> SEQUENCE: 49

Lys Trp Cys Phe Arg Val Cys Tyr Arg Gly Ile Cys Tyr Arg Arg Cys
1               5                   10                  15

Arg


<210> SEQ ID NO 50
<211> LENGTH: 17
<212> TYPE: PRT
<213> ORGANISM: Tachypleus gigas

<400> SEQUENCE: 50

Arg Trp Cys Phe Arg Val Cys Tyr Arg Gly Ile Cys Tyr Arg Lys Cys
1               5                   10                  15

Arg


<210> SEQ ID NO 51
<211> LENGTH: 129
<212> TYPE: PRT
<213> ORGANISM: Bufo bufo gagarizans

<400> SEQUENCE: 51

Met Ser Gly Arg Gly Lys Gln Gly Gly Lys Val Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ala Gln Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Val Arg Asn Asp Glu Glu Leu Asn Lys
                85                  90                  95

Leu Leu Gly Gly Val Thr Ile Ala Gln Gly Gly Val Leu Pro Asn Ile
            100                 105                 110

Gln Ala Val Leu Leu Pro Lys Thr Glu Ser Ser Lys Pro Ala Lys Ser
        115                 120                 125
```

```
Lys

<210> SEQ ID NO 52
<211> LENGTH: 21
<212> TYPE: PRT
<213> ORGANISM: Bufo bufo gagarizans

<400> SEQUENCE: 52

Thr Arg Ser Ser Arg Ala Gly Leu Gln Phe Pro Val Gly Arg Val His
1               5                   10                  15

Arg Leu Leu Arg Lys
            20


<210> SEQ ID NO 53
<211> LENGTH: 63
<212> TYPE: PRT
<213> ORGANISM: Bombyx mori

<400> SEQUENCE: 53

Met Asn Phe Val Arg Ile Leu Ser Phe Val Phe Ala Leu Val Leu Ala
1               5                   10                  15

Leu Gly Ala Val Ser Ala Ala Pro Glu Pro Arg Trp Lys Leu Phe Lys
            20                  25                  30

Lys Ile Glu Lys Val Gly Arg Asn Val Arg Asp Gly Leu Ile Lys Ala
        35                  40                  45

Gly Pro Ala Ile Ala Val Ile Gly Gln Ala Lys Ser Leu Gly Lys
    50                  55                  60


<210> SEQ ID NO 54
<211> LENGTH: 63
<212> TYPE: PRT
<213> ORGANISM: Bombyx mori

<400> SEQUENCE: 54

Met Asn Phe Ala Lys Ile Leu Ser Phe Val Phe Ala Leu Val Leu Ala
1               5                   10                  15

Leu Ser Met Thr Ser Ala Ala Pro Glu Pro Arg Trp Lys Ile Phe Lys
            20                  25                  30

Lys Ile Glu Lys Met Gly Arg Asn Ile Arg Asp Gly Ile Val Lys Ala
        35                  40                  45

Gly Pro Ala Ile Glu Val Leu Gly Ser Ala Lys Ala Ile Gly Lys
    50                  55                  60


<210> SEQ ID NO 55
<211> LENGTH: 63
<212> TYPE: PRT
<213> ORGANISM: Drosophila melanogaster

<400> SEQUENCE: 55

Met Asn Phe Tyr Lys Ile Phe Val Phe Val Ala Leu Ile Leu Ala Ile
1               5                   10                  15

Ser Ile Gly Gln Ser Glu Ala Gly Trp Leu Lys Lys Leu Gly Lys Arg
            20                  25                  30

Ile Glu Arg Ile Gly Gln His Thr Arg Asp Ala Thr Ile Gln Gly Leu
        35                  40                  45

Gly Ile Ala Gln Gln Ala Ala Asn Val Ala Ala Thr Ala Arg Gly
    50                  55                  60


<210> SEQ ID NO 56
<211> LENGTH: 31
```

<212> TYPE: PRT
<213> ORGANISM: Sus scrofa

<400> SEQUENCE: 56

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 57
<211> LENGTH: 13
<212> TYPE: PRT
<213> ORGANISM: Bos taurus

<400> SEQUENCE: 57

Ile Leu Pro Trp Lys Trp Pro Trp Trp Pro Trp Arg Arg
1               5                   10

<210> SEQ ID NO 58
<211> LENGTH: 34
<212> TYPE: PRT
<213> ORGANISM: Lactococcus lactis

<400> SEQUENCE: 58

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 59
<211> LENGTH: 20
<212> TYPE: PRT
<213> ORGANISM: Rana catesbeiana

<400> SEQUENCE: 59

Phe Leu Gly Gly Leu Ile Lys Ile Val Pro Ala Met Ile Cys Ala Val
1               5                   10                  15

Thr Lys Lys Cys
            20

<210> SEQ ID NO 60
<211> LENGTH: 25
<212> TYPE: PRT
<213> ORGANISM: Bos taurus

<400> SEQUENCE: 60

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 61
<211> LENGTH: 19
<212> TYPE: PRT
<213> ORGANISM: Sus scrofa
<220> FEATURE:
<221> NAME/KEY: misc_feature
<222> LOCATION: (19)..(19)
<223> OTHER INFORMATION: Xaa can be any naturally occurring amino acid

<400> SEQUENCE: 61

Arg Gly Gly Arg Leu Cys Tyr Cys Arg Arg Arg Phe Cys Val Cys Val
1               5                   10                  15

```
Gly Arg Xaa


<210> SEQ ID NO 62
<211> LENGTH: 16
<212> TYPE: PRT
<213> ORGANISM: Sus scrofa

<400> SEQUENCE: 62

Gly Gly Arg Leu Cys Tyr Cys Arg Arg Arg Phe Cys Ile Cys Val Gly
1               5                   10                  15


<210> SEQ ID NO 63
<211> LENGTH: 51
<212> TYPE: PRT
<213> ORGANISM: Homo sapiens

<400> SEQUENCE: 63

Met Lys Phe Phe Val Phe Ala Leu Ile Leu Ala Leu Met Leu Ser Met
1               5                   10                  15

Thr Gly Ala Asp Ser His Ala Lys Arg His His Gly Tyr Lys Arg Lys
            20                  25                  30

Phe His Glu Lys His His Ser His Arg Gly Tyr Arg Ser Asn Tyr Leu
        35                  40                  45

Tyr Asp Asn
    50


<210> SEQ ID NO 64
<211> LENGTH: 38
<212> TYPE: PRT
<213> ORGANISM: Macaca fascicularis

<400> SEQUENCE: 64

Asp Ser His Glu Glu Arg His His Gly Arg His Gly His His Lys Tyr
1               5                   10                  15

Gly Arg Lys Phe His Glu Lys His His Ser His Arg Gly Tyr Arg Ser
            20                  25                  30

Asn Tyr Leu Tyr Asp Asn
        35


<210> SEQ ID NO 65
<211> LENGTH: 33
<212> TYPE: PRT
<213> ORGANISM: Phyllomedusa sauvagei

<400> SEQUENCE: 65

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Thr
            20                  25                  30

Gln


<210> SEQ ID NO 66
<211> LENGTH: 34
<212> TYPE: PRT
<213> ORGANISM: Phyllomedusa sauvagei

<400> SEQUENCE: 66

Ala Leu Trp Phe Thr Met Leu Lys Lys Leu Gly Thr Met Ala Leu His
1               5                   10                  15

Ala Gly Lys Ala Ala Leu Gly Ala Ala Ala Asn Thr Ile Ser Gln Gly
            20                  25                  30
```

```
Thr Gln


<210> SEQ ID NO 67
<211> LENGTH: 30
<212> TYPE: PRT
<213> ORGANISM: Phyllomedusa sauvagei

<400> SEQUENCE: 67

Ala Leu Trp Lys Asn Met Leu Lys Gly Ile Gly Lys Leu Ala Gly Lys
1               5                   10                  15

Ala Ala Leu Gly Ala Val Lys Lys Leu Val Gly Ala Glu Ser
            20                  25                  30


<210> SEQ ID NO 68
<211> LENGTH: 21
<212> TYPE: PRT
<213> ORGANISM: Misgurnus anguillicaudatus

<400> SEQUENCE: 68

Arg Gln Arg Val Glu Glu Leu Ser Lys Phe Ser Lys Lys Gly Ala Ala
1               5                   10                  15

Ala Arg Arg Arg Lys
            20


<210> SEQ ID NO 69
<211> LENGTH: 27
<212> TYPE: PRT
<213> ORGANISM: Apis mellifera

<400> SEQUENCE: 69

Gly Ile Gly Ala Val Leu Lys Val Leu Thr Thr Gly Leu Pro Ala Leu
1               5                   10                  15

Ile Ser Trp Ile Ser Arg Lys Lys Arg Gln Gln
            20                  25


<210> SEQ ID NO 70
<211> LENGTH: 33
<212> TYPE: PRT
<213> ORGANISM: Pardachirus pavoninus

<400> SEQUENCE: 70

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Glu Gln
            20                  25                  30

Glu


<210> SEQ ID NO 71
<211> LENGTH: 33
<212> TYPE: PRT
<213> ORGANISM: Pardachirus pavoninus

<400> SEQUENCE: 71

Gly Phe Phe Ala Leu Ile Pro Lys Ile Ile Ser Ser Pro Ile Phe Lys
1               5                   10                  15

Thr Leu Leu Ser Ala Val Gly Ser Ala Leu Ser Ser Ser Gly Gly Gln
            20                  25                  30

Glu


<210> SEQ ID NO 72
<211> LENGTH: 176
```

```
<212> TYPE: PRT
<213> ORGANISM: Bos taurus

<400> SEQUENCE: 72

Met Glu Thr Gln Arg Ala Ser Leu Ser Leu Gly Arg Cys Ser Leu Trp
1               5                   10                  15

Leu Leu Leu Leu Gly Leu Val Leu Pro Ser Ala Ser Ala Gln Ala Leu
            20                  25                  30

Ser Tyr Arg Glu Ala Val Leu Arg Ala Val Asp Gln Phe Asn Glu Arg
        35                  40                  45

Ser Ser Glu Ala Asn Leu Tyr Arg Leu Leu Glu Leu Asp Pro Thr Pro
    50                  55                  60

Asn Asp Asp Leu Asp Pro Gly Thr Arg Lys Pro Val Ser Phe Arg Val
65                  70                  75                  80

Lys Glu Thr Asp Cys Pro Arg Thr Ser Gln Gln Pro Leu Glu Gln Cys
                85                  90                  95

Asp Phe Lys Glu Asn Gly Leu Val Lys Gln Cys Val Gly Thr Val Thr
            100                 105                 110

Leu Asp Pro Ser Asn Asp Gln Phe Asp Ile Asn Cys Asn Glu Leu Gln
        115                 120                 125

Ser Val Arg Phe Arg Pro Pro Ile Arg Arg Pro Pro Ile Arg Pro Pro
    130                 135                 140

Phe Tyr Pro Pro Phe Arg Pro Pro Ile Arg Pro Pro Ile Phe Pro Pro
145                 150                 155                 160

Ile Arg Pro Pro Phe Arg Pro Pro Leu Gly Pro Phe Pro Gly Arg Arg
                165                 170                 175


<210> SEQ ID NO 73
<211> LENGTH: 155
<212> TYPE: PRT
<213> ORGANISM: Bos taurus

<400> SEQUENCE: 73

Met Glu Thr Pro Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
            20                  25                  30

Ser Tyr Arg Glu Ala Val Leu Arg Ala Val Asp Gln Leu Asn Glu Gln
        35                  40                  45

Ser Ser Glu Pro Asn Ile Tyr Arg Leu Leu Glu Leu Asp Gln Pro Pro
    50                  55                  60

Gln Asp Asp Glu Asp Pro Asp Ser Pro Lys Arg Val Ser Phe Arg Val
65                  70                  75                  80

Lys Glu Thr Val Cys Ser Arg Thr Thr Gln Gln Pro Pro Glu Gln Cys
                85                  90                  95

Asp Phe Lys Glu Asn Gly Leu Leu Lys Arg Cys Glu Gly Thr Val Thr
            100                 105                 110

Leu Asp Gln Val Arg Gly Asn Phe Asp Ile Thr Cys Asn Asn His Gln
        115                 120                 125

Ser Ile Arg Ile Thr Lys Gln Pro Trp Ala Pro Pro Gln Ala Ala Arg
    130                 135                 140

Leu Cys Arg Ile Val Val Ile Arg Val Cys Arg
145                 150                 155


<210> SEQ ID NO 74
<211> LENGTH: 29
<212> TYPE: PRT
```

<213> ORGANISM: Ceratitis capitata

<400> SEQUENCE: 74

Ser Ile Gly Ser Ala Leu Lys Lys Ala Leu Pro Val Ala Lys Lys Ile
1               5                   10                  15

Gly Lys Ile Ala Leu Pro Ile Ala Lys Ala Ala Leu Pro
            20                  25

<210> SEQ ID NO 75
<211> LENGTH: 29
<212> TYPE: PRT
<213> ORGANISM: Ceratitis capitata

<400> SEQUENCE: 75

Ser Ile Gly Ser Ala Phe Lys Lys Ala Leu Pro Val Ala Lys Lys Ile
1               5                   10                  15

Gly Lys Ala Ala Leu Pro Ile Ala Lys Ala Ala Leu Pro
            20                  25

<210> SEQ ID NO 76
<211> LENGTH: 170
<212> TYPE: PRT
<213> ORGANISM: Homo sapiens

<400> SEQUENCE: 76

Met Lys Thr Gln Arg Asn Gly His Ser Leu Gly Arg Trp Ser Leu Val
1               5                   10                  15

Leu Leu Leu Leu Gly Leu Val Met Pro Leu Ala Ile Ile Ala Gln Val
            20                  25                  30

Leu Ser Tyr Lys Glu Ala Val Leu Arg Ala Ile Asp Gly Ile Asn Gln
        35                  40                  45

Arg Ser Ser Asp Ala Asn Leu Tyr Arg Leu Leu Asp Leu Asp Pro Arg
    50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
    130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170

<210> SEQ ID NO 77
<211> LENGTH: 170
<212> TYPE: PRT
<213> ORGANISM: Equus caballus

<400> SEQUENCE: 77

Met Glu Thr Gln Arg Asn Thr Arg Cys Leu Gly Arg Trp Ser Pro Leu
1               5                   10                  15

Leu Leu Leu Leu Gly Leu Val Ile Pro Pro Ala Thr Thr Gln Ala Leu
            20                  25                  30

Ser Tyr Lys Glu Ala Val Leu Arg Ala Val Asp Gly Leu Asn Gln Arg

```
        35                  40                  45

Ser Ser Asp Glu Asn Leu Tyr Arg Leu Leu Glu Leu Asp Pro Leu Pro
    50                  55                  60

Lys Gly Asp Lys Asp Ser Asp Thr Pro Lys Pro Val Ser Phe Met Val
65                  70                  75                  80

Lys Glu Thr Val Cys Pro Arg Ile Met Lys Gln Thr Pro Glu Gln Cys
                85                  90                  95

Asp Phe Lys Glu Asn Gly Leu Val Lys Gln Cys Val Gly Thr Val Ile
            100                 105                 110

Leu Asp Pro Val Lys Asp Tyr Phe Asp Ala Ser Cys Asp Glu Pro Gln
        115                 120                 125

Arg Val Lys Arg Phe His Ser Val Gly Ser Leu Ile Gln Arg His Gln
    130                 135                 140

Gln Met Ile Arg Asp Lys Ser Glu Ala Thr Arg His Gly Ile Arg Ile
145                 150                 155                 160

Ile Thr Arg Pro Lys Leu Leu Leu Ala Ser
                165                 170


<210> SEQ ID NO 78
<211> LENGTH: 159
<212> TYPE: PRT
<213> ORGANISM: Bos taurus

<400> SEQUENCE: 78

Met Glu Thr Gln Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
            20                  25                  30

Ser Tyr Arg Glu Ala Val Leu Arg Ala Val Asp Gln Leu Asn Glu Lys
        35                  40                  45

Ser Ser Glu Ala Asn Leu Tyr Arg Leu Leu Glu Leu Asp Pro Pro Pro
    50                  55                  60

Lys Glu Asp Asp Glu Asn Pro Asn Ile Pro Lys Pro Val Ser Phe Arg
65                  70                  75                  80

Val Lys Glu Thr Val Cys Pro Arg Thr Ser Gln Gln Ser Pro Glu Gln
                85                  90                  95

Cys Asp Phe Lys Glu Asn Gly Leu Leu Lys Glu Cys Val Gly Thr Val
            100                 105                 110

Thr Leu Asp Gln Val Gly Ser Asn Phe Asp Ile Thr Cys Ala Val Pro
        115                 120                 125

Gln Ser Val Gly Gly Leu Arg Ser Leu Gly Arg Lys Ile Leu Arg Ala
    130                 135                 140

Trp Lys Lys Tyr Gly Pro Ile Ile Val Pro Ile Ile Arg Ile Gly
145                 150                 155


<210> SEQ ID NO 79
<211> LENGTH: 156
<212> TYPE: PRT
<213> ORGANISM: Equus caballus

<400> SEQUENCE: 79

Met Glu Thr Gln Arg Asn Thr Arg Cys Leu Gly Arg Trp Ser Pro Leu
1               5                   10                  15

Leu Leu Leu Leu Gly Leu Val Ile Pro Pro Ala Thr Thr Gln Ala Leu
            20                  25                  30

Ser Tyr Lys Glu Ala Val Leu Arg Ala Val Asp Gly Leu Asn Gln Arg
        35                  40                  45
```

```
Ser Ser Asp Glu Asn Leu Tyr Arg Leu Leu Glu Leu Asp Pro Leu Pro
    50                  55                  60

Lys Gly Asp Lys Asp Ser Asp Thr Pro Lys Pro Val Ser Phe Met Val
65                  70                  75                  80

Lys Glu Thr Val Cys Pro Arg Ile Met Lys Gln Thr Pro Glu Gln Cys
                85                  90                  95

Asp Phe Lys Glu Asn Gly Leu Val Lys Gln Cys Val Gly Thr Val Ile
            100                 105                 110

Leu Gly Pro Val Lys Asp His Phe Asp Val Ser Cys Gly Glu Pro Gln
        115                 120                 125

Arg Val Lys Arg Phe Gly Arg Leu Ala Lys Ser Phe Leu Arg Met Arg
    130                 135                 140

Ile Leu Leu Pro Arg Arg Lys Ile Leu Leu Ala Ser
145                 150                 155


<210> SEQ ID NO 80
<211> LENGTH: 160
<212> TYPE: PRT
<213> ORGANISM: Ovis aries

<400> SEQUENCE: 80

Met Glu Thr Gln Arg Ala Ser Leu Ser Leu Gly Arg Cys Ser Leu Trp
1               5                   10                  15

Leu Leu Leu Leu Gly Leu Ala Leu Pro Ser Ala Ser Ala Gln Val Leu
            20                  25                  30

Ser Tyr Arg Glu Ala Val Leu Arg Ala Ala Asp Gln Leu Asn Glu Lys
        35                  40                  45

Ser Ser Glu Ala Asn Leu Tyr Arg Leu Leu Glu Leu Asp Pro Pro Pro
    50                  55                  60

Lys Gln Asp Asp Glu Asn Ser Asn Ile Pro Lys Pro Val Ser Phe Arg
65                  70                  75                  80

Val Lys Glu Thr Val Cys Pro Arg Thr Ser Gln Gln Pro Ala Glu Gln
                85                  90                  95

Cys Asp Phe Lys Glu Asn Gly Leu Leu Lys Glu Cys Val Gly Thr Val
            100                 105                 110

Thr Leu Asp Gln Val Arg Asn Asn Phe Asp Ile Thr Cys Ala Glu Pro
        115                 120                 125

Gln Ser Val Arg Gly Leu Arg Arg Leu Gly Arg Lys Ile Ala His Gly
    130                 135                 140

Val Lys Lys Tyr Gly Pro Thr Val Leu Arg Ile Ile Arg Ile Ala Gly
145                 150                 155                 160


<210> SEQ ID NO 81
<211> LENGTH: 12
<212> TYPE: PRT
<213> ORGANISM: Bos taurus

<400> SEQUENCE: 81

Arg Leu Cys Arg Ile Val Val Ile Arg Val Cys Arg
1               5                   10


<210> SEQ ID NO 82
<211> LENGTH: 30
<212> TYPE: PRT
<213> ORGANISM: Homo sapiens

<400> SEQUENCE: 82

Ala Cys Tyr Cys Arg Ile Pro Ala Cys Ile Ala Gly Glu Arg Arg Tyr
```

```
1               5                   10                  15

Gly Thr Cys Ile Tyr Gln Gly Arg Leu Trp Ala Phe Cys Cys
            20                  25                  30


<210> SEQ ID NO 83
<211> LENGTH: 29
<212> TYPE: PRT
<213> ORGANISM: Homo sapiens

<400> SEQUENCE: 83

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25


<210> SEQ ID NO 84
<211> LENGTH: 30
<212> TYPE: PRT
<213> ORGANISM: Homo sapiens

<400> SEQUENCE: 84

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30


<210> SEQ ID NO 85
<211> LENGTH: 33
<212> TYPE: PRT
<213> ORGANISM: Homo sapiens

<400> SEQUENCE: 85

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val


<210> SEQ ID NO 86
<211> LENGTH: 33
<212> TYPE: PRT
<213> ORGANISM: Oryctolagus cuniculus

<400> SEQUENCE: 86

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Pro Leu Cys Cys Arg
            20                  25                  30

Arg


<210> SEQ ID NO 87
<211> LENGTH: 33
<212> TYPE: PRT
<213> ORGANISM: Oryctolagus cuniculus

<400> SEQUENCE: 87

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg
```

<210> SEQ ID NO 88
<211> LENGTH: 34
<212> TYPE: PRT
<213> ORGANISM: Oryctolagus cuniculus

<400> SEQUENCE: 88

```
Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30

Arg Arg
```

<210> SEQ ID NO 89
<211> LENGTH: 34
<212> TYPE: PRT
<213> ORGANISM: Oryctolagus cuniculus

<400> SEQUENCE: 89

```
Gly Arg Cys Val Cys Arg Lys Gln Leu Leu Cys Ser Tyr Arg Glu Arg
1               5                   10                  15

Arg Ile Gly Asp Cys Lys Ile Arg Gly Val Arg Phe Pro Phe Cys Cys
            20                  25                  30

Pro Arg
```

<210> SEQ ID NO 90
<211> LENGTH: 34
<212> TYPE: PRT
<213> ORGANISM: Oryctolagus cuniculus

<400> SEQUENCE: 90

```
Val Ser Cys Thr Cys Arg Arg Phe Ser Cys Gly Phe Gly Glu Arg Ala
1               5                   10                  15

Ser Gly Ser Cys Thr Val Asn Gly Gly Val Arg His Thr Leu Cys Cys
            20                  25                  30

Arg Arg
```

<210> SEQ ID NO 91
<211> LENGTH: 33
<212> TYPE: PRT
<213> ORGANISM: Oryctolagus cuniculus

<400> SEQUENCE: 91

```
Val Phe Cys Thr Cys Arg Gly Phe Leu Cys Gly Ser Gly Glu Arg Ala
1               5                   10                  15

Ser Gly Ser Cys Thr Ile Asn Gly Val Arg His Thr Leu Cys Cys Arg
            20                  25                  30

Arg
```

<210> SEQ ID NO 92
<211> LENGTH: 32
<212> TYPE: PRT
<213> ORGANISM: Rattus norvegicus

<400> SEQUENCE: 92

```
Val Thr Cys Tyr Cys Arg Arg Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30
```

```
<210> SEQ ID NO 93
<211> LENGTH: 30
<212> TYPE: PRT
<213> ORGANISM: Rattus norvegicus

<400> SEQUENCE: 93

Cys Ser Cys Arg Tyr Ser Ser Cys Arg Phe Gly Glu Arg Leu Leu Ser
1               5                   10                  15

Gly Ala Cys Arg Leu Asn Gly Arg Ile Tyr Arg Leu Cys Cys
            20                  25                  30


<210> SEQ ID NO 94
<211> LENGTH: 31
<212> TYPE: PRT
<213> ORGANISM: Rattus norvegicus

<400> SEQUENCE: 94

Ala Cys Thr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20                  25                  30


<210> SEQ ID NO 95
<211> LENGTH: 31
<212> TYPE: PRT
<213> ORGANISM: Guinea pig

<400> SEQUENCE: 95

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30


<210> SEQ ID NO 96
<211> LENGTH: 67
<212> TYPE: PRT
<213> ORGANISM: Homo sapiens

<400> SEQUENCE: 96

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65


<210> SEQ ID NO 97
<211> LENGTH: 18
<212> TYPE: PRT
<213> ORGANISM: Macaca mulatta

<400> SEQUENCE: 97

Arg Cys Ile Cys Thr Arg Gly Phe Cys Arg Cys Leu Cys Arg Arg Gly
1               5                   10                  15

Val Cys


<210> SEQ ID NO 98
<211> LENGTH: 78
```

<212> TYPE: PRT
<213> ORGANISM: Helianthus annuus

<400> SEQUENCE: 98

```
Met Lys Ser Ser Met Lys Met Phe Ala Ala Leu Leu Leu Val Val Met
1               5                   10                  15

Cys Leu Leu Ala Asn Glu Met Gly Gly Pro Leu Val Val Glu Ala Arg
            20                  25                  30

Thr Cys Glu Ser Gln Ser His Lys Phe Lys Gly Thr Cys Leu Ser Asp
        35                  40                  45

Thr Asn Cys Ala Asn Val Cys His Ser Glu Arg Phe Ser Gly Gly Lys
    50                  55                  60

Cys Arg Gly Phe Arg Arg Arg Cys Phe Cys Thr Thr His Cys
65                  70                  75
```

<210> SEQ ID NO 99
<211> LENGTH: 78
<212> TYPE: PRT
<213> ORGANISM: Helianthus annuus

<400> SEQUENCE: 99

```
Met Lys Ser Ser Met Lys Met Phe Ala Ala Leu Leu Leu Val Val Met
1               5                   10                  15

Cys Leu Leu Ala Asn Glu Met Gly Gly Pro Leu Val Val Glu Ala Arg
            20                  25                  30

Thr Cys Glu Ser Gln Ser His Lys Phe Lys Gly Thr Cys Leu Ser Asp
        35                  40                  45

Thr Asn Cys Ala Asn Val Cys His Ser Glu Arg Phe Ser Gly Gly Lys
    50                  55                  60

Cys Arg Gly Phe Arg Arg Arg Cys Phe Cys Thr Thr His Cys
65                  70                  75
```

<210> SEQ ID NO 100
<211> LENGTH: 30
<212> TYPE: PRT
<213> ORGANISM: Macaca mulatta

<400> SEQUENCE: 100

```
Ala Cys Tyr Cys Arg Ile Pro Ala Cys Leu Ala Gly Glu Arg Arg Tyr
1               5                   10                  15

Gly Thr Cys Phe Tyr Met Gly Arg Val Trp Ala Phe Cys Cys
            20                  25                  30
```

<210> SEQ ID NO 101
<211> LENGTH: 37
<212> TYPE: PRT
<213> ORGANISM: Androctonus australis hector

<400> SEQUENCE: 101

```
Gly Phe Gly Cys Pro Phe Asn Gln Gly Ala Cys His Arg His Cys Arg
1               5                   10                  15

Ser Ile Arg Arg Arg Gly Gly Tyr Cys Ala Gly Leu Phe Lys Gln Thr
            20                  25                  30

Cys Thr Cys Tyr Arg
        35
```

<210> SEQ ID NO 102
<211> LENGTH: 38
<212> TYPE: PRT
<213> ORGANISM: Mytilus galloprovincialis
<220> FEATURE:

```
<221> NAME/KEY: misc_feature
<222> LOCATION: (28)..(28)
<223> OTHER INFORMATION: Xaa can be any naturally occurring amino acid

<400> SEQUENCE: 102

Gly Phe Gly Cys Pro Asn Asn Tyr Gln Cys His Arg His Cys Lys Ser
1               5                   10                  15

Ile Pro Gly Arg Cys Gly Gly Tyr Cys Gly Gly Xaa His Arg Leu Arg
            20                  25                  30

Cys Thr Cys Tyr Arg Cys
        35


<210> SEQ ID NO 103
<211> LENGTH: 54
<212> TYPE: PRT
<213> ORGANISM: Heuchera sanguinea

<400> SEQUENCE: 103

Asp Gly Val Lys Leu Cys Asp Val Pro Ser Gly Thr Trp Ser Gly His
1               5                   10                  15

Cys Gly Ser Ser Ser Lys Cys Ser Gln Gln Cys Lys Asp Arg Glu His
            20                  25                  30

Phe Ala Tyr Gly Gly Ala Cys His Tyr Gln Phe Pro Ser Val Lys Cys
        35                  40                  45

Phe Cys Lys Arg Gln Cys
    50


<210> SEQ ID NO 104
<211> LENGTH: 49
<212> TYPE: PRT
<213> ORGANISM: Clitoria ternatea

<400> SEQUENCE: 104

Asn Leu Cys Glu Arg Ala Ser Leu Thr Trp Thr Gly Asn Cys Gly Asn
1               5                   10                  15

Thr Gly His Cys Asp Thr Gln Cys Arg Asn Trp Glu Ser Ala Lys His
            20                  25                  30

Gly Ala Cys His Lys Arg Gly Asn Trp Lys Cys Phe Cys Tyr Phe Asn
        35                  40                  45

Cys


<210> SEQ ID NO 105
<211> LENGTH: 91
<212> TYPE: PRT
<213> ORGANISM: Mus musculus

<400> SEQUENCE: 105

Met Lys Lys Leu Val Leu Leu Phe Ala Leu Val Leu Leu Ala Phe Gln
1               5                   10                  15

Val Gln Ala Asp Ser Ile Gln Asn Thr Asp Glu Glu Thr Lys Thr Glu
            20                  25                  30

Glu Gln Pro Gly Glu Lys Asp Gln Ala Val Ser Val Ser Phe Gly Asp
        35                  40                  45

Pro Gln Gly Ser Ala Leu Gln Asp Ala Ala Leu Gly Trp Gly Arg Arg
    50                  55                  60

Cys Pro Gln Cys Pro Arg Cys Pro Ser Cys Pro Ser Cys Pro Arg Cys
65                  70                  75                  80

Pro Arg Cys Pro Arg Cys Lys Cys Asn Pro Lys
                85                  90
```

```
<210> SEQ ID NO 106
<211> LENGTH: 40
<212> TYPE: PRT
<213> ORGANISM: Bos taurus

<400> SEQUENCE: 106

Gln Gly Val Arg Asn Phe Val Thr Cys Arg Ile Asn Arg Gly Phe Cys
1               5                   10                  15

Val Pro Ile Arg Cys Pro Gly His Arg Arg Gln Ile Gly Thr Cys Leu
            20                  25                  30

Gly Pro Gln Ile Lys Cys Cys Arg
        35                  40


<210> SEQ ID NO 107
<211> LENGTH: 40
<212> TYPE: PRT
<213> ORGANISM: Bos taurus

<400> SEQUENCE: 107

Gln Gly Val Arg Asn Phe Val Thr Cys Arg Ile Asn Arg Gly Phe Cys
1               5                   10                  15

Val Pro Ile Arg Cys Pro Gly His Arg Arg Gln Ile Gly Thr Cys Leu
            20                  25                  30

Gly Pro Arg Ile Lys Cys Cys Arg
        35                  40


<210> SEQ ID NO 108
<211> LENGTH: 42
<212> TYPE: PRT
<213> ORGANISM: Bos taurus

<400> SEQUENCE: 108

Gln Gly Val Arg Asn His Val Thr Cys Arg Ile Tyr Gly Gly Phe Cys
1               5                   10                  15

Val Pro Ile Arg Cys Pro Gly Arg Thr Arg Gln Ile Gly Thr Cys Phe
            20                  25                  30

Gly Arg Pro Val Lys Cys Cys Arg Arg Trp
        35                  40


<210> SEQ ID NO 109
<211> LENGTH: 40
<212> TYPE: PRT
<213> ORGANISM: Bos taurus

<400> SEQUENCE: 109

Gln Val Val Arg Asn Pro Gln Ser Cys Arg Trp Asn Met Gly Val Cys
1               5                   10                  15

Ile Pro Ile Ser Cys Pro Gly Asn Met Arg Gln Ile Gly Thr Cys Phe
            20                  25                  30

Gly Pro Arg Val Pro Cys Cys Arg
        35                  40


<210> SEQ ID NO 110
<211> LENGTH: 41
<212> TYPE: PRT
<213> ORGANISM: Bos taurus

<400> SEQUENCE: 110

Gln Arg Val Arg Asn Pro Gln Ser Cys Arg Trp Asn Met Gly Val Cys
1               5                   10                  15

Ile Pro Phe Leu Cys Arg Val Gly Met Arg Gln Ile Gly Thr Cys Phe
```

```
            20                  25                  30

Gly Pro Arg Val Pro Cys Cys Arg Arg
        35                  40


<210> SEQ ID NO 111
<211> LENGTH: 42
<212> TYPE: PRT
<213> ORGANISM: Bos taurus

<400> SEQUENCE: 111

Gln Gly Val Arg Asn His Val Thr Cys Arg Ile Asn Arg Gly Phe Cys
1               5                   10                  15

Val Pro Ile Arg Cys Pro Gly Arg Thr Arg Gln Ile Gly Thr Cys Phe
            20                  25                  30

Gly Pro Arg Ile Lys Cys Cys Arg Ser Trp
        35                  40


<210> SEQ ID NO 112
<211> LENGTH: 40
<212> TYPE: PRT
<213> ORGANISM: Bos taurus

<400> SEQUENCE: 112

Gln Gly Val Arg Ser Tyr Leu Ser Cys Trp Gly Asn Arg Gly Ile Cys
1               5                   10                  15

Leu Leu Asn Arg Cys Pro Gly Arg Met Arg Gln Ile Gly Thr Cys Leu
            20                  25                  30

Ala Pro Arg Val Lys Cys Cys Arg
        35                  40


<210> SEQ ID NO 113
<211> LENGTH: 42
<212> TYPE: PRT
<213> ORGANISM: Bos taurus

<400> SEQUENCE: 113

Ser Gly Ile Ser Gly Pro Leu Ser Cys Gly Arg Asn Gly Gly Val Cys
1               5                   10                  15

Ile Pro Ile Arg Cys Pro Val Pro Met Arg Gln Ile Gly Thr Cys Phe
            20                  25                  30

Gly Arg Pro Val Lys Cys Cys Arg Ser Trp
        35                  40


<210> SEQ ID NO 114
<211> LENGTH: 38
<212> TYPE: PRT
<213> ORGANISM: Bos taurus

<400> SEQUENCE: 114

Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
            20                  25                  30

Lys Cys Cys Arg Ser Trp
        35


<210> SEQ ID NO 115
<211> LENGTH: 74
<212> TYPE: PRT
<213> ORGANISM: Zophobas atratus

<400> SEQUENCE: 115
```

```
Ser Leu Gln Gly Gly Ala Pro Asn Phe Pro Gln Pro Ser Gln Gln Asn
1               5                   10                  15

Gly Gly Trp Gln Val Ser Pro Asp Leu Gly Arg Asp Asp Lys Gly Asn
            20                  25                  30

Thr Arg Gly Gln Ile Glu Ile Gln Asn Lys Gly Lys Asp His Asp Phe
        35                  40                  45

Asn Ala Gly Trp Gly Lys Val Ile Arg Gly Pro Asn Lys Ala Lys Pro
    50                  55                  60

Thr Trp His Val Gly Gly Thr Tyr Arg Arg
65                  70


<210> SEQ ID NO 116
<211> LENGTH: 67
<212> TYPE: PRT
<213> ORGANISM: Homo sapiens

<400> SEQUENCE: 116

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65


<210> SEQ ID NO 117
<211> LENGTH: 40
<212> TYPE: PRT
<213> ORGANISM: Aedes aegypti

<400> SEQUENCE: 117

Ala Thr Cys Asp Leu Leu Ser Gly Phe Gly Val Gly Asp Ser Ala Cys
1               5                   10                  15

Ala Ala His Cys Ile Ala Arg Gly Asn Arg Gly Gly Tyr Cys Asn Ser
            20                  25                  30

Lys Lys Val Cys Val Cys Arg Asn
        35                  40


<210> SEQ ID NO 118
<211> LENGTH: 35
<212> TYPE: PRT
<213> ORGANISM: Mytilus edulis
<220> FEATURE:
<221> NAME/KEY: misc_feature
<222> LOCATION: (28)..(28)
<223> OTHER INFORMATION: Xaa can be any naturally occurring amino acid

<400> SEQUENCE: 118

Gly Phe Gly Cys Pro Asn Asp Tyr Pro Cys His Arg His Cys Lys Ser
1               5                   10                  15

Ile Pro Gly Arg Tyr Gly Gly Tyr Cys Gly Gly Xaa His Arg Leu Arg
            20                  25                  30

Cys Thr Cys
        35


<210> SEQ ID NO 119
<211> LENGTH: 40
```

<212> TYPE: PRT
<213> ORGANISM: Sarcophaga peregrina

<400> SEQUENCE: 119

```
Ala Thr Cys Asp Leu Leu Ser Gly Ile Gly Val Gln His Ser Ala Cys
1               5                   10                  15

Ala Leu His Cys Val Phe Arg Gly Asn Arg Gly Gly Tyr Cys Thr Gly
            20                  25                  30

Lys Gly Ile Cys Val Cys Arg Asn
        35                  40
```

<210> SEQ ID NO 120
<211> LENGTH: 95
<212> TYPE: PRT
<213> ORGANISM: Oryctolagus cuniculus

<400> SEQUENCE: 120

```
Met Arg Thr Leu Ala Leu Leu Ala Ala Ile Leu Leu Val Ala Leu Gln
1               5                   10                  15

Ala Gln Ala Glu His Val Ser Val Ser Ile Asp Glu Val Val Asp Gln
            20                  25                  30

Gln Pro Pro Gln Ala Glu Asp Gln Asp Val Ala Ile Tyr Val Lys Glu
        35                  40                  45

His Glu Ser Ser Ala Leu Glu Ala Leu Gly Val Lys Ala Gly Val Val
    50                  55                  60

Cys Ala Cys Arg Arg Ala Leu Cys Leu Pro Arg Glu Arg Arg Ala Gly
65                  70                  75                  80

Phe Cys Arg Ile Arg Gly Arg Ile His Pro Leu Cys Cys Arg Arg
                85                  90                  95
```

<210> SEQ ID NO 121
<211> LENGTH: 92
<212> TYPE: PRT
<213> ORGANISM: Mus musculus

<400> SEQUENCE: 121

```
Met Lys Pro Leu Val Leu Leu Ser Ala Leu Val Leu Leu Ser Phe Gln
1               5                   10                  15

Val Gln Ala Asp Pro Ile Gln Asn Thr Asp Glu Glu Thr Lys Thr Glu
            20                  25                  30

Glu Gln Ser Gly Glu Glu Asp Gln Ala Val Ser Val Ser Phe Gly Asp
        35                  40                  45

Arg Glu Gly Ala Ser Leu Gln Glu Glu Ser Leu Arg Asp Leu Val Cys
    50                  55                  60

Tyr Cys Arg Thr Arg Gly Cys Lys Arg Arg Glu Arg Met Asn Gly Thr
65                  70                  75                  80

Cys Arg Lys Gly His Leu Met Tyr Thr Leu Cys Cys
                85                  90
```

<210> SEQ ID NO 122
<211> LENGTH: 93
<212> TYPE: PRT
<213> ORGANISM: Mus musculus

<400> SEQUENCE: 122

```
Met Lys Thr Phe Val Leu Leu Ser Ala Leu Val Leu Leu Ala Phe Gln
1               5                   10                  15

Val Gln Ala Asp Pro Ile His Lys Thr Asp Glu Glu Thr Asn Thr Glu
            20                  25                  30
```

```
Glu Gln Pro Gly Glu Glu Asp Gln Ala Val Ser Ile Ser Phe Gly Gly
        35                  40                  45

Gln Glu Gly Ser Ala Leu His Glu Glu Leu Ser Lys Lys Leu Ile Cys
    50                  55                  60

Tyr Cys Arg Ile Arg Gly Cys Lys Arg Arg Glu Arg Val Phe Gly Thr
65                  70                  75                  80

Cys Arg Asn Leu Phe Leu Thr Phe Val Phe Cys Cys Ser
                85                  90


<210> SEQ ID NO 123
<211> LENGTH: 35
<212> TYPE: PRT
<213> ORGANISM: Mus musculus

<400> SEQUENCE: 123

Leu Arg Asp Leu Val Cys Tyr Cys Arg Ala Arg Gly Cys Lys Gly Arg
1               5                   10                  15

Glu Arg Met Asn Gly Thr Cys Arg Lys Gly His Leu Leu Tyr Met Leu
            20                  25                  30

Cys Cys Arg
        35


<210> SEQ ID NO 124
<211> LENGTH: 43
<212> TYPE: PRT
<213> ORGANISM: Pyrrhocoris apterus

<400> SEQUENCE: 124

Ala Thr Cys Asp Ile Leu Ser Phe Gln Ser Gln Trp Val Thr Pro Asn
1               5                   10                  15

His Ala Gly Cys Ala Leu His Cys Val Ile Lys Gly Tyr Lys Gly Gly
            20                  25                  30

Gln Cys Lys Ile Thr Val Cys His Cys Arg Arg
        35                  40


<210> SEQ ID NO 125
<211> LENGTH: 32
<212> TYPE: PRT
<213> ORGANISM: Rattus norvegicus

<400> SEQUENCE: 125

Val Thr Cys Tyr Cys Arg Ser Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30


<210> SEQ ID NO 126
<211> LENGTH: 31
<212> TYPE: PRT
<213> ORGANISM: Rattus norvegicus

<400> SEQUENCE: 126

Val Thr Cys Ser Cys Arg Thr Ser Ser Cys Arg Phe Gly Glu Arg Leu
1               5                   10                  15

Ser Gly Ala Cys Arg Leu Asn Gly Arg Ile Tyr Arg Leu Cys Cys
            20                  25                  30


<210> SEQ ID NO 127
<211> LENGTH: 34
<212> TYPE: PRT
<213> ORGANISM: Oryctolagus cuniculus
```

<400> SEQUENCE: 127

```
Gly Ile Cys Ala Cys Arg Arg Arg Phe Cys Leu Asn Phe Glu Gln Phe
1               5                   10                  15

Ser Gly Tyr Cys Arg Val Asn Gly Ala Arg Tyr Val Arg Cys Cys Ser
            20                  25                  30

Arg Arg
```

<210> SEQ ID NO 128
<211> LENGTH: 64
<212> TYPE: PRT
<213> ORGANISM: Pan troglodytes

<400> SEQUENCE: 128

```
Met Arg Val Leu Tyr Leu Leu Phe Ser Phe Leu Phe Ile Phe Leu Met
1               5                   10                  15

Pro Leu Pro Gly Val Phe Gly Gly Ile Ser Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60
```

<210> SEQ ID NO 129
<211> LENGTH: 64
<212> TYPE: PRT
<213> ORGANISM: Homo sapiens

<400> SEQUENCE: 129

```
Met Arg Val Leu Tyr Leu Leu Phe Ser Phe Leu Phe Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60
```

<210> SEQ ID NO 130
<211> LENGTH: 68
<212> TYPE: PRT
<213> ORGANISM: Homo sapiens

<400> SEQUENCE: 130

```
Met Arg Thr Ser Tyr Leu Leu Leu Phe Thr Leu Cys Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65
```

<210> SEQ ID NO 131
<211> LENGTH: 64
<212> TYPE: PRT
<213> ORGANISM: Capra hircus

<400> SEQUENCE: 131

```
Met Arg Leu His His Leu Leu Leu Val Leu Phe Phe Leu Val Leu Ser
1               5                   10                  15

Ala Gly Ser Gly Phe Thr Gln Gly Ile Arg Ser Arg Arg Ser Cys His
            20                  25                  30

Arg Asn Lys Gly Val Cys Ala Leu Thr Arg Cys Pro Arg Asn Met Arg
        35                  40                  45

Gln Ile Gly Thr Cys Phe Gly Pro Pro Val Lys Cys Cys Arg Lys Lys
    50                  55                  60


<210> SEQ ID NO 132
<211> LENGTH: 64
<212> TYPE: PRT
<213> ORGANISM: Capra hircus

<400> SEQUENCE: 132

Met Arg Leu His His Leu Leu Leu Ala Leu Phe Phe Leu Val Leu Ser
1               5                   10                  15

Ala Gly Ser Gly Phe Thr Gln Gly Ile Ile Asn His Arg Ser Cys Tyr
            20                  25                  30

Arg Asn Lys Gly Val Cys Ala Pro Ala Arg Cys Pro Arg Asn Met Arg
        35                  40                  45

Gln Ile Gly Thr Cys His Gly Pro Pro Val Lys Cys Cys Arg Lys Lys
    50                  55                  60


<210> SEQ ID NO 133
<211> LENGTH: 96
<212> TYPE: PRT
<213> ORGANISM: Macaca mulatta

<400> SEQUENCE: 133

Met Arg Thr Leu Val Ile Leu Ala Ala Ile Leu Leu Val Ala Leu Gln
1               5                   10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Val Ser Leu Ala
        35                  40                  45

Trp Asp Glu Ser Leu Ala Pro Lys Asp Ser Val Pro Gly Leu Arg Lys
    50                  55                  60

Asn Met Ala Cys Tyr Cys Arg Ile Pro Ala Cys Leu Ala Gly Glu Arg
65                  70                  75                  80

Arg Tyr Gly Thr Cys Phe Tyr Arg Arg Arg Val Trp Ala Phe Cys Cys
                85                  90                  95


<210> SEQ ID NO 134
<211> LENGTH: 96
<212> TYPE: PRT
<213> ORGANISM: Macaca mulatta

<400> SEQUENCE: 134

Met Arg Thr Leu Val Ile Leu Ala Ala Ile Leu Leu Val Ala Leu Gln
1               5                   10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Val Ser Leu Ala
        35                  40                  45

Trp Asp Glu Ser Leu Ala Pro Lys Asp Ser Val Pro Gly Leu Arg Lys
    50                  55                  60

Asn Met Ala Cys Tyr Cys Arg Ile Pro Ala Cys Leu Ala Gly Glu Arg
```

```
65                  70                  75                  80

Arg Tyr Gly Thr Cys Phe Tyr Leu Gly Arg Val Trp Ala Phe Cys Cys
                85                  90                  95


<210> SEQ ID NO 135
<211> LENGTH: 33
<212> TYPE: PRT
<213> ORGANISM: Mesocricetus auratus

<400> SEQUENCE: 135

Val Thr Cys Phe Cys Arg Arg Arg Gly Cys Ala Ser Arg Glu Arg His
1               5                   10                  15

Ile Gly Tyr Cys Arg Phe Gly Asn Thr Ile Tyr Arg Leu Cys Cys Arg
            20                  25                  30

Arg


<210> SEQ ID NO 136
<211> LENGTH: 31
<212> TYPE: PRT
<213> ORGANISM: Mesocricetus auratus

<400> SEQUENCE: 136

Cys Phe Cys Lys Arg Pro Val Cys Asp Ser Gly Glu Thr Gln Ile Gly
1               5                   10                  15

Tyr Cys Arg Leu Gly Asn Thr Phe Tyr Arg Leu Cys Cys Arg Gln
            20                  25                  30


<210> SEQ ID NO 137
<211> LENGTH: 39
<212> TYPE: PRT
<213> ORGANISM: Gallus gallus

<400> SEQUENCE: 137

Gly Arg Lys Ser Asp Cys Phe Arg Lys Asn Gly Phe Cys Ala Phe Leu
1               5                   10                  15

Lys Cys Pro Tyr Leu Thr Leu Ile Ser Gly Lys Cys Ser Arg Phe His
            20                  25                  30

Leu Cys Cys Lys Arg Ile Trp
        35


<210> SEQ ID NO 138
<211> LENGTH: 43
<212> TYPE: PRT
<213> ORGANISM: Allomyrina dichotoma

<400> SEQUENCE: 138

Val Thr Cys Asp Leu Leu Ser Phe Glu Ala Lys Gly Phe Ala Ala Asn
1               5                   10                  15

His Ser Leu Cys Ala Ala His Cys Leu Ala Ile Gly Arg Arg Gly Gly
            20                  25                  30

Ser Cys Glu Arg Gly Val Cys Ile Cys Arg Arg
        35                  40


<210> SEQ ID NO 139
<211> LENGTH: 31
<212> TYPE: PRT
<213> ORGANISM: Cavia porcellus

<400> SEQUENCE: 139

Arg Arg Cys Ile Cys Thr Thr Arg Thr Cys Arg Phe Pro Tyr Arg Arg
1               5                   10                  15
```

```
Leu Gly Thr Cys Ile Phe Gln Asn Arg Val Tyr Thr Phe Cys Cys
            20                  25                  30


<210> SEQ ID NO 140
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: The residues at these positions represent
      conservatively or nonconservatively substituted amino acids, and
      may be present or absent
<220> FEATURE:
<221> NAME/KEY: MISC_FEATURE
<222> LOCATION: (4)..(4)
<223> OTHER INFORMATION: The residue at this position represents a
      conservatively or nonconservatively substituted amino acid
<220> FEATURE:
<221> NAME/KEY: MISC_FEATURE
<222> LOCATION: (7)..(9)
<223> OTHER INFORMATION: The residues at these positions represent
      conservatively or nonconservatively substituted amino acids
<220> FEATURE:
<221> NAME/KEY: MISC_FEATURE
<222> LOCATION: (10)..(10)
<223> OTHER INFORMATION: The residue at this position represents a
      conservatively or nonconservatively substituted amino acid, and
      may be present or absent
<220> FEATURE:
<221> NAME/KEY: MISC_FEATURE
<222> LOCATION: (11)..(14)
<223> OTHER INFORMATION: The residues at these positions represent
      conservatively or nonconservatively substituted amino acids
<220> FEATURE:
<221> NAME/KEY: MISC_FEATURE
<222> LOCATION: (15)..(15)
<223> OTHER INFORMATION: The residue at this position represents a
      conservatively or nonconservatively substituted amino acid, and
      may be present or absent
<220> FEATURE:
<221> NAME/KEY: MISC_FEATURE
<222> LOCATION: (18)..(18)
<223> OTHER INFORMATION: The residue at this position represents a
      conservatively or nonconservatively substituted amino acid
<220> FEATURE:
<221> NAME/KEY: MISC_FEATURE
<222> LOCATION: (19)..(20)
<223> OTHER INFORMATION: The residues at these positions represent
      conservatively or nonconservatively substituted amino acids, and
      may be present or absent
<220> FEATURE:
<221> NAME/KEY: MISC_FEATURE
<222> LOCATION: (22)..(22)
<223> OTHER INFORMATION: The residue at this position represents a
      conservatively or nonconservatively substituted amino acid, and
      may be present or absent
<220> FEATURE:
<221> NAME/KEY: MISC_FEATURE
<222> LOCATION: (24)..(28)
<223> OTHER INFORMATION: The residues at these positions represent
      conservatively or nonconservatively substituted amino acids
<220> FEATURE:
<221> NAME/KEY: MISC_FEATURE
<222> LOCATION: (29)..(32)
<223> OTHER INFORMATION: The residues at these positions represent
      conservatively or nonconservatively substituted amino acids, and
      may be present or absent
<220> FEATURE:
<221> NAME/KEY: MISC_FEATURE
<222> LOCATION: (35)..(36)
<223> OTHER INFORMATION: The residues at these positions represent
      conservatively or nonconservatively substituted amino acids, and
      may be present or absent

<400> SEQUENCE: 140
```

```
Xaa Xaa Cys Xaa Cys Arg Xaa Xaa Xaa Xaa Cys Xaa Xaa Xaa Xaa Glu
1               5                   10                  15

Arg Xaa Xaa Xaa Cys Xaa Gly Xaa Xaa Xaa Xaa Xaa Xaa Xaa Xaa Xaa
            20                  25                  30

Cys Cys Xaa Xaa
        35


<210> SEQ ID NO 141
<211> LENGTH: 30
<212> TYPE: PRT
<213> ORGANISM: Human

<400> SEQUENCE: 141

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30


<210> SEQ ID NO 142
<211> LENGTH: 29
<212> TYPE: PRT
<213> ORGANISM: Human

<400> SEQUENCE: 142

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25


<210> SEQ ID NO 143
<211> LENGTH: 30
<212> TYPE: PRT
<213> ORGANISM: Human

<400> SEQUENCE: 143

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30


<210> SEQ ID NO 144
<211> LENGTH: 33
<212> TYPE: PRT
<213> ORGANISM: Human

<400> SEQUENCE: 144

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val


<210> SEQ ID NO 145
<211> LENGTH: 33
<212> TYPE: PRT
<213> ORGANISM: Rabbit

<400> SEQUENCE: 145

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Pro Leu Cys Cys Arg
            20                  25                  30
```

```
Arg


<210> SEQ ID NO 146
<211> LENGTH: 33
<212> TYPE: PRT
<213> ORGANISM: Rabbit

<400> SEQUENCE: 146

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg


<210> SEQ ID NO 147
<211> LENGTH: 34
<212> TYPE: PRT
<213> ORGANISM: Rabbit

<400> SEQUENCE: 147

Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30

Arg Arg


<210> SEQ ID NO 148
<211> LENGTH: 34
<212> TYPE: PRT
<213> ORGANISM: Rabbit

<400> SEQUENCE: 148

Gly Arg Cys Val Cys Arg Lys Gln Leu Leu Cys Ser Tyr Arg Glu Arg
1               5                   10                  15

Arg Ile Gly Asp Cys Lys Ile Arg Gly Val Arg Phe Pro Phe Cys Cys
            20                  25                  30

Pro Arg


<210> SEQ ID NO 149
<211> LENGTH: 33
<212> TYPE: PRT
<213> ORGANISM: Rabbit

<400> SEQUENCE: 149

Val Ser Cys Thr Cys Arg Arg Phe Ser Cys Gly Phe Gly Glu Arg Ala
1               5                   10                  15

Ser Gly Ser Cys Thr Val Asn Gly Val Arg His Thr Leu Cys Cys Arg
            20                  25                  30

Arg


<210> SEQ ID NO 150
<211> LENGTH: 33
<212> TYPE: PRT
<213> ORGANISM: Rabbit

<400> SEQUENCE: 150

Val Phe Cys Thr Cys Arg Gly Phe Leu Cys Gly Ser Gly Glu Arg Ala
1               5                   10                  15

Ser Gly Ser Cys Thr Ile Asn Gly Val Arg His Thr Leu Cys Cys Arg
            20                  25                  30
```

Arg

<210> SEQ ID NO 151
<211> LENGTH: 32
<212> TYPE: PRT
<213> ORGANISM: Rat

<400> SEQUENCE: 151

```
Val Thr Cys Tyr Cys Arg Arg Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30
```

<210> SEQ ID NO 152
<211> LENGTH: 30
<212> TYPE: PRT
<213> ORGANISM: Rat

<400> SEQUENCE: 152

```
Cys Ser Cys Arg Tyr Ser Ser Cys Arg Phe Gly Glu Arg Leu Leu Ser
1               5                   10                  15

Gly Ala Cys Arg Leu Asn Gly Arg Ile Tyr Arg Leu Cys Cys
            20                  25                  30
```

<210> SEQ ID NO 153
<211> LENGTH: 31
<212> TYPE: PRT
<213> ORGANISM: Rat

<400> SEQUENCE: 153

```
Ala Cys Thr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20                  25                  30
```

<210> SEQ ID NO 154
<211> LENGTH: 31
<212> TYPE: PRT
<213> ORGANISM: Guinea pig

<400> SEQUENCE: 154

```
Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30
```

<210> SEQ ID NO 155
<211> LENGTH: 0
<212> TYPE: DNA
<213> ORGANISM: Artificial Sequence
<220> FEATURE:
<223> OTHER INFORMATION: Synthetic

<400> SEQUENCE: 155

000

<210> SEQ ID NO 156
<211> LENGTH: 0
<212> TYPE: PRT
<213> ORGANISM: Artificial Sequence
<220> FEATURE:
<223> OTHER INFORMATION: Synthetic

<400> SEQUENCE: 156

000

<210> SEQ ID NO 157
<211> LENGTH: 714
<212> TYPE: DNA
<213> ORGANISM: Artificial Sequence
<220> FEATURE:
<223> OTHER INFORMATION: Synthetic

<400> SEQUENCE: 157

```
atggcctcct ttgtctctct gctcctggtt ggcatcctat tccatgccac ccaggccgtt      60

gtgatgaccc aaattccact ctccctgcct gtcagtcttg gagatcaagc ctccatctct     120

tgcagatcta gtcagagcct tgtacacagt aatggaaaca cctatttaca ttggtacctg     180

cagaagccag gccagtctcc aaaggtcctg atctacaaag tttccaaccg attttctggg     240

gtcccagaca ggttcagtgg cagtggatca gggacagatt tcacactcaa gatcagcaga     300

gtggaggctg aggatctggg agtttatttc tgctctcaaa gtacacatgt tccgctcacg     360

ttcggtgctg ggaccaagct ggagctgaaa cgggctgatg ctgcaccaac tgtatccatc     420

ttcccaccat ccagtgagca gttaacatct ggaggtgcct cagtcgtgtg cttcttgaac     480

aacttctacc ccaaagacat caatgtcaag tggaagattg atggcagtga acgacaaaat     540

ggcgtcctga acagttggac tgatcaggac agcaaagaca gcacctacag catgagcagc     600

accctcacgt tgaccaagga cgagtatgaa cgacataaca gctatacctg tgaggccact     660

cacaagacat caacttcacc cattgtcaag agcttcaaca ggaatgagtg ttag           714
```

<210> SEQ ID NO 158
<211> LENGTH: 237
<212> TYPE: PRT
<213> ORGANISM: Artificial Sequence
<220> FEATURE:
<223> OTHER INFORMATION: Synthetic

<400> SEQUENCE: 158

```
Met Ala Ser Phe Val Ser Leu Leu Leu Val Gly Ile Leu Phe His Ala
1               5                   10                  15

Thr Gln Ala Val Val Met Thr Gln Ile Pro Leu Ser Leu Pro Val Ser
            20                  25                  30

Leu Gly Asp Gln Ala Ser Ile Ser Cys Arg Ser Ser Gln Ser Leu Val
        35                  40                  45

His Ser Asn Gly Asn Thr Tyr Leu His Trp Tyr Leu Gln Lys Pro Gly
    50                  55                  60

Gln Ser Pro Lys Val Leu Ile Tyr Lys Val Ser Asn Arg Phe Ser Gly
65                  70                  75                  80

Val Pro Asp Arg Phe Ser Gly Ser Gly Ser Gly Thr Asp Phe Thr Leu
                85                  90                  95

Lys Ile Ser Arg Val Glu Ala Glu Asp Leu Gly Val Tyr Phe Cys Ser
            100                 105                 110

Gln Ser Thr His Val Pro Leu Thr Phe Gly Ala Gly Thr Lys Leu Glu
        115                 120                 125

Leu Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175
```

```
Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235


<210> SEQ ID NO 159
<211> LENGTH: 411
<212> TYPE: DNA
<213> ORGANISM: Artificial Sequence
<220> FEATURE:
<223> OTHER INFORMATION: Synthetic

<400> SEQUENCE: 159

atggagacag acacactcct gctatgggta ctgctgctct gggttccagg ttccactggt      60

gacacgcgtg atgttgtgat gacccaaatt ccactctccc tgcctgtcag tcttggagat     120

caagcctcca tctcttgcag atctagtcag agccttgtac acagtaatgg aaacacctat     180

ttacattggt acctgcagaa gccaggccag tctccaaagc tcctgatcta caaagtttcc     240

aaccgatttt ctggggtccc agacaggttc agtggcagtg gatcagggac agatttcaca     300

ctcaagatca gcagagtgga ggctgaggat ctgggagttt atttctgctc tcaaagtaca     360

catgttcctc cgtggacgtt tggtggaggc accaagctgg aaatcaaacg g              411


<210> SEQ ID NO 160
<211> LENGTH: 137
<212> TYPE: PRT
<213> ORGANISM: Artificial Sequence
<220> FEATURE:
<223> OTHER INFORMATION: Synthetic

<400> SEQUENCE: 160

Met Glu Thr Asp Thr Leu Leu Leu Trp Val Leu Leu Leu Trp Val Pro
1               5                   10                  15

Gly Ser Thr Gly Asp Thr Arg Asp Val Val Met Thr Gln Ile Pro Leu
            20                  25                  30

Ser Leu Pro Val Ser Leu Gly Asp Gln Ala Ser Ile Ser Cys Arg Ser
        35                  40                  45

Ser Gln Ser Leu Val His Ser Asn Gly Asn Thr Tyr Leu His Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Phe Cys Ser Gln Ser Thr His Val Pro Pro Trp Thr Phe Gly
        115                 120                 125

Gly Gly Thr Lys Leu Glu Ile Lys Arg
    130                 135


<210> SEQ ID NO 161
<211> LENGTH: 429
<212> TYPE: DNA
<213> ORGANISM: Artificial Sequence
<220> FEATURE:
<223> OTHER INFORMATION: Synthetic
```

<400> SEQUENCE: 161

```
atggagacag acacactcct gctatgggta ctgctgctct gggttccagg ttccactggt     60

gacacgcgtc agatccagtt ggtgcagtct ggacctgagc tgaagaagcc tggagagaca    120

gtcaagatct cctgcaaggc ttctgggtat accttcacaa actatggaat gaactgggtg    180

aagcaggctc caggaaaggg tttaaagtgg atgggctgga taaacaccaa cactggagag    240

ccaacatatg ctgaagagtt caaggggcgg tttgccttct ctttggaaac ctctgccagc    300

actgcctatt tgcagatcaa caacctcaaa aatgaggaca cggctacata tttctgtgca    360

agacacggtg gtaggagctg gtacttcgat gtctggggcg cagggaccac ggtcaccgtc    420

tcctcagcg                                                           429
```

<210> SEQ ID NO 162
<211> LENGTH: 143
<212> TYPE: PRT
<213> ORGANISM: Artificial Sequence
<220> FEATURE:
<223> OTHER INFORMATION: Synthetic

<400> SEQUENCE: 162

```
Met Glu Thr Asp Thr Leu Leu Leu Trp Val Leu Leu Leu Trp Val Pro
1               5                   10                  15

Gly Ser Thr Gly Asp Thr Arg Gln Ile Gln Leu Val Gln Ser Gly Pro
            20                  25                  30

Glu Leu Lys Lys Pro Gly Glu Thr Val Lys Ile Ser Cys Lys Ala Ser
        35                  40                  45

Gly Tyr Thr Phe Thr Asn Tyr Gly Met Asn Trp Val Lys Gln Ala Pro
    50                  55                  60

Gly Lys Gly Leu Lys Trp Met Gly Trp Ile Asn Thr Asn Thr Gly Glu
65                  70                  75                  80

Pro Thr Tyr Ala Glu Glu Phe Lys Gly Arg Phe Ala Phe Ser Leu Glu
                85                  90                  95

Thr Ser Ala Ser Thr Ala Tyr Leu Gln Ile Asn Asn Leu Lys Asn Glu
            100                 105                 110

Asp Thr Ala Thr Tyr Phe Cys Ala Arg His Gly Gly Arg Ser Trp Tyr
        115                 120                 125

Phe Asp Val Trp Gly Ala Gly Thr Thr Val Thr Val Ser Ser Ala
    130                 135                 140
```

<210> SEQ ID NO 163
<211> LENGTH: 393
<212> TYPE: DNA
<213> ORGANISM: Artificial Sequence
<220> FEATURE:
<223> OTHER INFORMATION: Synthetic

<400> SEQUENCE: 163

```
atggagacag acacactcct gctatgggta ctgctgctct gggttccagg ttccactggt     60

gacacgcgtg acattgtgat gacccagtct caaaaattca tgtccacatc agtaggagac    120

agggtcagcg tcacctgcaa ggccagtcag aatgtgggta ctaatgtagc ctggtttcaa    180

cagaaactag ggcaatctcc taaagcactg atttactcgg catcctaccg gttcagtgga    240

gtccctgatc gcttcacagg cagtggatct gggacagatt tcactctcac catcagcaat    300

gtgcagtctg aagacttggc agagtatttc tgtcagcaat ataacagctt tccattcacg    360

ttcggctcgg ggacaaagtt ggaaataaaa cgg                                393
```

<210> SEQ ID NO 164
<211> LENGTH: 131
<212> TYPE: PRT
<213> ORGANISM: Artificial Sequence
<220> FEATURE:
<223> OTHER INFORMATION: Synthetic

<400> SEQUENCE: 164

```
Met Glu Thr Asp Thr Leu Leu Leu Trp Val Leu Leu Leu Trp Val Pro
1               5                   10                  15

Gly Ser Thr Gly Asp Thr Arg Asp Ile Val Met Thr Gln Ser Gln Lys
            20                  25                  30

Phe Met Ser Thr Ser Val Gly Asp Arg Val Ser Val Thr Cys Lys Ala
        35                  40                  45

Ser Gln Asn Val Gly Thr Asn Val Ala Trp Phe Gln Gln Lys Leu Gly
    50                  55                  60

Gln Ser Pro Lys Ala Leu Ile Tyr Ser Ala Ser Tyr Arg Phe Ser Gly
65                  70                  75                  80

Val Pro Asp Arg Phe Thr Gly Ser Gly Ser Gly Thr Asp Phe Thr Leu
                85                  90                  95

Thr Ile Ser Asn Val Gln Ser Glu Asp Leu Ala Glu Tyr Phe Cys Gln
            100                 105                 110

Gln Tyr Asn Ser Phe Pro Phe Thr Phe Gly Ser Gly Thr Lys Leu Glu
        115                 120                 125

Ile Lys Arg
    130
```

<210> SEQ ID NO 165
<211> LENGTH: 417
<212> TYPE: DNA
<213> ORGANISM: Artificial Sequence
<220> FEATURE:
<223> OTHER INFORMATION: Synthetic

<400> SEQUENCE: 165

```
atggagacag acacactcct gctatgggta ctgctgctct gggttccagg ttccactggt     60

gacacgcgtc aggttcagct gcagcagtct gacgctgagt tggtgagacc tggggcttca    120

gtgaagatat cctgcaaacc ttctggctac accttcactg accatgctat tcactgggtg    180

aagcagaagc ctgaacaggg cctggaatgg attggatata tttctcccgg aaatggtgat    240

attaagtaca atgagaagtt caagggcaag gccacactga ctgcagacaa atcctccagc    300

actgcctaca tgcagctcaa cagcctgaca tctgaggatt ctgcagtgta tttctgtaaa    360

agatcctacg cccagtttgc ttactggggc caagggactc tggtcactgt ctctgcg       417
```

<210> SEQ ID NO 166
<211> LENGTH: 139
<212> TYPE: PRT
<213> ORGANISM: Artificial Sequence
<220> FEATURE:
<223> OTHER INFORMATION: Synthetic

<400> SEQUENCE: 166

```
Met Glu Thr Asp Thr Leu Leu Leu Trp Val Leu Leu Leu Trp Val Pro
1               5                   10                  15

Gly Ser Thr Gly Asp Thr Arg Gln Val Gln Leu Gln Gln Ser Asp Ala
            20                  25                  30

Glu Leu Val Arg Pro Gly Ala Ser Val Lys Ile Ser Cys Lys Pro Ser
        35                  40                  45
```

```
Gly Tyr Thr Phe Thr Asp His Ala Ile His Trp Val Lys Gln Lys Pro
    50                  55                  60

Glu Gln Gly Leu Glu Trp Ile Gly Tyr Ile Ser Pro Gly Asn Gly Asp
65                  70                  75                  80

Ile Lys Tyr Asn Glu Lys Phe Lys Gly Lys Ala Thr Leu Thr Ala Asp
                85                  90                  95

Lys Ser Ser Ser Thr Ala Tyr Met Gln Leu Asn Ser Leu Thr Ser Glu
            100                 105                 110

Asp Ser Ala Val Tyr Phe Cys Lys Arg Ser Tyr Ala Gln Phe Ala Tyr
        115                 120                 125

Trp Gly Gln Gly Thr Leu Val Thr Val Ser Ala
    130                 135
```

<210> SEQ ID NO 167
<211> LENGTH: 408
<212> TYPE: DNA
<213> ORGANISM: Artificial Sequence
<220> FEATURE:
<223> OTHER INFORMATION: Synthetic

<400> SEQUENCE: 167

```
atggagacag acacactcct gctatgggta ctgctgctct gggttccagg ttccactggt     60

gacacgcgta acattatgat gacacagtcg ccatcatctc tggctgtgtc tgcaggagaa    120

aaggtcacta tgagctgtaa gtccagtcaa agtgttttat acagttcaga tcagaagaac    180

tacttggcct ggtaccagca gaaaccaggg cagtctccta aactgctgat ctactgggca    240

tccactaggg aatctggtgt ccctgatcgc ttcacaggca gtggatctgg gacagatttt    300

actcttacca tcagcagtgt acaatctgaa gacctggcag tttattactg tcatcaatac    360

ctctcctcat tcacgttcgg ctcggggaca aagttggaaa tagaacgg                 408
```

<210> SEQ ID NO 168
<211> LENGTH: 136
<212> TYPE: PRT
<213> ORGANISM: Artificial Sequence
<220> FEATURE:
<223> OTHER INFORMATION: Synthetic

<400> SEQUENCE: 168

```
Met Glu Thr Asp Thr Leu Leu Leu Trp Val Leu Leu Leu Trp Val Pro
1               5                   10                  15

Gly Ser Thr Gly Asp Thr Arg Asn Ile Met Met Thr Gln Ser Pro Ser
            20                  25                  30

Ser Leu Ala Val Ser Ala Gly Glu Lys Val Thr Met Ser Cys Lys Ser
        35                  40                  45

Ser Gln Ser Val Leu Tyr Ser Ser Asp Gln Lys Asn Tyr Leu Ala Trp
    50                  55                  60

Tyr Gln Gln Lys Pro Gly Gln Ser Pro Lys Leu Leu Ile Tyr Trp Ala
65                  70                  75                  80

Ser Thr Arg Glu Ser Gly Val Pro Asp Arg Phe Thr Gly Ser Gly Ser
                85                  90                  95

Gly Thr Asp Phe Thr Leu Thr Ile Ser Ser Val Gln Ser Glu Asp Leu
            100                 105                 110

Ala Val Tyr Tyr Cys His Gln Tyr Leu Ser Ser Phe Thr Phe Gly Ser
        115                 120                 125

Gly Thr Lys Leu Glu Ile Glu Arg
    130                 135
```

<210> SEQ ID NO 169
<211> LENGTH: 420
<212> TYPE: DNA
<213> ORGANISM: Artificial Sequence
<220> FEATURE:
<223> OTHER INFORMATION: Synthetic

<400> SEQUENCE: 169

```
atggagacag acacactcct gctatgggta ctgctgctct gggttccagg ttccactggt     60

gacacgcgtg aggttcagct gcagcagtct ggggcagagc ttgtgaagcc aggggcctca    120

gtcaagttgt cctgcacagc ttctggcttc aacattatag acacctatat gcactgggtg    180

aaacagaggc ctgaacaggg cctggagtgg attggaagga ttgatcctgc gaatgataat    240

actaaatatg acccgaaatt ccagggcaag gccactataa cagctgacac atcctccaac    300

acagcctacc tgcagctcag cagcctgaca tctgaggaca ctgccgtcta ttactgtgcc    360

ctctttatta cgagggctat ggactactgg ggtcaaggaa cctcagtcac cgtctcctca    420
```

<210> SEQ ID NO 170
<211> LENGTH: 140
<212> TYPE: PRT
<213> ORGANISM: Artificial Sequence
<220> FEATURE:
<223> OTHER INFORMATION: Synthetic

<400> SEQUENCE: 170

```
Met Glu Thr Asp Thr Leu Leu Leu Trp Val Leu Leu Leu Trp Val Pro
1               5                   10                  15

Gly Ser Thr Gly Asp Thr Arg Glu Val Gln Leu Gln Gln Ser Gly Ala
            20                  25                  30

Glu Leu Val Lys Pro Gly Ala Ser Val Lys Leu Ser Cys Thr Ala Ser
        35                  40                  45

Gly Phe Asn Ile Ile Asp Thr Tyr Met His Trp Val Lys Gln Arg Pro
    50                  55                  60

Glu Gln Gly Leu Glu Trp Ile Gly Arg Ile Asp Pro Ala Asn Asp Asn
65                  70                  75                  80

Thr Lys Tyr Asp Pro Lys Phe Gln Gly Lys Ala Thr Ile Thr Ala Asp
                85                  90                  95

Thr Ser Ser Asn Thr Ala Tyr Leu Gln Leu Ser Ser Leu Thr Ser Glu
            100                 105                 110

Asp Thr Ala Val Tyr Tyr Cys Ala Leu Phe Ile Thr Arg Ala Met Asp
        115                 120                 125

Tyr Trp Gly Gln Gly Thr Ser Val Thr Val Ser Ser
    130                 135                 140
```

<210> SEQ ID NO 171
<211> LENGTH: 411
<212> TYPE: DNA
<213> ORGANISM: Artificial Sequence
<220> FEATURE:
<223> OTHER INFORMATION: Synthetic

<400> SEQUENCE: 171

```
atggagacag acacactcct gctatgggta ctgctgctct gggttccagg ttccactggt     60

gacacgcgtg atgttgtgat gacccaaatt ccactctccc tgcctgtcag tcttggagat    120

caagcctcca tctcttgcag atctagtcag agccttgtac acagtaatgg aaacacctat    180

ttacattggt acctgcagaa gccaggccag tctccaaagc tcctgatcta caaagtttcc    240

aaccgatttt ctggggtccc agacaggttc agtggcagtg gatcagggac agatttcaca    300
```

```
ctcaagatca gcagagtgga ggctgaggat ctgggagttt atttctgctc tcaaagtaca    360

catgttcctc cgtggacgtt cggtggaggc accaagctgg aaatcaaacg g             411


<210> SEQ ID NO 172
<211> LENGTH: 137
<212> TYPE: PRT
<213> ORGANISM: Artificial Sequence
<220> FEATURE:
<223> OTHER INFORMATION: Synthetic

<400> SEQUENCE: 172

Met Glu Thr Asp Thr Leu Leu Leu Trp Val Leu Leu Leu Trp Val Pro
1               5                   10                  15

Gly Ser Thr Gly Asp Thr Arg Asp Val Val Met Thr Gln Ile Pro Leu
            20                  25                  30

Ser Leu Pro Val Ser Leu Gly Asp Gln Ala Ser Ile Ser Cys Arg Ser
        35                  40                  45

Ser Gln Ser Leu Val His Ser Asn Gly Asn Thr Tyr Leu His Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Phe Cys Ser Gln Ser Thr His Val Pro Pro Trp Thr Phe Gly
        115                 120                 125

Gly Gly Thr Lys Leu Glu Ile Lys Arg
    130                 135


<210> SEQ ID NO 173
<211> LENGTH: 429
<212> TYPE: DNA
<213> ORGANISM: Artificial Sequence
<220> FEATURE:
<223> OTHER INFORMATION: Synthetic

<400> SEQUENCE: 173

atggagacag acacactcct gctatgggta ctgctgctct gggttccagg ttccactggt     60

gacacgcgtc agatccagtt ggtgcagtct ggacctgagc tgaagaagcc tggagagaca    120

gtcaagatct cctgcaaggc ttctgggtat accttcacaa actatggaat gaactgggtg    180

aagcaggctc caggaaaggg tttaaagtgg atgggctgga taaacaccaa cactggagag    240

ccaacatatg ctgaagagtt caaggggcgg tttgccttct ctttggaaac ctctgccagc    300

actgcctatt tgcagatcaa caacctcaaa aatgaggaca cggctacata tttctgtgca    360

agacacggtg gtaggagctg gtacttcgat gtctggggcg cagggaccac ggtcaccgtc    420

tcctcagct                                                            429


<210> SEQ ID NO 174
<211> LENGTH: 143
<212> TYPE: PRT
<213> ORGANISM: Artificial Sequence
<220> FEATURE:
<223> OTHER INFORMATION: Synthetic

<400> SEQUENCE: 174

Met Glu Thr Asp Thr Leu Leu Leu Trp Val Leu Leu Leu Trp Val Pro
1               5                   10                  15
```

```
Gly Ser Thr Gly Asp Thr Arg Gln Ile Gln Leu Val Gln Ser Gly Pro
            20                  25                  30

Glu Leu Lys Lys Pro Gly Glu Thr Val Lys Ile Ser Cys Lys Ala Ser
        35                  40                  45

Gly Tyr Thr Phe Thr Asn Tyr Gly Met Asn Trp Val Lys Gln Ala Pro
    50                  55                  60

Gly Lys Gly Leu Lys Trp Met Gly Trp Ile Asn Thr Asn Thr Gly Glu
65                  70                  75                  80

Pro Thr Tyr Ala Glu Glu Phe Lys Gly Arg Phe Ala Phe Ser Leu Glu
                85                  90                  95

Thr Ser Ala Ser Thr Ala Tyr Leu Gln Ile Asn Asn Leu Lys Asn Glu
            100                 105                 110

Asp Thr Ala Thr Tyr Phe Cys Ala Arg His Gly Gly Arg Ser Trp Tyr
        115                 120                 125

Phe Asp Val Trp Gly Ala Gly Thr Thr Val Thr Val Ser Ser Ala
    130                 135                 140


<210> SEQ ID NO 175
<211> LENGTH: 390
<212> TYPE: DNA
<213> ORGANISM: Artificial Sequence
<220> FEATURE:
<223> OTHER INFORMATION: Synthetic

<400> SEQUENCE: 175

atggagacag acacactcct gctatgggta ctgctgctct gggttccagg ttccactggt      60

gacacgcgtc aaattgttct cacccagtct ccagcaatca tgtctgcatc tccaggggag     120

aaggtcacca taacctgcag tgccagctca agtgtaagtt acatgcactg gttccagcag     180

aagccaggca cttctcccaa actctggatt tatagcacat ccaacctggc ttctggagtc     240

cctgctcgct tcagtggcag tggatctggg acctcttact ctctcacaat cagccgaatg     300

gaggctgaag atgctgccac ttattactgc cagcaaagga gtagttaccc acctacgttc     360

ggtgctggga ccaagctgga gctgaaacgg                                      390


<210> SEQ ID NO 176
<211> LENGTH: 130
<212> TYPE: PRT
<213> ORGANISM: Artificial Sequence
<220> FEATURE:
<223> OTHER INFORMATION: Synthetic

<400> SEQUENCE: 176

Met Glu Thr Asp Thr Leu Leu Leu Trp Val Leu Leu Leu Trp Val Pro
1               5                   10                  15

Gly Ser Thr Gly Asp Thr Arg Gln Ile Val Leu Thr Gln Ser Pro Ala
            20                  25                  30

Ile Met Ser Ala Ser Pro Gly Glu Lys Val Thr Ile Thr Cys Ser Ala
        35                  40                  45

Ser Ser Ser Val Ser Tyr Met His Trp Phe Gln Gln Lys Pro Gly Thr
    50                  55                  60

Ser Pro Lys Leu Trp Ile Tyr Ser Thr Ser Asn Leu Ala Ser Gly Val
65                  70                  75                  80

Pro Ala Arg Phe Ser Gly Ser Gly Ser Gly Thr Ser Tyr Ser Leu Thr
                85                  90                  95

Ile Ser Arg Met Glu Ala Glu Asp Ala Ala Thr Tyr Tyr Cys Gln Gln
            100                 105                 110

Arg Ser Ser Tyr Pro Pro Thr Phe Gly Ala Gly Thr Lys Leu Glu Leu
```

```
        115                 120                 125

Lys Arg
    130


<210> SEQ ID NO 177
<211> LENGTH: 423
<212> TYPE: DNA
<213> ORGANISM: Artificial Sequence
<220> FEATURE:
<223> OTHER INFORMATION: Synthetic

<400> SEQUENCE: 177

atggagacag acacactcct gctatgggta ctgctgctct gggttccagg ttccactggt      60

gacacgcgtg aggtccagct gcagcagtct ggacctgagc tagtgaagac tggggcttca     120

gtgaagatat cctgcaaggc ttctggttac tcattcactg gttactacat gcactgggtc     180

aagcagagcc atggaaagag ccttgagtgg attggatata ttagttgtta caatggtgct     240

actagctaca accagaagtt caagggcaag gccacattta ctgtagacac atcctccagc     300

acagcctaca tgcagttcaa cagcctgaca tctgaagact ctgcggtcta ttactgtgca     360

agatcgacta tgagggggt tatggactac tggggtcaag gaacctcagt caccgtctcc      420

tca                                                                   423


<210> SEQ ID NO 178
<211> LENGTH: 141
<212> TYPE: PRT
<213> ORGANISM: Artificial Sequence
<220> FEATURE:
<223> OTHER INFORMATION: Synthetic

<400> SEQUENCE: 178

Met Glu Thr Asp Thr Leu Leu Leu Trp Val Leu Leu Leu Trp Val Pro
1               5                   10                  15

Gly Ser Thr Gly Asp Thr Arg Glu Val Gln Leu Gln Gln Ser Gly Pro
            20                  25                  30

Glu Leu Val Lys Thr Gly Ala Ser Val Lys Ile Ser Cys Lys Ala Ser
        35                  40                  45

Gly Tyr Ser Phe Thr Gly Tyr Tyr Met His Trp Val Lys Gln Ser His
    50                  55                  60

Gly Lys Ser Leu Glu Trp Ile Gly Tyr Ile Ser Cys Tyr Asn Gly Ala
65                  70                  75                  80

Thr Ser Tyr Asn Gln Lys Phe Lys Gly Lys Ala Thr Phe Thr Val Asp
                85                  90                  95

Thr Ser Ser Ser Thr Ala Tyr Met Gln Phe Asn Ser Leu Thr Ser Glu
            100                 105                 110

Asp Ser Ala Val Tyr Tyr Cys Ala Arg Ser Thr Met Arg Gly Val Met
        115                 120                 125

Asp Tyr Trp Gly Gln Gly Thr Ser Val Thr Val Ser Ser
    130                 135                 140


<210> SEQ ID NO 179
<211> LENGTH: 7
<212> TYPE: PRT
<213> ORGANISM: Artificial Sequence
<220> FEATURE:
<223> OTHER INFORMATION: Synthetic

<400> SEQUENCE: 179

Lys Leu Ala Lys Lys Leu Ala
1               5
```

<210> SEQ ID NO 180
<211> LENGTH: 7
<212> TYPE: PRT
<213> ORGANISM: Artificial Sequence
<220> FEATURE:
<223> OTHER INFORMATION: Synthetic

<400> SEQUENCE: 180

Lys Leu Ala Lys Leu Ala Lys
1               5

<210> SEQ ID NO 181
<211> LENGTH: 21
<212> TYPE: PRT
<213> ORGANISM: Artificial Sequence
<220> FEATURE:
<223> OTHER INFORMATION: Synthetic

<400> SEQUENCE: 181

Lys Ala Leu Lys Ala Leu Lys Lys Ala Leu Lys Ala Leu Lys Lys Ala
1               5                   10                  15

Leu Lys Ala Leu Lys
            20

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Lys Leu Gly Lys Lys Leu Gly
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic

<400> SEQUENCE: 183

Lys Ala Ala Lys Lys Ala Ala
1               5

<210> SEQ ID NO 184
<211> LENGTH: 5
<212> TYPE: PRT
<213> ORGANISM: Artificial Sequence
<220> FEATURE:
<223> OTHER INFORMATION: Synthetic

<400> SEQUENCE: 184

Ser Gly Gly Gly Gly
1               5

<210> SEQ ID NO 185
<211> LENGTH: 15
<212> TYPE: PRT
<213> ORGANISM: Artificial Sequence
<220> FEATURE:
<223> OTHER INFORMATION: Synthetic

<400> SEQUENCE: 185

Ser Gly Gly Gly Gly Ser Gly Gly Gly Gly Ser Gly Gly Gly Gly

```
1               5                   10                  15


<210> SEQ ID NO 186
<211> LENGTH: 17
<212> TYPE: PRT
<213> ORGANISM: Artificial Sequence
<220> FEATURE:
<223> OTHER INFORMATION: Synthetic

<400> SEQUENCE: 186

Ser Gly Gly Gly Gly Ser Gly Gly Gly Gly Ser Gly Gly Gly Gly Ser
1               5                   10                  15

Pro


<210> SEQ ID NO 187
<211> LENGTH: 11
<212> TYPE: PRT
<213> ORGANISM: Artificial Sequence
<220> FEATURE:
<223> OTHER INFORMATION: Synthetic

<400> SEQUENCE: 187

Gly Gly Gly Gly Ser Gly Gly Gly Gly Gly Ser
1               5                   10


<210> SEQ ID NO 188
<211> LENGTH: 17
<212> TYPE: PRT
<213> ORGANISM: Artificial Sequence
<220> FEATURE:
<223> OTHER INFORMATION: Synthetic

<400> SEQUENCE: 188

Ser Ser Ser Ser Gly Ser Ser Ser Ser Gly Ser Ser Ser Ser Gly Ser
1               5                   10                  15

Pro
```

TARGETED CRYPTOSPORIDIUM BIOCIDES

CROSS REFERENCE TO RELATED APPLICATIONS

This application claims priority to U.S. provisional application 61/144,299, filed Jan. 13, 2009, which is herein incorporated by reference in its entirety. This application is also a continuation in part of Ser. No. 12/536,291, filed Aug. 5, 2009, now abandoned, which is a divisional of Ser. No. 11/545,601, filed Oct. 10, 2006, now abandoned, which is a continuation in part of Ser. No. 11/254,500, filed Oct. 20, 2005, now U.S. Pat. No. 7,566,447, which is a continuation in part of Ser. No. 10/844,837, filed May 13, 2004, now abandoned, which claims priority to 60/470,841, filed May 15, 2003, each of which are herein incorporated by reference in its entirety.

FIELD OF THE INVENTION

The present invention relates to fusion proteins comprising a microorganism targeting molecule (e.g., immunoglobulin) and a biocide. The present invention also relates to therapeutic and prophylactic methods of using a fusion protein comprising a microorganism targeting molecule and a biocide in diverse fields.

BACKGROUND OF THE INVENTION

Cryptosporidiosis, caused by *Cryptosporidium* spp., the apicomplexan parasite first described by Tyzzer 100 years ago (Tyzzer, Proc Soc Exp Biol Med 1907; 5:12-3), is amongst the most serious diarrheal diseases of humans and livestock species worldwide. *Cryptosporidium* is a Category B biothreat pathogen.

Cryptosporidiosis is an important burden on society. Human patients comprise three major groupings. Immunocompromised patients are most severely affected. Cryptosporidiosis is a serious complication of HIV AIDS, causing chronic diarrhea with weight loss and wasting. Infection may spread beyond the intestinal tract to other mucosae (Cama et al., J Infect Dis 2007 September 1; 196(5):684-91). Wider availability of antiretroviral drugs has reduced the threat of opportunistic infections with *Cryptosporidium* spp., but it remains an important complication of HIV, and especially so in developing countries where antiretroviral drugs are not as available. Other immunocompromised individuals, including cancer, transplant, and chemotherapy patients, are at risk (Sulzyc-Bielicka et al., J Parasitol 2007 June; 93(3):722-4; Hong et al., Pediatr Transplant 2007 February; 11(1):94-100).

Otherwise healthy patients, infected sporadically when exposed to *Cryptosporidium* contaminated water or fecally-contaminated food, typically develop severe debilitating stomach cramps and diarrhea that is self limiting and usually not fatal (Chappell et al., Am J Trop Med Hyg 1999 January; 60(1):157-64). Serologic studies indicate that approximately 20% of individuals in the US experience cryptosporidial infections in their youth, with much higher incidence, over 80%, in some areas (Kuhls et al., Clin Infect Dis 1994 May; 18(5):731-5; Leach et al., Am J Trop Med Hyg 2000 May; 62(5):656-61). Cryptosporidiosis is a leading cause of "travelers diarrhea" (Roy et al., J Clin Microbiol 2004 July; 42(7): 2944-51; Okhuysen, Clin Infect Dis 2001 Jul. 1; 33(1):110-4). Outbreaks have affected child daycare and elder-care centers (Naumova et al., Emerg Infect Dis 2003 April; 9(4): 418-25; Diers et al., J Parasitol 1989 August; 75(4):637-8). Large outbreaks have resulted from exposure to contaminated water, both drinking water or recreational water in water parks and swimming pools. Flooding events, such as follow hurricanes and heavy rains, place populations at high risk to exposure to *Cryptosporidium* from both human and animal fecal contaminated water (Sinigalliano et al., Proc Natl Acad Sci USA 2007 May 22; 104(21):9029-34).

Exposure to cattle can be an occupational risk for *C. parvum* infection (Gait et al., Vet Rec 2008 Jun. 28; 162(26):843-5). *C. hominis* and *C. parvum* are categorized as Category B pathogens because of their ability to cause large outbreaks of debilitating disease, and the very low infective dose (10-100 oocysts) of the highly resistant oocysts in healthy adults (Okhuysen et al., Int J Parasitol 2002 May; 32(5):517-25).

In tropical and developing countries *Cryptosporidium* spp are a common cause of diarrheal disease, especially among children living in impoverished conditions (Newman et al., Ann Intern Med 1994 Mar. 15; 120(6):500-5; Zu et al., Am J Trop Med Hyg 1994 July; 51(1):1-10; Jacobsen et al., J Health Popul Nutr 2007 December; 25(4):399-405).

In livestock cryptosporidiosis is an economically important disease especially in neonatal ruminants and *C. parvum* is one of the most common causes of diarrheal disease in calves under one month of age (Santin et al., In: Fayer R, Xiao L, eds. *Cryptosporidium* and Cryptosporidiosis. 2nd ed. Boca Raton: CRC, 2008). Cattle may become asymptomatic long term shedders of oocysts (Casemore et al., Cryptosporidiosis—Human and Animal Epidemiology. In: Fayer R. et al, ed. Cruptosporidium and Cryptosporidiosis. Boca Raton: CRC Press, 2002. p. 65-92). Cryptosporidiosis can be fatal to calves when accompanied by other enteropathogens, and other economic losses arise from lost productivity, increased labor and veterinary costs (de G et al., Int J Parasitol 1999 August; 29(8):1269-87). Infected animals shed large numbers of *C. parvum* oocysts and thus serve as a reservoir for direct and indirect infection of humans and other livestock.

Despite the significant disease and economic burden arising from cryptosporidiosis, and the screening of many drug compounds, there are currently no consistently effective drugs available (Abubakar et al., Br J Clin Pharmacol 2007 April; 63(4):387-93; Zardi et al., Chemotherapy 2005 July; 51(4):193-6; Zhu, Biochemistry. In: Fayer R, Xiao L, eds. *Cryptosporidium* and Cryptosporidiosis. 2nd ed. Boca Raton: CRC, 2008; Stockdale et al., Prophylaxis and Chemotherapy. In: Fayer R, Xiao L, eds. *Cryptosporidium* and Cryptosporidiosis. 2nd ed. Boca Raton: CRC, 2008). Genome information suggests *Cryptosporidium* lacks many drug targets found in other apicomplexan parasites (Zhu, 2008, supra).

A broad spectrum antiprotozoal thiazolide drug, Nitazoxanide (Alinia®, Romark), was approved in 2002 (children) and 2005 (adults) for cryptosporidiosis and giardiasis, however *Cryptosporidium* lacks the enzyme target for this drug and results are mixed (Zhu, supra). Paromomycin (Humatin® Parke Davis), used to treat amebiasis, is not highly effective against cryptosporidiosis in vivo, allowing continued oocyst shedding and occasionally leading to problematic biliary infections (Stockdale et al., supra). The consensus is that a therapy for cryptosporidiosis is still urgently needed (Tzipori et al., Trends Parasitol 2008 April; 24(4):184-9). Treatment now relies heavily on symptomatic and supportive measures, such as rehydration (Abubakar et al., supra).

A large number of potential therapeutic agents have been tested in animal models. A few drugs have been tested in the field for veterinary use. Halofuginone lactate (Halocur®, Intervet) has been approved for use in several European countries. Paromomycin sulphate (Gabbrovet®, Ceva Sante Animale) is only available as an injectable against bacterial infections in a couple of countries for piglets, calves and poultry. There is off-label use against *Cryptosporidium* and *Giardia*. These drugs are regarded as suppressive but not curative against *Cryptosporidium*.

Therefore, development of an effective therapeutic for cryptosporidium remains a major unresolved medical need. A well tolerated, highly effective drug to be administered orally would provide lifesaving benefit immunocompromised patients, and would provide relief from debilitating diarrhea and minimize spread to other patients. It would provide a means to manage large outbreaks, and in tropical countries would enhance the quality of life for many for whom sequential childhood diseases stunt physical and intellectual development. An effective anticryptosporidial which can be easily administered to young calves would have immediate economic benefits, and would reduce the reservoir for zoonotic infection.

SUMMARY OF THE INVENTION

The present invention relates to fusion proteins comprising a microorganism targeting molecule (e.g., immunoglobulin) and a biocide. The present invention also relates to therapeutic and prophylactic methods of using a fusion protein comprising a microorganism targeting molecule and a biocide in diverse fields.

For example, in some embodiments, the present invention provides a composition comprising a recombinant fusion protein, wherein said fusion protein comprises an immunoglobulin that binds to a *Cryptosporidium* spp., wherein the immunoglobulin comprises a pair of polypeptides comprising a heavy chain and a light chain and wherein the variable regions of said pair of polypeptides have amino acid sequences selected from, for example SEQ ID NOs: 34:36, 38:40 or 42:44 or sequences that are at least 90%, or at least 95% identical or similar to the aforementioned sequences; and wherein the immunoglobulin is joined to at least a portion of a protein biocide molecule. In some embodiments, the microorganism targeting molecule and the at least a portion of a protein biocide molecule are joined by a poly amino acid linker molecule from about 2 to 500 amino acids long (e.g., from about 5 to 100 amino acids long or about 10 to 30 amino acids long). In some embodiments, the poly amino acid linker molecule is composed of amino acids including, but not limited to Gly, Ser, Asn, Thr, Ala, and Pro. In some embodiments, the amino acid linker comprises a sequence of amino acid residues having the formula: $(Ser_n\text{-}Gly_x)_y$ wherein $n \geqq 1$, wherein $x \geqq 1$, and wherein $y \geqq 1$. In some embodiments, n=1, x=4, and $y \geqq 1$ (e.g., 1, 2, 3, 4, 5, 6, 7, or 8). In some embodiments, the protein biocide comprises at least an active portion of an enzyme. In some embodiments, the protein biocide is lysozyme, phopholipase A2, lactoferrin, lactoperoxidase, bacterial permeability increasing protein, lysostaphin, aprotinin, a cathelicidin or cathelicidin derived peptide (e.g., LL37), or a defensin (e.g., an alphadefensin or a betadefensin). In some embodiments, the pair of polypeptides have amino acid sequences selected, for example, SEQ ID NOs 2:10, 20:24, 26:32 or sequences that are at least 90%, or at least 95% identical or similar to the aforementioned sequences. In some embodiments, the fusion protein comprises immunoglobulin heavy chain having an amino acid sequence selected from, for example, SEQ ID NOs: 4, 6, 8, 14, 16, 18, 22, 28, or 30 or sequences that are at least 90%, or at least 95% identical or similar to the aforementioned sequences.

Some embodiments of the present invention provide a composition comprising a recombinant fusion protein, wherein the fusion protein comprises an immunoglobulin that binds to a *Cryptosporidium* spp., wherein said immunoglobulin comprises a pair of polypeptides comprising a heavy chain and a light chain having amino acid sequences selected from, for example, SEQ ID NOs: 10:6, 10:8, 10:4, 10:2, 158:4, 24:12, 24:14, 24:16, 24:18, 24:20, 24:22, 32:26, 32:28, 32:30 or sequences that are at least 95% identical to the aforementioned sequences.

Further embodiments of the present invention provide a vector construct comprising a nucleic acid sequence encoding a recombinant fusion protein, wherein said fusion protein comprises an immunoglobulin that binds to a *Cryptosporidium* spp., wherein the immunoglobulin comprises a pair of polypeptides comprising a heavy chain and a light chain and wherein the variable regions of said pair of polypeptides have amino acid sequences selected from, for example, SEQ ID NOs: 34:36, 38:40 or 42:44 or sequences that are at least 90%, or at least 95% identical or similar to the aforementioned sequences; joined to at least a portion of a protein biocide molecule. In some embodiments, the variable regions of said pair of polypeptides are encoded by a nucleic acid sequence selected from the group including, but not limited to SEQ ID NOs: 1:9, 23:11, 25:31 or 19:23 or sequences that are at least 90%, or at least 95% identical or similar to the aforementioned sequences. In some embodiments, the vector is a retroviral vector. In some embodiments, the vector is in a cell. In some embodiments, the cell is in a non human animal (e.g., a bovine).

Additional embodiments of the present invention provide a method of treating a subject, comprising: contacting a subject suspected of being infected with, at risk of being infected with or infected with a *Cryptosporidium* spp. or other apicomplexan protozoan with a recombinant fusion protein, wherein said fusion protein comprises an immunoglobulin that binds to a *Cryptosporidium* spp., wherein the immunoglobulin comprises a pair of polypeptides comprising a heavy chain and a light chain and wherein the variable regions of said pair of polypeptides have amino acid sequences selected from, for example SEQ ID NOs: SEQ ID NOs 2:10, 20:24, 26:32 160:162, 164:166, 168:170, 172:174 or 176:178 or sequences that are at least 90%, or at least 95% identical or similar to the aforementioned sequences; joined to at least a portion of a protein biocide molecule under conditions such that the recombinant fusion protein neutralizes the *Cryptosporidium* spp. or prevents infection by the *Cryptosporidium* spp. In some embodiments, the subject is a mammal (e.g., a human or a ruminant (e.g., bovine). In some embodiments, the fusion protein is delivered to the subject orally, in fluid pill or capsule form. In some embodiments, oral delivery comprises milk or a milk based fluid.

Other embodiments of the present invention provide a transgenic organism comprising a nucleic acid sequence encoding a recombinant fusion protein, wherein said fusion protein comprises an immunoglobulin that binds to a *Cryptosporidium* spp., wherein the immunoglobulin comprises a pair of polypeptides comprising a heavy chain and a light chain and wherein the variable regions of said pair of polypeptides have amino acid sequences selected from, for example SEQ ID NOs: SEQ ID NOs 2:10, 20:24, 26:32 160:162, 164:166, 168:170, 172:174 or 176:178 or sequences that are at least 90%, or at least 95% identical or similar to the aforementioned sequences; joined to at least a portion of a protein biocide molecule. In some embodiments, the transgenic organism is selected from an animal, a plant, or a microorganism.

DESCRIPTION OF THE FIGURES

FIG. 2 shows activity of candidate antimicrobial peptides against *C. parvum* sporozoite infectivity in vitro. Activity of MAb 3E2, lactoferrin (LF), lactoferrin pepsin-hydrolysate (LFH), lactoferricin B (LFB), LL37 (CAT), indolicidin (IND), β-defensin 1 (BD1), β-defensin 2 (BD2), lysozyme (LYZ), bee venom phospholipase A2 (PLA2), or phosphoinositol phospholipase C (PI-PLC) against *C. parvum* sporozoite infectivity for Caco-2 human intestinal epithelial cells in vitro.

FIG. 9 shows sequences of exemplary directed biocides and antibodies of the present invention.

FIG. 12 shows the efficacy of exemplary directed biocides of the present invention in a neonatal mouse model. Recombinant fusion products 3E2IgM monomer linked to LL37, 3E2 halfmer IgM linked toLL37, and 3E2 IgM hexamer linked to LL37 are compared to recombinant fusion 4H9-LL37 and a recombinant IgG immunoglobulin with the variable region from 3E2 (but no biocide fusion). Dosages are shown in mg/kg/day.

FIG. 14 shows a list of exemplary immunoglobulins and directed biocides of embodiments of the present invention.

DEFINITIONS

Figure 1:
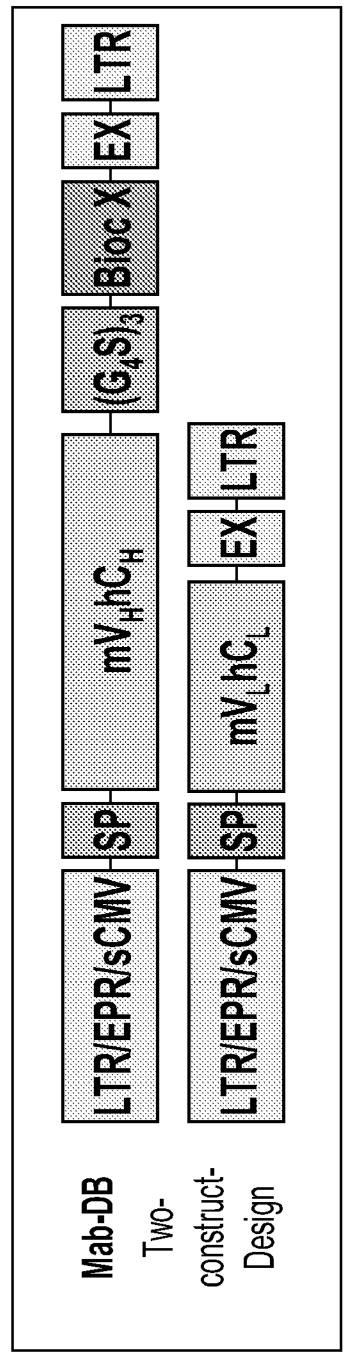
FIG. 1 shows genetic constructs for making mouse-human chimeric immunoglobulin biocide fusion protein using the MLV-based retroviral vector. LTR=long terminal repeat, EPR=extended packaging region, sCMV=simian cytomegalo virus promoter, SP=signal peptide, mVH=murine heavy chain variable region, mVL=murine light chain variable region, hCH=human heavy chain constant region, hCL=human light chain constant region, EX=RNA export signal, (G4S)3=glycine-serine linker, Bioc=biocide.

To facilitate an understanding of the present invention, a number of terms and phrases are defined below:

"A recombinant antibody that binds to a surface epitope of *Cryptosporidium* sp." refers to a recombinantly expressed monoclonal antibody that binds to a specific epitope on the surface of *Cryptosporidium* sp. Exemplary *Cryptosporidium* spp. epitopes include, but are not limited to, GP25-200, p23, CSL, or beta-mannosylated glycolipid. Exemplary recombinant monoclonal antibodies include, but are not limited to 3E2, which recognizes CSL, 1E10, which recognizes p23, 3H2, which recognizes GP25-200, 4H9, which recognizes GP25-200, 18.44, which recognizes beta-mannosylated glycolipid.

"Antigen binding protein" refers to proteins that bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries.

Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*. For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]).

In other embodiments, suitable monoclonal antibodies, including recombinant chimeric monoclonal antibodies and chimeric monoclonal antibody fusion proteins are prepared as described herein. According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity. In some embodiments, monoclonal antibodies are generated using the ABL-MYC method (See e.g., U.S. Pat. Nos. 5,705,150 and 5,244,656, each of which is herein incorporated by reference) (Neoclone, Madison, Wis.). ABL-MYC is a recombinant retrovirus that constitutively expresses v-abl and c-myc oncogenes. When used to infect antigen-activated splenocytes, this retroviral system rapidly induces antigen-specific plasmacytomas. ABL-MYC targets antigen-stimulated (Ag-stimulated) B-cells for transformation. Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent. Genes encoding antigen-binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

"Biocide" or "biocides," as used herein, refer to at least a portion of a naturally occurring or synthetic molecule (e.g., peptides) that directly kills or promotes the death and/or attenuation of, or otherwise neutralizes infectivity without killing (e.g., prevents growth and/or replication) of biological targets (e.g., bacteria, parasites, yeast, viruses, fungi, protozoans and the like). Examples of biocides include, but are not limited to, bactericides, viricides, fungicides, parasiticides, and the like.

"Cell type specific" as applied to a regulatory element refers to a regulatory element which is capable of directing selective expression of a nucleotide sequence of interest in a specific type of cell in the relative absence of expression of the same nucleotide sequence of interest in a different type of cell within the same tissue (e.g., cells infected with retrovirus, and more particularly, cells infected with BLV or HTLV). The term "cell type specific" when applied to a regulatory element also means a regulatory element capable of promoting selective expression of a nucleotide sequence of interest in a region within a single tissue. The cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

"Co-administration" refers to administration of more than one agent or therapy to a subject. Co-administration may be concurrent or, alternatively, the chemical compounds described herein may be administered in advance of or following the administration of the other agent(s). One skilled in the art can readily determine the appropriate dosage for co-administration. When co-administered with another therapeutic agent, both the agents may be used at lower dosages. Thus, co-administration is especially desirable where the claimed compounds are used to lower the requisite dosage of known toxic agents.

"*Cryptosporidium* sp." refers to any species of *Cryptosporidium*. Examples include, but are not limited to, *Cryptosporidium parvum* and *Cryptosporidium hominis*.

"Dairy animal," as used herein, refers to a milk producing non-human mammal that is larger than a laboratory rodent (e.g., a mouse). In preferred embodiments, the dairy animals produce large volumes of milk and have long lactating periods (e.g., cows or goats).

"Fusion protein," as used herein, refers to a single polypeptide that comprises one or more distinct functional units (e.g., polypeptides, linkers, etc.) joined in the same polypeptide chain. In some embodiments, fusion proteins comprise an immunoglobulin and a biocide. In some embodiments, fusion proteins comprise additional components such as, for example, linkers, signal sequences, etc. Fusion protein polypeptides may be assembled with other polypeptides to provide a functional protein (eg. a fusion protein immunoglobulin heavy chain with an immunoglobulin light chain).

In some embodiments a fusion protein is expressed as a single polypeptide from a single polynucleotide in a cell; in yet other embodiments a fusion protein is assembled by chemical synthesis from multiple polypeptides.

"Genome," as used herein, refers to the genetic material (e.g., chromosomes) of an organism or a host cell.

"Halfmer" or "halfmer immunoglobulin," as used herein refers to an immunoglobin comprising one light chain and one heavy chain. Halfmer immunoglobulins may be derived from an IgM or IgG or any other immunoglobulin (e.g., an immunoglobulin that normally assembles as units of two or more light chains and two or more heavy chains). To achieve the assembly as a halfmer three substitutions are made in each of the heavy and light chains from Cysteine to serine to remove the disulphide bonds.

"Host cell," as used herein, refers to any eukaryotic cell (e.g., mammalian cells, avian cells, amphibian cells, plant cells, fish cells, insect cells, yeast cells, and bacteria cells, and the like), whether located in vitro or in vivo (e.g., in a transgenic organism).

"In operable combination," "in operable order," and "operably linked," as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

"Internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801-809 [1994]; Meyer et al., J. Virol. 69: 2819-2824 [1995]; Jang et al., 1988, J. Virol. 62: 2636-2643 [1998]; Haller et al., J. Virol. 66: 5075-5086 [1995]). Vectors incorporating IRESs may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal promoter (e.g., cytomegalovirus promoter) or an inducible promoter (e.g., the inducible promoters of the present invention), which may be preferable depending on the use. The polycistronic message cassette can further comprise a cDNA or genomic DNA (gDNA) sequence operatively associated within the polylinker.

"Isolated," when used in relation to a nucleic acid, as in "an isolated oligonucleotide" refers to a nucleic acid sequence that is identified and separated from at least one contaminant nucleic acid with which it is ordinarily associated in its natural source. Isolated nucleic acids are nucleic acids present in a form or setting that is different from that in which they are found in nature. In contrast, non-isolated nucleic acids are nucleic acids such as DNA and RNA that are found in the state in which they exist in nature.

"Long terminal repeat" or "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

"Mammals," are defined herein as all animals which have mammary glands. In some embodiments, female mammals produce milk.

"Metaphylactic," as used herein, is used to describe the administration of a therapy or treatment (e.g., drug product) both before and during the active course of a disease. For example, in the case of cryptosporidiosis, metaphylactic it is used to describe a course of treatment which encompasses the period of potential exposure to the organism and the period of active parasite infection.

"Microorganism targeting molecule," as used herein, refers to any molecule (e.g., protein) that interacts with a microorganism (e.g., parasite). In preferred embodiments, the microorganism targeting molecule specifically interacts with microorganisms at the exclusion of non-microorganism host cells. Preferred microorganism targeting molecules interact with broad classes of microorganism (e.g., all bacteria or all gram positive or negative bacteria). However, the present invention also contemplates microorganism targeting molecules that interact with a specific species or sub-species of microorganism. In some embodiments, microorganism targeting molecules are antibodies (e.g., monoclonal antibodies directed towards PAMPS or monoclonal antibodies directed to specific organisms or serotype specific epitopes).

"Monomer IgM," as used herein, is used to describe the immunoglobulin structure which comprises two light chains and two heavy chains of immunoglobulin M in which two substitutions of cysteine for serine results in abrogation of the disulphide bond, and prevents the normal assembly into a hexamer (in absence of a J chain) or pentamer (if a J chain is present).

"Neutralization" and "pathogen neutralization," as used herein refer to destruction or inactivation (e.g., loss of virulence or infectivity) of a "pathogen" (e.g., *Cryptosporidium* spp.) thus preventing the pathogen's ability to initiate a disease state in a subject or cause degradation of a food product.

"Non-specific binding" and "background binding" when used in reference to the interaction of an antibody and an antigen refer to an interaction that is not dependent on the presence of a particular structure (i.e., the antibody is binding to antigens in general rather that a particular structure such as an epitope).

"Pharmaceutical composition" is intended to include the combination of an active agent with a carrier, inert or active, making the composition suitable for diagnostic or therapeutic use in vivo, in vivo or ex vivo.

"Pharmaceutically acceptable carrier" encompasses any of the standard pharmaceutical carriers, such as a phosphate buffered saline solution, water, and an emulsion, such as an oil/water or water/oil emulsion, and various types of wetting agents. The compositions also can include stabilizers and preservatives. For examples of carriers, stabilizers and adjuvants see Martin, Remington's Pharmaceutical Sciences, 15th Ed., Mack Publ. Co., Easton, Pa. (1975).

"Pharmaceutically acceptable salt" as used herein, relates to any pharmaceutically acceptable salt (acid or base) of a compound of the present invention, which, upon administration to a recipient, is capable of providing a compound of this invention or an active metabolite or residue thereof. As is known to those of skill in the art, "salts" of the compounds of the present invention may be derived from inorganic or organic acids and bases. Examples of acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds of the invention and their pharmaceutically acceptable acid.

"Polycistronic," as used herein, refers to an mRNA encoding more than one polypeptide chain (See, e.g., WO 93/03143, WO 88/05486, and European Pat. No. 117058, each of which is incorporated herein by reference). Likewise, the term "arranged in polycistronic sequence" refers to the arrangement of genes encoding two different polypeptide chains in a single mRNA.

"Promoter" and "enhancer" elements, as used herein, refer to transcriptional control signals in eukaryotes. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review See e.g., Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1$\alpha$ gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]). In preferred embodiments, inducible retroviral promoters are utilized.

A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one that is capable of directing a level of transcription of an operably linked nucleic acid sequence in the presence of a stimulus (e.g., heat shock, chemicals, etc.), which is different from the level of transcription of the operably linked nucleic acid sequence in the absence of the stimulus.

"Promoter/enhancer," as used herein, denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter. Regulatory elements may be tissue specific or cell specific. The term "tissue specific" as it applies to a regulatory element refers to a regulatory element that is capable of directing selective expression of a nucleotide sequence of interest to a specific type of tissue (e.g., mammary gland) in the relative absence of expression of the same nucleotide sequence(s) of interest in a different type of tissue (e.g., liver). Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

"Protein biocide" and "protein biocides," as used herein, refer to at least a portion of a naturally occurring or synthetic peptide or protein molecule that directly kills or promotes the death and/or attenuation of, or otherwise neutralizes infectivity without killing (e.g., prevents growth and/or replication) of biological targets (e.g., bacteria, parasites, yeast, viruses, fungi, protozoans and the like). Examples of biocides include, but are not limited to, bactericides, viricides, fungicides, parasiticides, and the like.

"Protein of interest," as used herein, refers to a protein encoded by a nucleic acid of interest.

"Pseudotyped retroviral vector," as used herein, refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola), which is associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

"Purified" or "to purify," as used herein, refers to the removal of undesired components from a sample. As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

"Regulatory element," as used herein, refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

"Retroviral vector," as used herein, refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells that are susceptible to infection by the retrovirus. Through well-known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

"Retrovirus," as used herein, refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell.

"RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which is incorporated herein by reference) and woodchuck mRNA processing enhancer (WPRE; WO 99/14310, incorporated herein by reference).

"Specific binding" or "specifically binding" when used in reference to the interaction of an antibody and an antigen means that the interaction is dependent upon the presence of a particular structure (i.e., the antigenic determinant or epitope) on the antigen; in other words the antibody is recognizing and binding to a specific structure rather than to antigens in general. For example, if an antibody is specific for epitope "A," the presence of a protein containing epitope A (or free, unlabelled A) in a reaction containing labeled "A" and the antibody will reduce the amount of labeled A bound to the antibody.

"Splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40. Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 by BamHI/BclI restriction fragment and directs both termination and polyadenylation (Sambrook, supra, at 16.6-16.7).

"Subject" is an animal such as vertebrate, including a mammal, a bird (e.g., a chicken) or a fish. In some embodiments, the vertebrate is a mammal (e.g., a human or a bovine). Mammals, however, are understood to include, but are not limited to, murines, simians, humans, bovines, cervids, equines, porcines, canines, felines etc.).

"Transgene," as used herein, means a nucleic acid sequence (e.g., encoding one or more fusion protein polypeptides), which is introduced into the genome of a transgenic organism. A transgene can include one or more transcriptional regulatory sequences and other nucleic acid, such as introns, that may be necessary for optimal expression and secretion of a nucleic acid encoding the fusion protein. A transgene can include an enhancer sequence. A fusion protein sequence can be operatively linked to a tissue specific promoter, e.g., mammary gland specific promoter sequence that results in the secretion of the protein in the milk of a transgenic mammal, a urine specific promoter, or an egg specific promoter.

"Transgenic animal," as used herein, is a non-human animal in which one or more, and preferably essentially all, of the cells of the animal contain a transgene introduced by way of human intervention, such as by transgenic techniques known in the art. The transgene can be introduced into the cell, directly or indirectly by introduction into a precursor of the cell, by way of deliberate genetic manipulation, such as by microinjection or by infection with a recombinant virus.

"Transgenic cell," as used herein, refers to a cell containing a transgene.

"Transgenic organism," as used herein, refers to a transgenic animal or plant.

"Vector," as used herein, refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors.

"Viral replicons" or "viral origins of replication" are elements sometimes included in eukaryotic expression vectors. Viral replicons are viral DNA sequences that allow for the extrachromosomal replication of a vector in a host cell expressing the appropriate replication factors. Vectors that contain either the SV40 or polyoma virus origin of replication replicate to high "copy number" (up to 104 copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

DETAILED DESCRIPTION OF THE INVENTION

Embodiments of the present invention provide therapeutic and prophylactic compositions directed to combating *Cryptosporidium* spp. infections in humans and other animals (e.g., agriculturally important animals such as cows).

In preferred embodiments, the present invention provides fusion proteins comprising microorganism targeting molecules (e.g., including, but not limited to, monoclonal antibodies) directed against *Cryptosporidium* spp. and methods of using and creating these molecules. In some of these embodiments, the antibodies are chimeras (e.g., murine-bovine). The present invention is not limited however to providing fusion proteins or chimeras.

In some embodiments, the fusion proteins comprise one or more portions of an immunoglobulin and a portion of a biocide molecule, such as bactericides, viricides, fungicides, parasiticides, and the like. In preferred embodiments, the present invention provides antibody biocide fusion proteins, wherein the biocide component comprises an enzyme such as human lysozyme, phospholipase A2 (groups I, II, V, X, and XII), lactoferrin, lactoperoxidase, and bacterial permeability increasing protein or an antibacterial peptide such as a cathelicidin, cathelicidin derived peptide, or defensin. In additional embodiments, the present provides fusion proteins comprising immune system complement proteins including cytokines such as the interferons (e.g., IFN-α, IFN-β, and IFN-γ) and the tumor necrosis factors (e.g., TNF-α, and TNF-β). In preferred embodiments, the antibody portion of these fusion proteins binds specifically to a *Cryptosporidium* spp.

In some embodiments, the fusion proteins of the present invention are purified from the lactational secretions of transgenic non-human mammals such as, cows, pigs, sheep, and goats. In particularly preferred embodiments, the transgenic animal is a cow. Consequently, the present invention further provides novel genetic constructs and methods of producing transgenic animals that express the compositions of the present invention in their lactation.

The present invention also provides methods of stably transfecting cell lines (e.g., mammalian) with vectors encoding the fusion proteins disclosed herein. In preferred embodiments, the constructs of the present invention allow complex multicistronic gene constructs to be stably inserted into cells (e.g., mammalian). The production of fusion proteins in mammalian cell lines (or in transgenic mammals) allows for their proper assembly and processing. Another method suitable for use in some embodiments of the present invention is protein production in mammalian tissue culture bioreactors.

Monoclonal antibodies are typically produced in mammalian cells to ensure correct processing, however mammalian tissue culture bioreactors are often expensive to operate thus placing products beyond mass applications. The ability to manufacture monoclonals in the milk of transgenic animals (e.g., bovines) is contemplated to expand the scope of monoclonal antibodies typically from individual medicine to applications for large populations. Production of the disclosed compositions in the milk of transgenic mammals (e.g., bovines) provides large quantities for economical distribution to food safety and processing operations. For instance, in preferred embodiments, the present invention contemplates that at reasonable expression levels of about one gram per liter of milk, a herd of 100 transgenic cows will produce about a metric ton of recombinant protein per year. This enables production of recombinant monoclonals at 100 fold less cost than in cell culture bioreactors. Accordingly, in preferred embodiments the present invention provides methods of creating transgenic bovines that produce the compositions of the present invention in their lactation.

In still further embodiments, the present invention provides fusion protein enriched colostrum, or colostrum like products, for use as milk substitutes and nutritional supplements for nursing mammals and in particular for nursing feedlot animals. In preferred embodiments, these compositions comprise the microorganism targeting molecule fusion proteins of the present invention.

In preferred embodiments, the compositions of the present invention comprise a targeting molecule, for example an immunoglobulin subunit (or portion thereof), a biocide molecule (or portion thereof), and a linker that connects the targeting molecule and the biocide molecule. In other preferred embodiments, the compositions further comprise a signaling molecule or sequence that predictably directs the composition to an intracellular or extracellular location.

The present invention further provides a recombinant fusion protein for treatment or prevention of a microbial infection wherein said recombinant fusion protein is delivered orally. In a preferred embodiment the recombinant fusion protein material is delivered in a liquid form, including delivery in milk or a milk based liquid or in colostrum. In other embodiments the oral delivery is accomplished by including the recombinant fusion protein in a capsule. In some forms of oral delivery the recombinant fusion protein is protected from gastrointestinal secretions by the inclusion of or co-treatment with an antacid (e.g., omeprazole, cimetidine). A particular embodiment includes the delivery of the recombinant fusion protein to neonatal calves and piglets as a supplement to milk or colostrum delivered in a bottle or bucket to the young animal.

I. Directed Biocides

As described above, embodiments of the present invention provide directed biocides comprising a targeting moiety (e.g., immunoglobulin) and a biocide. Examplary, non limiting examples of biocides are described below.

A. Microorganism Targeting Moiety

In some embodiments, the microorganism targeting moiety is an immunoglobulin. Immunoglobulins (antibodies) are proteins generated by the immune system to provide a specific molecule capable of complexing with an invading molecule commonly referred to as an antigen. Natural antibodies have two identical antigen-binding sites, both of which are specific to a particular antigen. The antibody molecule recognizes the antigen by complexing its antigen-binding sites with areas of the antigen termed epitopes. The epitopes fit into the conformational architecture of the antigen-binding sites of the antibody, enabling the antibody to bind to the antigen.

i. Immunoglobulins

The immunoglobulin molecule is composed of two identical heavy and two identical light polypeptide chains, held together by interchain disulfide bonds. Each individual light and heavy chain folds into regions of about 110 amino acids, assuming a conserved three-dimensional conformation. The light chain comprises one variable region (termed $V_L$) and one constant region ($C_L$), while the heavy chain comprises one variable region ($V_H$) and three constant regions ($C_H1$, $C_H2$ and $C_H3$). Pairs of regions associate to form discrete structures. In particular, the light and heavy chain variable regions, $V_L$ and $V_H$, associate to form an "$F_V$" area that contains the antigen-binding site.

The variable regions of both heavy and light chains show considerable variability in structure and amino acid composition from one antibody molecule to another, whereas the constant regions show little variability. Each antibody recognizes and binds an antigen through the binding site defined by the association of the heavy and light chain, variable regions into an $F_V$ area. The light-chain variable region $V_L$ and the heavy-chain variable region $V_H$ of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDRs from a light chain and the three CDRs from a corresponding heavy chain form the antigen-binding site.

Cleavage of naturally occurring antibody molecules with the proteolytic enzyme papain generates fragments that retain their antigen-binding site. These fragments, commonly known as Fab's (for Fragment, antigen binding site) are composed of the $C_L$, $V_L$, $C_H1$ and $V_H$ regions of the antibody. In the Fab the light chain and the fragment of the heavy chain are covalently linked by a disulfide linkage.

Monoclonal antibodies against target antigens (e.g., a cell surface protein, such as receptors) are produced by a variety of techniques including conventional monoclonal antibody methodologies such as the somatic cell hybridization techniques of Kohler and Milstein, Nature, 256:495 (1975). Although in some embodiments, somatic cell hybridization procedures are preferred, other techniques for producing monoclonal antibodies are contemplated as well (e.g., viral or oncogenic transformation of B lymphocytes).

The preferred animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Human monoclonal antibodies (mAbs) directed against human proteins can be generated using transgenic mice carrying the complete human immune system rather than-the mouse system. Splenocytes from the transgenic mice are immunized with the antigen of interest, which are used to produce hybridomas that secrete human mAbs with specific affinities for epitopes from a human protein. (See e.g., Wood et al., WO 91/00906, Kucherlapati et al., WO 91/10741; Lonberg et al., WO 92/03918; Kay et al., WO 92/03917 [each of which is herein incorporated by reference in its entirety]; N. Lonberg et al., Nature, 368:856-859 [1994]; L. L. Green et al., Nature Genet., 7:13-21 [1994]; S. L. Morrison et al., Proc. Nat. Acad. Sci. USA, 81:6851-6855 [1994]; Bruggeman et al., Immunol., 7:33-40 [1993]; Tuaillon et al., Proc. Nat. Acad. Sci. USA, 90:3720-3724 [1993]; and Bruggernan et al. Eur. J. Immunol., 21:1323-1326 [1991]).

Monoclonal antibodies can also be generated by other methods known to those skilled in the art of recombinant DNA technology (See e.g., Sastry et al., Proc. Nat. Acad. Sci. USA, 86:5728 [1989]; Huse et al., Science, 246:1275 [1989]; and Orlandi et al., Proc. Nat. Acad. Sci. USA, 86:3833 [1989]; U.S. Pat. No. 4,683,292; Orlandi, et al., Proc. Nat. Acad. Sci. USA, 86:3833-3837 [1989]; Sastry et al., Proc. Nat. Acad. Sci. USA, 86:5728-5732 [1989]; and Huse et al., Science, 246:1275 [1989]; U.S. Pat. No. 5,233,409 and U.S. Pat. No. 5,403,484, each of which is incorporated herein by reference in their entireties).

Chimeric mouse-human monoclonal antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 [each of which is herein incorporated by reference in its entirety]; Better et al., Science, 240:1041-1043 [1988]; Liu et al., Proc. Nat. Acad. Sci. USA, 84:3439-3443 [1987]; Liu et al., J. Immunol., 139:3521-3526 [1987]; Sun et al., Proc. Nat. Acad. Sci. USA, 84:214-218 [1987]; Nishimura et al., Canc. Res., 47:999-1005 [1987]; Wood et al., Nature, 314:446-449 [1985]; and Shaw et al., J. Natl. Cancer Inst., 80:1553-1559 [1988]).

The chimeric antibody can be further humanized by replacing sequences of the Fv variable region that are not directly involved in antigen binding with equivalent sequences from human Fv variable regions. General reviews of humanized chimeric antibodies are provided by S. L. Morrison, Science, 229:1202-1207 (1985) and by Oi et al., Bio. Techniques, 4:214 (1986). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-$GPII_bIII_a$ antibody producing hybridoma. The recombinant DNA encoding the chimeric antibody, or fragment thereof, can then be cloned into an appropriate expression vector.

Suitable humanized antibodies can alternatively be produced by CDR substitution (e.g., U.S. Pat. No. 5,225,539 (incorporated herein by reference in its entirety); Jones et al., Nature, 321:552-525 [1986]; Verhoeyan et al., Science, 239:1534 [1988]; and Beidler et al., J. Immunol., 141:4053 [1988]). All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method that is capable of replacing at least a portion of a CDR of a human antibody with a CDR derived from a non-human antibody. The human CDRs may be replaced with non-human CDRs; using oligonucleotide site-directed mutagenesis.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In preferred embodiments, the fusion proteins include a monoclonal antibody subunit (e.g., a human, murine, or bovine), or a fragment thereof, (e.g., an antigen binding fragment thereof). The monoclonal antibody subunit or antigen binding fragment thereof can be a single chain polypeptide, a dimer of a heavy chain and a light chain, a tetramer of two heavy and two light chains, or a pentamer (e.g., IgM). IgM is a pentamer of five monomer units held together by disulfide bonds linking their carboxyl-terminal (Cμ4/Cμ4) domains and Cμ3/Cμ3 domains. The pentameric structure of IgM provides 10 antigen-binding sites, thus serum IgM has a higher valency than other types of antibody isotypes. With its high valency, pentameric IgM is more efficient than other antibody isotypes at binding multidimensional antigens (e.g., viral particles and red blood cells. However, due to its large pentameric structure, IgM does not diffuse well and is usually found in low concentrations in intercellular tissue fluids. The J chain of IgM allows the molecule to bind to receptors on secretary cells, which transport the molecule across epithelial linings to the external secretions that bathe the mucosal surfaces. In some embodiments, of the present invention take advantage of the low diffusion rate of pentameric IgM to help concentrate the fusion proteins of present invention at a site of interest. In preferred embodiments, monoclonal IgM, and fusion and chimeric proteins thereof, are directed to destroying *Cryptosporidium parvum* and other types of parasitic pathogens.

In some embodiments, an IgA is utilized to make a directed biocide. IgA's are preferably produced using either one, two or three constructs. IgA made by use of two or three retrovector constructs. For example, a retroviral construct can be produced in which the J-chain expression is driven by the long terminal repeat (LTR) promoter, and expression of a heavy chain and light chain separated by an IRES sequence is driven by an internal promoter. In another example, the heavy chain and light chain are provided in one vector and the J chain is provided in another vector. In another example, a third construct expressing the secretory component truncated form from poly IgR is provided.

In still other embodiments, secretion of a directed biocide is enhanced by transfecting a cell producing a directed biocide with a vector (e.g., a retroviral vector) that expressed secretory component. See U.S. Pat. No. 6,300,104; Koteswarra and Morrison, Proc. Natl. Acad. Sci. USA 94:6364-68 (1997).

In some preferred embodiments, the monoclonal antibody is a murine antibody or a fragment thereof. In other preferred embodiments, the monoclonal antibody is a bovine antibody or a fragment thereof. For example, the murine antibody can be produced by a hybridoma that includes a B cell obtained from a transgenic mouse having a genome comprising a heavy chain transgene and a light chain transgene fused to an immortalized cell. The antibodies can be of various isotypes, including, but not limited to: IgG (e.g., IgG1, IgG2, IgG2a, IgG2b, IgG2c, IgG3, IgG4); IgM; IgA1; IgA2; $IgA_{sec}$; IgD; and IgE. In some preferred embodiments, the antibody is an IgG isotype. In other preferred embodiments, the antibody is an IgM isotype. The antibodies can be full-length (e.g., an IgG1, IgG2, IgG3, or IgG4 antibody) or can include only an antigen-binding portion (e.g., a Fab, $F(ab')_2$, Fv or a single chain Fv fragment).

In the case of IgM antibodies, which naturally assemble as pentamers or hexamers, substitution of 2 cysteines with serines removes the ability to form disulphide bonds linking the molecules into pentamers and thus permits the expression of monomeric molecules (two heavy chains two light chains). The present invention also contemplates the use of "halfmers" comprising one heavy chain and one light chain, thus providing one epitope binding site. In some embodiments, to achieve a halfmer, three cysteines are substituted with serines to remove disulphide bonds allowing a single light chain linked to a single heavy chain conformation (e.g., a "halfmer").

In some embodiments, the immunoglobulin subunit of the fusion proteins is a recombinant antibody (e.g., a chimeric or a humanized antibody), a subunit, or an antigen binding fragment thereof (e.g., has a variable region, or at least a complementarity determining region (CDR)).

In preferred embodiments, the immunoglobulin subunit of the fusion protein is monovalent (e.g., includes one pair of heavy and light chains, or antigen binding portions thereof). In other embodiments, the immunoglobulin subunit of the fusion protein is a divalent (e.g., includes two pairs of heavy and light chains, or antigen binding portions thereof). In preferred embodiments, the transgenic fusion proteins include an immunoglobulin heavy chain or a fragment thereof (e.g., an antigen binding fragment thereof).

In still other embodiments, the fusion proteins and/or or recombinant antibodies comprise an immunoglobulin having only heavy chains such as the HCAbs found in certain *Camelidae* (e.g., camels, dromedaries, and llamas) species, spotted ratfish, and nurse shark. While the present invention is not limited to any particular mechanisms, the present invention contemplates that there are differences between conventional antibodies and HCAbs in both the $V_H$ and $C_H$ regions. For instance, as reported by Muyldermans et al. and Nguyen et al., the sequences of HCAbs variable domains ($V_HH$) differ significantly from those of conventional antibodies ($V_H$). (S. Muyldermans et al., Protein, Eng., 7:1129-1135 [1994]; V. K. Nguyen et al., J. Mol. Biol., 275:413-418 [1998]; and V. K. Nguyen et al., Immunogenetics DOI 10.1007/s00251-002-0433-0 [2002]). Additionally, HCAbs lack the first domain of the constant region ($C_H$); the matured $V_HH$-DJ is directly joined to the hinge region. Separate sets of V and C genes encode conventional antibodies and HCAbs, however, conventional antibodies and HCAbs have some common D genes and appear to have identical $J_H$ regions. (V. K. Nguyen et al., EMBO J., 19:921-930 [2000]; and V. K. Nguyen et al., Adv. Immunol., 79:261-296 [2001]).

In yet other embodiments, IgM is used as the microorganism targeting molecule. IgMs bind with multiple epitopes, effectively enhancing the avidity of the binding. The genes for both SP-D and MBL of these molecules have been sequenced and both have been produced as recombinant molecules in full or truncated forms (Shrive et al., J Mol Biol 2003; 331: 509-23; Arora et al., J Biol Chem 2001; 276:43087-94).

In some embodiments, a system of hybridoma-like antibody preparation, developed by Neoclone (Madison, Wis.), is used in the production of monoclonal antibodies. Splenocytes from immunized mice are immortalized using a retrovector-mediated introduction of the abl-myc genes. On reintroduction into recipient mice one dominant immortalized B cell clone (plasmacytoma) outgrows all others and produces a monoclonal antibody in the ascitic fluid. The B cell clone can be harvested with the ascitic fluid that contains high concentration of monoclonal antibody. This process can be completed in 8-10 weeks.

In still further embodiments, murine IgG2b biocide fusions are utilized as directed biocides. The murine immunoglobulin gamma heavy chain isotype IgG2b has a substantially longer hinge region than the other IgG isotypes, which makes the Fc portion more flexible when bound to the antigen. Its human equivalent is the IgG3 isotype. The present invention is not limited to a particular mechanism. Indeed, an understanding of the mechanism of the present invention is not necessary to practice the present invention. Nonetheless, it is contemplated that a c-terminal fusion of a biocide to the IgG2b or human IgG3 heavy chain will extend its radius of activity and make it more likely that the biocide finds its target (substrate). This flexibility allows a construct with a very short or no linker at all for attachment of the fusion to the c-terminus (e.g., a very short stiff linker such as glycine-proline-proline-glycine or a flexible linker). In other embodiments, it is contemplated that an extended length linker will enhance the activity radius. It is contemplated that this additional flexibility allows for better binding of the biocide to its substrate present on the target organism's surface and therefore result in a greater efficacy of the antibody-biocide fusion.

Accordingly, in some embodiments, proteins of interest (e.g., biocides) are fused to murine IgG2b or human IgG3 sequences. The present invention is not limited to a particular protein of interest. In some embodiments, the protein of interest is a protein biocide (e.g. those described herein). However, the protein of interest is not limited to protein biocides. In other embodiments the protein of interest is an effector molecule for murine IgG2b or human IgG3. Examples include, but are not limited to, cytokines (e.g., INFγ, IL-2, IL-12, etc), receptors for cytokines and growth factors, ligands for receptors, and label or marker proteins (e.g., including, but not limited to, HRP, fluorescent molecules, biotin).

ii. Production of Recombinant Antibodies

The present invention contemplates obtaining hybridoma cell lines that produce monoclonal antibodies against *Cryptosporidium* spp. The cell lines are subsequently used to isolate the heavy and light chain genes that encode for pathogen specific monoclonal antibodies according to standard molecular biology methods. For example hybridomas developed to *Cryptosporidium* spp. are described by Riggs (M. W. Riggs, Microbes. Infect., 4:1067 [2002) and Schaefer (Infect Immun 2000; 68:2608-16).

In some embodiments, candidate monoclonal antibodies are chosen based upon their binding affinity to the pathogen of interest (e.g., *Cryptosporidium* spp.) as well as their binding specificity that in certain instances includes as many different pathogen serotypes as possible. In some other embodiments, candidate monoclonals preferably show no or only weak cross-reaction with other species of microorganism and mammalian cells.

These cultures are expanded and grown in flasks under the described conditions to allow production of approximately milligram amounts of purified monoclonal antibodies. In preferred embodiments, the antibodies are purified using any suitable protocol such as ammonium sulfate precipitation. In some embodiments, the purified monoclonal antibodies are used to perform various in vitro functionality tests. For example, the present invention contemplates using purified monoclonal antibodies to perform affinity and specificity tests in order to select for the antibodies that have the best binding properties to the surface of the pathogen of interest (e.g., *Cryptosporidium* spp.) and/or that include binding to a broad range of serotypes. Contemplated functionality tests include, but are not limited to, enzyme-linked immunosorbent assays (ELISA) and competitive ELISA assays. In one embodiment, varying concentrations of different monoclonal antibodies are allowed to bind to immobilized heat killed pathogens (e.g., *Cryptosporidium* spp. or *L. monocytogenes*). In another embodiment using a competitive assay, various concentrations of competing antigen are added to the wells of test plate and the binding of the monoclonal antibodies is measured. In yet another embodiment, quantitative immunofluorescence assays are used to allow the determination of binding affinity based on fluorescence intensity per cell. The present invention contemplates that by determining the affinity of the monoclonal antibodies based on their binding capacity to the pathogen of interest (e.g., *Cryptosporidium* spp. or *L. monocytogenes*), the present invention allows the selection of the one monoclonal antibody that is best for topical applications against viable pathogens.

Cells from the highest affinity hybridoma clone are used to extract total RNA with the purpose of isolating the monoclonal antibody-specific heavy and light chain gene transcripts. Upon total RNA extraction, the RNA is reverse transcribed using standard molecular biology kits and protocols, such as the RIBOCLONE cDNA synthesis system from Promega (Promega Corp., Madison, Wis.). Preferably, the procedures used create double stranded cDNA of all RNA transcripts in a cell, including the transcripts from the murine heavy and light chain genes. The total cDNA is used as a template to specifically amplify the mouse IgG2a heavy chain and the Igk light chain. Site-directed mutagenesis primers are used to amplify these sequences. The present invention contemplates that the use of these primers adds short sequences of DNA, and introduces suitable restriction sites thus allowing direct cloning of the product into the retrovector backbone.

In preferred embodiments, once the genes for the murine heavy and light chain have been isolated, they are separated by an IRES element and inserted into the retrovector expression system under the control of the simian cytomegalovirus and the bovine alpha-lactalbumin promoter. In particularly preferred embodiments, the genes for the murine heavy and light antibody chains are cloned into a retrovector expression system (e.g., under the control of the simian cytomegalovirus (sCMV)) or other suitable multigenic gene expression systems. This process allows for the production of cell lines that secrete high levels of the monoclonal antibodies.

Figure 10:
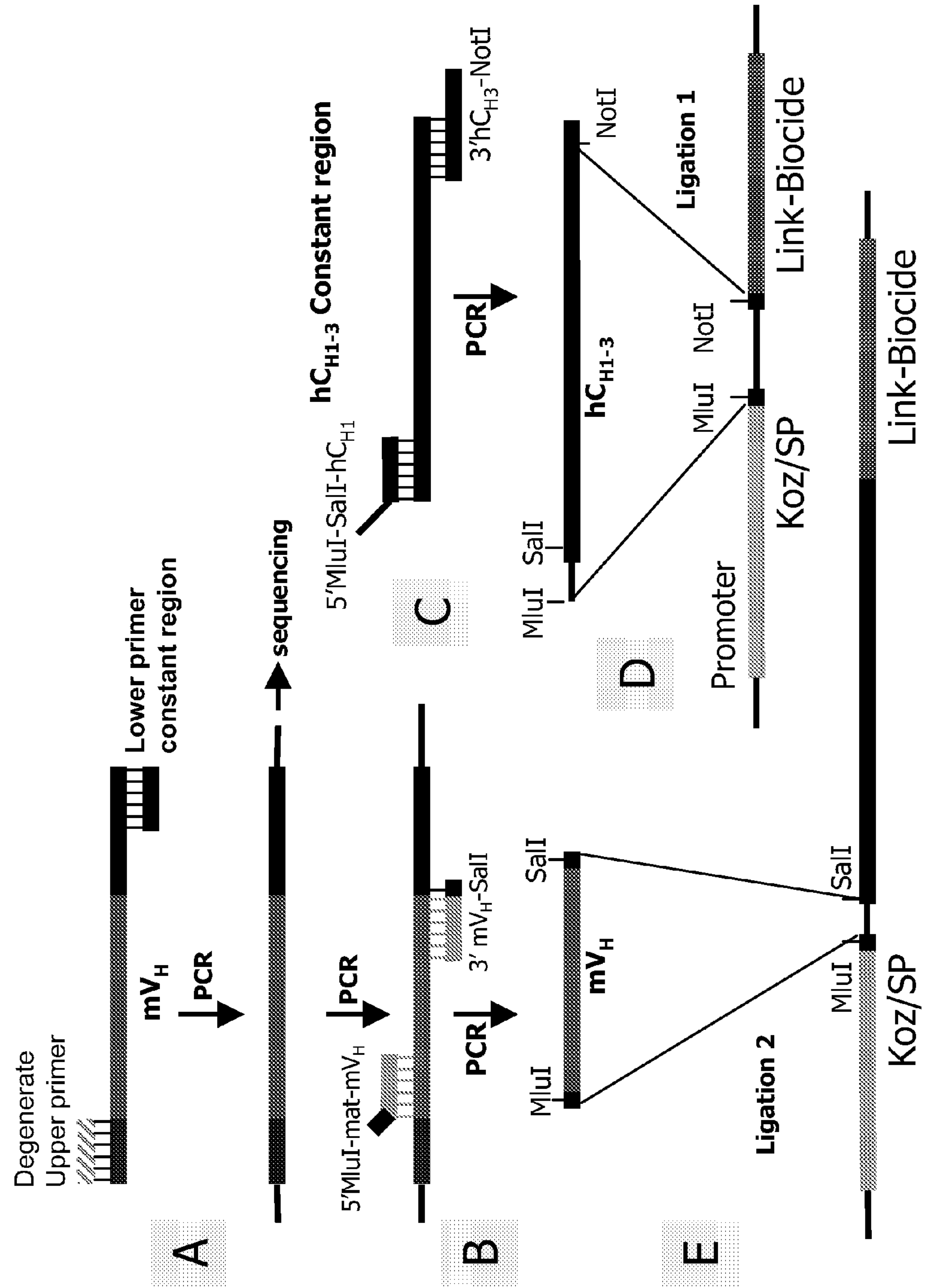
FIG. 10 shows assembly of mouse-human chimeric immunoglobulin biocide fusion protein coding sequence. A, Amplification of variable region using degenerate 5' primer and constant region 3' primer, resulting product is cloned and sequenced. B, Amplification of mature murine variable region with addition of restriction sites; C, Amplification of human constant region from human blood cDNA (Invitrogen, Carlsbad, Calif.) and addition of restriction sites; D, restriction site mediated ligation of hCH into retroviral backbone containing 3 different linker-biocide portions; E, ligation of mVH into retrovector backbone containing human constant heavy chain linked to various biocides. mVH=murine variable heavy chain, hCH1-3=human constant heavy chain region 1-3, Koz=Kozak element, SP=signal peptide
Figure 11:
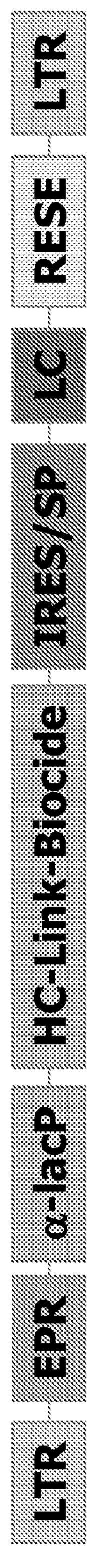
FIG. 11 shows an exemplary retrovector construct used for production of immunoglobulin biocide fusion protein in transgenic cows. Abbreviations used are: LTR, long terminal repeat; EPR, extended packaging region; α-lacP, alpha-lactalbumin promoter; SP, signal peptide; HC, antibody heavy chain; IRES, internal ribosome entry site from encephalomyocarditis virus; LC, antibody light chain; RESE, RNA export and stability element.
Figure 13:
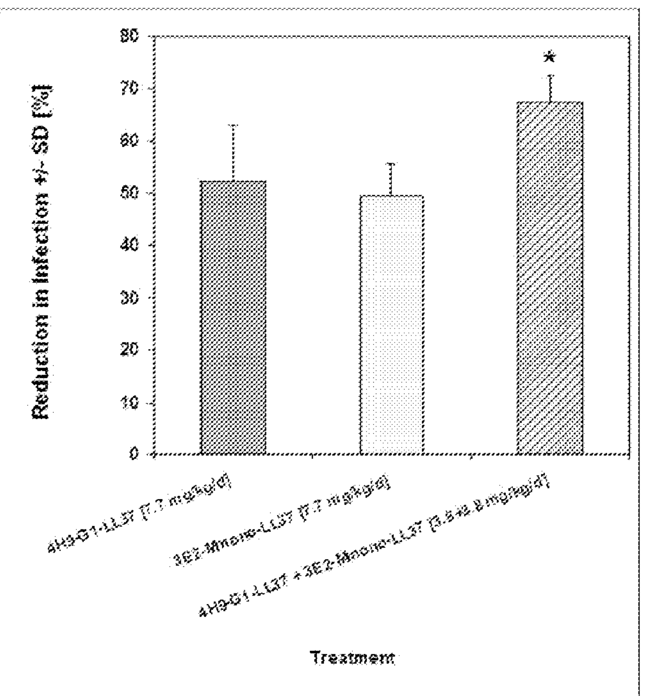
FIG. 13 shows the efficacy of combinatorial treatment with exemplary directed biocides of the present invention in a neonatal mouse model.

In particular, the heavy chain followed by an internal ribosome entry site (IRES) element are cloned into the retrovector backbone at the same site. Similarly, the light chain is then cloned into the retrovector backbone. Once the retroviral construct is complete, quality control sequencing will confirm that all the elements are present. The present invention contemplates that the use of the IRES element in between heavy and light chain genes yields fully functional antibodies expressed and secreted into the medium at exceptionally high levels (e.g., >100 pg/cell/day in CHO cells). In some preferred embodiments, after the retroviral constructs are complete, quality control sequencing is used to confirm that all the elements are present. The retrovector construct are then used to transform host cells along with the plasmid that encodes the vesicular stomatitis virus glycoprotein (VSV-G) used for pseudotyping the retrovirus. This procedure creates intermediate level viral titer that is used to infect production cell lines (e.g., 293H or CHO cells). The population of transduced cells are subjected to clonal selection based on the antibody levels present in the medium supernatant. The clone with the highest level of antibodies secreted into the supernatant is selected to produce milligram amounts of murine monoclonal antibody 4E8C12. In preferred embodiments, the recombinant antibodies are purified from cell supernatants using standard techniques well known to those in the art. FIG. 10 provide a diagram of the steps outlined above.

iii. Production of Recombinant Chimeric Antibodies

In some embodiments, the bovine IgG1 and IgG2 heavy chain genes are used to modify the constructs made above to produce constructs encoding chimeric bovine-murine antibodies. For example, in one contemplated embodiment, the constant portion of the murine heavy chain gene is replaced with the constant portion of the bovine heavy chain gene to create a chimeric bovine-murine monoclonal antibodies. A suitable bovine heavy chain IgG1 sequence may be selected from, but is not limited to, the following GenBank Accession Numbers: BD105809; S82409; U32264; U32263; U32262; U32261; U32260; U32259; U32258; U32257; U32256; U32255; U32254; U32253; U32252; U32251; U32250; U32249; U34749; U34748; U32852; U32851; U32850; U36824; U36823; S82407; X62917; X62916; and X16701. Likewise, a suitable bovine heavy chain IgG2 sequence may be selected from, but is not limited to, the following GenBank Accession Numbers: S82409; S82407; Z37506; and X16702. In preferred embodiments, GenBank Accession No. 5282409 (SEQ ID NO:1) provides bovine IgG1/IgG2 sequences. (See, I. Kacskovics and J. E. Butler, Mol. Immunol., 33(2):189-195 [1996]). Preferably, the murine IgG2a heavy chain gene will be replaced by the bovine sequence for IgG1 or IgG2a. Thus, modified with bovine IgG1/IgG2 sequences, the vectors described above are used in subsequent cloning steps.

In preferred embodiments, following sequence analysis of the construct, the constructs are used to create vectors for the transduction of production cell lines (e.g., 293H) and packaging cell lines (e.g., 293gp). Standard clonal analysis techniques are used to select for clones that produce high levels of the bovine-murine chimeric antibody. Once a top clone has been selected, enough chimeric antibody will be produced from this clone to conduct functionality tests with the derived chimeric monoclonal antibody.

In preferred embodiments, production cell lines that secrete high levels of the monoclonal antibodies are made from the above-mentioned constructs. The retroviral construct containing the chimeric murine-bovine monoclonal antibody genes are used to transduce at least one production cell line (e.g., the 293H production cell line). Upon transduction and expansion, the cell pool is subjected to limited dilution cloning to select for clones that produce high levels of the chimeric monoclonal antibody as determined by standard assay techniques (e.g., ELISA assays). One of the top clones is used to produce chimeric murine-bovine monoclonal antibodies in milligram amounts that are subsequently used in the functionality tests described below.

The present invention further contemplates the production of retrovector packaging cell lines that produce high titers of retrovector containing the gene for the monoclonal antibodies in preparation for making transgenic animals, such as bovines. For example, the retrovector construct containing the chimeric murine-bovine monoclonal antibody genes are used to transduce a packaging cell line (e.g., 293gp packaging cell line). The transduced packaging cell pool is then subjected to limiting dilution cloning and clones that produce the highest infectious viral titers are used for virus production. After a thorough quality control of the top virus titer producing clone, which ensures that the construct is complete, an appropriate amount of pseudotyped virus are purified and cryopreserved for use in oocyte injections.

B. Biocides

The present invention provides novel fusion proteins. In preferred embodiments, the recombinant fusion proteins comprise one or more biocide molecules (e.g., a bactericidal enzyme) attached to the antibody portion of the construct via a linking group. The specificity of the monoclonal antibody portion of the construct targets the biocide molecule to a *Cryptosporidium* spp.

One benefit of the specific targeting ability of the fusion protein construct is that it allows for relative accumulation of biocide at locations where the targeted pathogens are challenging the animal. Increasing the local concentration of biocide relative to the targeted pathogens enhances the biocidal activity of the fusion protein construct. In particular, the present invention contemplates that directing the biocide (e.g., lysozyme, PLA2, and the like) to the immediate vicinity of the pathogen (e.g., a bacterium) via the antibody portion of the construct effectively increasing the biocide's local concentration, thus providing a significantly greater biocidal (e.g., bactericidal) effect than administering biocide alone (parasiticidal compounds). For example in the case of lysozyme, the affinity constant ($K_m$) of lysozyme for its substrate is approximately $10^{-3}$ M, while that of phospholipase A2 is approximately $10^{-4}$ M. However, the $K_d$ of a monoclonal antibody is usually in the range of $10^{-8}$ M to $10^{-11}$ M, thus antibodies have about 5 orders of magnitude higher affinity for their substrates than do biocidal molecules alone. Therefore, preferred embodiments of the present invention utilize monoclonal antibodies (or portions thereof) to specifically direct biocide molecules to a target by taking advantage of the antibody's very high affinity for target pathogens. Additionally, directing the fusion protein constructs to target pathogens also reduces the possible deleterious effects to the animal caused by systemic administration of the biocidal molecules.

In preferred embodiments, the directed biocidal approach described herein uses a monoclonal antibody to direct a naturally occurring bactericidal enzyme to the target pathogen. In some of these embodiments, the bactericidal enzyme(s) are components of the innate immune system. One such preferred bactericidal enzyme is lysozyme.

Lysozyme is naturally present in mammalian tissues and in secretions such as tears and mucus. Lysozyme is also found in many foods including, egg whites, cow milk, and human colostrum. The enzyme is widely reported to have antibacterial properties. Lysozyme is a glycosidase that targets the polysaccharides of many bacterial cell walls rendering them more susceptible to osmotic lysis. Lysozyme is a 1,4-β-N-acetylmurmidase that cleaves the glycosidic bond between C-1 of N-acetylmuramic acid and C-4 of N-acetylglucosamine of the peptidoglycan layer present in many bacterial cell walls (See e.g., M. Schindler et al., Biochemistry, 16(3):423-431 [1977]). While it is not clear whether this cleavage contributes to the bactericidal action of lysozyme (K. During et al., FEBS Lett., 449(2-3):93-100 [1999]; and H. R. Ibrahim et al., FEBS Lett., 506(1):27-32 [2001]), it is widely accepted that lysozyme plays an important role in defense against bacterial infection. Lysozyme has also been shown to bind to the lipid A portion of bacterial endotoxin. This interaction prevents the endotoxin from inducing the release of inflammatory components by lymphocytes and macrophages (See e.g., B. Reusens-Billen et al., Diabetes Res. Clin. Pract., 23(2):85-94 [1994]; K. Takada et al., Infect. Immun, 62(4):1171-1175 [1994]; and K. Takada et al., Circ. Shock, 44(4):169-174 [1994]).

Other proteins that form part of the innate immune system, and especially those secreted by the intestinal Paneth cells, are contemplated for targeting the structural integrity of sporozoites. For example, phopholipase A2 (PLA2) is another naturally occurring bactericidal enzyme contemplated for use in certain embodiments of the present invention. Secretory type II phospholipase A2 (sPLA(2)-IIA) is a 14 kD enzyme synthesized in a number of gland cells, including Paneth cells of intestinal mucosa, prostate gland cells, and lacrimal glands. It is present in cellular secretions on mucosal surfaces including intestinal mucus, seminal plasma, and tears (X. D. Qu and R. I. Lehrer, Infect. Immun, 66:2791-2797 [1998]; and X. D. Qu et al., Infect. Immun, 64:5161-5165 [1996]). Evidence suggests that phopholipase A2 has an important antibacterial role in addition to its inflammatory mediating role (See e.g., A. G. Buckland and D. C. Wilton, Biochim. Biophys. Acta, 1488(1-2):71-82 [2000]). Elevated amounts of phospholipase A2 is found in patients with acute bacterial diseases (J. O. Gronoos et al., J. Infect. Dis., 185: 1767-1772 [2002]). The enzyme appears to effective in controlling *E. coli*. infections when expressed in transgenic mice (See e.g., V. J. Laine et al., Infect. Immun., 68(1):87-92 [2000]). While the present invention is not limited to any mechanisms, PLA2 appears to hydrolyze membrane phospholipids, thus destroying the membranes of invading microbes. PLA2 serves as a critical component of the innate immune system, functioning in combination with lysozyme and the defensins to provide an effective barrier to invasion by a diverse range of organisms.

Mammalian cells are generally highly resistant to sPLA(2) IIA (R. S. Koduri et al., J. Biol. Chem., 273:32142-32153 [1998]). The substrate specificity of the different members of the PLA2 family may be related to the differences in interfacial binding characteristics to charge-neutral phosphotidyl choline (PC) versus anionic phospholipids. Indeed, sPLA(2) family members sPLA2-V and -X bind efficiently and hydrolyze PC vesicles in vitro whereas the vesicles are a poor binding substrate for -IIA. Plasma membranes with a high PC content would therefore be stable in the presence of sPLA(2)-IIA. The composition of the phospholipids on the surface of the organism therefore contributes to the susceptibility of the organism to the action of sPLA2. Some parasitic eukaryotic organisms may evade the innate immune system by not stimulating the cells of the immune system to release biocidal enzymes and defensins (e.g., *G. lamblia* and *C. albicans* appear not to stimulate Paneth cells). However, one recent report suggests that *Plasmodium* is susceptible to sPLA2 (Type III, from bee venom) (Rodrigues et al., Insect Mol Biol 2008 April; 17(2):175-83). Type III sPLA2 has an activity that is similar to the type IIA enzyme, but is a slightly larger molecule having N- and C-terminal extensions. Systemically, sPLA(2)-IIA has a role in generalized inflammatory responses. In acute inflammation, the levels of the enzyme are elevated many hundreds of fold, however, it appears to have no adverse effect at epithelial surfaces. In vitro, sPLA(2) apparently has no deleterious effect on various types of cultured mammalian cells. Healthy transgenic mice chronically over-expressing sPLA(2)-IIA have been produced and exhibit an elevated resistance to infection by gram positive organisms (V. J. Laine et al., J. Immunol., 162:7402-7408 [1999]; and V. J. Laine et al., Infect, Immun, 68:87-92 [2000]).

A number of inhibitors have been identified that have activity against *C. parvum* by targeting the parasite's metabolic pathways. These include, but are not limited to, metalloprotease inhibitors (P. C. Okhuysen et al., Antimicrob. Agents Chemother., 40:2781-2784 [1996]) and serine protease antagonists (J. R. Formey et al., J. Parasitol., 82:638-640 [1996]). Other enzymes essential to *C. parvum* infectivity provide useful inhibitor targets. These include, for example, phosphoinositide 3-kinase (J. R. Formey et al., Infect. Immun, 67:844-852 [1999]) and cysteine proteinase (M. V. Nesterenko et al., Microbios., 83:77-88 [1995]).

Other naturally occurring bactericidal molecules (e.g., enzymes) contemplated for use in certain embodiments of the present invention, include, but are not limited to, lactoferrin, lactoperoxidase, bacterial permeability increasing protein (BPI), and Aprotinin. (See e.g., B. A. Mannion et al., J. Clin. Invest., 85(3):853-860 [1990]; A. Pellegrini et al., Biochem. Biophys. Res. Commun, 222(2):559-565 [1996]; and P. Prohinar et al., Mol. Microbiol., 43(6):1493-1504 [2002]).

In some embodiments of the present invention, the biocide component of the fusion protein comprises an antimicrobial polypeptide (See e.g., *Antimicrobial Peptide Protocols*, ed. W. M. Shafer, Humana Press, Totowa, NJ [1997]) or a pore forming agent. In some embodiments, the antimicrobial peptide or pore forming agent is a compound or peptide selected from the following: magainin (e.g., magainin I, magainin II, xenopsin, xenopsin precursor fragment, caerulein precursor fragment), magainin I and II analogs (PGLa, magainin A, magainin G, pexiganin, Z-12, pexigainin acetate, D35, MSI-78A, MG0 [K10E, K11E, F12W-magainin 2], MG2+[K10E, F12W-magainin-2], MG4+[F12W-magainin 2], MG6+ [f12W, E19Q-magainin 2 amide], MSI-238, reversed magainin II analogs [e.g., 53D, 87-ISM, and A87-ISM], Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME (1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 [(+/−)1-(4-aminobutyl)-6-benzylindane], PM2c [(+/−)-6-benzyl-1-(3-carboxypropyl)indane], PM3 [(+/−)1-benzyl-6-(4-aminobutyl)indane], tachyplesin, buforin I or II, misgurin, melittin, PR-39, PR-26, 9-phenylnonylamine, (KLAKKLA)n (SEQ ID NO. 179), (KLAKLAK)n (SEQ ID NO. 180), where n=1, 2, or 3, (KALKALK)3 (SEQ ID NO. 181), KLGKKLG)n (SEQ ID NO. 182), and KAAKKAA)n (SEQ ID NO. 183), wherein N=1, 2, or 3, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG1, 1bAMP, snakin, lipid transfer proteins, and plant defensins. In further embodiments, the antimicrobial polypeptide is a modified cathelicidin derived polypeptide (e.g., LL37, Ganz and Lehrer, 1997, Current Opinion in Hematology 4:53-58). Exemplary sequences for the above compounds are provided in Table 1. In some embodiments, the antimicrobial peptides are synthesized from L-amino acids, while in other embodiments, the peptides are synthesized from or comprise D-amino acids.

TABLE 1

Antimicrobial Peptides

| SEQ ID NO: | Name | Organism | Sequence |
|---|---|---|---|
| 45 | lingual antimicrobial peptide precursor (Magainin) | *Bos taurus* | MRLHHLLLALLFLVLSAGSGF TQGVRNSQSCRRNKGICVP IRCPGSMRQIGTCLGAQVKCC RRK |
| 46 | antimicrobial peptide PGQ | *Xenopus laevis* | GVLSNVIGYLKKLGTGALNAV LKQ |
| 47 | Xenopsin | *Xenopus laevis* | MYKGIFLCVLLAVICANSLAT PSSDADEDNDEVERYVRGW ASKIGQTLGKIAKVGLKELIQ PKREAMLRSAEAQGKRPWIL |

TABLE 1-continued

Antimicrobial Peptides

| SEQ ID NO: | Name | Organism | Sequence |
|---|---|---|---|
| 48 | magainin precursor | *Xenopus laevis* | MFKGLFICSLIAVICANALPQPEASADEDMDEREVRGIGKFLHSAGKFGKAFVGEIMKSKRDAEAVGPEAFADEDLDEREVRGIGKFLHSAKKFGKAFVGEIMNSKRDAEAVGPEAFADEDLDEREVRGIGKFLHSAKKFGKAFVGEIMNSKRDAEAVGPEAFADEDLDEREVRGIGKFLHSAKKFGKAFVGEIMNSKRDAEAVGPEAFADEDFDEREVRGIGKFLHSAKKFGKAFVGEIMNSKRDAEAVGPEAFADEDLDEREVRGIGKFLHSAKKFGK AFVGEIMNSKRDAEAVDDRRWVE |
| 49 | tachyplesin I | *Tachypleus gigas* | KWCFRVCYRGICYRRCR |
| 50 | tachyplesin II | *Tachypleus gigas* | RWCFRVCYRGICYRKCR |
| 51 | buforin I | *Bufo bufo gagarizans* | MSGRGKQGGKVRAKAKTRSSRAGLQFPVGRVHRLLRKGNYAQRVGAGAPVYLAAVLEYLTAEILELAGNAARDNKKTRIIPRHLQLAVRNDEELNKLLGGVTIAQGGVLPNIQAVLLPKTESSKPAKSK |
| 52 | buforin II | *Bufo bufo gagarizans* | TRSSRAGLQFPVGRVHRLLRK |
| 53 | cecropin A | *Bombyx mori* | MNFVRILSFVFALVLALGAVSAAPEPRWKLFKKIEKVGRNVRDGLIKAGPAIAVIGQAKSLGK |
| 54 | cecropin B | *Bombyx mori* | MNFAKILSFVFALVLALSMTSAAPEPRWKIFKKIEKMGRNIRDGIVKAGPAIEVLGSAKAIGK |
| 55 | cecropin C | *Drosophila melanogaster* | MNFYKIFVFVALILAISIGQSEAGWLKKLGKRIERIGQHTRDATIQGLGIAQQAANVAATARG |
| 56 | cecropin P1 | *Sus scrofa* | SWLSKTAKKLENSAKKRISEGIAIAIQGGPR |
| 57 | indolicidin | *Bos taurus* | ILPWKWPWWPWRR |
| 58 | nisin | *Lactococcus lactis* | ITSISLCTPGCKTGALMGCNMKTATCHCSIHVSK |
| 59 | ranalexin | *Rana catesbeiana* | FLGGLIKIVPAMICAVTKKC |
| 60 | lactoferricin B | *Bos taurus* | FKCRRWQWRMKKLGAPSITCVRRAF |
| 61 | protegrin-1 | *Sus scrofa* | RGGRLCYCRRRFCVCVGRX |
| 62 | protegrin-2 | *Sus scrofa* | GGRLCYCRRRFCICVG |
| 63 | histatin precursor | *Homo sapiens* | MKFFVFALILALMLSMTGADSHAKRHHGYKRKFHEKHHSHRGYRSNYLYDN |
| 64 | histatin 1 | *Macaca fascicularis* | DSHEERHHGRHGHHKYGRKFHEKHHSHRGYRSNYLYDN |

TABLE 1-continued

Antimicrobial Peptides

| SEQ ID NO: | Name | Organism | Sequence |
|---|---|---|---|
| 65 | dermaseptin | *Phyllomedusa sauvagei* | ALWKTMLKKLGTMALHAGKAALGAAADTISQTQ |
| 66 | dermaseptin 2 | *Phyllomedusa sauvagei* | ALWFTMLKKLGTMALHAGKAALGAAANTISQGTQ |
| 67 | dermaseptin 3 | *Phyllomedusa sauvagei* | ALWKNMLKGIGKLAGKAALGAVKKLVGAES |
| 68 | misgurin | *Misgurnus anguilli-caudatus* | RQRVEELSKFSKKGAAARRRK |
| 69 | melittin | *Apis mellifera* | GIGAVLKVLTTGLPALISWISRKKRQQ |
| 70 | pardaxin-1 | *Pardachirus pavoninus* | GFFALIPKIISSPLFKTLLSAVGSALSSSGEQE |
| 71 | pardaxin-2 | *Pardachirus pavoninus* | GFFALIPKIISSPIFKTLLSAVGSALSSSGGQE |
| 72 | bactenecin 5 precursor | *Bos taurus* | METQRASLSLGRCSLWLLLLGLVLPSASAQALSYREAVLRAVDQFNERSSEANLYRLLELDPTPNDDLDPGTRKPVSFRVKETDCPRTSQQPLEQCDFKENGLVKQCVGTVTLDPSNDQFDINCNELQSVRFRPPIRRPPIRPPFYPPFRPPIRPPIFPPIRPPFRPPLGPFPGRR |
| 73 | bactenecin precursor | *Bos taurus* | METPRASLSLGRWSLWLLLLGLALPSASAQALSYREAVLRAVDQLNEQSSEPNIYRLLELDQPPQDDEDPDSPKRVSFRVKETVCSRTTQQPPEQCDFKENGLLKRCEGTVTLDQVRGNFDITCNNHQSIRITKQPWAPPQAARLCRIVVIRVCR |
| 74 | ceratotoxin A | *Ceratitis capitata* | SIGSALKKALPVAKKIGKIALPIAKAALP |
| 75 | ceratotoxin B | *Ceratitis capitata* | SIGSAFKKALPVAKKIGKAALPIAKAAALP |
| 76 | cathelicidin antimicrobial peptide | *Homo sapiens* | MKTQRNGHSLGRWSLVLLLLGLVMPLAIIAQVLSYKEAVLRAIDGINQRSSDANLYRLLDLDPRPTMDGDPDTPKPVSFTVKETVCPRTTQQSPEDCDFKKDGLVKRCMGTVTLNQARGSFDISCDKDNKRFALLGDFFRKSKEKIGKEFKRIVQRIKDFLRNLVPRTES |
| 77 | myeloid cathelicidin 3 | *Equus caballus* | METQRNTRCLGRWSPLLLLLGLVIPPATTQALSYKEAVLRAVDGLNQRSSDENLYRLLELDPLPKGDKDSDTPKPVSFMVKETVCPRIMKQTPEQCDFKENGLVKQCVGTVILDPVKDYFDASCDEPQRVKRFHSVGSLIQRHQQMIRDKSEATRHGIRIITRPKLLLAS |
| 78 | myeloid antimicrobial peptide BMAP-28 | *Bos taurus* | METQRASLSLGRWSLWLLLLGLALPSASAQALSYREAVLRAVDQLNEKSSEANLYRLLELDPPPKEDDENPNIPKPVSFRVKETVCPRTSQQSPEQCDFKENGLLKECVGTVTLDQVGSNFDIT |

TABLE 1-continued

Antimicrobial Peptides

| SEQ ID NO: | Name | Organism | Sequence |
|---|---|---|---|
| | | | CAVPQSVGGLRSLGRKILRAW KKYGPIIVPIIRIG |
| 79 | myeloid cathelicidin 1 | *Equus caballus* | METQRNTRCLGRWSPLLLLLG LVIPPATTQALSYKEAVLR AVDGLNQRSSDENLYRLLELD PLPKGDKDSDTPKPVSFMVKE TVCPRIMKQTPEQCDFKENGL VKQCVGTVILGPVKDHFDVSC GEPQRVKRFGRLAKSFLRMRI LLPRRKILLAS |
| 80 | SMAP 29 | *Ovis aries* | METQRASLSLGRCSLWLLLLG LALPSASAQVLSYREAVLRAA DQLNEKSSEANLYRLLELDPP PKQDDENSNIPKPVSFRVKET VCPRTSQQPAEQCDFKENGLL KECVGTVTLDQVRNNFDITCA EPQSVRGLRRLGRKIAHGVKK YGPTVLRIIRIAG |
| 81 | BNP-1 | *Bos taurus* | RLCRIVVIRVCR |
| 82 | HNP-1 | *Homo sapiens* | ACYCRIPACIAGERRYGTCIY QGRLWAFCC |
| 83 | HNP-2 | *Homo sapiens* | CYCRIPACIAGERRYGTCIYQ GRLWAFCC |
| 84 | HNP-3 | *Homo sapiens* | DCYCRIPACIAGERRYGTCIY QGRLWAFCC |
| 85 | HNP-4 | *Homo sapiens* | VCSCRLVFCRRTELRVGNCLI GGVSFTYCCTRV |
| 86 | NP-1 | *Oryctolagus cuniculus* | VVCACRRALCLPRERRAGFCR IRGRIHPLCCRR |
| 87 | NP-2 | *Oryctolagus cuniculus* | VVCACRRALCLPLERRAGFCR IRGRIHPLCCRR |
| 88 | NP-3A | *Oryctolagus cuniculus* | GICACRRRFCPNSERFSGYCR VNGARYVRCCSRR |
| 89 | NP-3B | *Oryctolagus cuniculus* | GRCVCRKQLLCSYRERRIGDC KIRGVRFPFCCPR |
| 90 | NP-4 | *Oryctolagus cuniculus* | VSCTCRRFSCGFGERASGSCT VNGGVRHTLCCRR |
| 91 | NP-5 | *Oryctolagus cuniculus* | VFCTCRGFLCGSGERASGSCT INGVRHTLCCRR |
| 92 | RatNP-1 | *Rattus norvegicus* | VTCYCRRTRCGFRERLSGACG YRGRIYRLCCR |
| 93 | Rat-NP-3 | *Rattus norvegicus* | CSCRYSSCRFGERLLSGACRL NGRIYRLCC |
| 94 | Rat-NP-4 | *Rattus norvegicus* | ACTCRIGACVSGERLTGACGL NGRIYRLCCR |
| 95 | GPNP | Guinea pig | RRCICTTRTCRFPYRRLGTCI FQNRVYTFCC |
| 96 | beta defensin-3 | *Homo sapiens* | MRIHYLLFALLFLFLVPVPGH GGIINTLQKYYCRVRGGRC AVLSCLPKEEQIGKCSTRGRK CCRRKK |
| 97 | theta defensin-1 | *Macaca mulatta* | RCICTRGFCRCLCRRGVC |
| 98 | defensin CUA1 | *Helianthus annuus* | MKSSMKMFAALLLVVMCLLAN EMGGPLVVEARTCESQSHKFK GTCLSDTNCANVCHSERFSGG KCRGFRRRCFCTTHC |
| 99 | defensin SD2 | *Helianthus annuus* | MKSSMKMFAALLLVVMCLLAN EMGGPLVVEARTCESQSHKFK GTCLSDTNCANVCHSERFSGG KCRGFRRRCFCTTHC |
| 100 | neutrophil defensin 2 | *Macaca mulatta* | ACYCRIPACLAGERRYGTCFY MGRVWAFCC |
| 101 | 4 KDA defensin | *Androctonus australis hector* | GFGCPFNQGACHRHCRSIRRR GGYCAGLFKQTCTCYR |
| 102 | defensin | *Mytilus gallopro-vincialis* | GFGCPNNYQCHRHCKSIPGRC GGYCGGXHRLRCTCYRC |
| 103 | defensin AMP1 | *Heuchera sanguinea* | DGVKLCDVPSGTWSGHCGSSS KCSQQCKDREHFAYGGACH YQFPSVKCFCKRQC |
| 104 | defensin AMP1 | *Clitoria ternatea* | NLCERASLTWTGNCGNTGHCD TQCRNWESAKHGACHKRGN WKCFCYFNC |
| 105 | cysteine-rich cryptdin-1 homolog | *Mus musculus* | MKKLVLLFALVLLAFQVQADS IQNTDEETKTEEQPGEKDQAV SVSFGDPQGSALQDAALGWGR RCPQCPRCPSCPSCPRC PRC PRCKCNPK |
| 106 | beta-defensin-9 | *Bos taurus* | QGVRNFVTCRINRGFCVPIRC PGHRRQIGTCLGPQIKCCR |
| 107 | beta-defensin-7 | *Bos taurus* | QGVRNFVTCRINRGFCVPIRC PGHRRQIGTCLGPRIKCCR |
| 108 | beta-defensin-6 | *Bos taurus* | QGVRNHVTCRIYGGFCVPIRC PGRTRQIGTCFGRPVKCCRRW |
| 109 | beta-defensin-5 | *Bos taurus* | QVVRNPQSCRWNMGVCIPISC PGNMRQIGTCFGPRVPCCR |
| 110 | beta-defensin-4 | *Bos taurus* | QRVRNPQSCRWNMGVCIPFLC RVGMRQIGTCFGPRVPCCRR |
| 111 | beta-defensin-3 | *Bos taurus* | QGVRNHVTCRINRGFCVPIRC PGRTRQIGTCFGPRIKCCRSW |
| 112 | beta-defensin-10 | *Bos taurus* | QGVRSYLSCWGNRGICLLNRC PGRMRQIGTCLAPRVKCCR |
| 113 | beta-defensin-13 | *Bos taurus* | SGISGPLSCGRINGGVCIPIR CPVPMRQIGTCFGRPVKCCRS W |
| 114 | beta-defensin-1 | *Bos taurus* | DFASCHTNGGICLPNRCPGHM IQIGICFRPRVKCCRSW |
| 115 | coleoptericin | *Zophobas atratus* | SLQGGAPNFPQPSQQNGGWQV SPDLGRDDKGNTRGQIEIQNK GKDHDFNAGWGKVIRGPNKAK PTWHVGGTYRR |
| 116 | beta defensin-3 | *Homo sapiens* | MRIHYLLFALLFLFLVPVPGH GGIINTLQKYYCRVRGGRCAV LSCLPKEEQIGKCSTRGRKCC RRKK |
| 117 | defensin C | *Aedes aegypti* | ATCDLLSGFGVGDSACAAHCI ARGNRGGYCNSKKVCVCRN |

TABLE 1-continued

Antimicrobial Peptides

| SEQ ID NO: | Name | Organism | Sequence |
|---|---|---|---|
| 118 | defensin B | *Mytilus edulis* | GFGCPNDYPCHRHCKSIPGRYGGYCGGXHRLRCTC |
| 119 | sapecin C | *Sarcophaga peregrina* | ATCDLLSGIGVQHSACALHCVFRGNRGGYCTGKGICVCRN |
| 120 | macrophage antibiotic peptide MCP-1 | *Oryctolagus cuniculus* | MRTLALLAAILLVALQAQAEHVSVSIDEVVDQQPPQAEDQDVAIYVKEHESSALEALGVKAGVVCACRRALCLPRERRAG FCRIRGRIHPLCCRR |
| 121 | cryptdin-2 | *Mus musculus* | MKPLVLLSALVLLSFQVQADPIQNTDEETKTEEQSGEEDQAVSVSFGDREGASLQEESLRDLVCYCRTRGCKRRERMNGT CRKGHLMYTLCC |
| 122 | cryptdin-5 | *Mus musculus* | MKTFVLLSALVLLAFQVQADPIHKTDEETNTEEQPGEEDQAVSISFGGQEGSALHEELSKKLICYCRIRGCKRRERVFGTCRNLFLTFVFCCS |
| 123 | cryptdin 12 | *Mus musculus* | LRDLVCYCRARGCKGRERMNGTCRKGHLLYMLCCR |
| 124 | defensin | *Pyrrhocoris apterus* | ATCDILSFQSQWVTPNHAGCALHCVIKGYKGGQCKITVCHCRR |
| 125 | defensin R-5 | *Rattus norvegicus* | VTCYCRSTRCGFRERLSGACGYRGRIYRLCCR |
| 126 | defensin R-2 | *Rattus norvegicus* | VTCSCRTSSCRFGERLSGACRLNGRIYRLCC |
| 127 | defensin NP-6 | *Oryctolagus cuniculus* | GICACRRRFCLNFEQFSGYCRVNGARYVRCCSRR |
| 128 | beta-defensin-2 | *Pan troglodytes* | MRVLYLLFSFLFIFLMPLPGVFGGISDPVTCLKSGAICHPVFCPRRYKQIGTCGLPGTKCCKKP |
| 129 | beta-defensin-2 | *Homo sapiens* | MRVLYLLFSFLFIFLMPLPGVFGGIGDPVTCLKSGAICHPVFCPRRYKQIGTCGLPGTKCCKKP |
| 130 | beta-defensin-1 | *Homo sapiens* | MRTSYLLLFTLCLLLSEMASGGNFLTGLGHRSDHYNCVSSGGQCLYSACPIFTKIQGTCYRGKAKCCK |
| 131 | beta-defensin-1 | *Capra hircus* | MRLHHLLLVLFFLVLSAGSGFTQGIRSRRSCHRNKGVCALTRCPRNMRQIGTCFGPPVKCCRKK |
| 132 | beta defensin-2 | *Capra hircus* | MRLHHLLLALFFLVLSAGSGFTQGIINHRSCYRNKGVCAPARCPRNMRQIGTCHGPPVKCCRKK |
| 133 | defensin-3 | *Macaca mulatta* | MRTLVILAAILLVALQAQAEPLQARTDEATAAQEQIPTDNPEVVVSLAWDESLAPKDSVPGLRKNMACYCRIPACLAGER RYGTCFYRRRVWAFCC |
| 134 | defensin-1 | *Macaca mulatta* | MRTLVILAAILLVALQAQAEPLQARTDEATAAQEQIPTDNPEVVVSLAWDESLAPKDSVPGLRKNMACYCRIPACLAGER RYGTCFYLGRVWAFCC |
| 135 | neutrophil defensin 1 | *Mesocricetus auratus* | VTCFCRRRGCASRERHIGYCRFGNTIYRLCCRR |
| 136 | neutrophil defensin 1 | *Mesocricetus auratus* | CFCKRPVCDSGETQIGYCRLGNTFYRLCCRQ |
| 137 | Gallinacin 1-alpha | *Gallus gallus* | GRKSDCFRKNGFCAFLKCPYLTLISGKCSRFHLCCKRIW |
| 138 | defensin | *Allomyrina dichotoma* | VTCDLLSFEAKGFAANHSLCAAHCLAIGRRGGSCERGVCICRR |
| 139 | neutrophil cationic peptide 1 | *Cavia porcellus* | RRCICTTRTCRFPYRRLGTCIFQNRVYTFCC |

In some embodiments of the present invention, the antimicrobial polypeptide is a defensin. In preferred embodiments, the compositions of the present invention comprise one or more defensins. In some of these embodiments, the antimicrobial polypeptide defensin is BNP1 (also known as bactanecin and bovine dodecapeptide). In certain embodiments, the defensin comprises the following consensus sequence: (SEQ ID NO:140-$X_1CN_1CRN_2CN_3ERN_4CN_5GN_6CCX_2$, wherein N and X represent conservatively or nonconservatively substituted amino acids and $N_1=1$, $N_2=3$ or 4, $N_3=3$ or 4, $N_4=1$, 2, or 3, $N_6=5$-9, $X_1$ and $X_2$ may be present, absent, or equal from 1-2. The present invention is not limited to any particular defensin. Representative defensins are provided in Tables 1 and 2.

TABLE 2

Defensins

| SEQ ID NO | Name | Organism | Sequence |
|---|---|---|---|
| 141 | HNP-1 | Human | ACYCRIPACIAGERRYGTCIYQGRLWAFCC |
| 142 | HNP-2 | Human | CYCRIPACIAGERRYGTCIYQGRLWAFCC |
| 143 | HNP-3 | Human | DCYCRIPACIAGERRYGTCIYQGRLWAFCC |
| 144 | HNP-4 | Human | VCSCRLVFCRRTELRVGNCLIGGVSFTYCCTRV |
| 145 | NP-1 | Rabbit | VVCACRRALCLPRERRAGFCRIRGRIHPLCCRR |
| 146 | NP-2 | Rabbit | VVCACRRALCLPLERRAGFCRIRGRIHPLCCRR |
| 147 | NP-3A | Rabbit | GICACRRRFCPNSERFSGYCRVNGARYVRCCSRR |

TABLE 2-continued

| Defensins | | | |
|---|---|---|---|
| SEQ ID NO | Name | Organism | Sequence |
| 148 | NP-3B | Rabbit | GRCVCRKQLLCSYRERRIGDCKIRGVR FPFCCPR |
| 149 | NP-4 | Rabbit | VSCTCRRFSCGFGERASGSCTVNGVRH TLCCRR |
| 150 | NP-5 | Rabbit | VFCTCRGFLCGSGERASGSCTINGVRH TLCCRR |
| 151 | RatNP-1 | Rat | VTCYCRRTRCGFRERLSGACGYRGRIY RLCCR |
| 152 | Rat-NP-3 | Rat | CSCRYSSCRFGERLLSGACRLNGRIYRL CC |
| 153 | Rat-NP-4 | Rat | ACTCRIGACVSGERLTGACGLNGRIYR LCCR |
| 154 | GPNP | Guinea pig | RRCICTTRTCRFPYRRLGTCIFQNRVYT FCC |

In general, defensins are a family of highly cross-linked, structurally homologous antimicrobial peptides found in the azurophil granules of polymorphonuclear leukocytes (PMN's) with homologous peptides being present in macrophages. (See e.g., Selsted et al., Infect. Immun., 45:150-154 [1984]). Originally described as "Lysosomal Cationic Peptides" in rabbit and guinea pig PMN (Zeya et al., Science, 154:1049-1051 [1966]; Zeya et al., J. Exp. Med., 127:927-941 [1968]; Zeya et al., Lab. Invest., 24:229-236 [1971]; Selsted et al., [1984], supra.), this mixture was found to account for most of the microbicidal activity of the crude rabbit PMN extract against various microorganisms (Zeya et al., [1966], supra; Lehrer et al., J. Infect. Dis., 136:96-99 [1977]; Lehrer et al., Infect. Immun., 11:1226-1234 [1975]). Six rabbit neutrophil defensins have been individually purified and are designated NP-1, NP-2, NP-3A, NP-3B, NP-4, and NP-5. Their amino acid sequences were determined, and their broad spectra of activity were demonstrated against a number of bacteria (Selsted et al., Infect. Immun., 45:150-154 [1984]), viruses (Lehrer et al., J. Virol. 54:467 [1985]), and fungi (Selsted et al., Infect. Immun, 49:202-206 [1985]; Segal et al., 151:890-894 [1985]). Defensins have also been shown to possess mitogenic activity (e.g., Murphy et al., J. Cell. Physiol., 155:408-13 [1993]).

Four peptides of the defensin family have been isolated from human PMN's and are designated HNP-1, HNP-2, HNP-3, and HNP-4 (Ganz et al., J. Clin. Invest., 76:1427-1435 [1985]; Wilde et al., J. Biol. Chem., 264:11200-11203 [1989]). The amino acid sequences of HNP-1, HNP-2, and HNP-3 differ from each other only in their amino terminal residues, while each of the human defensins are identical to the six rabbit peptides in 10 or 11 of their 29 to 30 residues. These are the same 10 or 11 residues that are shared by all six rabbit peptides. Human defensin peptides have been shown to share with the rabbit defensins a broad spectrum of antimicrobial activity against bacteria, fungi, and enveloped viruses (Ganz et al., [1985], supra).

Three defensins designated RatNP-1, RatNP-2, and RatNP-4, have been isolated from rat. (Eisenhauer et al., Infection and Immunity, 57:2021-2027 [1989]). A guinea pig defensin (GPNP) has also been isolated, purified, sequenced and its broad spectrum antimicrobial properties verified (Selsted et al., Infect. Immun., 55:2281-2286 [1987]). Eight of its 31 residues were among those invariant in six rabbit and three human defensin peptides. The sequence of GPNP also included three nonconservative substitutions in positions otherwise invariant in the human and rabbit peptides. Of the defensins tested in a quantitative assay HNP-1, RatNP-1, and rabbit NP-1 possess the most potent antimicrobial properties, while NP-5 possesses the least amount of antimicrobial activity when tested against a panel of organisms in stationary growth phase. (Selsted et al., Infect. Immun., 45:150-154 [1984]; Ganz et al., J. Clin. Invest. 76:1427-1435 [1985]). Defensin peptides are further described in U.S. Pat. Nos. 4,543,252; 4,659,692; and 4,705,777 (each of which is incorporated herein by reference).

Accordingly, in some embodiments, the compositions of the present invention comprise one or more defensins selected from the group consisting of SEQ ID NOs: 37-95.

In preferred embodiments, suitable antimicrobial peptides comprise all or part of the amino acid sequence of a known peptide, more preferably incorporating at least some of the conserved regions identified in Table 2. In particularly preferred embodiments, the antimicrobial peptides incorporate at least one of the conserved regions, more usually incorporating two of the conserved regions, preferably conserving at least three of the conserved regions, and more preferably conserving four or more of the conserved regions. In preferred embodiments, the antimicrobial peptides comprise fifty amino acids or fewer, although there may be advantages in increasing the size of the peptide above that of the natural peptides in certain instances. In certain embodiments, the peptides have a length in the range from about 10 to 50 amino acids, preferably being in the range from about 10 to 40 amino acids, and most preferably being in the range from about 30 to 35 amino acids which corresponds generally to the length of the natural defensin peptides.

In some embodiments, the present invention provides antibodies (or portions thereof) fused to biocidal molecules (e.g., lysozyme) (or portions thereof) suitable for use with processed food products as a whey based coating applied to food packaging and/or as a food additive. In still other embodiments, the compositions of the present invention are formulated for use as disinfectants for use in food processing facilities. Additional embodiments of the present invention provide human and animal therapeutics.

C. Linkers

In preferred embodiments, the transgenic fusion proteins comprise a targeting molecule (e.g., immunoglobulin heavy chain (or fragment thereof) and a light chain or (a fragment thereof)) connected to a biocide molecule by a linker. In preferred embodiments, the targeting molecule is linked via a peptide linker or is directly fused (e.g., covalently bonded) to the biocide molecule. In preferred embodiments, the transgenic fusion proteins assemble into dimeric, trimeric, tetrameric, pentameric, hexameric or higher polymeric complexes.

In preferred embodiments, the present invention provides retroviral constructs that encode in operable configuration an immunoglobulin (or portion thereof), a biocide molecule (or portion thereof), and a linker group that connects the immunoglobulin and the biocide. In some of these embodiments, the linker group comprises one amino acid moiety (e.g., $X_n$; wherein X is any amino acid or amino acid derivative; and n=1). In some of these embodiments, the linker group comprises at least one amino acid moiety (e.g., $X_n$; wherein X is any amino acid or amino acid derivative; and $n \geqq 2$). Similarly, in other embodiments, the linker group comprises two or more repeating amino acids (e.g., $X_nY_z$; wherein X and Y are any amino acid or amino acid derivative; and n≧1 and z≧1). In still further embodiments, the linker group comprises two or more repeating amino acids that form a repeating unit (e.g., $(X_nY_z)_r$; wherein r≧1). The present invention is not intended to be limited, however, to the aforementioned linker groups. Those skilled in the art will appreciate that a number of other linker group configurations and compositions find use in certain embodiments of the present invention.

In particularly preferred embodiments, the linker group used has one or more of the following characteristics: 1) sufficient length and flexibility to allow for the rotation of the targeting molecule (e.g., immunoglobulin) and the biocide molecule (e.g., lysozyme) relative to one another; 2) a flexible extended conformation; 3) a propensity for developing ordered secondary or tertiary structures that interact with functional components; 4) nonreactive with the functional components of the construct (e.g., minimal hydrophobic or charged character to react with the functional protein domains); 5) sufficient resistant to degradation (e.g., digestion by proteases); and 6) allows the fusion protein to form a complex (e.g., a di-, tri-, tetra-, penta-, or higher multimeric complex) while retaining biological (e.g., biocidal) activity. The linker sequence should separate the target molecule and the biocide molecule of the fusion protein by a distance sufficient to ensure that each component properly folds into its secondary and tertiary structures.

In preferred embodiments, the peptide linker is from about 2 to 500, more preferably of from about 50 to 100, and even more preferably, from about 10 to 30 amino acids long. A polypeptide linker sequence of about 20 amino acids provides a suitable separation of functional protein domains, although longer or shorter linker sequences are contemplated. For example, in particularly preferred embodiments, the peptide linker is between 17 to 20 amino acids in length.

The present invention further contemplates peptide linkers comprised of the following amino acids: Gly, Ser, Asn, Thr or Ala. Typical surface amino acids in flexible protein regions include Gly, Ser, and Asn. The present invention contemplates that various amino acid sequence permutations of Gly, Ser, and optionally Asn, provide suitable linker sequences. However, the present invention is not limited to peptide linkers comprised of the aforementioned amino acids. For example, in some embodiments, the peptide linkers comprise further uncharged polar amino acids (e.g., Gln, or Tyr) and/or nonpolar amino acids (e.g., Val, Leu, Ileu, Pro, Phe, Met, Trp, Cys).

In some preferred embodiments, the peptide linker comprises one (or more) Gly-Ser elements. For example, in some of these embodiments, the peptide linker has the formula $(Ser_n\text{-}Gly_x)_y$, wherein n and x≧1, and y≧1. In some preferred embodiments, the peptide linker has the formula $(Ser\text{-}Gly_4)_y$ (SEQ ID NO. 184), wherein y=1, 2, 3, 4, 5, 6, 7, 8 or more. In some other preferred embodiments, the peptide linker includes a sequence having the formula $(Ser\text{-}Gly_4)_3$ (SEQ ID NO. 185). In still other preferred embodiments, the peptide linker comprises a sequence of the formula $((Ser\text{-}Gly_4)_3\text{-}Ser\text{-}Pro)$ (SEQ ID NO. 186). Other peptide linker sequences are contemplated, including, but not limited to, $Gly_4SerGly_5Ser$ (SEQ ID NO. 187), and $((Ser_4\text{-}Gly)_3\text{-}Ser\text{-}Pro)$ (SEQ ID NO. 188).

In still further embodiments, the target molecule and the biocidal molecule comprising the fusion protein are fused directly without a linker sequence. In some embodiments, linker sequences are unnecessary where the fusion protein components have non-essential N- or C-terminal amino acid regions that separate functional domains and prevent steric interference.

II. Constructs and Production

A. Retroviruses and Retroviral Vectors

Retroviruses (family Retroviridae) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses that infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other poi gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses is well known in the art and this has allowed the adaptation of the retroviral genome to produce retroviral vectors. The production of a recombinant retroviral vector carrying a gene of interest is typically achieved in two stages. First, the gene of interest is inserted into a retroviral vector which contains the sequences necessary for the efficient expression of the gene of interest (including promoter and/or enhancer elements which may be provided by the viral long terminal repeats [LTRs] or by an internal promoter/enhancer and relevant splicing signals), sequences required for the efficient packaging of the viral RNA into infectious virions (e.g., the packaging signal [Psi], the tRNA primer binding site [−PBS], the 3' regulatory sequences required for reverse transcription [+PBS] and the viral LTRs). The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); the resulting virus is said to be replication defective.

Second, following the construction of the recombinant vector, the vector DNA is introduced into a packaging cell line. Packaging cell lines provide viral proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus [VSV]). The transfected packaging cell will then produce viral particles that contain the membrane-associated protein expressed by the transfected packaging cell line; these viral particles, which contain viral genomic RNA derived from one virus encapsidated by the envelope proteins of another virus are said to be pseudotyped virus particles.

Viral vectors, including recombinant retroviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

Commonly used recombinant retroviral vectors are derived from the amphotropic Moloney murine leukemia virus (MoMLV) (Miller and Baltimore, Mol. Cell. Biol., 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (Markowitz et al., J. Virol., 62:1120 [1988]).

Despite these advantages, existing retroviral vectors based upon MoMLV are limited by several intrinsic problems: 1) they do not infect non-dividing cells (Miller et al., Mol. Cell. Biol., 10:4239 [1992]), 2) they produce low titers of the recombinant virus (Miller and Rosman, BioTechn., 7: 980 [1989]; and Miller, Nature 357: 455 [1992]) and 3) they infect certain cell types (e.g., human lymphocytes) with low efficiency (Adams et al., Proc. Natl. Acad. Sci. USA 89:8981 [1992]). The low titers associated with MoMLV-based vectors has been attributed, at least in part, to the instability of the virus-encoded envelope protein. Concentration of retrovirus stocks by physical means (e.g., ultracentrifugation and ultrafiltration) leads to a severe loss of infectious virus.

Other commonly used retrovectors are derived from lentiviruses including, but not limited to, human immunodeficiency virus (HIV) or feline immunodeficiency virus (FIV). Lentivirus vectors have the advantage of being able to infect non replicating cells.

The low titer and inefficient infection of certain cell types by retro vectors has been overcome by the use of pseudotyped retroviral vectors which contain the G protein of VSV as the membrane associated protein. Unlike retroviral envelope proteins which bind to a specific cell surface protein receptor to gain entry into a cell, the VSV G protein interacts with a phospholipid component of the plasma membrane (Mastromarino et al., J. Gen. Virol., 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al., Proc. Natl. Acad. Sci. USA, 90:8033 [1993]).

The VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV.

The present invention is not limited to the use of the VSV G protein when a viral G protein is employed as the heterologous membrane-associated protein within a viral particle. Sequences encoding other G proteins derived from other members of the Rhabdoviridae family may be used; sequences encoding numerous rhabdoviral G proteins are available from the GenBank database.

The majority of retroviruses can transfer or integrate a double-stranded linear form of the virus (the provirus) into the genome of the recipient cell only if the recipient cell is cycling (i.e., dividing) at the time of infection. Retroviruses that have been shown to infect dividing cells exclusively, or more efficiently, include MLV, spleen necrosis virus, Rous sarcoma virus human immunodeficiency virus, and other lentiviral vectors.

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J., 12:2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

B. Production of Proteins in Mammalian Cell Culture

In certain embodiments, the production of *Cryptosporidium* spp.-specific monoclonal antibody fusion proteins is conducted in a retrovector gene product expression system. In an initial step, the transduced production cell pool is subjected to clonal analysis to select the top fusion protein producing clones. Preferably, the retrovector construct is used to transform host cells along with the plasmid that encodes the vesicular stomatitis virus glycoprotein (VSV-G) used for pseudotyping the retrovirus. This procedure creates intermediate level viral titer used to infect production cell lines (e.g., 293H and CHO cells among others). The population of transduced cells is then subjected to a clonal selection, based on antibody fusion protein levels present in the medium supernatant.

In additional embodiments, the selected clones are then expanded and used to produce sufficient quantities of *Cryptosporidium* spp.-specific fusionprotein products to perform one or more functionality studies.

The clone with the highest level of antibody secreted into the supernatant is then chosen to produce milligram amounts of recombinant fusion protein against *Cryptosporidium* spp. Additional experiments with the purified fusion protein products are then conducted.

C. Production of Transgenic Animals with Retrovectors

The nuclear envelope of a cell breaks down during meiosis as well as during mitosis. Meiosis occurs only during the final stages of gametogenesis. Applications of retrovector transfer to create transgenic animals exploit the breakdown of the nuclear envelope during meiosis to permit the integration of recombinant retroviral DNA and permit for the first time the use of unfertilized oocytes (i.e., pre-fertilization and pre-maturation oocytes) as the recipient cell for retroviral gene transfer for the production of transgenic animals. Because infection of unfertilized oocytes permits the integration of the recombinant provirus prior to the division of the one cell embryo, all cells in the embryo will contain the proviral sequences. FIG. 14 describes exemplary constructs for production of directed biocides in transgenic organisms.

Exemplary methods are described, for example, by Chan et al (Proc Natl Acad Sci U S A 1998 Nov. 24; 95(24):14028-33), and U.S. Pat. No. 7,138,562, U.S. Pat. No. 6,548,740, U.S. Pat. No. 6,291,740, U.S. Pat. No. 6,080,912, US20030221206A1, US20020129393A1, and US20010044937A1, each of which is herein incorporated by reference.

Briefly, high titer retrovector containing the construct for the protein of interest is introduced into the perivitelline space of oocytes which have not undergone the final stages of gametogenesis. The injected oocytes are then permitted to complete maturation and subjected to in vitro fertilization.

Retroviral vectors capable of infecting the desired species of non-human animal, which can be grown and concentrated to very high titers (e.g., $1\times10^8$ cfu/ml) are preferentially employed. The use of high titer virus stocks allows the introduction of a defined number of viral particles into the perivitelline space of each injected oocyte. The perivitelline space of most mammalian oocytes can accommodate about 10 picoliters of injected fluid (those in the art know that the volume that can be injected into the perivitelline space of a mammalian oocyte or zygote varies somewhat between species as the volume of an oocyte is smaller than that of a zygote and thus, oocytes can accommodate somewhat less than can zygotes).

The vector used may contain one or more genes encoding a protein of interest; alternatively, the vector may contain sequences that produce anti-sense RNA sequences or ribozymes. The infectious virus is microinjected into the perivitelline space of oocytes (including pre-maturation oocytes) or one cell stage zygotes.

The virus stock may be titered and diluted prior to microinjection into the perivitelline space so that the number of proviruses integrated in the resulting transgenic animal is controlled.

Following injection matured oocytes are fertilized by the addition of spermatozoa and the fertilized embryos are incubated for 7-8 days prior to transfer to a hormonally synchronized recipient surrogate mother. Pregnancy in such a surrogate is carried to term and the offspring may be delivered by natural vaginal birth or via cesarean section. The presence of the transgene in the offspring is detected after birth by PCR testing for the transgene presence in samples from multiple tissues (e.g., blood, skin, etc.).

D. Expression in the Milk of Transgenic Animals

The present invention also provides transgenic animals that are capable of expressing foreign proteins in their milk, urine and blood. The transgene is stable and shown to be passed from a transgenic founder bull or cow to its offspring. In addition, the transgenic animals produced according to the present invention express foreign proteins in their body fluids (e.g., milk, blood, and urine).

In order to achieve the expression of the protein of interest (e.g., fusion protein or directed biocide) in the desired tissue (e.g., in the mammary epithelium to achieve secretion in milk) the retrovector construct is designed to include a tissue specific promoter which restricts the expression of the gene of interest to the preferred tissue In some embodiments, the promoter used for mammary specific expression is derived from a milk protein (e.g., alphalactalbumin, betaglobulinm, whey acid protein or casein). For direction of expression to other tissues other tissue specific promoters may be preferred.

III. Uses of *Cryptosporidium* spp. Directed Biocides

As described above, embodiments of the present invention provide directed biocides against *Cryptosporidium* spp. (e.g., *Cryptosporidium parvum* and *Cryptosporidium hominus*).

The present invention provides antibody-based fusion protein products that effectively control acute *Cryptosporidium* spp. infections. The present invention contemplates that the efficacy of compositions and methods of treatment comprising administering antibodies specifically developed against *Cryptosporidium* spp. epitopes and combined as a fusion protein with a protein biocide as a fusion is distinguishable from the host-produced antibodies in protection against natural infection, which depends on competent cell mediated immune responses (M. Riggs, Microbes Infect., 4:1067 [2002]).

Preferred embodiments provide compositions and methods for administering immunoglobulin based biocides against *Cryptosporidium* spp. infections. In some embodiments the product is applied as an oral therapeutic effective against *Cryptosporidium* spp. for treatment of cryptosporidiosis in immunocompromised patients, and immunocompetent individuals infected in sporadic outbreaks or when exposed in travel. In other embodiments the product is used as an oral therapeutic delivered in a cold chain independent or tolerant formulation suitable for administration to children in tropical countries. In yet another embodiment the product is applied as an oral milk supplement for neonatal calves, to reduce the impact of clinical cryptosporidiosis in cattle and to reduce the reservoir of *Cryptosporidium* spp. for infection of man. In some embodiments, directed biocides are used as a prophylactic or preventative treatment against *Cryptosporidium* spp. (e.g., by administering to a subject at risk of being infected with *Cryptosporidium* spp.).

In some of these embodiments, the present invention provides orally administered monoclonal antibody compositions that specifically target pathogens (e.g., parasites) and either prevent infection, or reduce an existing infection to subclinical levels and abbreviate existing clinical effects.

In some embodiments, the present invention provides monoclonal antibodies against defined apical complex and surface-exposed antigens to specifically neutralize infective stages of *Cryptosporidium* spp. in vitro and in vivo. The present invention also provides previously unavailable recombinant antibodies to *Cryptosporidium* spp. Prior to the present invention, high cost and inefficient production systems for recombinant and hybridoma monoclonals alike have generally removed widespread immunoprophylaxis and/or immunotherapies for cryptosporidiosis from serious clinical consideration.

Some preferred embodiments of the present invention make use of an extensive bank of hybridoma lines directed to cryptosporidial antigens. A large number of *Cryptosporidium* spp antigens of distinct function have been identified and characterized. (M. W. Riggs, Microbes. Infect., 4:1067 [2002]). Several antigens in particular have shown potential for independent targeting to neutralize sporozoite and merozoite infectivity, including, but not limited to, CSL, P23, and GP25-200. Briefly, CSL (~1300 kDa) is an apical complex-derived glycoprotein expressed on the surface of sporozoite and merozoite infective stages. After antibody binding to CSL, sporozoites release the antigen in membranous antibody-CSL complexes and are rendered non-infective. (M. W. Riggs et al., J. Immunol., 158:1787-1795 [1997]). Since CSL has been shown to contain a ligand for a surface receptor on human intestinal epithelial cells (See, R. C. Langer and M. W. Riggs, Infect. Immun, 67:5282-5291 [1999]; and R. C. Langer et al., Infect. Immun, 69:1661-1670 [2001]), blocking of CSL is contemplated to account for the efficacy of anti-CSL antibodies in inhibiting sporozoite attachment. P23 (~23 kDa) is a surface protein of sporozoites and merozoites believed to be involved in motility and invasion processes (See, L. E. Perryman et al., Vaccine, 17:2142-2149 [1999]). Monospecific antibodies to P23 have been shown to curtail disease in neonatal calves. (L. E. Perryman et al., supra). GP25-200 is a glycoprotein complex of variable size, found in the apical complex and on the surface of sporozoites and merozoites. (M. W. Riggs et al., supra). Schaefer et al. demonstrated that when hybridoma derived monoclonal antibodies to CSL, P23, and GP25-200 were applied singly, or in combination, significant sporozoite neutralization could be obtained. (D. A. Schaefer et al., Infect. Immun, 68:2608-2616 [2000]).

In some embodiments, optimal protection against oocyst challenge in neonatal mice is achieved by targeting multiple epitopes. Additional preferred embodiments provide fusion proteins comprising cryptosporocidal enzymes and antibodies, or portions thereof, including, but not limited to, 3E2, 18.44 and 4H9.

In other embodiments, monoclonal antibody 3E2 is utilized. 3E2 recognizes the CSL antigen, a ~1300 kDa apical complex-derived glycoprotein expressed on the surface of sporozoite and merozoite infective stages. After antibody binding to CSL, sporozoites release the antigen in membranous antibody-CSL complexes and are rendered non-infective (Riggs et al., J Immunol 1997; 158:1787-95). Since CSL has been shown to contain a ligand for a surface receptor on human intestinal epithelial cells (Langer and Riggs, Infect Immun 1999; 67:5282-91; Langer et al., J. Immunol. 1997; 158:1787).

Experiments conducted during the course of development of the present invention demonstrated that several biocides had *Cryptosporidium* spp. sporozoite killing activity, as well as the ability to reduce *Cryptosporidium* spp. infectivity. The biocides evaluated have the further advantage of showing minimal toxicity against human cells. In some embodiments, the methods and compositions of the present invention find use in the treatment of subjects (e.g., humans) infected with a *Cryptosporidium* spp. In other embodiments, the present invention provides methods of preventing infection with a *Cryptosporidium* spp. by administering a composition of the present invention to a subject at risk of infection with a *Cryptosporidium* spp.

IV. Pharmaceutical Compositions

The present invention provides novel methods and compositions for treating or preventing diseases characterized by pathogenic infection comprising administering subjects (e.g., bovines, humans, other mammals, and other vertebrates) a pharmaceutical and/or nutraceutical composition comprising chimeric recombinant antibodies either in food based (e.g., milk or whey protein) carriers, or common pharmaceutical carriers, including any sterile, biocompatible pharmaceutical carrier (e.g., saline, buffered saline, dextrose, water, and the like) to subjects.

In some embodiments the composition is applied to individuals exposed or likely to have been exposed to a given microorganism as a prophylactic treatment; in other embodiments the composition is applied to combat clinical or subclinical disease as a therapeutic. In yet others embodiments, it is applied to individuals in a group who are at various stages of infection as a metaphylactic treatment.

In some embodiments, the methods of the present invention comprise administering the compositions of the present invention in suitable pharmaceutical carriers. In some embodiments, these pharmaceutical compositions contain a mixture of at least two types of antibody-biocide compositions co-administered to a subject. In still further embodiments, the pharmaceutical compositions comprise a plurality of antibody-biocide compositions administered to a subject under one or more of the following conditions: at different periodicities, different durations, different concentrations, different administration routes, etc.

Depending on the condition being treated, these pharmaceutical compositions are formulated and administered systemically or locally. Techniques for formulation and administration are found in the latest edition of "Remington's Pharmaceutical Sciences" (Mack Publishing Co, Easton Pa.). Accordingly, the present invention contemplates administering pharmaceutical compositions in accordance with acceptable pharmaceutical delivery methods and preparation techniques.

In some embodiments, present compositions are formulated for parenteral administration, including intravenous, subcutaneous, intramuscular, and intraperitoneal. In some embodiments, these compositions optionally include aqueous solutions (i.e., water-soluble forms). Additionally, suspensions of the active compounds may also be prepared as oily injection suspensions as appropriate. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

In other embodiments, the present compositions are formulated using pharmaceutically acceptable carriers and in suitable dosages for oral administration. Such carriers enable the compositions to be formulated as tablets, pills, capsules, dragees, liquids, gels, syrups, slurries, suspensions and the like, for oral or nasal ingestion by a patient to be treated.

Pharmaceutical preparations for oral use can be obtained by combining the active compounds (e.g., chimeric antibody biocide fusion proteins) with a solid excipient, optionally grinding the resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc.; cellulose such as methyl cellulose, hydroxypropylmethyl-cellulose, or sodium carboxymethylcellulose; and gums including arabic and tragacanth; and proteins such as gelatin and collagen. If desired disintegrating or solubilizing agents may be added, such as the cross-linked polyvinyl pyrrolidone, agar, alginic acid or a salt thereof such as sodium alginate.

Ingestible formulations of the present compositions may further include any material approved by the United States Department of Agriculture for inclusion in foodstuffs and substances that are generally recognized as safe (GRAS), such as, food additives, flavorings, colorings, vitamins, minerals, and phytonutrients. The term "phytonutrients" as used herein, refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

Compositions of the present invention that can be used orally include push-fit capsules made of gelatin, as well as soft, sealed capsules made of gelatin and a coating such as glycerol or sorbitol. The push-fit capsules can contain the active ingredients mixed with fillers or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers. In some embodiments, capsules are enterically coated (e.g., methyl cellulose) to prevent opening in the stomach.

In some embodiments of the present invention, therapeutic agents are administered to a patient alone, or in combination with one or more other drugs or therapies (e.g., antibiotics and antiviral agents etc.) or in pharmaceutical compositions where it is mixed with excipient(s) or other pharmaceutically acceptable carriers. In one embodiment of the present invention, the pharmaceutically acceptable carrier is pharmaceutically inert. In some embodiments, therapeutic agents are administered in combination with antacids (e.g., omprazole, cimetidine) to protect the protein during gastric passage.

Pharmaceutical compositions suitable for use in the present invention include compositions wherein the active ingredients are contained in an effective amount to achieve the intended purpose. For example, an effective amount of therapeutic compound(s) may be that amount that destroys or disables pathogens as compared to control pathogens.

In addition to the active ingredients, preferred pharmaceutical compositions optionally comprise pharmaceutically acceptable carriers, such as, excipients and auxiliaries that facilitate processing of the active compounds into preparations that can be used pharmaceutically.

In some embodiments, the pharmaceutical compositions used in the methods of the present invention are manufactured according to well-known and standard pharmaceutical manufacturing techniques (e.g., by means of conventional mixing, dissolving, granulating, dragee-making, levigating, emulsifying, encapsulating, entrapping or lyophilizing processes).

Dosing is dependent on severity and responsiveness of the disease state to be treated, with the course of treatment lasting from several days to several months, or until a cure is effected or a diminution of the disease state is achieved. Optimal dosing schedules are calculated from measurements of composition accumulation in the subject's body. The administering physician can easily determine optimum dosages, dosing methodologies and repetition rates. Optimum dosages may vary depending on the relative potency of compositions agents, and can generally be estimated based on the $EC_{50}$s found to be effective in in vitro and in vivo animal models. Additional factors that may be taken into account, include the severity of the disease state; the age, weight, and gender of the subject; the subject's diet; the time and frequency of administration; composition combination(s); possible subject reaction sensitivities; and the subject's tolerance/response to treatments. In general, dosage is from 0.001 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the therapeutic agent is administered in maintenance doses, ranging from 0.001 μg to 100 g per kg of body weight, once or more daily, weekly, or other period.

For any compound used in the methods of the invention, the therapeutically effective dose can be estimated initially from cell culture assays. Then, preferably, dosage can be formulated in animal models (particularly murine or rat models) to achieve a desirable circulating concentration range that results in increased PKA activity in cells/tissues characterized by undesirable cell migration, angiogenesis, cell migration, cell adhesion, and/or cell survival. A therapeutically effective dose refers to that amount of compound(s) that ameliorate symptoms of the disease state (e.g., pathogenic infection). Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from cell culture assays and additional animal studies can be used in formulating a range of dosage, for example, mammalian use (e.g., humans). The dosage of such compounds lies preferably, however the present invention is not limited to this range, within a range of circulating concentrations that include the $ED_{50}$ with little or no toxicity.

Guidance as to particular dosages and methods of delivery is provided in the literature (See, U.S. Pat. Nos. 4,657,760; 5,206,344; or 5,225,212, all of which are herein incorporated by reference in their entireties). Administration of some agents to a patient's bone marrow may necessitate delivery in a manner different from intravenous injections.

EXAMPLES

The present invention provides the following non-limiting examples to further describe certain contemplated embodiments of the present invention.

Example 1

Molecular Engineering to Make Anticryptosporidial Recombinant Antibodies and Antibody Biocide Fusions Hybridoma cell lines, established at the University of Arizona (Schaefer et al., Infect Immun 2000 May; 68(5):2608-16), for 3 different antibodies (3E2, 4H9, 18.44), plus a non-cryptosporidial hybridoma, 166, for a control (Ziegler H K, Orlin Calif. Analysis of *Listeria monocytogenes* antigens with monoclonal antibodies. Clin Invest Med 1984; 7(4):239-42) were the starting material for total RNA extraction. Total RNA was reverse transcribed into cDNA and used as a template for PCR. Separate sets of degenerate primers were used to either amplify the heavy chain or the light chain variable coding region. Since the degenerate primers anneal to the signal peptide region of the immunoglobulin coding regions, the endogenous hybridoma-derived signal peptide was replaced with a standard signal peptide used for all constructs. The resulting PCR products were cloned into a PCR cloning vector and sequenced. The genes for the light chains were assembled in the same fashion. A list of the antibodies and epitopes used in this example are provided in Table 3. FIG. 14 shows a list of constructs and SEQ ID NOs.

TABLE 3

DB and rMab produced and tested in this project

| Antibody | Epitope on *C. parvum* sporozoites | DB type |
|---|---|---|
| 4H9 | GP25-500 | 4H9-G1 |
| | | 4H9-G1-LL37 |
| | | 4H9-G2b-LL37 |
| | | 4H9-G1-PLA2 |
| 18.44 | CPS-500 | 18.44-G1 |
| | | 18.44-G1-PLA2 |
| | | 18.44-G1-LL37 |
| 3E2 | CSL | 3E2-M |
| 166 | N/A | 166-G2b-LL37 |

Grafting of Variable Region Coding Sequence onto Various Different Immunoglobulin Isotypes Immunoglobulin constant region was obtained from hybridoma cDNA using primers to the known constant region. The constant regions were combined with the variable regions by overlap PCR. A variety of DB types were constructed. The 4H9 variable region was grafted onto either an IgG1 or an IgG2b isotype constant region by a series of overlap PCR steps. Both of these isotype versions were tested an no changes in the binding pattern with *C. parvum* sporozoites in vitro were observed demonstrating that grafting these variable regions onto different isotypes has no impact on binding specificity.

Linking of Immunoglobulins to Various Different Biocides

One particular antibody can be fused to various different biocides to achieve efficacy. 4H9-G1-LL37 and 4H9-G1-PLA2 fusions were constructed and demonstrated good efficacy with both biocides. The gene for human phospholipase A2 group IIA was obtained from the ATCC gene collection (MGC-14516). The coding region for the 37 amino acid active portion of human hCAP-18 and the linker were assembled by PCR amplification of 3 long overlapping oligomers that were based on Genbank NM_004345. The fusion was done via overlap PCR of heavy chain constant region with the desired linker biocide coding sequence. The fully assembled heavy chain-biocide fusion was then cloned into the mammalian retrovector. Examplary antibody-biocide fusions of combinations of three specificities with two isotypes and two biocides are shown in Table 1. Additional DB variations using the 3E2 specificity with either a hexamer, monomer or halfmer constant region linked to the LL37 biocide were also generated.

For control purposes, cell lines that secrete either pentameric or hexameric IgM 3E2 standalone antibody (without a biocide fusion) were generated. To achieve the pentameric version of IgM, which is the predominant form in the serum of mammals, a J-chain is needed. The J-chain should be expressed in the same cell line that secretes the IgM heavy and light chain. CHO cells were transduced first with a retroviral construct containing the gene for the J-chain (extracted from the hybridoma cell line by use of primers specific to Genbank Accession NM_152839). The J-chain producing pool was then transduced with the constructs for 3E2 light chain followed by 3E2 heavy chain. Upon clonal selection a clonal cell line producing recombinant pentameric 3E2 antibody at the correct size of approximately 900 kDa as determined by Western immunoblot (data not shown). We also made a clonal cell line lacking the J-chain in which the IgM immunoglobulin spontaneously assembles into a hexamer form with a molecular weight of approximately 1180 kDa. Both recombinant versions of 3E2, hexamer and pentamer, were effective at neutralizing infection in mice. This the first time an IgM hexameric form of an anti-cryptosporidium antibody has demonstrated neutralizing activity.

Creation of Stable Production Cell Lines

FIG. 2. shows the basic functional elements of the constructs. Due to the extremely high gene transfer efficiency of the retroviral system no resistance genes are needed for selection of transduced mammalian host cells. The simian CMV promoter was used as the main driver of expression of the transgene. An RNA export element derived from the woodchuck hepatitis virus was also included in the constructs. Both the assembled light chain gene and the heavy chain-linker-biocide gene were cloned into separate MLV-based retrovectors. First, the retroviral construct containing the light chain gene of interest was co-transfected with plasmid containing the gene for vesicular stomatitis glycoprotein into GP2-293 packaging cells (Clontech, Mountain View, Calif.) to produce infectious replication-incompetent pseudotyped retrovector particles. These were harvested by centrifugation, then used to transduce CHO cells. Ten days after transduction, cell pools were analyzed by ELISA to detect light chain. Upon confirmation of secreted light chain, clonal analysis was done and the top producing clones selected. In a second step, top light chain producing clones were transduced with the heavy chain construct to make full size antibodies. Clonal analysis was repeated and top clones producing full size antibody products selected. Products from top clones were used mostly unprocessed for in vitro and in vivo testing. In some experiments, cell culture supernatants were concentrated up to 20 fold using Amicon Centricon Plus-20 (Millipore, Billerica, Mass. 01821) to match protein concentrations of different products in one assay.

Scale-Up of Manufacturing

In Cell Culture

To meet the product demand of different experimental test systems (in vitro, neonatal mouse, or neonatal pig) different cell culture production systems were employed. For small scale testing in our in vitro systems, standard tissue culture flasks were used to grow volumes up to 30 ml per flask (T150). Product for mouse trials was grown in 500 ml Erlenmeyer shaker flasks that grow volumes of up to 180 ml. The next production vessel is a single-use culture bag (MantaRay, Wheaton Science, Millville, N.J.) with a capacity of 500 ml to 1000 ml.

To supply the product for the pig trials (see below), Wave Biotech (GE, Piscataway, N.J.) disposable bags up to 25 L working volume were used. The Wave Biotech system is scaleable up to 500 L working volume for use as seed train or actual production vessels. Expression levels of up to 200 mg/L were achieved. This indicates that with eventual optimization of growth parameters under cGMP conditions the cells would yield upwards of a gram per liter. For the downstream processing a pilot scale tangential-flow filtration system for clarification, concentration and dialysis of up to 25 L of cell suspension was built. In some applications, purified protein is lyophilized.

In Transgenic Animals

The tissue culture constructs were adapted for expression under a mammary specific promoter in the milk of transgenic cattle. The initial focus was on the production of 4H9-G1-LL37 and 4H9-G1-PLA2. High titer concentrated retrovector is used to achieve transgenic embryos by perivitelline space injection of oocytes prior to in vitro fertilization (Chan et al., Proc Natl Acad Sci USA 1998 Nov. 24; 95(24):14028-33). Constructs comprising the alphalac promoter were utilized to obtain mammary specific expression (SEQ ID NOs157-158). A qPCR-based methodology was used to predict the number of infectious particles injected into each oocyte. Typically between 15 and 40 particles are injected per oocyte. After injection of retrovector the oocytes were fertilized in vitro and matured until day 7 at which time they were either transferred into a surrogate mother cow, or analyzed for the presence of the transgene. A protocol was developed to reliably determine transgenic rates in isolated single bovine embryos using a nested PCR approach.

Selection of the Best Biocide Candidates

Ten antimicrobial peptides (from a variety of commercial sources) were screened for anti-cryptosporidial activity based on their previously reported in vitro activity against various bacteria or protozoa (Ganz, Antimicrobial polypeptides. J Leukoc Biol 2004 January; 75(1):34-8; Giacometti et al., Antimicrob Agents Chemother 2000 December; 44(12):3473-5; Giacometti et al., J Antimicrob Chemother 2003 April; 51(4):843-7; Lehrer et al., Curr Opin Immunol 1999 February; 11(1):23-7; Martin et al., J Leukoc Biol 1995 August; 58(2):128-36; McGwire et al., J Infect Dis 2003 Jul. 1; 188(1):146-52; Murdock et al., J Appl Microbiol 2002; 93(5):850-6; Wade et al., Proc Natl Acad Sci USA 1990 June; 87(12):4761-5;

Tanaka et al., Exp Parasitol 1995 December; 81(4):614-7; Tarver et al., Infect Immun 1998 March; 66(3):1045-56; Zaalouk et al., Infect Immun 2004 May; 72(5):2772-9). Their activity was evaluated using an in vitro infectivity assay that involves measurement of the infectious potential of sporozoites on Caco-2 cells upon exposure to the biocides (FIG. 2). Neutralizing MAb 3E2 (hybridoma product) was included as a positive control. With the exception of lactoferrin and lyzozyme, each peptide had highly significant activity against *C. parvum* sporozoite infectivity at the lowest concentration evaluated (2.5 μM). No detectable toxicity towards the host cells was detected at that concentration using an LDH release assay (Promega). Based on these data, PLA2 and LL37 were identified as the two leading biocide candidates on which to focus initial effort for production of DBs.

Visualization of DB Impact on Viability

Figure 3:
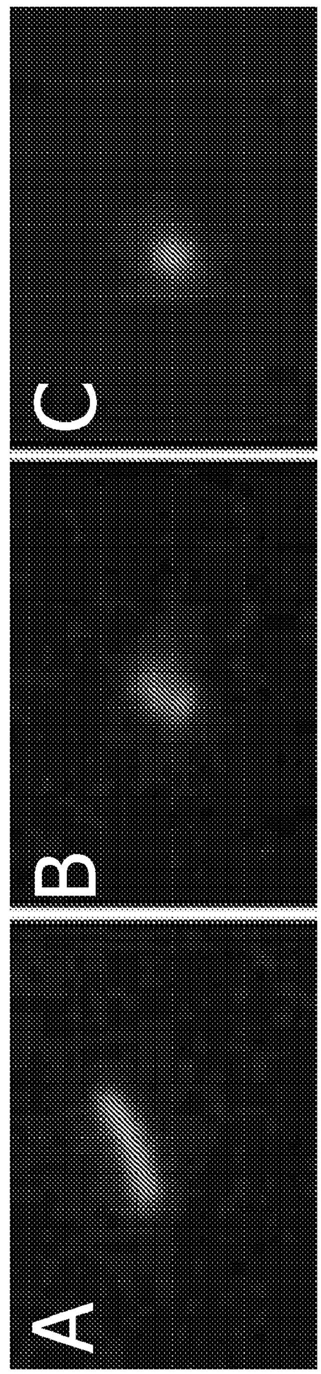
FIG. 3 shows fluorescence photomicrographs demonstrating the effect of immunoglobulin biocide fusion protein 4H9-G2b-LL37 and control antibody 4H9-G2b on sporozoite viability as determined by the addition of fluorescein diacetate and propidium iodide. A, exposure of sporozoites to 4H9-G1 control antibody during 30 min. B, exposure of sporozoites to immunoglobulin biocide fusion protein 4H9-G2b-LL37 during 5 minutes. C, exposure of sporozoites to 4H9-G2b-LL37 for 30 minutes.

As soon as the first DB were created, in vitro testing was initiated to measure direct effect on viability of sporozoites. An immunofluorescent sporozoite viability assay was established. FIG. 3 shows the comparison of treatment with 4H9 recombinant antibody alone and treatment with 4H9-G1-LL37 fusion protein.

Figure 4:
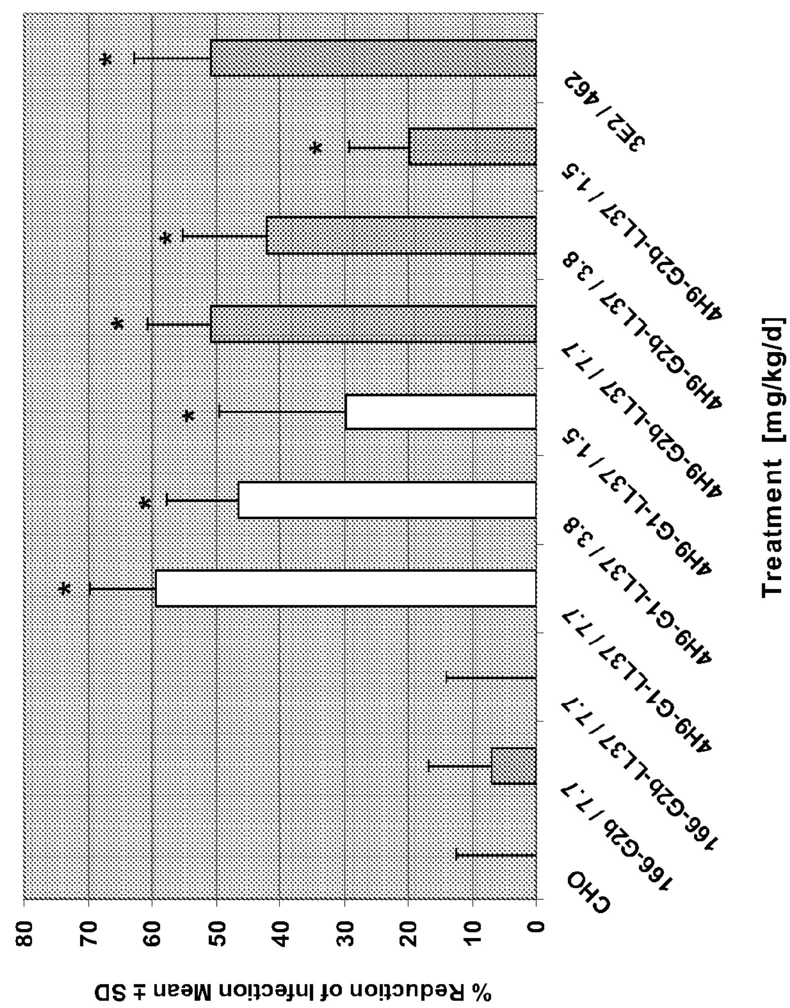
FIG. 4 shows dose response testing of oral immunoglobulin biocide fusion protein against intestinal infection in *C. parvum* oocyst challenged mice. Dosages are expressed in milligrams per kilogram per day

Efficacy Testing in Neonatal Mouse Model Using Various Dosing and Combinatorial Regimens First, dosage of fusion protein in the in vivo neonatal mouse model was established by comparing it to a hybridoma derived form of the established neutralizing antibody 3E2. The control non-specific fusion protein166-G2b-LL37 and recombinant 166-G2b were also tested to measure potential contribution of the biocide portion when fused to an antibody that does not bind to *Cryptosporidium*. Neonatal mice were inoculated with $5\times10^4$ purified oocysts by gastric intubation and the first dose of treatment was given concomitantly with the oocyst challenge to make sure therapeutic antibody products were available at the time of excystation. Treatment was given orally every 12 hours for a total of 9 treatments. 92-94 hours post challenge, mice were sacrificed and gut sections prepared for histology followed by infectious stage scoring. FIG. 4 shows a typical outcome of an in vivo reduction of infection experiment in neonatal mice. The neutralizing Mab 3E2 demonstrates good efficacy when given at a high dose of 462 mg/kg/day. Comparatively, both DB (4H9-G1-LL37, 4H9-G2b-LL37) tested, show similar or higher reduction of infection but at doses that are approximately 60-times lower (7.7 mg/kg/d) than the 3E2 dose. Dose dependency of DB efficacy is shown by two lower doses of 3.8 mg/kg/d and 1.5 mg/kg/d. None of the controls resulted in any significant reduction of infection when compared to control mice treated with CHO cell supernatant. These data indicate that several DB are highly efficient at reducing infection in the neonatal mouse model at doses that are much lower than the current benchmark neutralizing antibody 3E2. Heretofore, hybridoma-derived 3E2 has been considered the reference standard for comparison in developing new anti-cryptosporidial antibody based products (Riggs et al., J Immunol 1997 Feb. 15; 158(4):1787-95; Schaefer et al., Infect Immun 2000 May; 68(5):2608-16).

Figure 5:
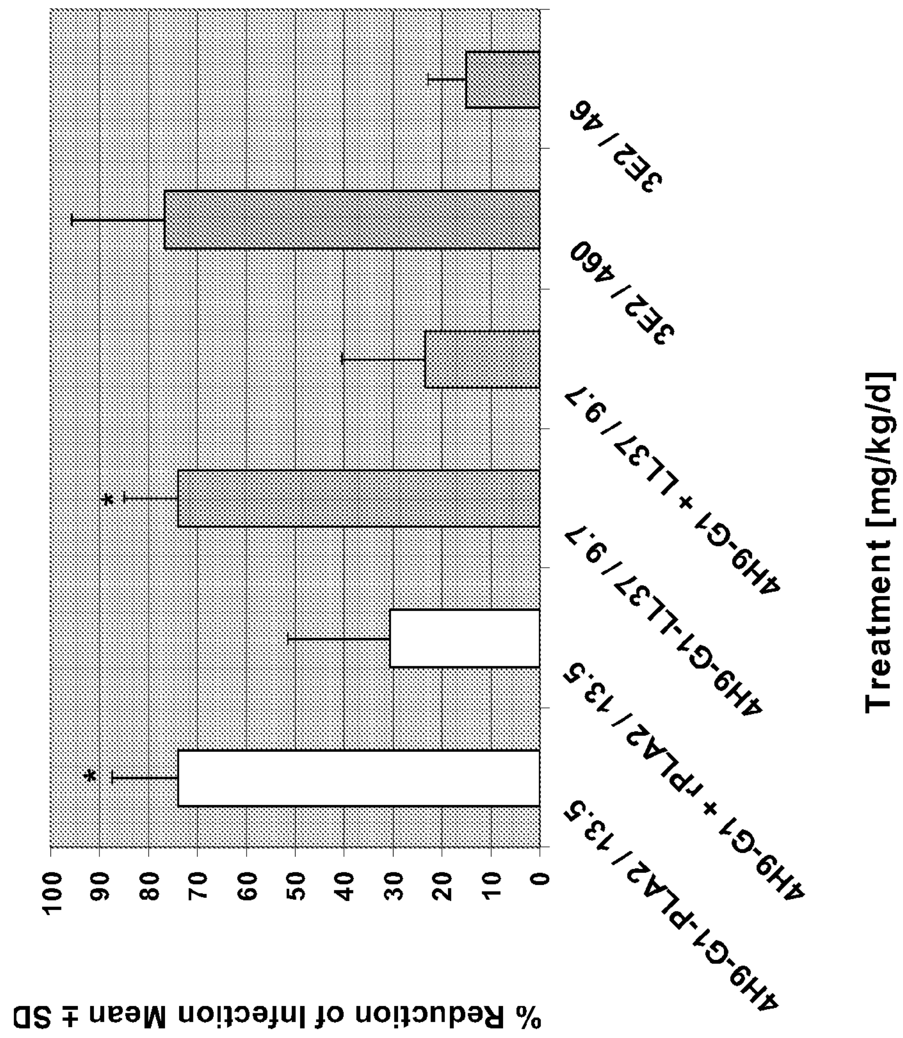
FIG. 5 shows inhibition of infection in neonatal mice. Recombinant fusion proteins 4H9-LL37 and 4H9 PLA2 are compared to the component products (recombinant immunoglobulin and biocide) added separately and to hybridoma-expressed non recombinant 3E2 IgM immunoglobulin.

Immunoglobulin-Biocide Fusion Protein Exerts Significantly Higher In Vivo Efficacy than Antibody and Biocide Given as Separate Molecules Recombinant versions of the 4H9 monoclonal antibody and synthetically produced LL-37 peptide or purified PLA2 were used to compare the efficacy of the individual components of the biocides to the fusion protein. These components were given to neonatal mice at concentrations that were equimolar to the fusion protein. Several mouse trials were performed to establish the superior functionality of the fusion protein over antibody plus biocide given as separate molecules. FIG. 5 shows that the in vivo therapeutic activity of an antibody-biocide fusion is significantly greater than that of the individual molecules mixed together. For example, 4H9-G1-LL37 given at 9.7 mg/kg/d had significantly greater in vivo therapeutic efficacy than MAb 4H9 given at 9.7 mg/kg/d in combination with an equimolar amount of LL-37. Similarly, 4H9-G1-PLA2 given at 13.5 mg/kg/d showed superior reduction of infection than an equimolar combination of 4H9 and PLA2.

These data demonstrate that the fusion of an antibody to a biocide has led to a new, more efficient mechanism of membrane disruption than the biocide itself could achieve.

Efficacy Testing in Neonatal Pig Model with Monitoring of Clinical Parameters

Figure 6:
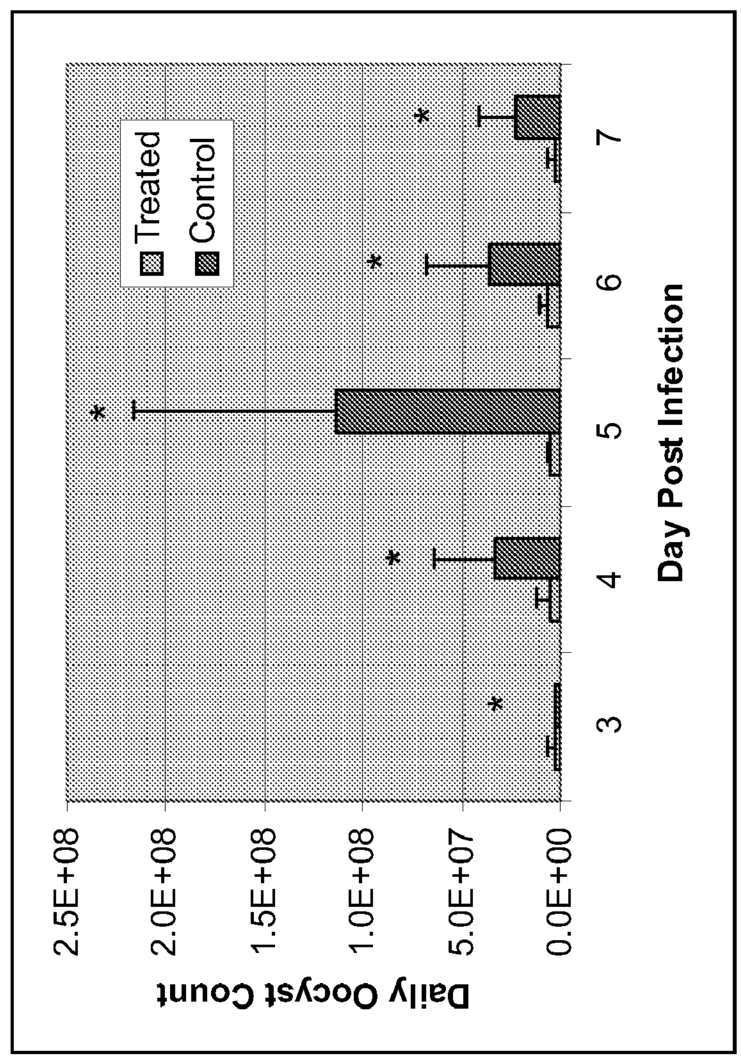
FIG. 6 shows efficacy of 4H9-G2b-LL37 given at 37.5 mg/kg/day against *C. parvum* propagation in piglets—Daily oocyst production.
Figure 7:
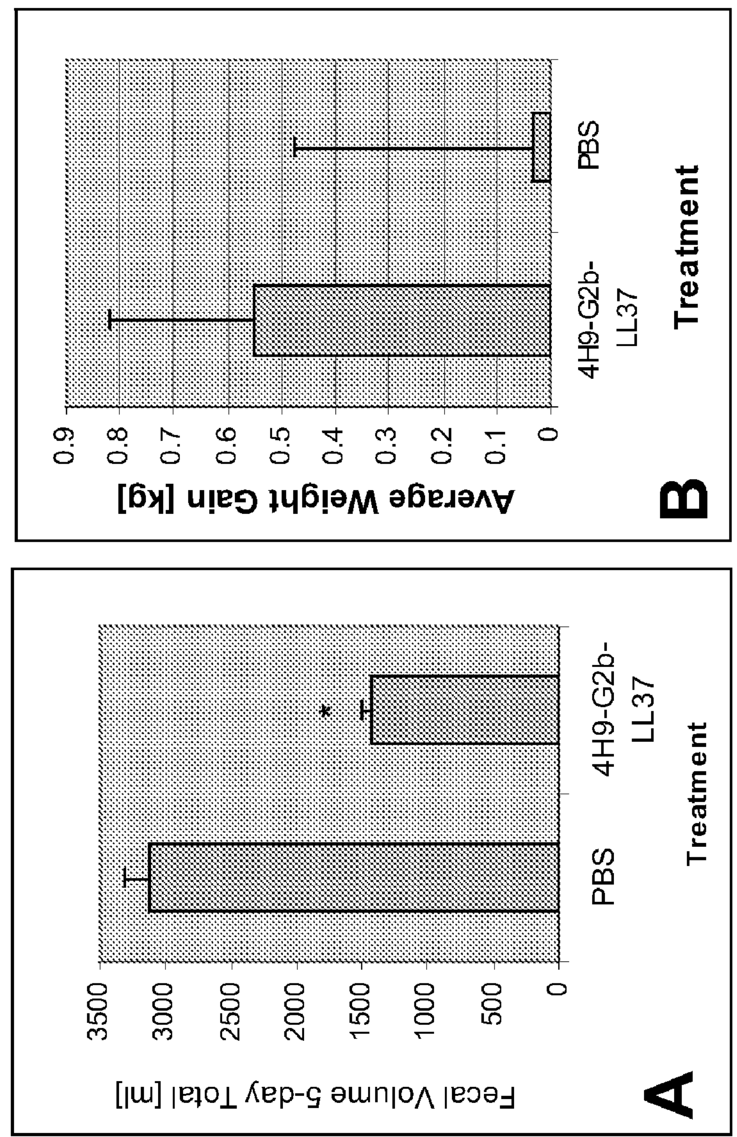
FIG. 7 shows A, Efficacy of 25 mg/dose oral solution form 4H9-G1-cat5 against *C. parvum* Diarrhea in piglets—Total fecal volume group means. B, Efficacy of 37.5 mg/kg/day dose oral solution form 4H9-G2b-LL37 against cryptosporidiosis in piglets—Average Weight Gain.

Nine neonatal piglet trials were performed. Seven trials were performed to test 4H9-G2b-LL37 and two trials to test 4H9-G1-PLA2. Dosing trials for 4H9-G2b-LL37 in piglets were performed using 1.5 mg/kg/d (enteric-coated capsule form), 4.5 mg/kg/d (solution form), or 37.5 mg/kg/d (solution form) doses. Statistically significant efficacy was observed for one or more evaluation parameters at all dosages. However, the 37.5 mg/kg/d dose trial demonstrated the greatest overall efficacy against *C. parvum* infection and clinical disease. At this dose, the treated piglets shed significantly less oocysts compared to the control group (FIG. 6). Reduction of oocyst shedding contributed to reduced transmission and reduction in the reservoir for infection of other livestock and humans. Fecal volume produced by each piglet was determined. FIG. 7A shows overall averages of fecal volume for each treatment group over the 5-day period of the trial. A significantly smaller fecal volume occurred in the 4H9-G2b-LL37-treated group when compared the PBS treated control which. During the 7-day trial period (FIG. 7B) treated animals gained on average 0.5 kg, whereas control animals gained only 0.03 kg. Weight gain occurring despite a severe infection challenge is an excellent efficacy indicator for a *C. parvum* treatment.

Figure 8:
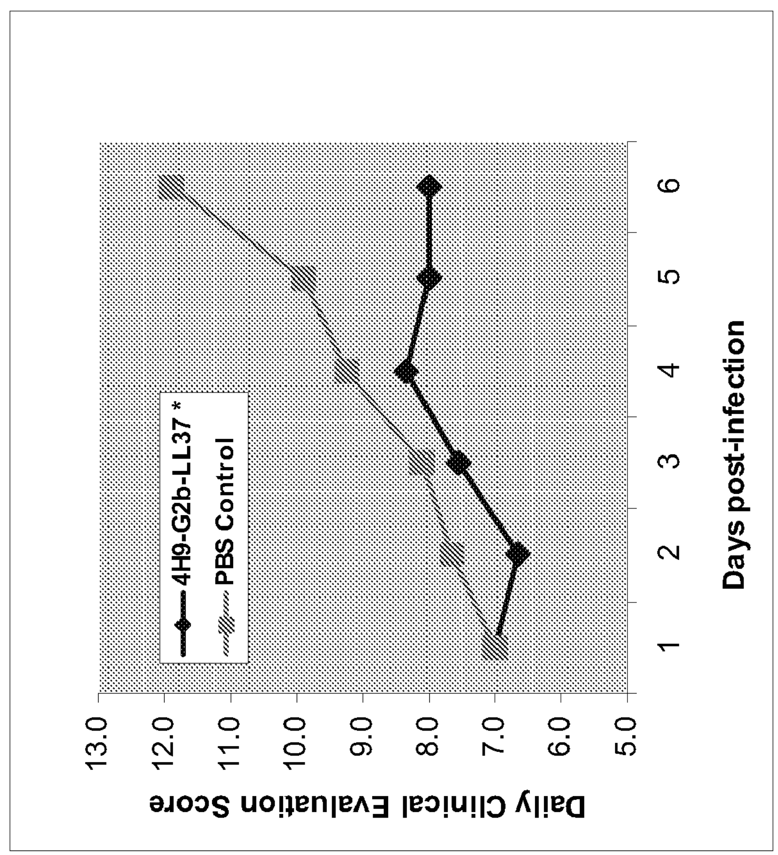
FIG. 8 shows efficacy of 37.5 mg/kg/d oral dose of 4H9-G2b-LL37 against cryptosporidiosis in piglets—Daily Clinical Evaluation Scores reflecting clinical comportment comprises a composite score for each of fecal consistency, willingness to rise, hydration status, appetite, stance when up, attitude, where a higher score reflects a worsened clinical status.

Clinical scores for each individual piglet in each treatment group were further determined FIG. 8 shows that clinical symptoms in the 4H9-G2b-LL37-treated group improve over the course of 5 days while the control animals get sicker (higher score based on assessment of fecal consistency, willingness to rise, hydration status, appetite, stance when up, attitude). The clinical scoring shows that the reduction of fecal volume and oocyst shedding combined with weight gain indeed results in an overall health improvement in treated animals which is ultimately the goal of a new treatment. The data collected in the pig clinical model shows unequivocably that immunoglobulin biocide fusion protein offer an effective new anti-cryptosporidial agent.

Example 2

Methods

This example describes exemplary methods for the development of additional directed biocides.

Chimeric Human-Mouse Immunoglobulin Fusion Protein that Bind to Both *C. hominis* and *C. parvum*

Six candidate MAb were selected based on i) specific binding to the surface of sporozoites of both species; ii) expression level in the hybridoma cell line; iii) specificity for 4 different surface antigens. Prior to molecular engineering, supernatants from hybridoma cell lines are tested for required optimal expression levels (recombinant antibodies derived from low expressing hybridoma cell lines tend to be expressed at low levels in CHO cell expression system). Total RNA is extracted from freshly grown hybridoma cells. RNA is reverse transcribed using oligo dT primer to generate cDNA from mRNA transcripts. This cDNA is used for extraction of the immunoglobulin variable coding region of the heavy and light chains. In some embodiments, the Ig-Primer Set kit from Novagen (EMD Biosciences, San Diego, Calif.). The use of degenerate PCR primers (FIG. 10 A) allows the extraction of variable region DNA for both heavy and light chain from reverse transcribed RNA (cDNA). The PCR products obtained are cloned and sequences are verified.

In the next step (FIG. 10B) the mature variable region coding sequence is defined and restriction sites are added to both ends for cloning using mutagenesis PCR. The human constant region is PCR-amplified out of human blood cDNA and restriction digested (FIG. 10C). The constant region is restriction enzyme digested and ligated in-frame into a set of existing retrovector constructs (FIG. 10D) that already contain the linker-biocide portion (e.g., LL37, PLA2 or HBD2). The constant region is restriction enzyme digested and ligated in-frame into a set of existing retrovector constructs (FIG. 10D) that already contain the linker-biocide portion (e.g., LL37, PLA2 or HBD2). The biocide portions from these vectors were obtained either by DNA synthesis (Blue Heron Biotechnology, Bothell, Wash.) based on Genbank information (accession numbers: LL37=NM_004345; HBD2=AF071216) or obtained from the ATCC mammalian gene colletion (hPLA2 group IIA=MGC-14516). These constructs become the destination plasmids for the variable regions. FIG. 10E shows the final cloning step of adding the variable region to the human heavy chain-biocide destination construct. The light chain is isolated from hybridoma cDNA in a similar fashion. Given the shortness of the light chain sequence, the murine variable region will be fused to the human constant light chain region by overlap extension PCR and the chimeric light chain cloned into the retrovector backbone. The basic elements of the retroviral vector are shown in FIG. 1. The light chain and heavy chains are cloned into separate vectors. Every construct is thoroughly sequenced, analyzed and compared to the theoretical maps. Once the construct has passed QC it moves to cell culture.

Production of Human-Mouse Chimeric Anti- *Cryptosporidium* Immunoglobulin Biocide Fusion Protein and Chimeric Control Antibodies in Stable Cell Lines The constructs created are transitioned to cell culture using a retroviral vector. The retroviral gene transfer system achieves very high gene transfer rates precluding the need to use selection markers. Retrovector particles are made using a packaging cell line that produces the capsid, and reverse transcriptase and integrase enzymes. Retrovector constructs for the transgene and VSVg construct for the pseudotype are co-transfected into the packaging cell line which produces pseudotyped retrovector particles. These are harvested by supra-speed centrifugation and concentrated vector used to transduce Chinese hamster ovary (CHO) cells. The transduced cell pools undergo limiting dilution cloning and resulting clones are analyzed for expression of the product. Typically about 200 clones are analyzed. The top-producing clones are selected and expanded. A clonal cell line usually contains multiple copies of the transgene and is stable over at least 60 passages. As soon as a clone is identified as a "top clone" it is cryopreserved and backed up at two locations. Established clonal cell lines are then be grown at volumes that meet the demands of the downstream tests.

Confirm Binding to *Cryptosporidium* sporozoites

The first test uses the immunofluorescence assay (IFA) to visualize binding patterns of antibodies on the surface of sporozoites. Briefly, viable, excysted *C. parvum* or *C. hominis* preparations are incubated with either chimeric immunoglobulin biocide fusion protein or chimeric control antibody cell supernatant at increasing serial twofold dilutions. After a 30 minute incubation at 4° C., sporozoites are washed, incubated with fluorescein-conjugated affinity-purified goat anti-human IgG-Fc (Bethyl Laboratories, Montgomery, Tex.), and washed again prior to examination by epifluorescence microscopy. Candidates that show correct binding proceed to further testing as described below.

Purification Strategy for Chimeric Immunoglobulin Biocide Fusion Protein Products for Testing in In Vivo Models.

Once immunoglobulin biocide fusion protein candidates to be tested in the animal models are evaluated using the purification strategy outlined below. Initially, for in vitro evaluation and first round testing in mice cells are removed from the cell suspension (clarification) and the resulting supernatant is used. Most of the in vitro and in vivo data shown above have been obtained with cell supernatant (Example 1). In some embodiments, protein A chromatography and additional polishing steps including size exclusion viral clearance and lyophilization are performed prior to testing the product.

Since the constructs are mouse-human chimerics they comprise a human Fc portion that is known to interact with protein A from *Staphylococcus aureus* (Hjelm et al., FEBS Lett 1972 Nov. 15; 28(1):73-6; Kronvall et al., J Immunol 1970 December; 105(6):1353-9; Kronvall et al., J Immunol 1970 November; 105(5): 1116-23). Protein A affinity purification is a widely used purification strategy for human antibodies and is used for most therapeutic antibodies on the market today (Shukla et al., J Chromatogr B Analyt Technol Biomed Life Sci 2007 Mar. 15; 848(1):28-39). It is contemplated that an initial single step purification step over a protein A column will result in a product that is at least 98% pure.

Advanced purification steps are done with candidates that have undergone successful selection in the gerbil mode. Large batches (20 L or more) are produced using the Wave Bioreactor (GE, Piscataway, N.J.) to create enough starting material for testing multiple step purification schemes. The first step is cell clarification by tangential-flow filtration using a 0.2 micron hollow fiber cartridge with a 1.15 m2 surface area adequate for processing pilot scale volumes. The resulting clear solution will then be applied onto a 200 ml protein A affinity column (MabSelect, GE, Piscataway, N.J.) capable of binding up to 6 g of recombinant chimeric product, followed by a wash and elution step. The eluted product is usually of a high degree of purity (~98%). Eluted affinity purified product is analyzed using gel electrophoresis under reducing and non-reducing conditions to differentiate between heavy and light chain components of the immunoglobulin biocide fusion protein. This provides information regarding the amount of fully vs. partially assembled product as well as any aggregates, which are frequently observed in mammalian culture systems.

Further steps to remove impurities from Protein A purified material are selected depending on which polishing step is best for the specific product. These steps include anion, cation exchange or hydroxylapatite chromatography, depending on the charge of the product at a certain pH. Since some of the biocides that are linked to the antibodies are heavily charged and others are not, it is contemplated that different polishing strategies may be used for every product. The first polishing step is followed by a second polishing step consisting of size exclusion or hydrophobic interaction chromatography that reduces impurities to <0.1%.

As a final step we will include a size exclusion viral clearance step using Viresolve filters (Millipore, Billerica, Mass.). These filters are proven to remove various viruses including MLV. Viresolve products have Drug Master files to expedite FDA approval for new biotherapeutic products.

Additional testing of the purified product is conducted to gather information regarding the ability of the immunoglobulin biocide fusion protein products to retain activity upon undergoing lyophilization. Several grams of highly purified product from each of the remaining candidates are subjected to a standard industrial lyophilization procedure. Lyophilized material is then tested in the mouse model first to confirm activity before final testing is done in the pig model.

Determine the Effect of Immunoglobulin Biocide Fusion Protein B on *C. hominis* and *C. parvum* Viability and Infectivity In Vitro.

The Iowa *C. parvum* isolate (Heine et al., J Infect Dis 1984 November; 150(5):768-75) (bovine origin) has been maintained in the Parasitology Core laboratory at the University of Arizona since 1987 by propagation in newborn *Cryptosporidium*-free calves (Riggs et al., Infect Immun 1987 September; 55(9):2081-7; Riggs et al., J Immunol 1989 Aug. 15; 143(4):1340-5; Arrowood et al., J Parasitol 1987 April; 73(2): 314-9). This well-characterized isolate was used to sequence the *C. parvum* genome (Abrahamsen et al., Science 2004 Apr. 16; 304(5669):441-5), and is infectious for humans and animal models, including neonatal mice and pigs (Riggs et al., Infect Immun 1987 September; 55(9):2081-7; Riggs et al., J Immunol 1989 Aug. 15; 143(4):1340-5). The infectivity and pathogenicity of this isolate for humans have been well characterized (DuPont et al., N Engl J Med 1995 Mar. 30; 332 (13):855-9). The Iowa *C. parvum* isolate are obtained by ongoing propagation in newborn calves as previously described (Riggs et al., Infect Immun 1987 September; 55(9): 2081-7; Arrowood et al., J Parasitol 1987 April; 73(2):314-9). Oocysts are isolated from the feces of experimentally infected calves, and stored in 2.5% KCr2O7 (4° C.) (Riggs et al., Infect Immun 1987 September; 55(9):2081-7). To obtain isolated sporozoites, oocysts are hypochlorite-treated prior to excystation, then passed through a sterile polycarbonate filter (Riggs et al., Infect Immun 1987 September; 55(9):2081-7). For animal experiments, oocysts are used within 30 days of isolation and disinfected with 1% peracetic acid prior to administration (Riggs et al., Infect Immun 1994 May; 62(5): 1927-39). *C. hominis* oocysts (TU-502 isolate), free of exogenous enteropathogens, are obtained from the laboratory of Dr. Saul Tzipori (see attached letter). The TU-502 isolate is of human origin and has been propagated for over 5 years (Akiyoshi et al., Infect Immun 2003 October; 71(10):5765-71). This isolate is considered a reference isolate for *C. hominis*. TU-502 was the isolate used to sequence the *C. hominis* genome (Xu et al., Nature 2004 Oct. 28; 431(7012):1107-12) and its infectivity and pathogenicity for humans is well-characterized (Chappell et al., G. Am J Trop Med Hyg 1999 January; 60(1):157-64).

Immunoglobulin Biocide Fusion Protein Impact on Viability In Vitro

To quantify parasiticidal activity of immunoglobulin biocide fusion protein, sporozoite viability after in vitro incubation with individual immunoglobulin biocide fusion protein is assessed using fluorescein diacetate (FDA) and propidium iodide (PI) as previously described (Arrowood et al., Antimicrob Agents Chemother 1991 February; 35(2):224-7). In brief, freshly excysted *C. parvum* or *C. hominis* sporozoites are incubated (15 min, 37° C.) in PBS containing individual immunoglobulin biocide fusion protein (0.6 μM) or spent CHO cell medium (n=3). Heat killed (20 sec, 100° C.) sporozoites are used as an internal control. FDA (4 μg/ml final concentration) and PI (3 μg/ml final concentration) is added to the sporozoite preparations, incubated further (5 min, 21° C.), then examined by epifluorescence microscopy. A minimum of 100 sporozoites is counted for each preparation to determine the percent reduction in viability [(untreated sporozoite mean viability−immunoglobulin biocide fusion protein treated sporozoite mean viability)÷untreated sporozoite mean viability]×100]. Data is analyzed by Student's one-tailed t test.

Immunoglobulin Biocide Fusion Protein Impact on Infectivity In Vitro

To quantify specific neutralizing activity of immunoglobulin biocide fusion protein, an in vitro sporozoite infectivity assay is performed as previously described (Langer et al., Infect Immun 1999 October; 67(10):5282-91). For this assay, freshly excysted *C. parvum* or *C. hominis* sporozoites will be incubated (15 min, 37° C.) in medium (RPMI 1640 with 10% FBS) containing individual immunoglobulin biocide fusion protein (0.06 μM final concentration) (n=3), then inoculated onto individual HCT-8 cell monolayers (human ileocecal adenocarcinoma cells; ATCC CCL244). Prior to inoculation, HCT-8 monolayers will have been grown to ~90% confluency on glass coverslips. For comparison, control monolayers will be inoculated with sporozoites which have been identically incubated with 1) Spent CHO cell medium, or 2) neutralizing MAb 3E2. After incubation (2 h, 37° C.), inoculation medium will be aspirated and replaced with RPMI 1640 after gentle washing with medium. At 24 h post-inoculation, coverslip monolayers are washed, fixed, blocked, and processed for immunofluorescence assay (IFA) using MAb 4B10 and AlexaFluor488 affinity-purified goat anti-mouse IgM to detect intracellular stages. HCT-8 cells are counterstained with Evan's Blue stain. MAb 4B10, prepared against *C. parvum* as previously described (Riggs et al., J Immunol 1997 Feb. 15; 158(4):1787-95) also specifically recognizes *C. hominis* (Sturbaum et al., Mol Biochem Parasitol 2008 June; 159(2): 138-41) and binds all parasite stages in HCT-8 cells through 72 h post-inoculation (Langer et al., 1999, supra). Processed coverslips are mounted using DABCO then systematically examined by the same investigator using epifluorescence microscopy to directly quantitate the number of intracellular stages per monolayer to determine the mean percent reduction in infection ([mean # of intracellular stages from treated sample/mean # of intracellular stages from control]×100%) is calculated. Data is analyzed by Student's one-tailed t test.

To determine that anticryptosporidial activity detected is parasite-specific and not due to a toxic effect of immunoglobulin biocide fusion proteins on the host cell monolayers, an LDH release assay is performed. Replicate (n=3) HCT-8 monolayers are grown as previously described (Langer et al., 1999, supra), washed with phosphate-buffered saline (PBS), then incubated (2 h, 37° C.) with individual immunoglobulin biocide fusion protein at either 0.6 μM or 6 μM in PBS according to the manufacturer's instructions (CytoTox 96® Non-Radioactive Cytotoxicity Assay Kit; Promega, Madison, Wis.). Control monolayers are incubated in parallel with PBS alone. Following incubation, lactate dehydrogenase (LDH) is measured in supernatant harvested from individual wells, and monolayers lysed with 0.1% Triton X-100 according to the manufacturer's instructions to calculate cytotoxicity.

Determine the In Vivo Efficacy of Immunoglobulin Biocide Fusion Protein Against *C. parvum* in the Neonatal Mouse and Against *C. hominis* and *C. parvum* in the Immunosuppressed Gerbil Infection Model.

Each immunoglobulin biocide fusion protein that has demonstrated specific binding to *C. hominis* and *C. parvum* by IFA, and in vitro activity against both *C. hominis* and *C. parvum* in the above assays is further evaluated in vivo. For *C. parvum*, immunoglobulin biocide fusion protein are evaluated individually for the ability to reduce intestinal infection levels using the neonatal mouse model as described next. Neonatal mice cannot be infected with *C. hominis*.

Immunoglobulin Biocide Fusion Protein Efficacy Against *C. parvum* in Neonatal Mice A previously described neonatal mouse model (Riggs et al., Infect Immun 1987 September; 55(9):2081-7; Schaefer et al., Infect Immun 2000 May; 68(5):2608-16) is used as follows: Groups of 10-12 eight-day-old SPF ICR mice (Harlan) are infected with $5\times10^4$ purified *C. parvum* oocysts (50× mouse ID50) by gastric intubation. At the time of challenge, 3 hours post-challenge, and every 12 hours thereafter, mice are administered individual immunoglobulin biocide fusion protein in liquid form by gastric intubation for a total of 9 treatments averaging a dosage of 10 mg/kg/day per mouse based on prior effective doses of immunoglobulin biocide fusion protein (see data above). Cimetidine (10 mg/kg/d) is included with all treatments to neutralize gastric pH. For comparison, additional groups of 10-12 eight-day-old control mice are identically infected and treated with 1) control chimeric MAb that corresponds to immunoglobulin biocide fusion protein, 2) neutralizing MAb 3E2 (600 mg/kg/d), or 3) irrelevant concentration-matched chimeric MAb. Mice are euthanized at 92-94 hours post-infection. The jejunum, ileum, cecum, and colon are collected from each mouse and processed for histopathology. Sections are coded and examined by the same investigator, without knowledge of treatment group, for *C. parvum* stages in mucosal epithelium. Infection scores (0, no infection; 1, <33 to 66% of mucosa infected; and 3, >66% of mucosa infected) are assigned to longitudinal sections representing the entire length of (i) terminal jejunum, (ii) ileum, (iii) cecum, and (iv) proximal colon, then summed to an infection score (0-12) for each mouse (54). Additionally, all intestinal sections and sections of stomach, liver, and kidney from mice treated with antibody-biocide fusions is examined by an ACVP Board-Certified Veterinary Pathologist to determine if any lesions suggestive of biocide-host toxicity are present. Infection scores for treated and control mice will be used to calculate the mean % reduction of infection. Data is analyzed by Student's one-tailed t test.

Immunoglobulin biocide fusion protein candidates with high efficacy in this mouse model are produced in larger batches for purification as described above. Mouse studies are repeated comparing cell culture supernatant to purified versions of the same immunoglobulin biocide fusion protein. These studies measure the impact of purification procedures on the activity of the immunoglobulin biocide fusion protein. Purified candidates that show efficacy against *C. parvum* in mice are further examined in the gerbil model for activity against *C. hominis*

Immunoglobulin Biocide Fusion Protein Efficacy Against *C. hominis* or *C. parvum* in Gerbils Candidates selected using the neonatal mouse model are tested in gerbils for their efficacy against *C. hominis* and *C. parvum*. The top two performers are defined based on efficacy against both *C. hominis* and *C. parvum*, and based on binding to different antigens from among the four antigen targets under study.

To quantify the in vivo efficacy of chimeric immunoglobulin biocide fusion protein against *C. hominis* or *C. parvum* infection, an immunosuppressed gerbil model developed by (Baishanbo et al., Infect Immun 2005 August; 73(8):5252-5) is used. Groups of five four-week-old SPF Mongolian Gerbils (Meriones unguiculatus) (Charles River Labs) are injected IP with 0.8 mg of dexamethasone every second day for 10 days pre-oocyst inoculation to day 10 post-oocyst inoculation, for a total of 20 days. Following day 10 of dexamethasone treatment, gerbils are inoculated with $5\times10^4$ purified *C. hominis* TU-502 or *C. parvum* oocysts by oral intubation. At the time of oocyst inoculation, 3 hours post-inoculation, and every 12 hours thereafter, gerbils are administered individual immunoglobulin biocide fusion proteins in liquid form by intubation for a total of 22 treatments. The dosage is based on the effective dose in mice, approximately 10 mg/kg/d. Cimetidine (10 mg/kg) is included with all treatments to neutralize gastric pH. For comparison, groups of five four-week-old control gerbils are identically immunosuppressed, infected and treated with 1) chimeric MAb corresponding to the immunoglobulin biocide fusion protein, 2) neutralizing MAb 3E2 given at 600 mg/kg/d, or 3) irrelevant concentration-matched chimeric MAb. Gerbils are euthanized at 10 d post infection. The distal jejunum, ileum, cecum, and proximal colon are collected from each gerbil from identically sampled sites and processed for histopathology. Sections are coded and examined by the same investigator, without knowledge of treatment group, for *C. hominis* or *C. parvum* stages in mucosal epithelium. Infection scores (0, no infection; 1, <33 to 66% of mucosa infected; and 3, >66% of mucosa infected) are assigned to longitudinal sections from each of the above four intestinal sites then summed to an infection score (0-12) for each gerbil. Additionally, all intestinal sections and sections of stomach, liver, and kidney from gerbils treated with immunoglobulin biocide fusion proteins are examined to determine if any lesions suggestive of immunoglobulin biocide fusion protein toxicity are present. Infection scores for treated and control gerbils are used to calculate the mean % reduction of infection. Data are analyzed by Student's one-tailed t test.

In Vivo Efficacy of Immunoglobulin Biocide Fusion Protein Against *C. hominis* and *C. parvum* in the Neonatal Pig Clinical Model To quantify the in vivo efficacy of immunoglobulin biocide fusion proteins selected from testing in mouse and gerbil models, a SPF neonatal pig clinical model is used. SPF male Yorkshire hybrid piglets (S and S Swine for Biomedical Research, Ramona Calif.) are hand-caught during parturition ("snatch farrowed") from sows in which the perineum has been thoroughly cleaned using standard methods equivalent to pre-surgical preparation. Methods and precautions to prevent piglet exposure to an exogenous source of *C. parvum* and other potential diarrheal agents are used (Riggs et al., Infect Immun 1987 September; 55(9):2081-7; Perryman et al., Vaccine 1999 Apr. 23; 17(17):2142-9; Perryman et al., Mol Biochem Parasitol 1996 Oct. 1; 80(2):137-47). Piglets are fed commercial, antibiotic-free sow milk-replacer (Soweena Litter Life, Merrick) to which has been added a commercial antiserum against *E. coli* and *Clostridium perfringens* type C (Novartis Animal Health), and transported in autoclaved crates to the University of Arizona BSL 2 isolation facility. Following arrival at BSL-2 isolation facilities, piglets are assigned to either treatment (4 piglets) or control groups (4 piglets) by blind code. Group assignments and coding are made by an independent third party not involved in conducting the experiments, data collection, or interpretation of results. Personnel involved with the experiments have no knowledge of piglet group assignments; codes are revealed only at completion of the study. Dedicated separate BSL-2 rooms are used for all *C. hominis* and *C. parvum* piglet trials. Rooms are disinfected with ammonia and allowed to air dry for at least 96 hours prior to and after each trial to inactivate any residual *Cryptosporidium* or other microbial agents.

For the neonatal pig studies purified immunoglobulin biocide fusion protein is used. Since these products are suspended in a diluent and >98% pure, the diluent is used as the control treatment.

Evaluation for efficacy against *C. hominis* and *C. parvum* is determined in separate experiments but using identical protocols as follows. At 48 to 50 hours after birth, groups of 4 piglets per immunoglobulin biocide fusion protein are challenged by oral inoculation with $1\times10^7$ purified, viable *C. hominis* TU-502 oocysts, or $1\times10^7$ purified, viable *C. parvum* Iowa oocysts. To allow accurate comparisons between activities of the immunoglobulin biocide fusion protein constructs to be evaluated, the concentration of each are standardized on an equimolar basis. At challenge, and three hours after challenge, piglets are administered individual 25 mg doses of immunoglobulin biocide fusion protein orally. Every 8 hours thereafter, piglets are treated identically until the end of the trial on day 10 post-infection for an overall dose average of 37 mg/kg/d. For comparison, a group of 4 control piglets are identically infected and treated with the immunoglobulin biocide fusion protein diluent. Prilosec® OTC (Omeprazole, 1 mg/kg, Astra-Merck) is administered three hours prior to oocyst challenge and thereafter once per day to neutralize gastric pH (Foss et al., Vaccine 1999 Feb. 26; 17(7-8):788-801). Piglets are confined individually, in elevated metabolic isolation cages equipped with fecal collection pans, and maintained on milk replacer for the duration of the trial. To prevent urine from contaminating feces for subsequent analyses, high absorbancy human pediatric diapers are positioned around the abdomen, completely covering the preputial orifice, and fastened on the back of each piglet to collect urine. These are changed at each 8 hour treatment interval. This method has been successfully used in previous piglet studies. Piglets are examined twice daily by a veterinarian, without knowledge of treatment group, and assigned numerical scores based on clinical assessment for symptoms of depression, anorexia, and dehydration. Piglet weights at the time of infection, daily, and at the end of the experiment are also recorded. The total volume of feces excreted and percent dry matter for successive 24 h collections are determined to provide an objective, quantitative index of diarrhea volume and severity for each piglet. Fecal samples are examined for oocysts prior to challenge and daily thereafter by IFA using oocyst-specific MAb 4D3 to determine pre-patent and patent periods as previously described (Riggs et al., Antimicrob Agents Chemother 2002 February; 46(2):275-82). Total oocyst counts (# oocysts per ml of feces×total ml feces) for each piglet are determined from samples of well-mixed feces collected over successive 24 h periods. Feces from each piglet are examined for possible bacterial and viral enteropathogens by standard methods used in the Arizona Veterinary Diagnostic Laboratory. Piglets are euthanized on day 10 post-infection, or before if clinically indicated. Sections of duodenum, jejunum, ileum, cecum, and colon from identically sampled sites in each piglet are collected, and examined histologically without knowledge of treatment group by an ACVP Board-Certified Veterinary Pathologist. Villous length to crypt depth ratios and the density of organisms per unit length of mucosa are determined as previously described (Heine et al., J Infect Dis 1984 November; 150(5):768-75; Riggs et al., Infect Immun 1994 May; 62(5):1927-39). Infection scores of 0, 1, 2, or 3 (0, no infection; 1, <33 to 66% of mucosa infected; and 3, >66% of mucosa infected) are assigned to longitudinal sections from the (i) duodenum, (ii) proximal, mid and distal jejunum, (iii) ileum, (iv) cecum, and (v) proximal and distal colon, then summed to obtain an infection score for each piglet. Additionally, all intestinal sections, and sections of stomach, liver, myocardium, and kidney from piglets treated with immunoglobulin biocide fusion proteins are examined by an ACVP Board-Certified Pathologist to determine if any lesions suggestive of biocide-host toxicity are present. Clinical, parasitologic, and histologic data are analyzed statistically by ANOVA using the General Linear Modes Program of SAS.

Production of Murine Immunoglobulin Biocide Fusion Protein Using the Transgenic Bovine Platform Multiple transgenic lines are generated for production of murine immunoglobulin biocide fusion protein for use as an oral animal health product active against *C. parvum*. Milk from transgenic offspring, harvested by hormonal induction is used to evaluate product efficacy. FIG. 12 shows the construct design for transgenic expression. The constitutive sCMV promoter used in cell culture expression is replaced with the lactation inducible α-lactalbumin promoter which restricts expression of the transgene to the lactating mammary epithelial cells, resulting in secretion into the milk (Bleck et al., Gene 1993 Apr. 30; 126(2):213-8; Bleck et al., J Dairy Sci 1994 July; 77(7):1897-904; Bleck et al., J Anim Sci 1998 December; 76(12):3072-8). High titer pseudotyped vector is made for injection into the very small perivitelline space of the oocyte. The pseudotyped VSVg vector envelope stabilizes the vector during concentration for injection in picoliter amounts. The packaging lines established and tested for the 4H9-G1-PLA2 immunoglobulin biocide fusion protein are used. When retrovector derived from these packaging lines is concentrated and injected into oocytes typical achieving transgenic embryo rates are >85% and >50% blastocyst development rates, not significantly lower than non-injected controls.

Obtain Murine Immunoglobulin Biocide Fusion Protein from the Milk of Transgenic Cows.

Shortly after puberty transgenic heifers are hormonally induced to lactate. Milk containing immunoglobulin biocide fusion protein products is analysed and tested in the in vitro and mouse model. A protocol has been developed and recently re-tested to achieve induction of lactation. Briefly, heifers are subject to a short "simulated pregnancy" using progestins and estrogen to induce mammary development and then milk secretion initiated upon removal of these hormones. This provides milk from transgenic offspring to test approximately a year sooner than can be obtained by waiting for completion of a pregnancy.

Milk produced from transgenic animals is centrifuged to remove the fat prior to analysis for the murine immunoglobulin biocide fusion protein product. Recombinant product in the milk is tested first for binding to *C. parvum* using the IFA immunoglobulin biocide fusion protein activity is then be assessed by the in vitro infectivity assay using the HCT-8 host cell model followed by testing in a mouse trial as described above.

Processing of Transgenic Milk

The dairy industry routinely uses spray-drying to produce milk powder at very large scales. Many colostrum replacement products are processed by spray-drying and retain activity of the protective immunoglobulins. Several investigators have shown that monoclonal antibodies are mostly unaffected by this procedure (Maa et al., Pharm Res 1998 May; 15(5): 768-75; Abdul-Fattah et al., J Pharm Sci 2007 August; 96(8): 1886-916). In some embodiments, batches of transgenic milk are spray dried using a laboratory scale spray dryer (Buchi Corporation, New Castle, Del.). The obtained milk powder is then tested in an in vitro and in vivo mouse model to test if activity has been retained.

Efficacy Testing of Murine Immunoglobulin Biocide Fusion Protein in the Calf Model.

Calf trials are conducted to measure efficacy against *C. parvum*. Reduction of oocyst shedding and clinical symptoms is closely monitored. The immediate goal of large scale production of *C. parvum*-reactive murine immunoglobulin biocide fusion protein in the milk of transgenic animals is to create an inexpensive recombinant product that can be administered orally to calves after birth as a prophylactic treatment for the reduction of the *Cryptosporidium* reservoir. It is known unprocessed supernatant from cell culture production is highly efficacious when given orally to both mice and pigs (see data above) so it is expected that unprocessed milk product are equally active. However for field use a powder that can be mixed into colostrum or milk replacer is preferable to a liquid product. Spray-dried milk containing immunoglobulin biocide fusion protein product is used to conduct a calf trial.

The calf trial are conducted as a partly blinded, controlled, randomized study with 4 cohorts of 4 animals that are sequentially enrolled in the trial. Cohorts of four 1-day-old Holstein bull calves are obtained from the same production unit of approximately 2400 dairy cows for each calf trial. Calves are collected immediately upon calving, onto plastic sheeting to prevent contamination with enteropathogens, and transported to a large sterile Varikennel® transport crate containing autoclaved straw.

Once the trial animals arrive at the University of Arizona facility, they are confined to individual elevated calf stalls located in two separate containment rooms to allow separation of treatment groups. All animals of this trial are infected with $1\times10^7$ of *Cryptosporidium parvum* on day 0, when animals are 36-48 hours old. In each cohort of 4 animals, 2 are treated orally with immunoglobulin biocide fusion protein product and 2 receive a spray-dried control milk. To conduct a blinded study, personnel responsible for the calf trials do not know which group receives the treatment or placebo. The dosing is as follows: The two immunoglobulin biocide fusion protein-treated animals receive 75 mg (active substance weight) of spray-dried immunoglobulin biocide fusion protein per dose at each of the following time points: At time of challenge; 4 h, 24 h, 36 h, 48 h and 72 h post challenge (total of 6 doses=450 mg of immunoglobulin biocide fusion protein). Control animals are treated with spray-dried milk that was processed identically to transgenic milk. Each animal receives 1 g of sodium bicarbonate along with treatment to reduce stomach acidity. This is to avoid potential damage of the immunoglobulin biocide fusion protein product by abomasal pH induced inactivation. Calves are given a commercial colostrum replacer (Acquire®, APC Inc., Ankemy, Iowa) right after birth and upon arrival at study facility. Beginning at 24 h of age, all calves are maintained on reconstituted antibiotic-free milk replacer twice daily until the termination of the experiment at day 10 post challenge. The calves are examined once daily by a veterinarian. The following variables are assessed: Clinical symptoms; General health observations (willingness to rise, stance, rectal temperature, appetite, attitude, hydration status); presence or absence of diarrhea; fecal consistency (numeral scores); Coprological examinations (daily oocyst counts, fecal volume, presence of bacterial and viral enteropathogens (days 0 and 10). Other observations that are conducted: bodyweight on arrival and on termination, mortality, necropsy (at the end of the 10 day trial or for each mortality case).

Example 3

Activity of Directed Biocides Against *C. hominis*

Figure 15:
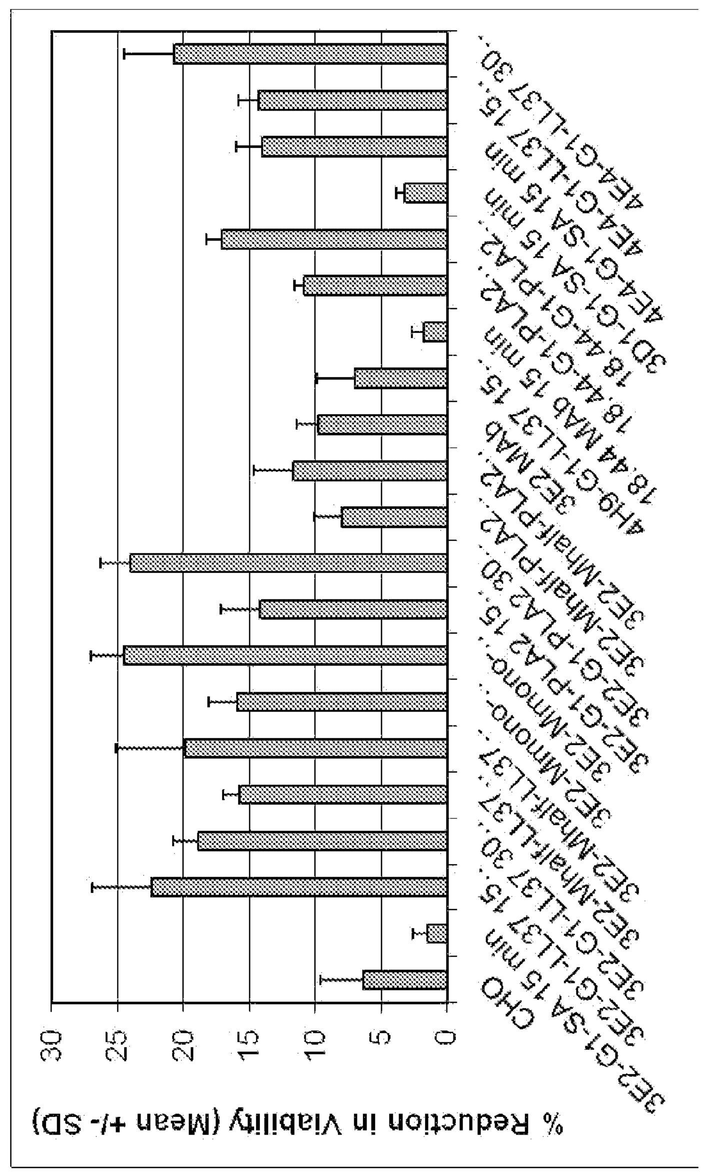
FIG. 15 shows viability of *C. hominis* after exposure to directed biocides.

This Example describes the in vitro killing of *C. hominis* by directed biocides. Experiments were performed as described in Example 2 above. Results are shown in FIG. 15. FIG. 15 shows in vitro viability of *C. hominis* upon exposure to directed biocides.

Example 4

4H9 Efficacy in Calves

This Example describes the efficacy of 4H9 directed biocides in calves. Experiments were performed as described in Example 2 above with the following modifications:

Calves:

4 sequential cohorts of 4 calves each; 2 treatment, 2 control. Holstein bull calves were collected at birth without contamination. Weight range 37-50 kg. Calves were clostrum fed (commercial powdered replacement) and entered into study at 36-48 hours of age.

Treatment and Challenge:

Challenged with $5\times10^7$ *C. parvum* oocysts

Treatment: 4H9-G1-LL37, 50K ultrafiltered, dialyzed against PBS, concentrated, frozen once Control: spent CHO medium, 50K ultrafiltered, dialyzed against PBS, concentrated, frozen once Regimen: concomitant with challenge, then after challenge, then twice daily for 4 days (0, 4, 24, 36, 48, 60, 72, 84, 96 hours)

Dose 4 days of treatment at 6.5 mg/kg/d (average)

Total of 9 treatments, Total dose per calf/trial: 520 mg

Figure 16:
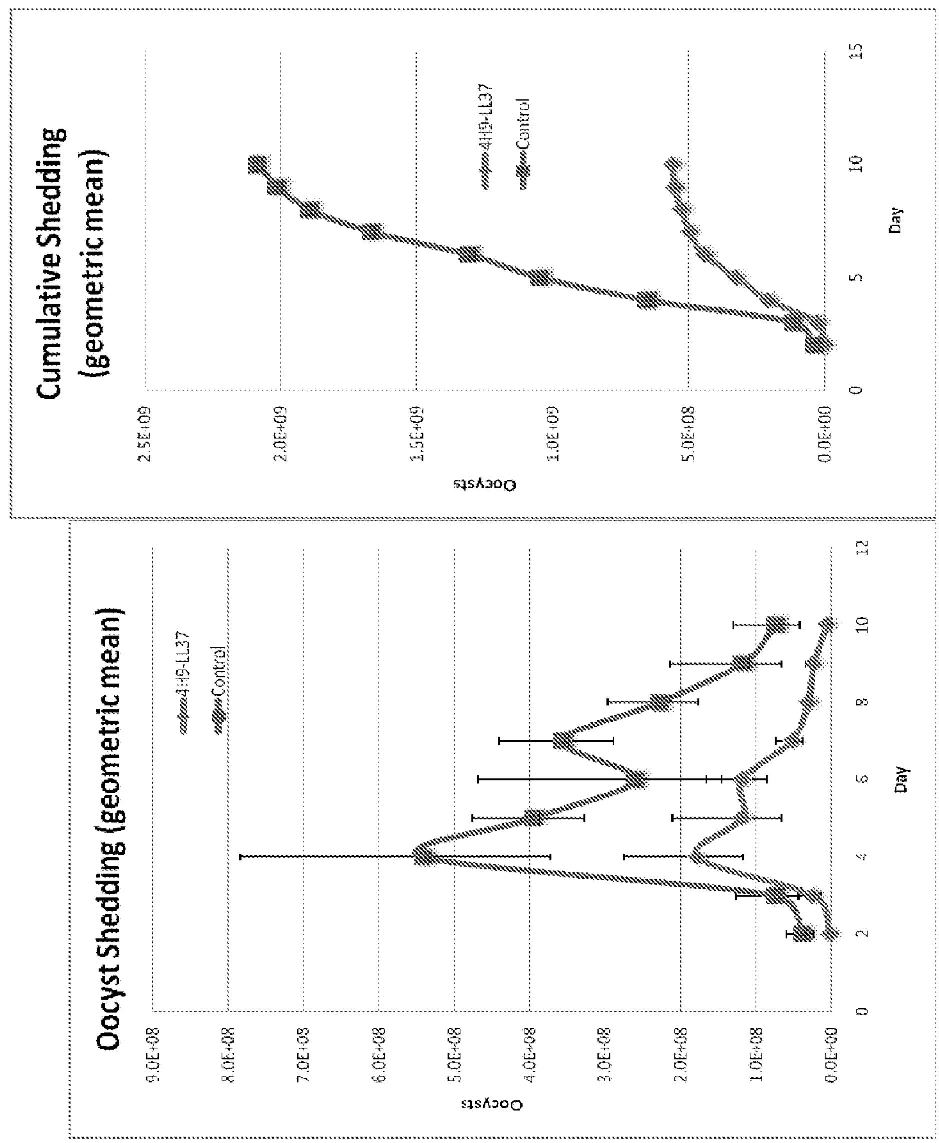
FIG. 16 summarizes oocyst shedding data treatment of calves using 4H9-LL37.
Figure 17:
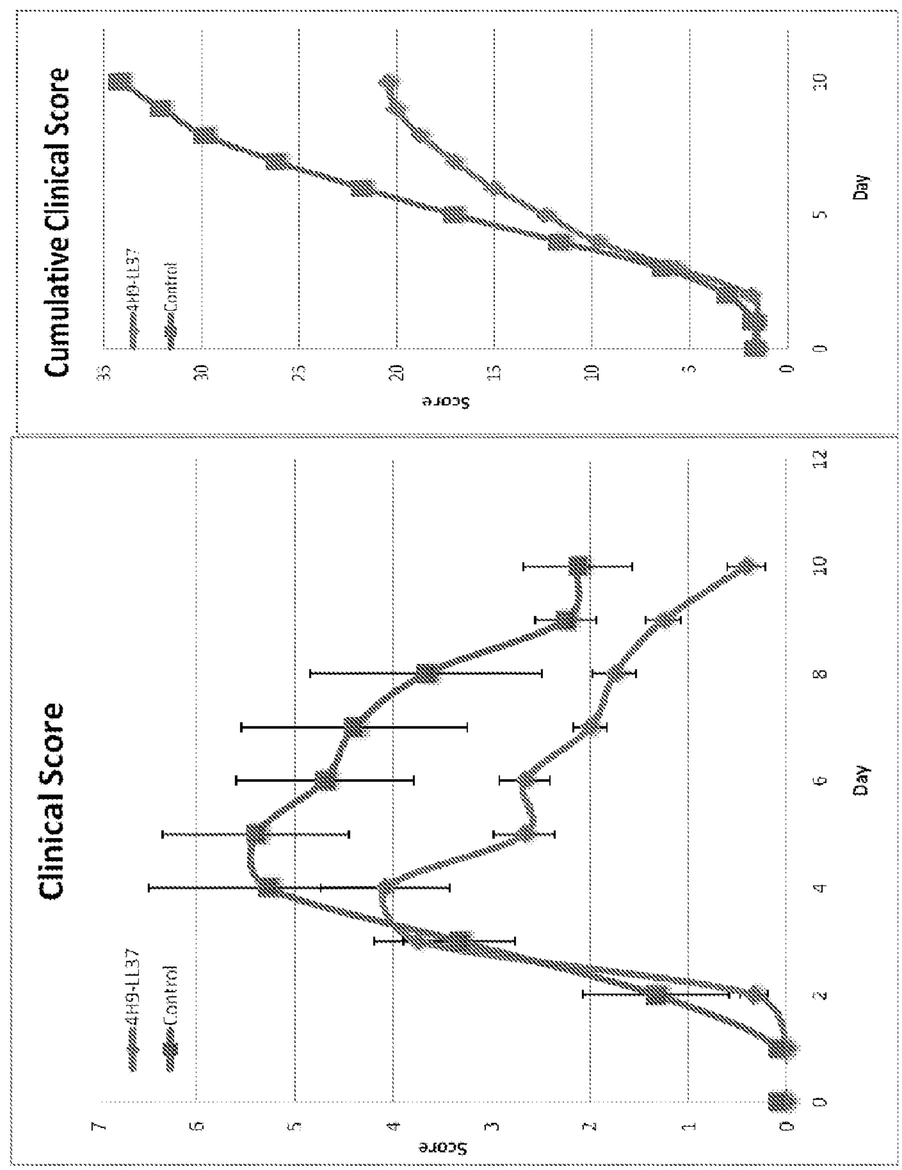
FIG. 17 summarizes clinical score results for animals given 4H9-LL37.

Results are shown in FIGS. 16 and 17. FIG. 16 summarizes the oocyst shedding data for the calf experiments using geometric mean and SEM data. The cumulative curve at the right is equivalent to an 'area-under-curve.' FIG. 17 summarizes the clinical score results. Animals given the 4H9-LL37 product show improvement in clinical score over time.

Treated animals showed a 90% reduction in oocysts in feces. Treatment with 4H9-LL37 shows significant differences in all clinical scoring parameters. The treated animals maintained appetite and voluntarily consumed more fluids. Fecal volume was unchanged in treated animals, but consistency was improved (diarrhea reduced). All 4H9-G1-LL37- treated calves showed strong (1:100 Titer) presence of mouse immunoglobulin in their serum on day 10, as well as presence of fusion in feces. No mouse immunoglobulin was detected in control calves. Circulating 4H9-G1-LL37 was shown to bind to *C. parvum* sporozoites in vitro.

Example 5

Directed Biocide Activity in Mice

Materials and Methods

Hybridomas

Three hybridomas producing antibodies directed to different neutralization-sensitive antigens on *Cryptosporidium parvum* were previously created (Riggs et al., 1989. J. Immunol. 143:1340-1345; Riggs et al., 1999. Infect. Immun. 67:1317-1322; Riggs et al., 1987. Infect Immun 55:2081-2087; Riggs et al., 1997. J. Immunol. 158:1787-1795; Schaefer et al., 2000. Infect Immun 68:2608-2616) (Table 1). MAb 3E2 was included as a positive control. As an isotype control antibody MAb 166 directed to *Listeria monocytogenes* was used (Ziegler and Orlin. 1984. Clin. Invest Med. 7:239-242). Hybridoma-derived and recombinant MAb 166 do not bind to *C. parvum* sporozoites as determined by immunofluorescence assay (IFA).

Assembly of Genetic Constructs

Total RNA was isolated from hybridoma cells (RNeasy kit Qiagen Inc. Valencia, Calif.) and reverse transcribed into cDNA using oligo dT primers (AffinityScript cDNA synthesis kit, Stratagene, La Jolla, Calif.) Immunoglobulin variable region genes were amplified from cDNA using degenerate upper primers semi-specific for the signal peptide region combined with lower primers specific for the constant region (Novagen Ig-primer set, EMD Biosciences, San Diego, Calif.) and the PCR products obtained were cloned (Strataclone PCR cloning kit, Stratagene, La Jolla, Calif.). Multiple clones derived from the same PCR product were sequenced to test for PCR-derived mutations and correct reading frame using Lasergene (DNAstar Inc., Madison, Wis.) and compared with sequences in Genbank to confirm that they were of mouse immunoglobulin origin. Immunoglobulin gene constant regions were extracted from hybridoma cDNA using primers (oligonucleotides obtained from Integrated DNA Technologies, Coralville, Iowa) to the known constant sequence of either murine IgG1 or IgG2b isotype. The $(G_4 5)_3$ linker, including flanking regions compatible with heavy chain sequence at the 5'-end and biocide sequence at the 3'-end, was synthesized by Blue Heron Biotechnology (Bothell, Wash.). The gene for human phospholipase A2 group IIA (PLA2) was obtained from the ATCC gene collection (MGC-14516). The coding region for LL37, the active portion of human cathelicidin hCAP-18 was assembled by PCR amplification of three long overlapping oligomers that were based on Genbank NM__004345. The RNA export and stabilization element (RESE) is based on the woodchuck hepatitis virus RNA export element and enhances RNA export from the nucleus in the absence of RNA splicing (Zufferey et al., 1999. J Virol. 73:2886-2892).

To engineer the various IgM-based constructs, the variable and constant regions were isolated from the 3E2 hybridoma cell line as described above and a full size IgM molecule was constructed. In the absence of the J-chain, IgM spontaneously forms hexamers which we confirmed by size analysis using polyacrylamide gel electrophoresis (PAGE). Once binding of the 3E2 hexamer to sporozoites was confirmed by IFA (described below), the 3E2 sequences were used to construct monomeric and halfmeric fusion proteins. This was achieved by eliminating two or three of the interchain disulfide bonds in the IgM heavy chain genes. This was done as described by Wiersma et al (Wiersma and Shulman. 1995. J. Immunol. 154:5265-5272) using site-directed mutagenesis PCR to introduce the requisite cysteine to serine codon changes of the nucleotide sequence C337S+C414S+C575S to make halfmers and C414S+C475S to make monomers.

All elements were assembled in a series of overlap PCR reactions and the final product containing flanking restriction endonuclease sites was cloned into a murine leukemia virus (MLV) based replication incompetent retroviral expression system (Pantropic Retroviral Vector System, Clontech, Mountain View, Calif.) modified to include the simian cytomegalovirus (CMV) promoter (GenBank Accession U38308) (FIG. 1). Due to the very high gene transfer rates into mammalian host cells achieved with the retroviral system, the $Neo^r$ gene for selection was not essential and was removed from the retrovector backbone.

To confirm the production of correctly assembled recombinant antibody biocide fusion products, PAGE was performed under both reducing and non-reducing conditions, followed by Western blotting using an affinity purified goat anti-mouse IgG antibody or anti-mouse IgM antibody (Bethyl Laboratories, Montgomery, Tex.).

Sequences were deposited in GenBank under Accession numbers GU126674 (4H9 heavy chain variable region mRNA), GU126675 (4H9 light chain variable region mRNA), GU126676 (3E2 heavy chain variable region), GU126677 (3E2 light chain variable region), GU126678 (18.44 heavy chain variable region) and GU126679 (18.44 light chain variable region).

Expression in Cell Culture

The retroviral construct containing the gene of interest was co-transfected with plasmid containing the gene for vesicular stomatitis glycoprotein into GP2-293 packaging cells (Pantropic Retroviral Expression system, Clontech, Mountain View, Calif.) to produce infectious replication-incompetent pseudotyped retrovector particles. These were harvested by centrifugation (75,000×g) and resuspended for 2 h, then used to transduce CHO cells. Vector was removed and replaced with fresh SFM4 (Hyclone, Logan, Utah) medium after 16 h. Ten to twelve days after transduction cell pools were analyzed by ELISA for the detection of recombinant products using a heavy chain capture and light chain signal generation (Bethyl Laboratories, Montgomery, Tex.). Upon confirmation of presence of correctly assembled immunoglobulins, individual cells were isolated in 96 well plates by limiting dilution. After 12 days, supernatants were re-analyzed and the highest producing clones were selected and expanded. Recombinant products were produced in standard tissue culture flasks or 500 ml Erlenmeyer flasks with agitation. Typically, cultures were harvested after 8-10 days of incubation, cells removed by double-centrifugation (400×g for 10 min, 6000×g for 10 min), and supernatants analyzed to determine product concentration using ELISA co-detection of immunoglobulin heavy and light chain. Recombinant products or hybridoma-derived MAbs used for these studies were either prepared from unprocessed cell culture supernatants or supernatants concentrated up to 3 fold using Amicon Centricon Plus-20 (Millipore, Billerica, Mass.) to provide equal protein concentrations.

The recombinant products expressed are described using the following nomenclature: variable region source-recombinant isotype-biocide, for instance 4H9-G1-LL37. Recombinant products lacking a biocide fusion are described as variable region source-recombinant isotype, for instance 4H9-

G1. Hybridoma derived MAbs are described as hybridoma name MAb, for instance 3E2 MAb.

*Cryptosporidium parvum* Oocyst Source

The Iowa *C. parvum* isolate (Heine et al., 1984. J Infect Dis 150:768-775) has been maintained since 1988 by propagation in newborn *Cryptosporidium*-free Holstein bull calves (Riggs et al., 1989; supra; Riggs et al., 1987; supra) which were the source of oocysts for all experiments. Oocysts were isolated from calf feces by sucrose density gradient centrifugation and stored in 2.5% $KCr_2O_7$ (4° C.) (Arrowood et al., 1996. J Eukaryot. Microbiol. 43:89 S; Riggs et al., 1987; supra). For challenge of neonatal mice, oocysts were used within 30 days of isolation and disinfected with 1% peracetic acid immediately prior to administration (Riggs et al., 1994. Infect Immun 62:1927-1939). To obtain isolated sporozoites for use in vitro, oocysts were hypochlorite-treated prior to excystation, (37° C., 0.15% [wt/vol] taurocholate, 1 h), then passed through a sterile polycarbonate filter (2.0 μm pore size; Poretics, Livermore, Calif.) and used immediately (Riggs et al., 1987; supra; Schaefer et al., 2000. Infect Immun 68:2608-2616). Oocyst excystation was determined immediately prior to mouse administration, or to obtain isolated sporozoites, and always exceeded 90%.

Assays for Binding of Recombinant Products to Sporozoites and In Vitro Assessment of Viability.

For immunofluorescence assays to assess binding, excysted sporozoites were aliquoted onto Teflon-coated multiwell glass slides, air-dried, and then gently heat fixed. Individual wells were incubated (30 min, 37° C.) with concentration-matched recombinant fusion products, recombinant antibody, isotype-matched control MAb of irrelevant specificity, or CHO cell supernatant control, washed with PBS, incubated with fluorescein-conjugated affinity-purified goat anti-mouse IgM/IgG/IgA (Kirkegaard & Perry, Gaithersburg, Md.), washed, and then examined by epifluorescence microscopy.

To quantify parasiticidal activity of recombinant products, sporozoite viability after in vitro incubation with individual products was assessed using fluorescein diacetate (FDA) and propidium iodide (PI) as previously described (Arrowood et al., 1991. Antimicrob. Agents Chemother. 35:224-227; Carryn et al., International Journal of Antimicrobial Agents 24, 117. 2004). In brief, freshly excysted sporozoites were incubated (15 min, 37° C.) in CHO medium containing individual recombinant products (50 μg/ml) or spent CHO cell medium (n=3). Heat killed (20 sec, 100° C.) sporozoites were used as an internal control. FDA (8 μg/ml final concentration) and PI (3 μg/ml final concentration) were added to the sporozoite preparations, incubated further (30 min, 21° C.), then examined in fluid phase wet mounts by epifluorescence microscopy. A minimum of 100 sporozoites were counted for each preparation to determine the percent reduction in viability [(CHO-treated sporozoite mean viability−recombinant product-treated sporozoite mean viability)÷CHO-treated sporozoite mean viability]×100. The mean values for test and control preparations were examined for significant differences using JMP software and ANOVA analysis of variance (SAS, Cary, N.C.).

Evaluation of Recombinant Products for Efficacy In Vivo

Groups of 10 eight-day-old SPF ICR mice were administered, by gastric intubation, $5\times10^4$ oocysts ($50\times MID_{50}$) (Riggs et al., 1987, supra) concurrently with recombinant antibody fusions or combinations of individual MAbs and biocides (100 concentration range 10-100 μg/ml). At 3 and every 12 h thereafter, mice received additional treatments (100 concentration range 10-100 μg/ml) by gastric intubation for a total of nine treatments. Cimetidine (10 mg/kg) was included with all treatments. Groups of 10 eight-day-old control mice were treated identically with CHO cell culture supernatant or recombinant antibody alone. After euthanasia at 92-94 h p.i., the jejunum, ileum, cecum, and colon were collected, coded, and examined histologically by the same investigator, without knowledge of treatment group, for *C. parvum* stages in mucosal epithelium. Scores of 0, 1, 2 or 3 (0, no infection; 1, <33% of mucosa infected; 2, 33 to 66% of mucosa infected; and 3, >66% of mucosa infected) were assigned to longitudinal sections representing the entire length of (i) terminal jejunum, (ii) ileum, (iii) cecum, and (iv) colon, then summed to obtain an infection score (0 to 12) for each mouse (Riggs et al., 1989; supra; Riggs et al., 1997; supra). Percent reduction of infection was calculated as [(Control mean infection score−product mean infection score)÷Control mean infection score×100]. The control treatment in all in vivo experiments was CHO cell culture supernatant.

Experimental results were analyzed in JMP version 8 (SAS Institute Cary, N.C.) by ANOVA. Differences between means were tested with a Tukey-Kramer HSD with alpha=0.05.

All mice were maintained in BSL2 biocontainment at the University of Arizona and in accordance with the PHS Guide for the Care and Use of Laboratory Animals.

Results.

Production of Recombinant Antibodies and Antibody-Biocide Fusions

Recombinant protein fusions comprising monoclonal antibodies and biocides were assembled using the basic retroviral constructs shown in FIG. 1. Use of the retroviral system allowed the generation of stable cell lines for all the recombinant products shown in Table 4 in a short period of time. Cell supernatant-containing products were tested in the in vitro assay and the neonatal mouse model. All products showed the expected sizes on Western blots for either heavy chains alone, heavy chain-biocide fusions or kappa light chains (data not shown). Binding specificity of the recombinant 4H9, 3E2 and 18.44-derived products for *C. parvum* sporozoites, and lack of binding of recombinant 166-derived products, was confirmed by immunofluorescence assay. Table 4 shows the recombinant products and control antibodies tested.

Direct Effects of Antibody Biocide Fusion Proteins on Sporozoite Viability

Figure 18:
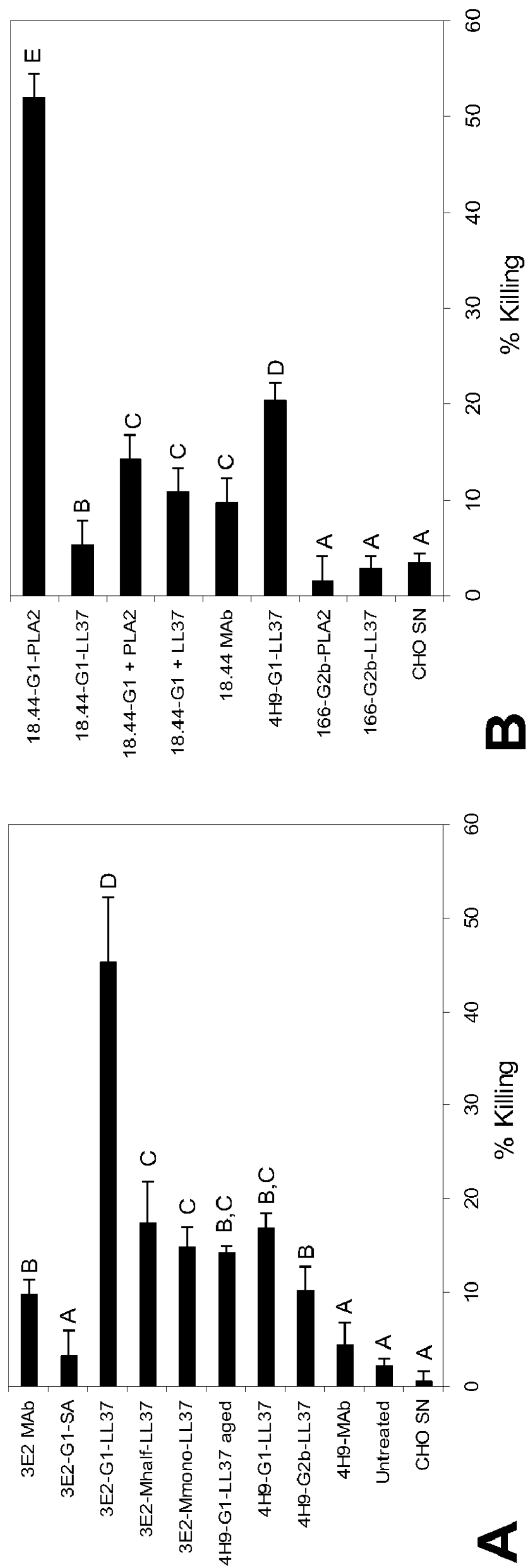
FIG. 18 shows In vitro killing of *C. parvum* sporozoites by fusion proteins. A, each component was used at 50 μg/ml except 3E2-G1-LL37 (1.5 μg/ml). B, each component was used at 25 μg/ml, PLA2 and LL37 were used at equimolar concentrations. CHO SN=spent CHO cell medium, Untreated=untreated sporozoites in PBS. MAb indicates use of native hybridoma-derived antibody as control. Means±SEM and ANOVA of triplicate wells are shown. Bars not connected by the same letter are significantly different (alpha=0.05).

An in vitro viability assay was performed using various different versions of antibody-biocide fusions comprising the 3E2 (anti-CSL), 4H9 (anti-GP25-200) and 18.44 (anti CPS-500) specificities combined with the LL37 and PLA2 biocides (FIG. 18). This assessment showed that antibody-biocide fusions targeting any one of these three different antigens on the sporozoite surface mediate significantly higher efficacy at killing sporozoites in vitro than their stand-alone antibody counterparts. Size-reduced versions of antibodies comprising an IgM monomer (two heavy chains+two light chains), and IgM halfmer (one heavy chain+one light chain) fused to LL37 were designed. The 3E2-based fusions showed significantly increased efficacy at killing sporozoite in vitro when compared to the hybridoma-derived 3E2 MAb (FIG. 18A).

The 3E2-G1-LL37 fusion showed high efficacy in vitro. The 4H9-G1-LL37 was subjected to long-term storage at 4° C. over a period of 3 months to evaluate stability. Storage resulted in a loss of activity of only 2.6%, indicating good stability under refrigeration temperatures. The 4H9-G1-PLA2 fusion was also tested in this series but did not show any direct effect on the viability of *C. parvum* sporozoites in vitro. FIG. 18B shows the effects on sporozoite viability of 18.44 MAb, alone and in combination with PLA2 or LL37, compared to the corresponding 18.44 MAb-biocide fusions. The 18.44-G3 MAb itself exhibited a low rate of sporozoite killing, which increased slightly by simultaneous application of the MAb with recombinant PLA2 as individual, non-fused molecules. However, when 18.44 was expressed as an IgG1 with PLA2 as a C-terminal fusion, the Resulting 18.44-G1-PLA2 fusion protein showed an approximately 3.5 fold increase in activity over that of 18.44 and PLA2 tested in combination. The 51% reduction in sporozoite viability achieved by 18.44-G1-PLA2 is one of the strongest detected in the in vitro assay. The 18.44-G1-LL37 fusion protein exhibited a lower activity than the 18.44-G1-PLA2 fusion. The outcome of this experiment demonstrated that antibody biocide fusions have a direct and greater impact on sporozoite survival in vitro compared to the corresponding stand-alone antibodies.

Figure 19:
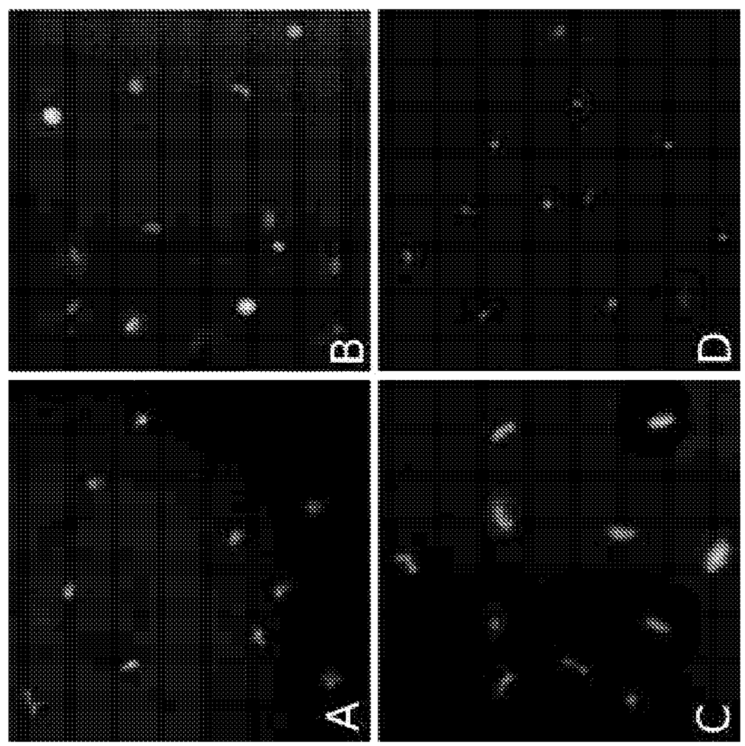
FIG. 19 shows fluorescence photomicrographs showing the effect of various fusion proteins and monoclonal antibody controls. A, representative picture of *C. parvum* sporozoites after an exposure of 30 min to either PBS, CHO cell supernatant, 4H9-G1, 4H9-G2b, 18,44 MAb, 4H9-G1-PLA2, 3E2-G1, or 3E2-MAb. B, representative picture of *C. parvum* sporozoites after an exposure of 30 min to either 4H9-G2b-LL37, 4H9-G1-LL37, 3E2-G1-LL37, 3E2-Mhalf-LL37 or 3E2-Mmono-LL37. C, *C. parvum* sporozoites after an exposure of 30 min to 18.44-G1-PLA2. D, heat-killed sporozoites.

To evaluate morphological effects, sporozoites were exposed to various fusion proteins for 30 minutes and then analyzed by immunofluorescence. FIG. 19A shows a representative result of sporozoites exposed to either CHO cell supernatant, monoclonal antibodies or the 4H9-G1-PLA2 fusion. FIG. 19B is representative for the activity shown by all LL37 fusions tested. The observation of spherical shapes and increased number of dead cells are indicative of the degenerative process associated with disturbance of the osmoregulatory system in the sporozoite.

Figure 20:
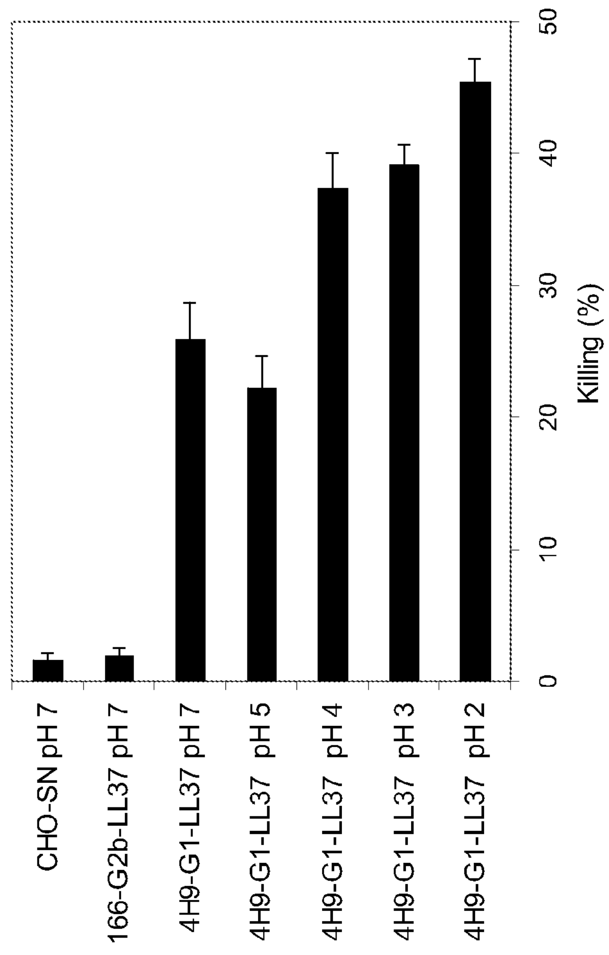
FIG. 20 shows In vitro killing of *C. parvum* sporozoites with low pH-treated 4H9-G1-LL37.

The effect of pH on the stability of 4H9-G1-LL37 was investigated. After incubation at various pHs (PBS at pH 2, 3, 4, 5, 7) at 37° C. for 90 min, the fusion protein samples were neutralized to pH 7 and tested in vitro for their direct effect on sporozoite viability. There was no decrease in effectiveness of the fusion protein following low pH treatment (FIG. 20). The efficacy of 4H9-G1-LL37 almost doubled after exposure at pH 2.

Fusion Proteins Inhibit Initiation of *C. parvum* Infection in Neonatal Mice.

Figure 21:
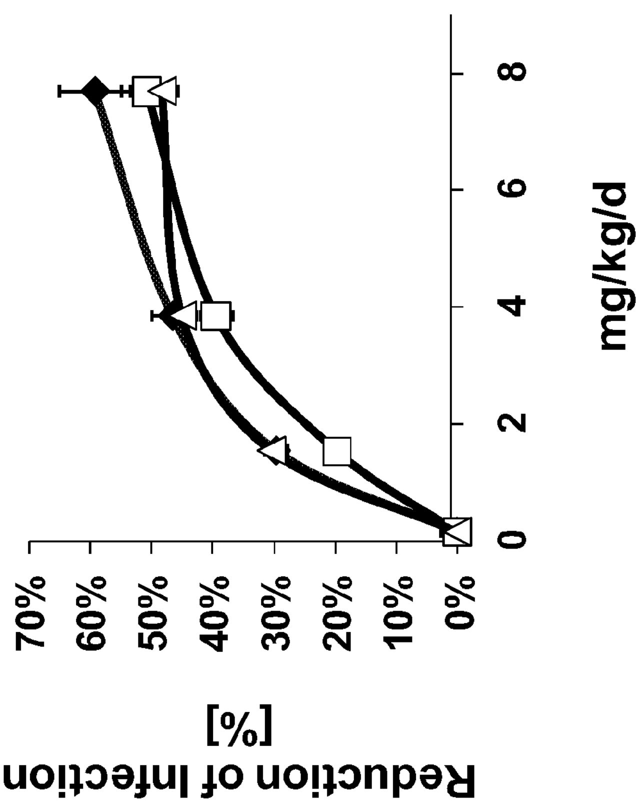
FIG. 21 shows dose dependent efficacy of different fusion proteins given orally against *C. parvum* infection in neonatal mice.

Cell culture-derived supernatants containing recombinant fusion proteins 4H9-G1-LL37, 4H9-G2b-LL37 and 18.44-G1-PLA2, and control 3E2 MAb were orally administered to neonatal mice concomitantly with the oocyst-challenge. Increasing dosages of fusion proteins lead to a greater prophylactic effect on infection as determined by intestinal section scoring to quantify intracellular *C. parvum* stages (FIG. 21). The dose response patterns of 4H9 fusion proteins in both the IgG1 and IgG2b formats were similar. A similar dose response pattern was also observed with the 18.44-G1-PLA2 fusion protein. The efficacy of all three fusions leveled off as the dose was increased to 7.7 mg/kg/day. The CHO cell supernatant (spent medium) controls had no significant effect on infection levels. MAb 3E2 IgM pentamer positive control had to be used at a dosage of 462 mg/kg/day to induce a reduction of initiation of infection of 37% (lower dosages resulted in insignificant reduction of initiation of infection). No adverse effects of the treatments were observed based on clinical appearance, growth and suckling response. Further, no evidence of host toxicity was observed based on histopathological evaluation of intestinal sections for morphologic changes.

The above data clearly show that multiple recombinant fusion proteins differing either in their binding specificity or in their biocide component, are efficacious at reducing *C. parvum* infection in neonatal mice. Furthermore, the 4H9 and 18.44 fusions have significantly greater neutralizing activity than the hybridoma antibody 3E2 used as a comparator, showing efficacy at doses that are 60-fold lower.

Antibody-Biocide Fusions are More Effective than the Sum of their Parts at Reducing Initiation of Infection in the Neonatal Mouse Model In vitro data presented in FIG. 18B showed that selected antibody biocide fusions are significantly more effective at killing sporozoites than an equimolar matched mixture of single antibody and single biocide molecules. To further extend these observations, the efficacy of antibody plus biocide administered as separate molecules were compared with that of a fusion of the two molecules against a *C. parvum* oocyst challenge in neonatal mice. The effectiveness of the fusion molecules was significantly greater than that of individual MAb and biocide components given as separate molecules at equimolar amounts (Table 5). The 4H9-biocide fusion molecules reduced intestinal infection by 74-81%, whereas the reduction achieved with a combination of 4H9-G1 plus PLA2 was 31%, and with 4H9-G1 plus LL37 was 23%. The 4H9-G1-LL37, 4H9-G2b-LL37, and 4H9-G1-PLA2 fusions were approximately equivalent in efficacy.

Antibody Biocide Fusions Directed to Different Epitopes have a Synergistic Effect Various fusion proteins were created using the variable region of anti-CSL MAb 3E2 (Table 4). 3E2 IgM monomer and 3E2 IgM halfmer fusions with LL37 were compared to the 4H9-biocide fusion molecules in the neonatal mouse model. When the 3E2-M monomer-LL37 was given to mice at a dose of 7.7 mg/kg/day, a significant reduction of initiation of infection over control treatment was observed, demonstrating that the activity of antibody fusion proteins in vivo can be mediated through different surface exposed epitopes. This observation further broadens the number of potential targets on the sporozoite surface for fusion protein-mediated neutralization. The most effective molecule of the series was the 3E2-Mhalfmer-LL37 fusion which reduced infection by 82% at a relatively low dose. It was previously observed that combinations of MAbs targeting different neutralization-sensitive antigens can provide significant additive efficacy over that of the individual MAbs (Schaefer et al., 2000, supra). Therefore the effect of a combined fusion protein treatment targeting two distinct epitopes was evaluated. When 4H9-G1-LL37 and 3E2-Mmono-LL37 were given together, each at half the dose used individually (3.8 mg/kg/d), a significant increase in efficacy over 3E2-Mmono-LL37 used alone at the 7.7 mg/kg/d dose was observed indicating a synergistic effect (Table 6).

TABLE 4

| Antibody | Epitope Specificity | Hybridoma Isotype | Recombinant Isotype | Peptide | Enzyme | mol wt [kDa] |
|---|---|---|---|---|---|---|
| 4H9 | *C. parvum* sporozoites | IgG1 | IgG1 | LL37 | | 158 |
| | GP25-500 | | IgG1 | | sPLA2 IIa | 177 |
| | | | IgG1 | — | — | 147 |
| | | | IgG2b | LL37 | | 160 |
| 3E2 | *C. parvum* sporozoites | IgM | IgM Monomer | LL37 | | 190 |
| | CSL | | IgM Halfmer | LL37 | | 95 |
| | | | IgG1 | — | — | 147 |
| | | | IgG1 | LL37 | | 158 |
| | | | N/A | — | — | 970 |

TABLE 4-continued

| Antibody | Epitope Specificity | Hybridoma Isotype | Recombinant Isotype | Peptide | Enzyme | mol wt [kDa] |
|---|---|---|---|---|---|---|
| 18.44 | *C. parvum* sporozoites | IgG3 | IgG1 | LL37 | | 158 |
| | CPS-500 | | IgG1 | | sPLA2 IIa | 177 |
| | | | N/A | — | — | 147 |
| 166 | *L. monocytogenes* | IgG2b | IgG2b | LL37 | | 159 |
| | cell wall | | IgG2b | | sPLA2 IIa | 178 |
| | | | IgG2b | — | — | 148 |

TABLE 5

| Treatment | Dose [mg/kg/d] MAb/Fusion | Dose [mg/kg/d] Biocide | N | Mean Infection Score | Std Error | % Infection Reduction | ANOVA[1] |
|---|---|---|---|---|---|---|---|
| CHO supernant negative control | NA | NA | 10 | 6.40 | 0.34 | 0% | A, B |
| 4H9-G1-LL37 | 9.7 | | 9 | 1.67 | 0.36 | 74% | D |
| 4H9-G2b-LL37 | 8.0 | | 9 | 1.22 | 0.36 | 81% | D |
| 4H9-G1-PLA2 | 13.5 | | 9 | 1.67 | 0.36 | 74% | D |
| 4H9-G1 + LL37 | 9.7 | 0.2 | 10 | 4.90 | 0.34 | 23% | B, C |
| 4H9-G1 + rPLA2 | 13.5 | 1.0 | 9 | 4.44 | 0.36 | 31% | C |
| 3E2 MAb | 46.5 | | 9 | 5.44 | 0.36 | 15% | A, B, C |
| 3E2 MAb | 465.0 | | 10 | 1.50 | 0.34 | 77% | D |

[1]Treatments not connected by same letter are significantly different (alpha = 0.05)

TABLE 6

| Treatment | Dose [mg/kd/d] | Mean Infection Score | Std Error | Infection Reduction | ANOVA[1] | | | | | |
|---|---|---|---|---|---|---|---|---|---|---|
| CHO SN | NA | 8.65 | 0.28 | 0% | A | | | | | |
| 3E2-G1 | 7.7 | 5.4 | 0.28 | 38% | | B | | | | |
| 3E2-Mmono-LL37 | 7.7 | 4.5 | 0.28 | 48% | | B | C | D | | |
| 4H9-G1-LL37 | 7.7 | 3.7 | 0.28 | 57% | | | | D | E | |
| 4H9-G1-LL37 + 3E2-Mmono-LL37 | 3.8 + 3.8 | 2.9 | 0.28 | 66% | | | | | E | F |
| 3E2-Mhalf-LL37 | 2.5 | 1.6 | 0.28 | 82% | | | | | | F |

[1]Treatments not connected by same letter are significantly different (alpha = 0.05)

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising a recombinant fusion protein, wherein said fusion protein comprises an immunoglobulin comprising a pair of polypeptides comprising a heavy chain and a light chain having the amino acid sequences selected from the group consisting of SEQ ID NOs: 10:6, 10:8, 10:4, 158:4, 24:14, 24:16, 24:18, 24:20, 24:22, 32:26, 32:28 and 32:30.

2. A method of treating a subject, comprising: contacting a subject suspected of being infected with or infected with *Cryptosporidium parvum* with the recombinant fusion protein of claim 1.

3. The method of claim 2, wherein said subject is a mammal.

4. The method of claim 3, wherein said mammal is selected from the group consisting of a bovine or a human.

* * * * *

UNITED STATES PATENT AND TRADEMARK OFFICE

CERTIFICATE OF CORRECTION

PATENT NO. : 8,394,379 B2
APPLICATION NO. : 12/686879
DATED : March 12, 2013
INVENTOR(S) : Imboden et al.

It is certified that error appears in the above-identified patent and that said Letters Patent is hereby corrected as shown below:

On the title page

Item (73) of the front page of the patent reads:

(73) Assignee: ioGenetics, LLC, Madison, WI (US)

when in fact it should read:

(73) Assignees: ioGenetics, LLC, Madison, WI (US);
Arizona Board of Regents on Behalf of The University of Arizona, Tucson, AZ (US)

Signed and Sealed this
Twentieth Day of October, 2015

Michelle K. Lee

Michelle K. Lee
*Director of the United States Patent and Trademark Office*